United States Patent
Maeda et al.

(10) Patent No.: US 12,378,567 B2
(45) Date of Patent: Aug. 5, 2025

(54) AROGENATE DEHYDROGENASE POLYNUCLEOTIDES, POLYPEPTIDES AND METHODS OF USING THE SAME

(71) Applicant: Wisconsin Alumni Research Foundation, Madison, WI (US)

(72) Inventors: Hiroshi A. Maeda, Madison, WI (US); Samuel Lopez-Nieves, Madison, WI (US); Marcos Viana de Oliveira, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/932,337

(22) Filed: Feb. 16, 2018

(65) Prior Publication Data
US 2018/0265880 A1 Sep. 20, 2018

Related U.S. Application Data

(60) Provisional application No. 62/459,798, filed on Feb. 16, 2017.

(51) Int. Cl.
| | |
|---|---|
| *A01H 5/00* | (2018.01) |
| *C07H 21/04* | (2006.01) |
| *C12N 15/00* | (2006.01) |
| *C12N 15/82* | (2006.01) |
| *C12P 13/22* | (2006.01) |

(52) U.S. Cl.
CPC .......... *C12N 15/8251* (2013.01); *A01H 5/00* (2013.01); *C07H 21/04* (2013.01); *C12N 15/00* (2013.01); *C12P 13/22* (2013.01); *C12Y 103/01043* (2013.01)

(58) Field of Classification Search
None
See application file for complete search history.

(56) References Cited

U.S. PATENT DOCUMENTS

| | | | |
|---|---|---|---|
| 7,396,664 | B2 | 7/2008 | Daly et al. |
| 9,029,636 | B2 | 5/2015 | Wu et al. |
| 9,701,977 | B2 | 7/2017 | Maeda et al. |
| 2015/0150157 | A1 | 5/2015 | Maeda et al. |
| 2018/0216083 | A1 | 8/2018 | Maeda et al. |

FOREIGN PATENT DOCUMENTS

WO WO 2002/090523 11/2002

OTHER PUBLICATIONS

Dohm et al., UnitProt Database, Acc. No. A0A0K9QIW7, Nature, 505: 546-549, 2014.*
Ploux, O., UniProt Database, Acc. No. A0A1U8YMX3, Jun. 7, 2017.*
Maeda, H., et al. Prephenate aminotransferase directs plant phenylalanine biosynthesis via arogenate. Nat. Chem. Biol. 7, 19-22 (2011).
Millgate, A. G. et al. Analgesia: Morphine-pathway block in top1 poppies. Nature 431, 413-414 (2004).
Raman, S., et al., Evolution-guided optimization of biosynthetic pathways. Proc. Natl. Acad. Sci. U. S. A. 111, 17803-17808 (2014).
Reyes-Prieto, A. & Moustafa, A. Plastid-localized amino acid biosynthetic pathways of Plantae are predominantly composed of non-cyanobacterial enzymes. Sci. Rep. 2, 955 (2012).
Rippert, P., et al., Engineering plant shikimate pathway for production of tocotrienol and improving herbicide resistance. Plant Physiol. 134, 92-100 (2004).
Rippert, P. & Matringe, M. Molecular and biochemical characterization of an Arabidopsis thaliana arogenate dehydrogenase with two. Plant Mol. Biol. 48, 361-368 (2002).
Rippert, P. & Matringe, M. Purification and kinetic analysis of the two recombinant arogenate dehydrogenase isoforms of *Arabidopsis thaliana*. 2002 European Journal of Biochemistry 269: 4753-4761.
Rippert, P., et al., Tyrosine and Phenylalanine are Synthesized within the Plastids in *Arabidopsis*. Plant Physiol. 149, 1251-1260 (2009).
Rubin, J. L. et al., "Enzymology of L-Tyrosine Biosynthesis in Mung Bean (*Vigna radiata* [L.] Wilczek)," 1979 Plant Physiol. 64:727-734.
Sariaslani, F. S. Development of a combined biological and chemical process for production of industrial aromatics from renewable resources. Annu. Rev. Microbiol. 61, 51-69 (2007).
Schenck, C.A., et al. Tyrosine biosynthesis, metabolism, and catabolism in plants. Phytochemistry. May 2018; 149:82-102.
Schenck, C.A., et al. "Conserved molecular mechanism of TyrA dehydrogenase substrate specificity underlying alternative tyrosine biosynthetic pathways in plants and microbes." (2017) Frontiers in Molecular biosciences.
Schenck, C.A., et al., Molecular Basis of the evolution of alternative tyrosine biosynthetic routes in plants. 2017 Nature Chemical Biology 13: 1029-1035.
Schenck, C.A., et al. Non-plastidic, tyrosine-insensitive prephenate dehydrogenases from legumes, 2017 Nature Chemical Biology, 2015, pp. 52-57, vol. 11.
Siehl, D.L. "The Biosynthesis of Tryptophan, Tyrosine, and Phenylalanine from Chorismate," 1999 Plant Amino Acids: Biochemistry and Biotechnology, Edited by Bijay K. Singh, pp. 171-204.
Song, J., et al., The TyrA family of aromatic-pathway dehydrogenases in phylogenetic context. BMC Biol. 3, 13 (2005).
Sun, W., et al. The Crystal Structure of Aquifex aeolicus Prephenate Dehydrogenase Reveals the Mode of Tyrosine Inhibition. J. Biol. Chem. 284, 13223-13232 (2009).
Tattersall, D.B., et al., Resistance to an herbivore through engineered cyanogenic glucoside synthesis. 2001 Science 293: 1826-1828.

(Continued)

*Primary Examiner* — Phuong T Bui
(74) *Attorney, Agent, or Firm* — Quarles & Brady, LLP

(57) ABSTRACT

The invention generally relates to arogenate dehydrogenase polynucleotides and methods of using the same. More specifically, the invention relates in part to compositions including arogenate dehydrogenase polynucleotides from beet varieties and other Caryophyllales species and methods of using the same.

13 Claims, 32 Drawing Sheets
(1 of 32 Drawing Sheet(s) Filed in Color)
Specification includes a Sequence Listing.

(56) References Cited

OTHER PUBLICATIONS

Vannelli, T., et al., Production of p-hydroxycinnamic acid from glucose in *Saccharomyces cerevisiae* and *Escherichia coli* by expression of heterologous genes from plants and fungi. Metab. Eng. 9, 142-151 (2007).
Wang, Y., et al., Metabolic engineering of flavonoids in plants and microorganisms. Appl. Microbiol. Biotechnol. 91, 949-956 (2011).
Yang, Y., et al. Dissecting molecular evolution in the highly diverse plant clade Caryophyllales using transcriptome sequencing. 2015 Molecular Biology and Evolution, 32, 2001-2014.
Office Action for U.S. Appl. No. 14/548,216, dated Mar. 28, 2016.
Office Action for U.S. Appl. No. 14/548,216, dated Nov. 25, 2016.
Ambawat, S. et al., MYB transcription factor genes as regulators for plant responses: An overview. Physiol. Mol. Biol. Plants 19, 307-321 (2013).
Azeredo, H.M.C. Betalains: properties, sources, applications, and stability—a review. 2009. International Journal of Food Science and Technology. 44:2365-76.
Bate-Smith, E. C. The phenolic constituents of plants and their taxonomic significance. J. Linn. Soc., Bot. 58, 95-173 (1962).
Beaudoin, G. A. W. & Facchini, P. J. Benzylisoquinoline alkaloid biosynthesis in opium poppy. Planta 240, 19-32 (2014).
Bentley, R. (University of S. The Shikimate Pathway—A Metabolic Tree with Many Branches. Crit Rev Biochem Mol Biol 25, 307-84 (1990).
Bonner, C. A. et al., Cohesion group approach for evolutionary analysis of TyrA, a protein family with wide-ranging substrate specificities. Microbiol. Mol. Biol. Rev. MMBR 72, 13-53 (2008).
Bonner, C. A. et al., Distinctive enzymes of aromatic amino acid biosynthesis that are highly conserved in land plants are also present in the chlorophyte alga *Chlorella sorokiniana*. Plant Cell Physiol. 36, 1013-1022 (1995).
Bonvin, J. et al., Biochemical characterization of prephenate dehydrogenase from the hyperthermophilic bacterium *Aquifex aeolicus*. Protein Sci. 15, 1417-32 (2006).
Brockington, S.F., et al., Phylogeny of the Caryophyllales sensu lato: Revisiting hypotheses on pollination biology and perianth differentiation in the core Caryophyllales. 2009 International Journal of Plant Sciences 170: 627-643.
Brockington, S.F., et al., Lineage-specific gene radiations underlie the evolution of novel betalain pigmentation in Caryophyllales. New Phytol. 207, 1170-1180 (2015).
Brockington, S.F., et al., Complex pigment evolution in the Caryophyllales. New Phytol. 190, 854-864 (2011).
Byng, G. et al., Enzymology of L-tyrosine biosynthesis in corn(*Zea mays*). Phytochem istry 20, 1289-1292 (1981).
Chávez-Béjar, M. I. et al. Metabolic engineering of *Escherichia coli* for L-tyrosine production by expression of genes coding for the chorismate mutase domain of the native chorismate mutase-prephenate dehydratase and a cyclohexadienyl dehydrogenase from Zymomonas mobilis. Appl. Environ. Microbiol. 74, 3284-3290 (2008).
Christinet, L., Characterization and functional identification of a novel plant 4,5-extradiol dioxygenase involved in betalain pigment biosynthesis in Portulaca grandiflora. Plant Physiol 134, 265-274 (2004).
Connelly, J. A. & Conn, E. E. Tyrosine biosynthesis in Sorghum bicolor: isolation and regulatory properties of arogenate dehydrogenase. Verlag der Zeitschrift fur Natwforsch. 41c,69-78 ( 1986).
Dal Cin, V. et al. Identification of Genes in the Phenylalanine Metabolic Pathway by Ectopic Expression of a MYB Transcription Factor in Tomato Fruit. Plant Cell 23, 2738-2753 (2011).
Delaux, P.M. et al., Comparative phylogenomics uncovers the impact of symbiotic associations on host genome evolution. 2014 PLoS Genetics 10: e1004487.
Des Marais, D. L. To betalains and back again: A tale of two pigments. New Phytol. 207, 939-941 (2015).

Dohm, J. C. et al., The genome of the recently domesticated crop plant sugar beet (*Beta vulgaris*). Nature 505, 546-9 (2014).
Dornfeld, C. et al. Phylobiochemical characterization of class-Ib aspartate/prephenate aminotransferases reveals evolution of the plant arogenate phenylalanine pathway. Plant Cell 26, 3101-3114 (2014).
Facchini, P. J. Alkaloid biosynthesis in plants: Biochemistry, cell biology, molecular regulation, and metabolic engineering applications. Annu. Rev. Plant Physiol. Plant Mol. Biol. 52, 29-66 (2001).
Gaines, C. G., et al., L-Tyrosine regulation and biosynthesis via arogenate dehydrogenase in suspension-cultured cells of Nicotiana silvestris Speg. et Comes. Planta 156,233-240 (1982).
Galanie, S. et al., Complete biosynthesis of opioids in yeast. DOI: 10.1126/science.aac9373, Published Online Aug. 13, 2015.
Gamborg, O.L. & Keeley, F. W. Aromatic metabolism in plants I.A study of the prephenate dehydrogenase from bean plants. Biochim. Biophys .Acta 115,65-72 ( 1966).
Greenberg, A.K. & Donoghue, M.J. Molecular systematics and character evolution in Caryophyllaceae. 2011 TAXON 60: 1637-1652.
Hagel, J. M. & Facchini, P. J. Benzylisoquinoline alkaloid metabolism: a century of discovery and a brave new world. Plant Cell Physiol. 54, 647-672 (2013).
Hatlestad, G. J. et al., The beet Y locus encodes an anthocyanin MYB-like protein that activates the betalain red pigment pathway. Nat. Genet. 47, 92-6 (2015).
Hernández-Ledesma, P., et al. A taxonomic backbone for the global synthesis of species diversity in the angiosperm order Caryophyllales. Willdenowia 45, 281-383 (2015).
Hunter, S. C. & Cahoon, E. B. Enhancing vitamin E in oilseeds: unraveling tocopherol and tocotrienol biosynthesis. Lipids 42, 97-108 (2007).
Khan, M. I. Plant Betalains: Safety, Antioxidant Activity, Clinical Efficacy, and Bioavailability. Compr. Rev. Food Sci. Food Saf. 15, 316-330 (2015).
Kristensen, C. et al., Metabolic engineering of dhurrin in transgenic *Arabidopsis* plants with marginal inadvertent effects on the metabolome and transcriptome. 2015 Proceedings of the National Academy of Sciences of the United States of America 102: 1779-1784.
Kutchan, T. M. Alkaloid biosynthesis: The basis for metabolic engineering of medicinal plants. Plant Cell 7, 1059-1070 (1995).
Lee, C.-H., et al., Betalains, phase II enzyme-inducing components from red beetroot (*Beta vulgaris* L.) extracts. Nutr. Cancer 53, 91-103 (2005).
Lee, E.J., et al., Betalain and Betaine Composition of Greenhouse- or Field-Produced Beetroot ( *Beta vulgaris* L.) and Inhibition of HepG2 Cell Proliferation. J Agric Food Chem 62, 1324-1331 (2014).
Legrand, P. et al., Biochemical Characterization and Crystal Structure of Synechocystis Arogenate Dehydrogenase Provide Insights into Catalytic Reaction. 2006 Structure 14: 767-776.
Leuchtenberger, W., et al., Biotechnological production of amino acids and derivatives: current status and prospects. Appl. Microbiol. Biotechnol. 69, 1-8 (2005).
Lopez-Nieves, S. et al. "Relaxation of tyrosine pathway regulation underlies the evolution of betalain pigmentation in caryophylales." (2017) New Phytologist.
Lütke-Eversloh, T. & Stephanopoulos, G. Feedback inhibition of chorismate mutase/prephenate dehydrogenase (TyrA) of *Escherichia coli*: generation and characterization of tyrosine-insensitive mutants. Appl. Environ. Microbiol. 71, 7224-7228 (2005).
Lütke-Eversloh, T. et al., Perspectives of biotechnological production of L-tyrosine and its applications. Appl. Microbiol. Biotechnol. 77, 751-762 (2007).
Mabry, T. The betacyanins, a new class of red violet pigments, and their phylogenetic significance. (Roland Press, 1964).
Maeda, H. & Dudareva, N. The Shikimate Pathway and Aromatic Amino Acid Biosynthesis in Plants. Annu. Rev. Plant Biol 63, 73-105 (2012).
Boerjan W, Ralph J, and Baucher M (2003) Lignin Biosynthesis. Annu Rev Plant Biol, 54:519-546.

(56) References Cited

OTHER PUBLICATIONS

Corea OR, Ki C, Cardenas CL, Kim SJ, Brewer SE, Patten AM, Davin LB, and Lewis NG (2012) Arogenate Dehydratase Isoenzymes Profoundly and Differentially Modulate Carbon Flux into Lignins. J Biol Chem, 287:11446-11459.

Herrmann, KM (1995) The Shikimate Pathway: Early Steps in the Biosynthesis of Aromatic Compounds. Plant Cell, 7:907-919.

Holding DR et al. 2010. Identification and characterization of the maize arogenate dehydrogenase gene family. Journal of Experimental Botany. 61(13):3663-73.

Keller, B., Keller, E. & Lingens, F. Arogenate dehydrogenase from Streptomyces phaeochromogenes—purification and properties. Biol. Chem. Hoppe. Seyler 366, 1063-1066 (1985).

Maeda H.A. (2016) Lignin biosynthesis: Tyrosine shortcut in grasses. Nature Plants 2, 16080.

Rinaldi R, Jastrzebski R, Clough MT, Ralph J, Kennema M, Bruijnincx PC, Weckhuysen BM. Paving the Way for Lignin Valorisation: Recent Advances in Bioengineering, Biorefining and Catalysis. Angew Chem Int Ed Engl. Jul. 11, 2016;55(29):8164-215.

Tohge T, Watanabe M, Hoefgen R, and Fernie AR (2013) Shikimate and Phenylalanine Biosynthesis in the Green Lineage. Front Plant Sci, 4:62.

Tzin V, and Galili G (2010) New Insights into the Shikimate and Aromatic Amino Acids Biosynthesis Pathways in Plants. Mol Plant, 3:956-972.

Vogt T., Phenylpropanoid biosynthesis. Mol. Plant 3, 2-20 (2010).

Voll LM, Allaire EE, Fiene G, and Weber AP (2004) The Arabidopsis Phenylalanine Insensitive Growth Mutant Exhibits a Deregulated Amino Acid Metabolism. Plant Physiol, 136:3058-3069.

Watts, K.T., Lee, P.C. and Schmidt-Dannert, C. (2006) Biosynthesis of plant-specific stilbene polyketides in metabolically engineered *Escherichia coli*. BMC Biotechnol., 6, 22.

Webby CJ, Jiao W, Hutton RD, Blackmore NJ, Baker HM, Baker EN, Jameson GB, Parker EJ. Synergistic allostery, a sophisticated regulatory network for the control of aromatic amino acid biosynthesis in *Mycobacterium tuberculosis*. J Biol Chem. Oct. 1, 2010;285(40):30567-76.

Yoo H., Widhalm J. R., Qian Y., Maeda H., Cooper B. R., Jannasch A. S., Gonda I., Lewinsohn E., Rhodes D., Dudareva N., An alternative pathway contributes to phenylalanine biosynthesis in plants via a cytosolic tyrosine: phenylpyruvate aminotransferase. Nat. Commun. 4, 2833 (2013).

\* cited by examiner

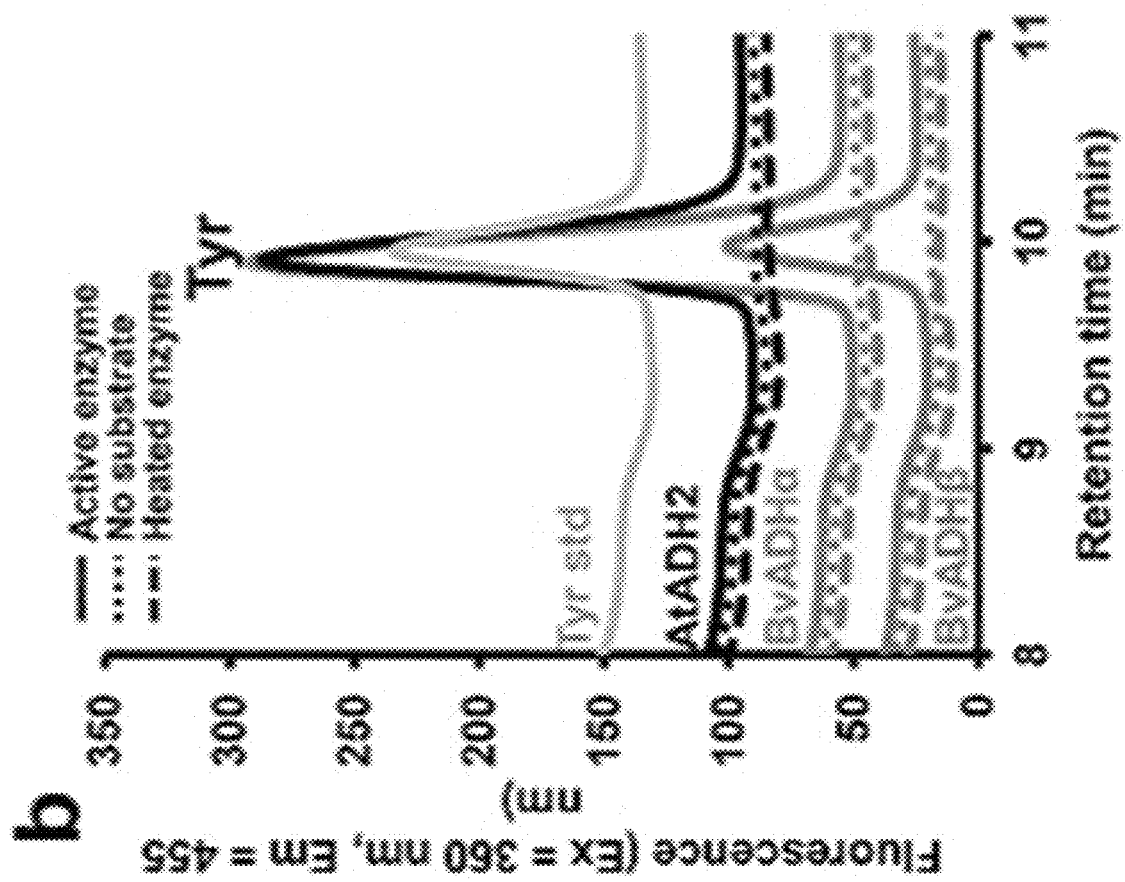

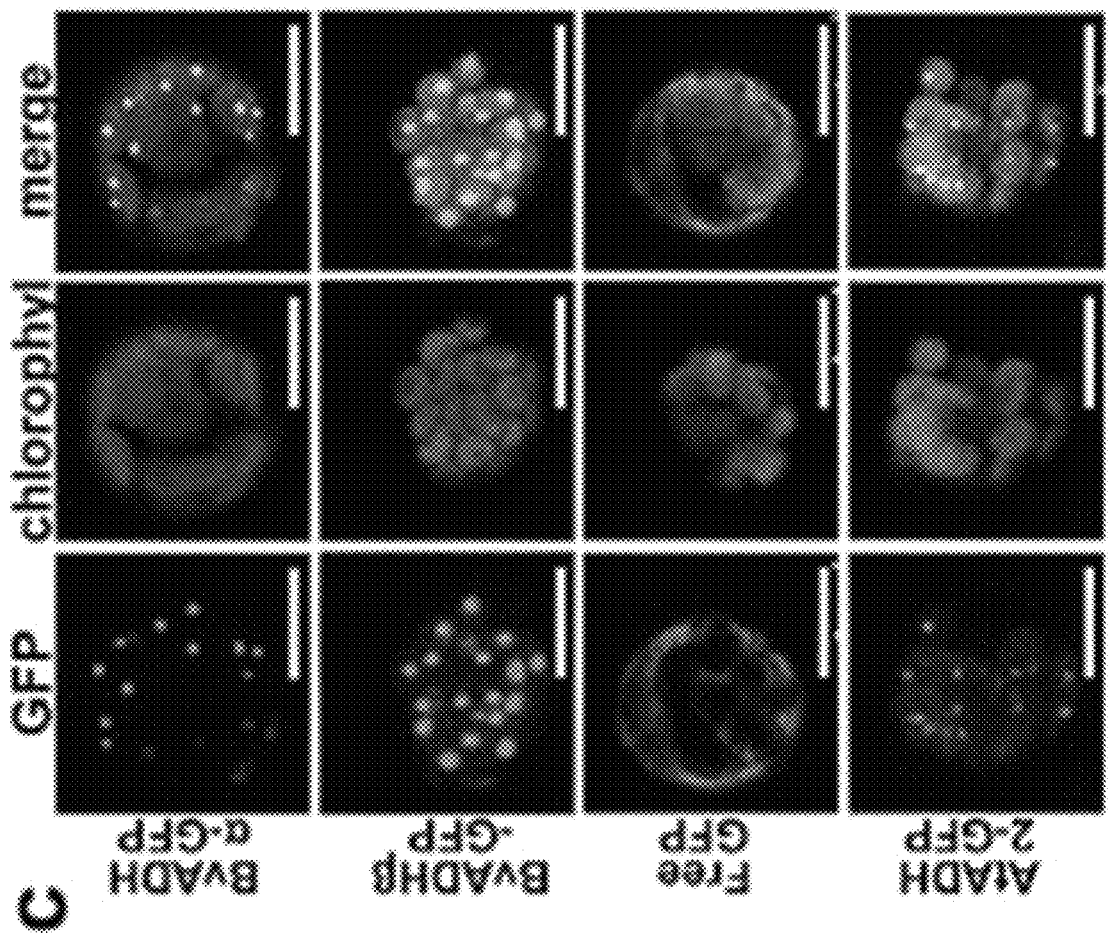

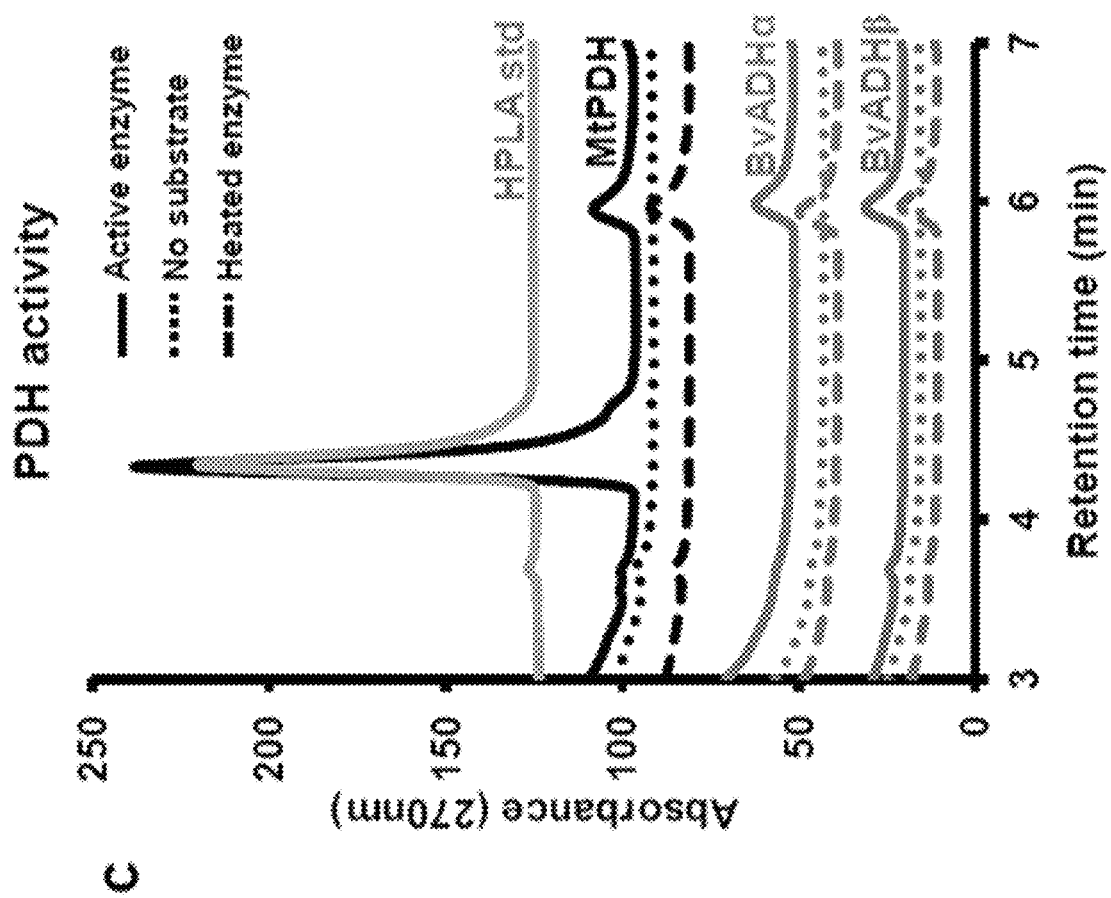

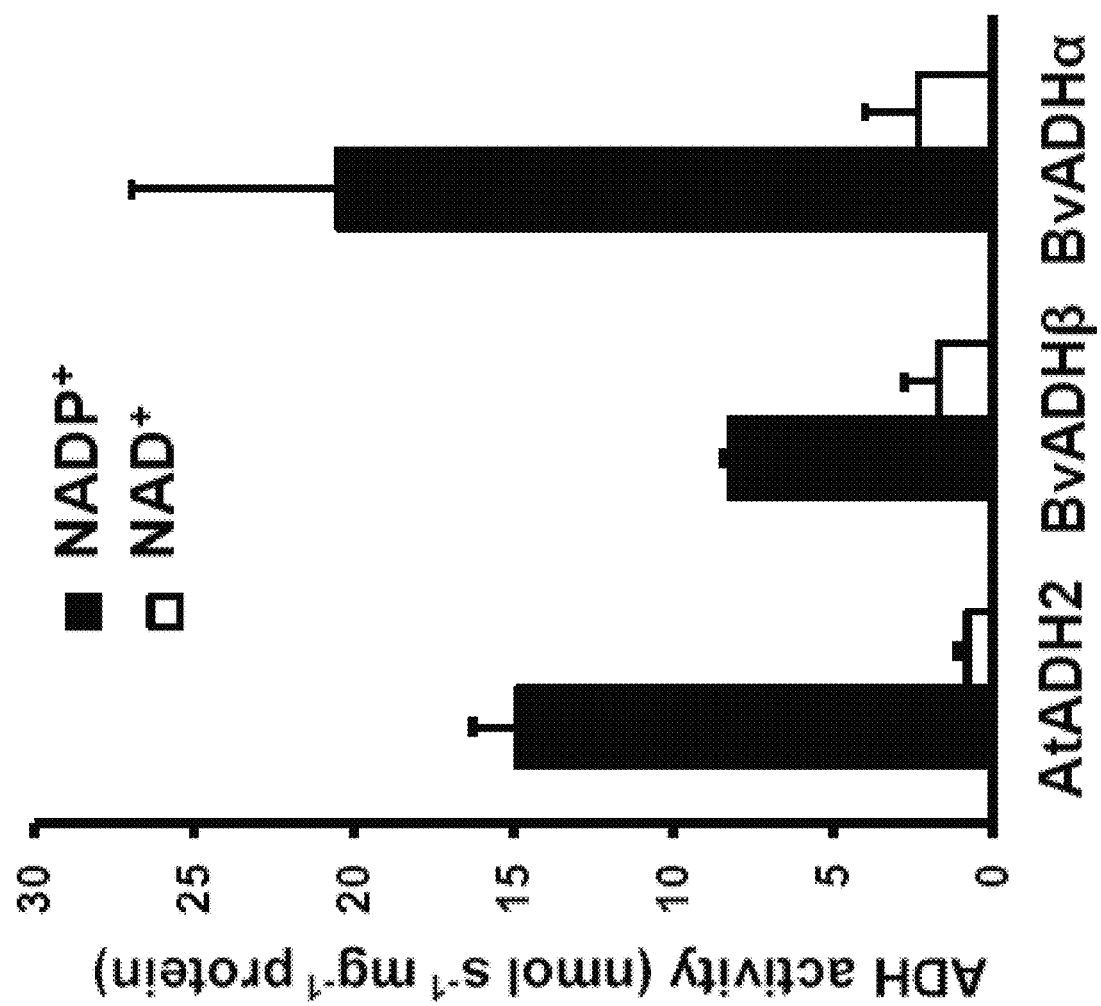

Fig. 5A-1

**a) Nucleotide sequence alignment of *BvADHα***

```
Redbeet_BvADHα      1   ATGATTTCACTCTCTTCTTTTCATCCTTCCTCCACCACCGCCACCGCCAC
Yellowbeet_BvADHα   1   ATGATTTCACTCTCTTCTTTTCATCCTTCCTCCACCACCGCCACCGCCAC
Whitebeet_BvADHα    1   ATGATTTCACTCTCTTCTTTTCATCCTTCCTCCACCACCGCCACCGCCAC
Sugarbeet_BvADHα    1   ATGATTTCACTCTCTTCTTTTCATCCTTCCTCCACCACCGCCACCGCCAC
Seabeet_BvADHα      1   ATGATTTCACTCTCTTCTTTTCATCCTTCCTCCACCACCGCCACCGCCAC Redbeet_BvADHα     51   CGCCGCCGCCGCCACC-----------------------------ACCCACC
Yellowbeet_BvADHα  51   CGCCGCCGCCGCCACC-----------------------------ACCCACC
Whitebeet_BvADHα   51   CGCCGCCGCCGCCACC-----------------------------ACCCACC
Sugarbeet_BvADHα   51   CGCCGCCACCGCCACC-----------------------------ACCCACC
Seabeet_BvADHα     51   CGCCGCCACCGCCACCGCCACCGCCACCGCCACCGCCACCGCCACACCCACC Redbeet_BvADHα     74   CACCTCAACAATGTCCCGCTTTTTCCTCTCCTCCGTCGCATCTCTCGCTT
Yellowbeet_BvADHα  74   CACCTCAACAATGTCCCGCTTTTTCCTCTCCTCCGTCGCATCTCTCGCTT
Whitebeet_BvADHα   74   CACCACAACAATGTCCCGCTTTTTCCTCTCCTCCGTCGCATCTCTCGCTT
Sugarbeet_BvADHα   74   CACCACAACAATGTCCCGCTTTTTCCTCTCCTCCATCGCATCTCTCGCTT
Seabeet_BvADHα    101   CACCACAACAATGTCCCGCTTTTTCCTCTCCTCCATCGCATCTCTCGCTT Redbeet_BvADHα    124   CCTTTACGCCACCCTCGCCAACACCTTGTAGTTCGGTGCGGTGGAGGTGG
Yellowbeet_BvADHα 124   CCTTTACGCCACCCTCGCCAACACCTTGTAGTTCGGTGCGGTGGAGGTGG
Whitebeet_BvADHα  124   CCTTTACGCCACCCTCGCCAACACCTTGTAGTTCGGTGCGGTGGAGGTGG
Sugarbeet_BvADHα  124   CCTTTACGCCACCCTCGCCAACACCTTGTAGTTCGGTGCGGTGGAGGTGG
Seabeet_BvADHα    151   CCTTTACGCCACCCTCGCCAACACCTTGTAGTTCGGTGCGGTGGAGGTGG Redbeet_BvADHα    174   TTCGGCCTCCGAATCGGTATTTAACCGTGATAGTGCTGCTACTCGTGTTT
Yellowbeet_BvADHα 174   TTCGGCCTCCGAATCGGTATTTAACCGTGATAGTGCTGCTACTCGTGTTT
Whitebeet_BvADHα  174   TTCGGCCTCCGAATCGGTATTTAACCGTGATAGTGCTGCTACTCGTGTTT
Sugarbeet_BvADHα  174   TTCGGCCTCCGAATCGGTATTTAACCGTGATAGTGCTGCTACTCGTGTTT
Seabeet_BvADHα    201   TTCGGCCTCCGAATCGGTATTTAACCGTGATAGTGCTGCTACTCGTGTTT Redbeet_BvADHα    224   CTAATGATCATCTTGACGTTAGTAAAAGAGATGTTAAGCTTAAGATTGCT
Yellowbeet_BvADHα 224   CTAATGATCATCTTGACGTTAGTAAAAGAGATGTTAAGCTTAAGATTGCT
Whitebeet_BvADHα  224   CTAATGATCATCTTGACGTTAGTAAAAGAGATGTTAAGCTTAAGATTGCT
Sugarbeet_BvADHα  224   CTAATGATCATCTTGACGTTAGTAAAAGAGATGTTAAGCTTAAGATTGCT
Seabeet_BvADHα    251   CTAATGATCATCTTGACGTTAGTAAAAGAGATGTTAAGCTTAAGATTGCT Redbeet_BvADHα    274   ATTATTGGGTTTGGTAACTTTGGCCAGTTTTTGGCTAAGACAATGGCTAA
Yellowbeet_BvADHα 274   ATTATTGGGTTTGGTAACTTTGGCCAGTTTTTGGCTAAGACAATGGCTAA
Whitebeet_BvADHα  274   ATTATTGGGTTTGGTAACTTTGGCCAGTTTTTGGCTAAGACAATGGCTAA
Sugarbeet_BvADHα  274   ATTATTGGGTTTGGTAACTTTGGCCAGTTTTTGGCTAAGACAATGGCTAA
Seabeet_BvADHα    301   ATTATTGGGTTTGGTAACTTTGGCCAGTTTTTGGCTAAGACAATGGCTAA Redbeet_BvADHα    324   GCAAGGTCATAGAGTGTTGGCTTACTCACGCTCGGACTACTCCCGCGCTG
Yellowbeet_BvADHα 324   GCAAGGTCATAGAGTGTTGGCTTACTCACGCTCGGACTACTCCCGCGCTG
Whitebeet_BvADHα  324   GCAAGGTCATAGAGTGTTGGCTTACTCACGCTCGGACTACTCCCGCGCTG
Sugarbeet_BvADHα  324   GCAAGGTCATAGAGTGTTGGCTTACTCACGCTCGGACTACTCCCGCGCTG
Seabeet_BvADHα    351   GCAAGGTCATAGAGTGTTGGCTTACTCACGCTCGGACTACTCCCGCGCTG
```

Fig. 5A-2

```
Redbeet_BvADHα      374  CTAAGGAGATCGGCGTCGAGTATTTTACTGACGCCGATGACCTCTGCGAG
Yellowbeet_BvADHα   374  CTAAGGAGATCGGCGTCGAGTATTTTACTGACGCCGATGACCTCTGCGAG
Whitebeet_BvADHα    374  CTAAGGAGATCGGCGTCGAGTATTTTACTGACGCCGATGACCTCTGCGAG
Sugarbeet_BvADHα    374  CTAAGGAGATCGGCGTCGAGTATTTTACTGACGCCGATGACCTCTGCGAG
Seabeet_BvADHα      401  CTAAGGAGATCGGCGTCGAGTATTTTACTGACGCCGATGACCTCTGCGAG Redbeet_BvADHα      424  GAGCACCCTGAGGTTATTCTGTTGTGCACATCCATCCTCTCAACGGAGAA
Yellowbeet_BvADHα   424  GAGCACCCTGAGGTTATTCTGTTGTGCACATCCATCCTCTCAACGGAGAA
Whitebeet_BvADHα    424  GAGCACCCTGAGGTTATTCTGTTGTGCACGTCCATCCTCTCAACGGAGAA
Sugarbeet_BvADHα    424  GAGCACCCTGAGGTTATTCTTTTGTGCACGTCCATCCTCTCAACGGAGAA
Seabeet_BvADHα      451  GAGCACCCTGAGGTTATTCTTTTGTGCACGTCCATCCTCTCAACGGAGAA Redbeet_BvADHα      474  GGTCCTCCGATCACTCCCCCTCCACCGGCTCCGTCGTTCAACCCTCTTTG
Yellowbeet_BvADHα   474  GGTCCTCCGATCACTCCCCCTCCACCGGCTCCGTCGTTCAACCCTCTTTG
Whitebeet_BvADHα    474  GGTCCTCCGATCACTCCCCCTCCACCGGCTCCGTCGTTCAACCCTCTTTG
Sugarbeet_BvADHα    474  GGTCCTCCGATCACTCCCCCTCCACCGGCTCCGTCGTTCAACCCTCTTTG
Seabeet_BvADHα      501  GGTCCTCCGATCACTCCCCCTCCACCGGCTCCGTCGTTCAACCCTCTTTG Redbeet_BvADHα      524  CGGATGTTCTCTCGGTCAAGGAATTTCCTCGATCGCTCTTCCTTCAACTA
Yellowbeet_BvADHα   524  CGGATGTTCTCTCGGTCAAGGAATTTCCTCGATCGCTCTTCCTTCAACTA
Whitebeet_BvADHα    524  CGGATGTTCTCTCGGTCAAGGAATTTCCTCGATCGCTCTTCCTTCAACTA
Sugarbeet_BvADHα    524  CGGATGTTCTCTCGGTCAAGGAATTTCCTCGATCGCTCTTCCTTCAACTA
Seabeet_BvADHα      551  CGGATGTTCTCTCGGTCAAGGAATTTCCTCGATCGCTCTTCCTTCAACTA Redbeet_BvADHα      574  CTTCCTAAGGACTTTGATATCCTATGCACCCACCCTATGTTTGGCCCAGA
Yellowbeet_BvADHα   574  CTTCCTAAGGACTTTGATATCCTATGCACCCACCCTATGTTTGGCCCAGA
Whitebeet_BvADHα    574  CTTCCTAAGGACTTTGATATCCTATGCACCCACCCTATGTTTGGCCCAGA
Sugarbeet_BvADHα    574  CTTCCTAAGGACTTTGATATCCTATGCACCCACCCTATGTTTGGCCCAGA
Seabeet_BvADHα      601  CTTCCTAAGGACTTTGATATCCTATGCACCCACCCTATGTTTGGCCCAGA Redbeet_BvADHα      624  CTCGGGCAAAGACGGGTGGGGTGGACTACCTTTTGTGTTCGATAAAGTTA
Yellowbeet_BvADHα   624  CTCGGGCAAAGACGGGTGGGGTGGACTACCTTTTGTGTTCGATAAAGTTA
Whitebeet_BvADHα    624  CTCGGGCAAAGACGGGTGGGGTGGACTACCTTTTGTGTTCGATAAAGTTA
Sugarbeet_BvADHα    624  CTCGGGCAAAGACGGGTGGGGTGGACTACCTTTTGTGTTTGATAAAGTTA
Seabeet_BvADHα      651  CTCGGGCAAAGACGGGTGGGGTGGACTACCTTTTGTGTTTGATAAAGTTA Redbeet_BvADHα      674  GAGTCGGATCAGATCAGAGTCGGACATCTCGTGCTGAGGCATTCCTAGAC
Yellowbeet_BvADHα   674  GAGTCGGATCAGATCAGAGTCGGACATCTCGTGCTGAGGCATTCCTAGAC
Whitebeet_BvADHα    674  GAGTCGGATCAGATCAGAGTCGGACATCTCGTGCTGAGGCATTCCTAGAC
Sugarbeet_BvADHα    674  GAGTCGGATCAGATCAGAGTCGGACATCTCGTGCTGAGGCATTCCTAGAC
Seabeet_BvADHα      701  GAGTCGGATCAGATCAGAGTCGGACATCTCGTGCTGAGGCATTCCTAGAC Redbeet_BvADHα      724  GTGTTTAGGAATGCCGGGTGTAGGATGGTGGAAATGAGTTGTGTTGATCA
Yellowbeet_BvADHα   724  GTGTTTAGGAATGCCGGGTGTAGGATGGTGGAAATGAGTTGTGTTGATCA
Whitebeet_BvADHα    724  GTGTTTAGGAATGCCGGGTGTAGGATGGTGGAAATGAGTTGTGTTGATCA
Sugarbeet_BvADHα    724  GTGTTTAGGAATGCCGGGTGTAGGATGGTGGAAATGAGTTGTGTTGATCA
Seabeet_BvADHα      751  GTGTTTAGGAATGCCGGGTGTAGGATGGTGGAAATGAGTTGTGTTGATCA
```

Fig. 5A-3

```
Redbeet_BvADHα      774  TGACAAGCATGCAGCCGGGTCTCAATTTATTACACATATGATGGGACGAG
Yellowbeet_BvADHα   774  TGACAAGCATGCAGCCGGGTCTCAATTTATTACACATATGATGGGACGAG
Whitebeet_BvADHα    774  TGACAAGCATGCAGCCGGGTCTCAATTTATTACACATATGATGGGACGAG
Sugarbeet_BvADHα    774  TGACAAGCATGCAGCCGGGTCTCAATTTATTACACATATGATGGGACGAG
Seabeet_BvADHα      801  TGACAAGCATGCAGCCGGGTCTCAATTTATTACACATATGATGGGACGAG Redbeet_BvADHα      824  TTTTGGAGAAATTGGCCTTGGAAAATACACCAATTAATACAAAAGGGTAC
Yellowbeet_BvADHα   824  TTTTGGAGAAATTGGCCTTGGAAAATACACCAATTAATACAAAAGGGTAC
Whitebeet_BvADHα    824  TTTTGGAGAAATTGGCCTTGGAAAATACACCAATTAATACAAAAGGGTAC
Sugarbeet_BvADHα    824  TTTTGGAGAAATTGGCCTTGGAAAATACACCAATTAATACAAAAGGGTAC
Seabeet_BvADHα      851  TTTTGGAGAAATTGGCCTTGGAAAATACACCAATTAATACAAAAGGGTAC Redbeet_BvADHα      874  GAAAGTTTGTTAAAATTGGTGGATAATACTGCAAGGGATAGTTTTGAGTT
Yellowbeet_BvADHα   874  GAAAGTTTGTTAAAATTGGTGGATAATACTGCAAGGGATAGTTTTGAGTT
Whitebeet_BvADHα    874  GAAAGTTTGTTAAAATTGGTGGATAATACTGCAAGGGATAGTTTTGAGTT
Sugarbeet_BvADHα    874  GAAAGTTTGTTAAAATTGGTGGATAATACTGCAAGGGATAGTTTTGAGTT
Seabeet_BvADHα      901  GAAAGTTTGTTAAAATTGGTGGATAATACTGCAAGGGATAGTTTTGAGTT Redbeet_BvADHα      924  GTTTTACGGGTTGTTTTTGTACAATAAAAATGCAATGGAGCAATTGGATA
Yellowbeet_BvADHα   924  GTTTTACGGGTTGTTTTTGTACAATAAAAATGCAATGGAGCAATTGGATA
Whitebeet_BvADHα    924  GTTTTACGGGTTGTTTTTGTACAATAAAAATGCAATGGAGCAATTGGATA
Sugarbeet_BvADHα    924  GTTTTATGGGTTGTTTTTGTACAATAAAAATGCAATGGAGCAATTGGATA
Seabeet_BvADHα      951  GTTTTATGGGTTGTTTTTGTACAATAAAAATGCAATGGAGCAATTGGATA Redbeet_BvADHα      974  GAATGGATTGGGCTTTCGAGATGGTAAAAAAGCAACTTTCGGGATATTTG
Yellowbeet_BvADHα   974  GAATGGATTGGGCTTTCGAGATGGTAAAAAAGCAACTTTCGGGATATTTG
Whitebeet_BvADHα    974  GAATGGATTGGGCTTTCGAGATGGTAAAAAAGCAACTTTCGGGATATTTG
Sugarbeet_BvADHα    974  GAATGGATTGGGCTTTCGAGATGGTAAAAAAGCAACTTTCGGGATATTTG
Seabeet_BvADHα     1001  GAATGGATTGGGCTTTCGAGATGGTAAAAAAGCAACTTTCGGGATATTTG Redbeet_BvADHα     1024  CATGATCTTGTTAGAAAACAATTGATGTTGGAGGGTAATAATGATCAAGC
Yellowbeet_BvADHα  1024  CATGATCTTGTTAGAAAACAATTGATGTTGGAGGGTAATAATGATCAAGC
Whitebeet_BvADHα   1024  CATGATCTTGTTAGAAAACAATTGATGTTGGAGGGTAATAATGATCAAGC
Sugarbeet_BvADHα   1024  CATGATCTTGTTAGAAAACAATTGATGTTGGAGGGTAATAATGATCAAGC
Seabeet_BvADHα     1051  CATGATCTTGTTAGAAAACAATTGATGTTGGAGGGTAATAATGATCAAGC Redbeet_BvADHα     1074  TGAGGTTACTTTTGACAAACCATTGATGCTTCCTTCTCCTACTATTAATC
Yellowbeet_BvADHα  1074  TGAGGTTACTTTTGACAAACCATTGATGCTTCCTTCTCCTACTATTAATC
Whitebeet_BvADHα   1074  TGAGGTTACTTTTGACAAACCATTGATGCTTCCTTCTCCTACTATTAATC
Sugarbeet_BvADHα   1074  TGAGGTTACTTTTGACAAACCATTAATGCTTCCTTCTCCTACTATTAATC
Seabeet_BvADHα     1101  TGAGGTTACTTTTGACAAACCATTAATGCTTCCTTCTCCTACTATTAATC Redbeet_BvADHα     1124  CTCCACAAATAGTTCCCTCTGCTGATATGGCTGAGAAGAAGCATGATTTA
Yellowbeet_BvADHα  1124  CTCCACAAATAGTTCCCTCTGCTGATATGGCTGAGAAGAAGCATGATTTA
Whitebeet_BvADHα   1124  CTCCACAAATAGTTCCCTCTGCTGATATGGCTGAGAAGAAGCATGATTTA
Sugarbeet_BvADHα   1124  CTCCACAAATAGTTCCTTCTGCTGATATGGCTGAGAAGAAGCATGATTTA
Seabeet_BvADHα     1151  CTCCACAAATAGTTCCTTCTGCTGATATGGCTGAGAAGAAGCATGATTTA
```

Fig. 5A-4

```
Redbeet_BvADHα      1174 GTGGTGGTTAATGGTACTAGATAG
Yellowbeet_BvADHα   1174 GTGGTGGTTAATGGTACTAGATAG
Whitebeet_BvADHα    1174 GTGGTGGTTAATGGTACTAGATAG
Sugarbeet_BvADHα    1174 GTGGTGGTTAATGGTACTAGATAG
Seabeet_BvADHα      1201 GTGGTGGTTAATGGTACTAGATAG
```

Fig. 5B-1 b) Nucleotide sequence alignment of *BvADHβ*

```
Sugarbeet_BvADHβ    1  ATGCTTTCTCTCTCCTCCACAACCACCGCAAAACCCTCGCCGTCGCCATC
Yellowbeet_BvADHβ   1  ATGCTTTCTCTCTCCTCCACAACCACCGCAAAACCCTCGCCGTCGCCATC
Redbeet_BvADHβ      1  ATGCTTTCTCTCTCCTCCACAACCACCGCAAAACCCTCGCCGTCGCCATC
Whitebeet_BvADHβ    1  ATGCTTTCTCTCTCCTCCACAACCACCGCAAAACCCTCGCCGTCGCCATC
Seabeet_BvADHβ      1  ATGCTTTCTCTCTCCTCCACAACCACCGCAAAACCCTCGCCGTCGCCATC Sugarbeet_BvADHβ   51  TCCGGCGAATTTTCCGGCGAAACTTTCTTCTCTCTCCACCATCACCACCA
Yellowbeet_BvADHβ  51  TCCGGCGAATTTTCCGGCGAAACTTTCTTCTCTCTCCACCATCACCACCA
Redbeet_BvADHβ     51  TCCGGCGAATTTTCCGGCGAAACTTTCTTCTCTCTCCACCATCACCACCA
Whitebeet_BvADHβ   51  TCCGGCGAATTTTCCGGCGAAACTTTCTTCTCTCTCCACCATCACCACCA
Seabeet_BvADHβ     51  TCCGGCGAATTTTCCGGCAAAACTTTCTTCTCTCTCCACCATCACCACCA Sugarbeet_BvADHβ  101  CTCTCTCTTTCTCTCCTCGCCGGAGATATTTTCATGGCGTCAAAACCCTA
Yellowbeet_BvADHβ 101  CTCTCTCTTTCTCTCCTCGCCGGAGATATTTTCATGGCGTCAAAACCCTA
Redbeet_BvADHβ    101  CTCTCTCTTTCTCTCCTCGCCGGAGATATTTTCATGGCGTCAAAACCCTA
Whitebeet_BvADHβ  101  CTCTCTCTTTCTCTCCTCGCCGGAGATATTTTCATGGCGTCAAAACCCTA
Seabeet_BvADHβ    101  CTATCTCTTTCTCTCCTCGCCGGAGATATTTTCATGGCGTCAAAACCCTA Sugarbeet_BvADHβ  151  ACAATTCGCAGCATCGACGCCGCACAATTCTTCGATTACGAATCAAAACT
Yellowbeet_BvADHβ 151  ACAATTCGCAGCATCGACGCCGCACAATTCTTCGATTACGAATCAAAACT
Redbeet_BvADHβ    151  ACAATTCGCAGCATCGACGCCGCACAATTCTTCGATTACGAATCAAAACT
Whitebeet_BvADHβ  151  ACAATTCGCAGCATCGACGCCGCACAATTCTTCGATTACGAATCAAAACT
Seabeet_BvADHβ    151  ACAATTCGCAGCATCGACGCTGCACAATTCTTCGATTACGAATCAAAACT Sugarbeet_BvADHβ  201  TGCCGCCATTAACACAACCTCTTCGTCTTCATCTTCATCTTATTCGAAGC
Yellowbeet_BvADHβ 201  TGCCGCCATTAACACAACCTCTTCGTCTTCATCTTCATCTTATTCGAAGC
Redbeet_BvADHβ    201  TGCCGCCATTAACACAACCTCTTCGTCTTCATCTTCATCTTATTCGAAGC
Whitebeet_BvADHβ  201  TGCCGCCATTAACACAACCTCTTCGTCTTCATCTTCATCTTATTCGAAGC
Seabeet_BvADHβ    201  CGCCGCCATTAACACAACCTCTTCATCTACATCTTCATCTTATTCGAAAC Sugarbeet_BvADHβ  251  TCAAAATCGCAATCGTAGGGTTCGGAAATTACGGACAATTTCTCGCGAAA
Yellowbeet_BvADHβ 251  TCAAAATCGCAATCGTAGGGTTCGGAAATTACGGACAATTTCTCGCGAAA
Redbeet_BvADHβ    251  TCAAAATCGCAATCGTAGGGTTCGGAAATTACGGACAATTTCTCGCGAAA
Whitebeet_BvADHβ  251  TCAAAATCGCAATCGTAGGGTTCGGAAATTACGGACAATTTCTCGCGAAA
Seabeet_BvADHβ    251  TCAAAATCGCAATCGTAGGGTTCGGAAATTACGGACAATTTCTCGCGAAA Sugarbeet_BvADHβ  301  ACCCTAGTTTCTCAAGGTCATACTGTTCTCGCTTATTCTCGCTCTGATTA
Yellowbeet_BvADHβ 301  ACCCTAGTTTCTCAAGGTCATACTGTTCTCGCTTATTCTCGCTCTGATTA
Redbeet_BvADHβ    301  ACCCTAGTTTCTCAAGGTCATACTGTTCTCGCTTATTCTCGCTCTGATTA
Whitebeet_BvADHβ  301  ACCCTAGTTTCTCAAGGTCATACTGTTCTCGCTTATTCTCGCTCTGATTA
Seabeet_BvADHβ    301  ACCCTAGTTTCTCAAGGTCATACTGTTCTCGCTTATTCTCGCTCTGATTA Sugarbeet_BvADHβ  351  CTCTAAAATCGCTGCGAATCTCGGCGTTTCTTACTTTTCTGATCCTGATG
Yellowbeet_BvADHβ 351  CTCTAAAATCGCTGCGAATCTCGGCGTTTCTTACTTTTCTGATCCTGATG
Redbeet_BvADHβ    351  CTCTAAAATCGCTGCGAATCTCGGCGTTTCTTACTTTTCTGATCCTGATG
Whitebeet_BvADHβ  351  CTCTAAAATCGCTGCGAATCTCGGCGTTTCTTACTTTTCTGATCCTGATG
Seabeet_BvADHβ    351  CTCTAAAATCGCTGCGAATCTCGGCGTTTCTTACTTTTCTGATCCTGATG
```

Fig. 5B-2

```
Sugarbeet_BvADHβ    401 ATCTTTGCGAAGAACATCCTGAGGTAATTATGTTGTGTACTTCGATTTTA
Yellowbeet_BvADHβ   401 ATCTTTGCGAAGAACATCCAGAGGTAATTATGTTGTGTACTTCGATTTTA
Redbeet_BvADHβ      401 ATCTTTGCGAAGAACATCCTGAGGTAATTATGTTGTGTACTTCGATTTTA
Whitebeet_BvADHβ    401 ATCTTTGCGAAGAACATCCTGAGGTAATTATGTTGTGTACTTCGATTTTA
Seabeet_BvADHβ      401 ATCTTTGCGAAGAACATCCTGAGGTAATTATGTTGTGTACTTCGATTTTA Sugarbeet_BvADHβ    451 TCAACTGAAGTTATGTTGAATTCGTTACCATTGCAGCGACTTAAACGATC
Yellowbeet_BvADHβ   451 TCAACTGAAGTTATGTTGAATTCGTTACCATTGCAGCGACTTAAACGATC
Redbeet_BvADHβ      451 TCAACTGAAGTTATGTTGAATTCGTTACCATTGCAGCGACTTAAACGATC
Whitebeet_BvADHβ    451 TCAACTGAAGTTATGTTGAATTCGTTACCATTGCAGCGACTTAAACGATC
Seabeet_BvADHβ      451 TCAACTGAAGTTATGTTGAATTCGTTACCATTGCAGCGACTTAAACGATC Sugarbeet_BvADHβ    501 GACGCTTTTTGTTGATGTTTTATCGGTGAAAGAATTTCCGCGTAATTGT
Yellowbeet_BvADHβ   501 GACGCTTTTTGTTGATGTTTTATCGGTGAAAGAATTTCCGCGTAATTGT
Redbeet_BvADHβ      501 GACGCTTTTTGTTGATGTTTTATCGGTGAAAGAATTTCCGCGTAATTGT
Whitebeet_BvADHβ    501 GACGCTTTTTGTTGATGTTTTATCGGTGAAAGAATTTCCGCGTAATTGT
Seabeet_BvADHβ      501 GACGCTTTTTGTTGATGTTTTATCGGTGAAAGAATTTCCGCGTAATTGT Sugarbeet_BvADHβ    551 TTCTTCAAACTTTACCGTCTGATTTTGATATATTATGTACTCATCCTATG
Yellowbeet_BvADHβ   551 TTCTTCAAACTTTACCGTCTGATTTTGATATATTATGTACTCATCCTATG
Redbeet_BvADHβ      551 TTCTTCAAACTTTACCGTCTGATTTTGATATATTATGTACTCATCCTATG
Whitebeet_BvADHβ    551 TTCTTCAAACTTTACCGTCTGATTTTGATATATTATGTACTCATCCTATG
Seabeet_BvADHβ      551 TTCTTCAAACTTTACCGTCTGATTTTGATATATTATGTACTCATCCTATG Sugarbeet_BvADHβ    601 TTTGGGCCTGAATCTGGGAAAAATGGTTGGGGAAGTTTGCCTTTTGTTTA
Yellowbeet_BvADHβ   601 TTTGGGCCTGAATCTGGGAAAAATGGTTGGGGAAGTTTGCCTTTTGTTTA
Redbeet_BvADHβ      601 TTTGGGCCTGAATCTGGGAAAAATGGTTGGGGAAGTTTGCCTTTTGTTTA
Whitebeet_BvADHβ    601 TTTGGGCCTGAATCTGGGAAAAATGGTTGGGGAAGTTTGCCTTTTGTTTA
Seabeet_BvADHβ      601 TTTGGGCCTGAATCTGGGAAAAATGGTTGGGGAAGTTTGCCTTTTGTTTA Sugarbeet_BvADHβ    651 TGATAAGGTTAGGATTGGGAAAGATGAGGGTAGAATTAAGAGATGTGAGA
Yellowbeet_BvADHβ   651 TGATAAGGTTAGGATTGGGAAAGATGAGGGTAGAATTAAGAGATGTGAGA
Redbeet_BvADHβ      651 TGATAAGGTTAGGATTGGGAAAGATGAGGGTAGAATTAAGAGATGTGAGA
Whitebeet_BvADHβ    651 TGATAAGGTTAGGATTGGGAAAGATGAGGGTAGAATTAAGAGATGTGAGA
Seabeet_BvADHβ      651 TGATAAGGTTAGGATTGGGAAAGATGAGGGTAGAATTAAGAGATGTGAGA Sugarbeet_BvADHβ    701 GTTTTTGGATGTTTTTAGGAGAGAAGGTTGTAGGGTTGAGGAAATGACT
Yellowbeet_BvADHβ   701 GTTTTTGGATGTTTTTAGGAGAGAAGGTTGTAGGGTTGAGGAAATGACT
Redbeet_BvADHβ      701 GTTTTTGGATGTTTTTAGGAGAGAAGGTTGTAGGGTTGAGGAAATGACT
Whitebeet_BvADHβ    701 GTTTTTGGATGTTTTTAGGAGAGAAGGTTGTAGGGTTGAGGAAATGACT
Seabeet_BvADHβ      701 GTTTTTGGATGTTTTTAGGAGAGAAGGTTGTAGGGTTGAGGAAATGACT Sugarbeet_BvADHβ    751 TGTGCTGAGCATGATAAGTTTGCAGCAGGGTCTCAGTTTATAACACATTT
Yellowbeet_BvADHβ   751 TGTGCTGAGCATGATAAGTTTGCAGCAGGGTCTCAGTTTATAACACATTT
Redbeet_BvADHβ      751 TGTGCTGAGCATGATAAGTTTGCAGCAGGGTCTCAGTTTATAACACATTT
Whitebeet_BvADHβ    751 TGTGCTGAGCATGATAAGTTTGCAGCAGGGTCTCAGTTTATAACACATTT
Seabeet_BvADHβ      751 TGTGCTGAGCATGATAAGTTTGCAGCAGGGTCTCAGTTTATTACACATTT
```

Fig. 5B-3

```
Sugarbeet_BvADHβ    801  CTTAGGGAGGGTTTTGGAGAAGCTTGATTTGGAGGATACGCCGATTAATA
Yellowbeet_BvADHβ   801  CTTAGGGAGGGTTTTGGAGAAGCTTGATTTGGAGGATACGCCGATTAATA
Redbeet_BvADHβ      801  CTTAGGGAGGGTTTTGGAGAAGCTTGATTTGGAGGATACGCCGATTAATA
Whitebeet_BvADHβ    801  CTTAGGGAGGGTTTTGGAGAAGCTTGATTTGGAGGATACGCCGATTAATA
Seabeet_BvADHβ      801  CTTAGGGAGGGTTTTGGAGAAGCTTGATTTGGAGGATACGCCGATTAATA Sugarbeet_BvADHβ    851  CGAAAGGGTATGAGAGTTTGTTGAATTTGGTGGATAATACGTCGAAGGAT
Yellowbeet_BvADHβ   851  CGAAAGGGTATGAGAGTTTGTTGAATTTGGTGGATAATACGTCGAAGGAT
Redbeet_BvADHβ      851  CGAAAGGGTATGAGAGTTTGTTGAATTTGGTGGATAATACGTCGAAGGAT
Whitebeet_BvADHβ    851  CGAAAGGGTATGAGAGTTTGTTGAATTTGGTGGATAATACGTCGAAGGAT
Seabeet_BvADHβ      851  CGAAAGGGTATGAGAGTTTGTTGAATTTGGTGGATAATACGTCGAAGGAT Sugarbeet_BvADHβ    901  AGTTTCGAGTTGTTTTATGGGTTGTTTTTGTATAATCAGAATGCTATGGA
Yellowbeet_BvADHβ   901  AGTTTCGAGTTGTTTTATGGGTTGTTTTTGTATAATCAGAATGCTATGGA
Redbeet_BvADHβ      901  AGTTTCGAGTTGTTTTATGGGTTGTTTTTGTATAATCAGAATGCTATGGA
Whitebeet_BvADHβ    901  AGTTTCGAGTTGTTTTATGGGTTGTTTTTGTATAATCAGAATGCTATGGA
Seabeet_BvADHβ      901  AGTTTCGAGTTGTTTTATGGGTTGTTTTTGTATAATCAGAATGCTATGGA Sugarbeet_BvADHβ    951  GCAGTTAGAGAGGTTAGATTGGGCGTTTGAGTTGGTTAAGAAGCAATTGT
Yellowbeet_BvADHβ   951  GCAGTTAGAGAGGTTAGATTGGGCGTTTGAGTTGGTTAAGAAGCAATTGT
Redbeet_BvADHβ      951  GCAGTTAGAGAGGTTAGATTGGGCGTTTGAGTTGGTTAAGAAGCAATTGT
Whitebeet_BvADHβ    951  GCAGTTAGAGAGGTTAGATTGGGCGTTTGAGTTGGTTAAGAAGCAATTGT
Seabeet_BvADHβ      951  GCAGTTAGAGAGGTTAGATTGGGCATTTGAGTTGGTTAAGAAGCAATTGT Sugarbeet_BvADHβ   1001  TTGGACACTTGCATGGGTTGCTAAGGAAACAGTTGTTTGGGTTTTCTGAG
Yellowbeet_BvADHβ  1001  TTGGACACTTGCATGGGTTGCTAAGGAAACAGTTGTTTGGGTTTTCTGAG
Redbeet_BvADHβ     1001  TTGGACACTTGCATGGGTTGCTAAGGAAACAGTTGTTTGGGTTTTCTGAG
Whitebeet_BvADHβ   1001  TTGGACACTTGCATGGGTTGCTAAGGAAACAGTTGTTTGGGTTTTCTGAG
Seabeet_BvADHβ     1001  TTGGACACTTGCATGGGTTGCTAAGGAAACAGTTGTTTGGGTTTTCTGAG Sugarbeet_BvADHβ   1051  ATAGATGAACGTATTGGGAAGGCGAAGGAGATCAAATTTCTCTCTGATGC
Yellowbeet_BvADHβ  1051  ATAGATGAACGTATTGGGAAGGCGAAGGAGATCAAATTTCTCTCTGATGC
Redbeet_BvADHβ     1051  ATAGATGAACGTATTGGGAAGGCGAAGGAGATCAAATTTCTCTCTGATGC
Whitebeet_BvADHβ   1051  ATAGATGAACGTATTGGGAAGGCGAAGGAGATCAAATTTCTCTCTGATGC
Seabeet_BvADHβ     1051  ATAGATGAACGTATTGGGAAGGCGAAGGAGATCAAATTTCTCTCTGATGC Sugarbeet_BvADHβ   1101  TGCAGAACAGAATGGCTCTGCCTTGTCTGCTAGGGAGAATGCAAATTCGG
Yellowbeet_BvADHβ  1101  TGCAGAACAGAATGGCTCTGCCTTGTCTGCTAGGGAGAATGCAAATTCGG
Redbeet_BvADHβ     1101  TGCAGAACAGAATGGCTCTGCCTTGTCTGCTAGGGAGAATGCAAATTCGG
Whitebeet_BvADHβ   1101  TGCAGAACAGAATGGCTCTGCCTTGTCTGCTAGGGAGAATGCAAATTCGG
Seabeet_BvADHβ     1101  TGCAGAACAGAATGGCTCTGCCTTGTCTGCTAGGGAGAATGCAAATTCGG Sugarbeet_BvADHβ   1151  AGACAAATTGA
Yellowbeet_BvADHβ  1151  AGACAAATTGA
Redbeet_BvADHβ     1151  AGACAAATTGA
Whitebeet_BvADHβ   1151  AGACAAATTGA
Seabeet_BvADHβ     1151  AGACAAATTGA
```

Fig. 5C-1 c) Amino acid sequence alignment of BvADHα

```
Redbeet_BvADHα      1   MISLSSFHPSSTTATATAAAAT----------THPPQQCPAFSSPPSHLSL
Whitebeet_BvADHα    1   MISLSSFHPSSTTATATAAAAT----------THPPQQCPAFSSPPSHLSL
Yellowbeet_BvADHα   1   MISLSSFHPSSTTATATAAAAT----------THPPQQCPAFSSPPSHLSL
Sugarbeet_BvADHα    1   MISLSSFHPSSTTATATAATAT----------THPPQQCPAFSSPPSHLSL
Seabeet_BvADHα      1   MISLSSFHPSSTTATATAATATATAATATATTHPPQQCPAFSSPPSHLSL Redbeet_BvADHα     42   PLRHPRQHLVVRC GGGGSASESVFNRDSAATRVSNDHLDVSKRDVKLKIA
Whitebeet_BvADHα   42   PLRHPRQHLVVRCGGGGSASESVFNRDSAATRVSNDHLDVSKRDVKLKIA
Yellowbeet_BvADHα  42   PLRHPRQHLVVRCGGGGSASESVFNRDSAATRVSNDHLDVSKRDVKLKIA
Sugarbeet_BvADHα   42   PLRHPRQHLVVRCGGGGSASESVFNRDSAATRVSNDHLDVSKRDVKLKIA
Seabeet_BvADHα     51   PLRHPRQHLVVRC GGGGSASESVFNRDSAATRVSNDHLDVSKRDVKLKIA Redbeet_BvADHα     92   IIGFGNFGQFLAKTMAKQGHRVLAYSRSDYSRAAKEIGVEYFTDADDLCE
Whitebeet_BvADHα   92   IIGFGNFGQFLAKTMAKQGHRVLAYSRSDYSRAAKEIGVEYFTDADDLCE
Yellowbeet_BvADHα  92   IIGFGNFGQFLAKTMAKQGHRVLAYSRSDYSRAAKEIGVEYFTDADDLCE
Sugarbeet_BvADHα   92   IIGFGNFGQFLAKTMAKQGHRVLAYSRSDYSRAAKEIGVEYFTDADDLCE
Seabeet_BvADHα    101   IIGFGNFGQFLAKTMAKQGHRVLAYSRSDYSRAAKEIGVEYFTDADDLCE Redbeet_BvADHα    142   EHPEVILLCTSILSTEKVLRSLPLHRLRRSTLFADVLSVKEFPRSLFLQL
Whitebeet_BvADHα  142   EHPEVILLCTSILSTEKVLRSLPLHRLRRSTLFADVLSVKEFPRSLFLQL
Yellowbeet_BvADHα 142   EHPEVILLCTSILSTEKVLRSLPLHRLRRSTLFADVLSVKEFPRSLFLQL
Sugarbeet_BvADHα  142   EHPEVILLCTSILSTEKVLRSLPLHRLRRSTLFADVLSVKEFPRSLFLQL
Seabeet_BvADHα    151   EHPEVILLCTSILSTEKVLRSLPLHRLRRSTLFADVLSVKEFPRSLFLQL Redbeet_BvADHα    192   LPKDFDILCTHPMFGPDSGKDGWGGLPFVFDKVRVGSDQSRISRAEAFLD
Whitebeet_BvADHα  192   LPKDFDILCTHPMFGPDSGKDGWGGLPFVFDKVRVGSDQSRISRAEAFLD
Yellowbeet_BvADHα 192   LPKDFDILCTHPMFGPDSGKDGWGGLPFVFDKVRVGSDQSRISRAEAFLD
Sugarbeet_BvADHα  192   LPKDFDILCTHPMFGPDSGKDGWGGLPFVFDKVRVGSDQSRISRAEAFLD
Seabeet_BvADHα    201   LPKDFDILCTHPMFGPDSGKDGWGGLPFVFDKVRVGSDQSRISRAEAFLD Redbeet_BvADHα    242   VFRNAGCRMVEMSCVDHDKHAAGSQFITHMMGRVLEKLALENTPINTKGY
Whitebeet_BvADHα  242   VFRNAGCRMVEMSCVDHDKHAAGSQFITHMMGRVLEKLALENTPINTKGY
Yellowbeet_BvADHα 242   VFRNAGCRMVEMSCVDHDKHAAGSQFITHMMGRVLEKLALENTPINTKGY
Sugarbeet_BvADHα  242   VFRNAGCRMVEMSCVDHDKHAAGSQFITHMMGRVLEKLALENTPINTKGY
Seabeet_BvADHα    251   VFRNAGCRMVEMSCVDHDKHAAGSQFITHMMGRVLEKLALENTPINTKGY Redbeet_BvADHα    292   ESLLNLVDNTARDSFELFYGLFLYNKNAMEQLDRMDWAFEMVKKQLSGYL
Whitebeet_BvADHα  292   ESLLNLVDNTARDSFELFYGLFLYNKNAMEQLDRMDWAFEMVKKQLSGYL
Yellowbeet_BvADHα 292   ESLLNLVDNTARDSFELFYGLFLYNKNAMEQLDRMDWAFEMVKKQLSGYL
Sugarbeet_BvADHα  292   ESLLNLVDNTARDSFELFYGLFLYNKNAMEQLDRMDWAFEMVKKQLSGYL
Seabeet_BvADHα    301   ESLLNLVDNTARDSFELFYGLFLYNKNAMEQLDRMDWAFEMVKKQLSGYL Redbeet_BvADHα    342   HDLVRKQLMLEGNNDQAEVTFDKPLMLPSPTINPPQIVPSADMAEKKHDL
Whitebeet_BvADHα  342   HDLVRKQLMLEGNNDQAEVTFDKPLMLPSPTINPPQIVPSADMAEKKHDL
Yellowbeet_BvADHα 342   HDLVRKQLMLEGNNDQAEVTFDKPLMLPSPTINPPQIVPSADMAEKKHDL
Sugarbeet_BvADHα  342   HDLVRKQLMLEGNNDQAEVTFDKPLMLPSPTINPPQIVPSADMAEKKHDL
Seabeet_BvADHα    351   HDLVRKQLMLEGNNDQAEVTFDKPLMLPSPTINPPQIVPSADMAEKKHDL
```

Fig. 5C-2

```
Redbeet_BvADHα      392  VVVNGTR
Whitebeet_BvADHα    392  VVVNGTR
Yellowbeet_BvADHα   392  VVVNGTR
Sugarbeet_BvADHα    392  VVVNGTR
Seabeet_BvADHα      401  VVVNGTR
```

Fig. 5D d) Amino acid sequence alignment of BvADHβ

```
Sugarbeet_BvADHβ    1  MLSLSSTTTAKPSPSPSPANFPAKLSSLSTITTTLSFSPRRRYFHGVKTL
Yellowbeet_BvADHβ   1  MLSLSSTTTAKPSPSPSPANFPAKLSSLSTITTTLSFSPRRRYFHGVKTL
Redbeet_BvADHβ      1  MLSLSSTTTAKPSPSPSPANFPAKLSSLSTITTTLSFSPRRRYFHGVKTL
Whitebeet_BvADHβ    1  MLSLSSTTTAKPSPSPSPANFPAKLSSLSTITTTLSFSPRRRYFHGVKTL
Seabeet_BvADHβ      1  MLSLSSTTTAKPSPSPSPANFPAKLSSLSTITTTISFSPRRRYFHGVKTL Sugarbeet_BvADHβ   51  TIRSIDAAQFFDYESKLAAINTTSSSSSSSYSKLKIAIVGFGNYGQFLAK
Yellowbeet_BvADHβ  51  TIRSIDAAQFFDYESKLAAINTTSSSSSSSYSKLKIAIVGFGNYGQFLAK
Redbeet_BvADHβ     51  TIRSIDAAQFFDYESKLAAINTTSSSSSSSYSKLKIAIVGFGNYGQFLAK
Whitebeet_BvADHβ   51  TIRSIDAAQFFDYESKLAAINTTSSSSSSSYSKLKIAIVGFGNYGQFLAK
Seabeet_BvADHβ     51  TIRSIDAAQFFDYESKLAAINTTSSSTSSSYSKLKIAIVGFGNYGQFLAK Sugarbeet_BvADHβ  101  TLVSQGHTVLAYSRSDYSKIAANLGVSYFSDPDDLCEEHPEVIMLCTSIL
Yellowbeet_BvADHβ 101  TLVSQGHTVLAYSRSDYSKIAANLGVSYFSDPDDLCEEHPEVIMLCTSIL
Redbeet_BvADHβ    101  TLVSQGHTVLAYSRSDYSKIAANLGVSYFSDPDDLCEEHPEVIMLCTSIL
Whitebeet_BvADHβ  101  TLVSQGHTVLAYSRSDYSKIAANLGVSYFSDPDDLCEEHPEVIMLCTSIL
Seabeet_BvADHβ    101  TLVSQGHTVLAYSRSDYSKIAANLGVSYFSDPDDLCEEHPEVIMLCTSIL Sugarbeet_BvADHβ  151  STEVMLNSLPLQRLKRSTLFVDVLSVKEFPRNLFLQTLPSDFDILCTHPM
Yellowbeet_BvADHβ 151  STEVMLNSLPLQRLKRSTLFVDVLSVKEFPRNLFLQTLPSDFDILCTHPM
Redbeet_BvADHβ    151  STEVMLNSLPLQRLKRSTLFVDVLSVKEFPRNLFLQTLPSDFDILCTHPM
Whitebeet_BvADHβ  151  STEVMLNSLPLQRLKRSTLFVDVLSVKEFPRNLFLQTLPSDFDILCTHPM
Seabeet_BvADHβ    151  STEVMLNSLPLQRLKRSTLFVDVLSVKEFPRNLFLQTLPSDFDILCTHPM Sugarbeet_BvADHβ  201  FGPESGKNGWGSLPFVYDKVRIGKDEGRIKRCESFLDVFRREGCRVEEMT
Yellowbeet_BvADHβ 201  FGPESGKNGWGSLPFVYDKVRIGKDEGRIKRCESFLDVFRREGCRVEEMT
Redbeet_BvADHβ    201  FGPESGKNGWGSLPFVYDKVRIGKDEGRIKRCESFLDVFRREGCRVEEMT
Whitebeet_BvADHβ  201  FGPESGKNGWGSLPFVYDKVRIGKDEGRIKRCESFLDVFRREGCRVEEMT
Seabeet_BvADHβ    201  FGPESGKNGWGSLPFVYDKVRIGKDEGRIKRCESFLDVFRREGCRVEEMT Sugarbeet_BvADHβ  251  CAEHDKFAAGSQFITHFLGRVLEKLDLEDTPINTKGYESLLNLVDNTSKD
Yellowbeet_BvADHβ 251  CAEHDKFAAGSQFITHFLGRVLEKLDLEDTPINTKGYESLLNLVDNTSKD
Redbeet_BvADHβ    251  CAEHDKFAAGSQFITHFLGRVLEKLDLEDTPINTKGYESLLNLVDNTSKD
Whitebeet_BvADHβ  251  CAEHDKFAAGSQFITHFLGRVLEKLDLEDTPINTKGYESLLNLVDNTSKD
Seabeet_BvADHβ    251  CAEHDKFAAGSQFITHFLGRVLEKLDLEDTPINTKGYESLLNLVDNTSKD Sugarbeet_BvADHβ  301  SFELFYGLFLYNQNAMEQLERLDWAFELVKKQLFGHLHGLLRKQLFGFSE
Yellowbeet_BvADHβ 301  SFELFYGLFLYNQNAMEQLERLDWAFELVKKQLFGHLHGLLRKQLFGFSE
Redbeet_BvADHβ    301  SFELFYGLFLYNQNAMEQLERLDWAFELVKKQLFGHLHGLLRKQLFGFSE
Whitebeet_BvADHβ  301  SFELFYGLFLYNQNAMEQLERLDWAFELVKKQLFGHLHGLLRKQLFGFSE
Seabeet_BvADHβ    301  SFELFYGLFLYNQNAMEQLERLDWAFELVKKQLFGHLHGLLRKQLFGFSE Sugarbeet_BvADHβ  351  IDERIGKAKEIKFLSDAAEQNGSALSARENANSETN
Yellowbeet_BvADHβ 351  IDERIGKAKEIKFLSDAAEQNGSALSARENANSETN
Redbeet_BvADHβ    351  IDERIGKAKEIKFLSDAAEQNGSALSARENANSETN
Whitebeet_BvADHβ  351  IDERIGKAKEIKFLSDAAEQNGSALSARENANSETN
Seabeet_BvADHβ    351  IDERIGKAKEIKFLSDAAEQNGSALSARENANSETN
```

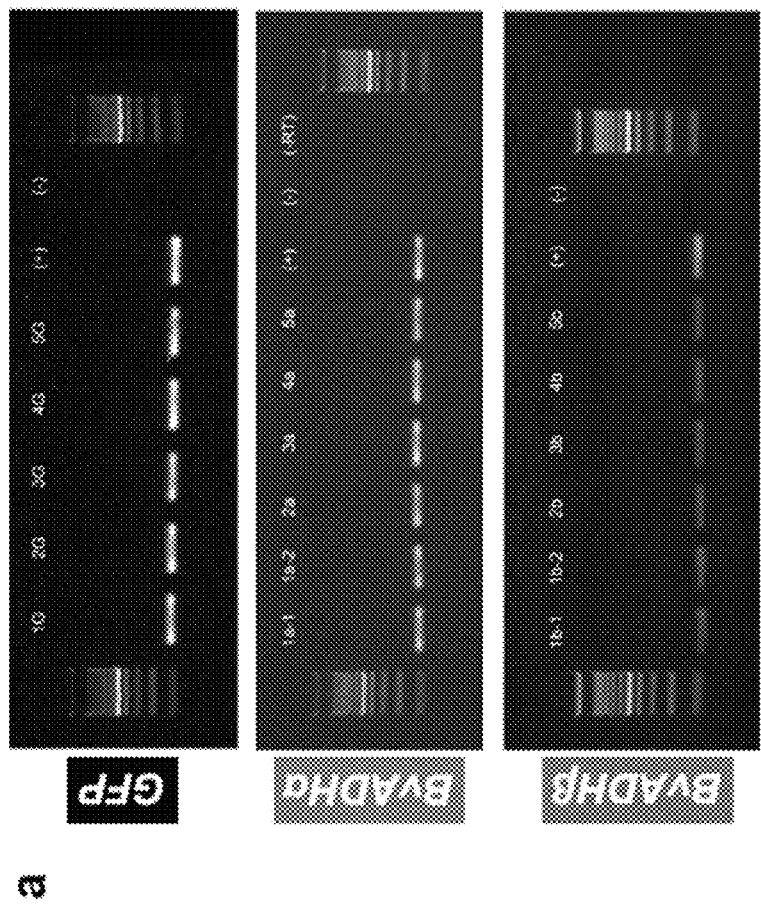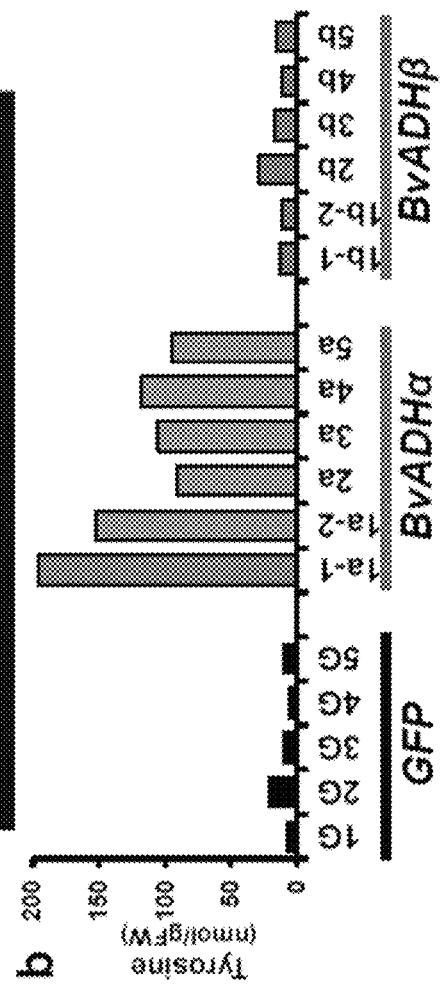
Fig. 9A
Fig. 9B

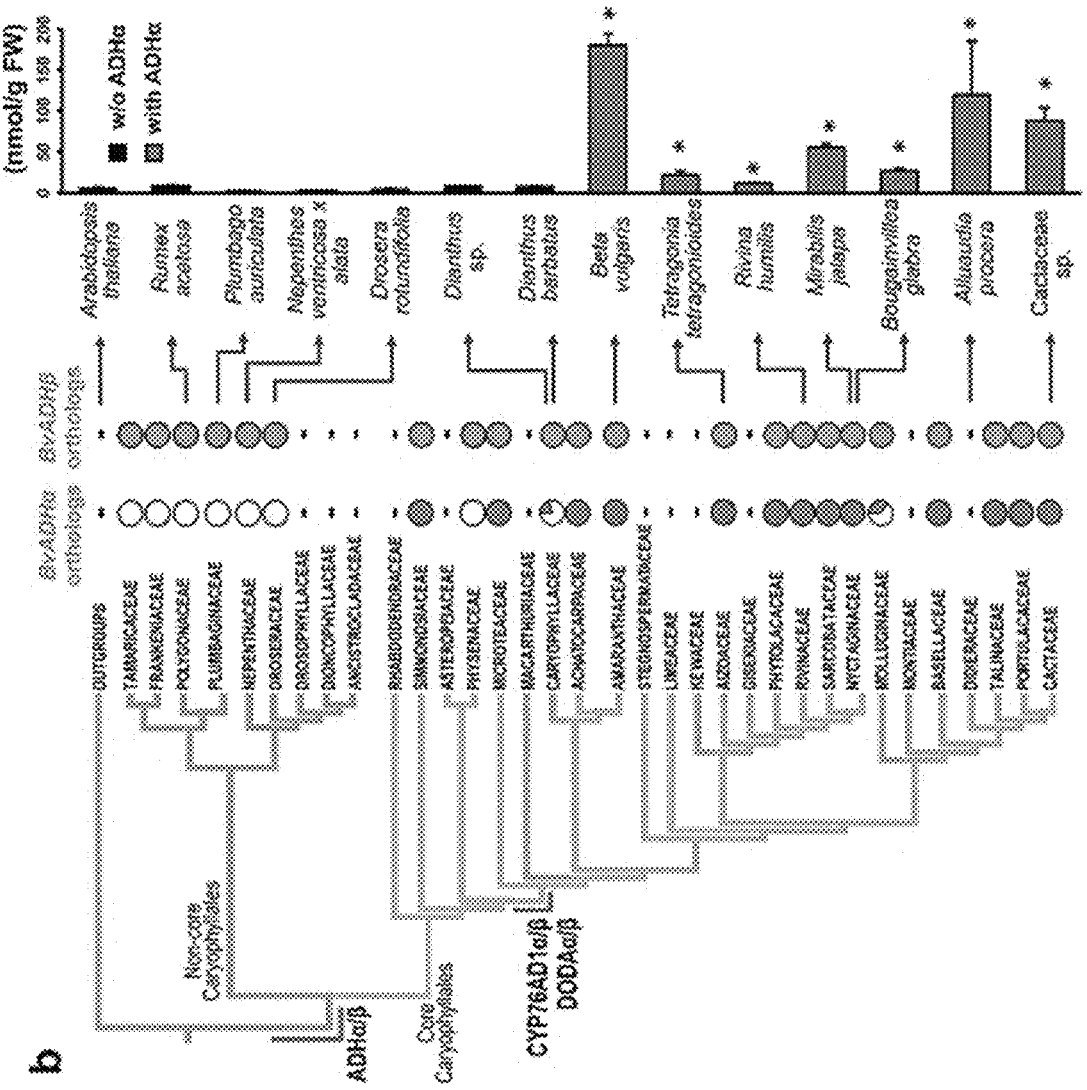

SEQUENCE LISTING

```
<160> NUMBER OF SEQ ID NOS: 94

<210> SEQ ID NO 1
<211> LENGTH: 398
<212> TYPE: PRT
<213> ORGANISM: Beta vulgaris
<220> FEATURE:
<221> NAME/KEY: misc_feature
<222> LOCATION: (1)..(398)
<223> OTHER INFORMATION: BvADH-alpha Big Buck sugar beet variety

<400> SEQUENCE: 1

Met Ile Ser Leu Ser Ser Phe His Pro Ser Ser Thr Thr Ala Thr Ala
1               5                   10                  15

Thr Ala Ala Thr Ala Thr Thr His Pro Pro Gln Gln Cys Pro Ala Phe
            20                  25                  30

Ser Ser Pro Pro Ser His Leu Ser Leu Pro Leu Arg His Pro Arg Gln
        35                  40                  45

His Leu Val Val Arg Cys Gly Gly Gly Ser Ala Ser Glu Ser Val
    50                  55                  60

Phe Asn Arg Asp Ser Ala Ala Thr Arg Val Ser Asn Asp His Leu Asp
65                  70                  75                  80

Val Ser Lys Arg Asp Val Lys Leu Lys Ile Ala Ile Ile Gly Phe Gly
                85                  90                  95

Asn Phe Gly Gln Phe Leu Ala Lys Thr Met Ala Lys Gln Gly His Arg
            100                 105                 110

Val Leu Ala Tyr Ser Arg Ser Asp Tyr Ser Arg Ala Ala Lys Glu Ile
        115                 120                 125

Gly Val Glu Tyr Phe Thr Asp Ala Asp Leu Cys Glu Glu His Pro
    130                 135                 140

Glu Val Ile Leu Leu Cys Thr Ser Ile Leu Ser Thr Glu Lys Val Leu
145                 150                 155                 160

Arg Ser Leu Pro Leu His Arg Leu Arg Arg Ser Thr Leu Phe Ala Asp
                165                 170                 175

Val Leu Ser Val Lys Glu Phe Pro Arg Ser Leu Phe Leu Gln Leu Leu
            180                 185                 190

Pro Lys Asp Phe Asp Ile Leu Cys Thr His Pro Met Phe Gly Pro Asp
        195                 200                 205

Ser Gly Lys Asp Gly Trp Gly Leu Pro Phe Val Phe Asp Lys Val
    210                 215                 220

Arg Val Gly Ser Asp Gln Ser Arg Thr Ser Arg Ala Glu Ala Phe Leu
225                 230                 235                 240

Asp Val Phe Arg Asn Ala Gly Cys Arg Met Val Glu Met Ser Cys Val
                245                 250                 255

Asp His Asp Lys His Ala Ala Gly Ser Gln Phe Ile Thr His Met Met
```

```
                    260                 265                 270
Gly Arg Val Leu Glu Lys Leu Ala Leu Glu Asn Thr Pro Ile Asn Thr
            275                 280                 285

Lys Gly Tyr Glu Ser Leu Leu Asn Leu Val Asp Asn Thr Ala Arg Asp
        290                 295                 300

Ser Phe Glu Leu Phe Tyr Gly Leu Phe Leu Tyr Asn Lys Asn Ala Met
305                 310                 315                 320

Glu Gln Leu Asp Arg Met Asp Trp Ala Phe Glu Met Val Lys Lys Gln
                325                 330                 335

Leu Ser Gly Tyr Leu His Asp Leu Val Arg Lys Gln Leu Met Leu Glu
            340                 345                 350

Gly Asn Asn Asp Gln Ala Glu Val Thr Phe Asp Lys Pro Leu Met Leu
        355                 360                 365

Pro Ser Pro Thr Ile Asn Pro Pro Gln Ile Val Pro Ser Ala Asp Met
    370                 375                 380

Ala Glu Lys Lys His Asp Leu Val Val Val Asn Gly Thr Arg
385                 390                 395
```

<210> SEQ ID NO 2
<211> LENGTH: 398
<212> TYPE: PRT
<213> ORGANISM: Beta vulgaris
<220> FEATURE:
<221> NAME/KEY: misc_feature
<222> LOCATION: (1)..(398)
<223> OTHER INFORMATION: BvADH-alpha W357B red beet variety

<400> SEQUENCE: 2

```
Met Ile Ser Leu Ser Ser Phe His Pro Ser Ser Thr Thr Ala Thr Ala
1               5                   10                  15

Thr Ala Ala Ala Thr Thr His Pro Pro Gln Gln Cys Pro Ala Phe
            20                  25                  30

Ser Ser Pro Pro Ser His Leu Ser Leu Pro Leu Arg His Pro Arg Gln
        35                  40                  45

His Leu Val Val Arg Cys Gly Gly Gly Gly Ser Ala Ser Glu Ser Val
    50                  55                  60

Phe Asn Arg Asp Ser Ala Ala Thr Arg Val Ser Asn Asp His Leu Asp
65                  70                  75                  80

Val Ser Lys Arg Asp Val Lys Leu Lys Ile Ala Ile Gly Phe Gly
                85                  90                  95

Asn Phe Gly Gln Phe Leu Ala Lys Thr Met Ala Lys Gln Gly His Arg
            100                 105                 110

Val Leu Ala Tyr Ser Arg Ser Asp Tyr Ser Arg Ala Ala Lys Glu Ile
        115                 120                 125

Gly Val Glu Tyr Phe Thr Asp Ala Asp Leu Cys Glu Glu His Pro
    130                 135                 140

Glu Val Ile Leu Leu Cys Thr Ser Ile Leu Ser Thr Glu Lys Val Leu
145                 150                 155                 160

Arg Ser Leu Pro Leu His Arg Leu Arg Arg Ser Thr Leu Phe Ala Asp
                165                 170                 175

Val Leu Ser Val Lys Glu Phe Pro Arg Ser Leu Phe Leu Gln Leu Leu
            180                 185                 190

Pro Lys Asp Phe Asp Ile Leu Cys Thr His Pro Met Phe Gly Pro Asp
        195                 200                 205

Ser Gly Lys Asp Gly Trp Gly Gly Leu Pro Phe Val Phe Asp Lys Val
    210                 215                 220
```

```
Arg Val Gly Ser Asp Gln Ser Arg Thr Ser Arg Ala Glu Ala Phe Leu
225                 230                 235                 240

Asp Val Phe Arg Asn Ala Gly Cys Arg Met Val Glu Met Ser Cys Val
                245                 250                 255

Asp His Asp Lys His Ala Ala Gly Ser Gln Phe Ile Thr His Met Met
            260                 265                 270

Gly Arg Val Leu Glu Lys Leu Ala Leu Glu Asn Thr Pro Ile Asn Thr
        275                 280                 285

Lys Gly Tyr Glu Ser Leu Leu Asn Leu Val Asp Asn Thr Ala Arg Asp
    290                 295                 300

Ser Phe Glu Leu Phe Tyr Gly Leu Phe Leu Tyr Asn Lys Asn Ala Met
305                 310                 315                 320

Glu Gln Leu Asp Arg Met Asp Trp Ala Phe Glu Met Val Lys Lys Gln
                325                 330                 335

Leu Ser Gly Tyr Leu His Asp Leu Val Arg Lys Gln Leu Met Leu Glu
            340                 345                 350

Gly Asn Asn Asp Gln Ala Glu Val Thr Phe Asp Lys Pro Leu Met Leu
        355                 360                 365

Pro Ser Pro Thr Ile Asn Pro Pro Gln Ile Val Pro Ser Ala Asp Met
370                 375                 380

Ala Glu Lys Lys His Asp Leu Val Val Val Asn Gly Thr Arg
385                 390                 395

<210> SEQ ID NO 3
<211> LENGTH: 398
<212> TYPE: PRT
<213> ORGANISM: Beta vulgaris
<220> FEATURE:
<221> NAME/KEY: misc_feature
<222> LOCATION: (1)..(398)
<223> OTHER INFORMATION: BvADH-alpha Blankoma white beet variety

<400> SEQUENCE: 3

Met Ile Ser Leu Ser Ser Phe His Pro Ser Ser Thr Thr Ala Thr Ala
1               5                   10                  15

Thr Ala Ala Ala Thr Thr His Pro Pro Gln Gln Cys Pro Ala Phe
                20                  25                  30

Ser Ser Pro Pro Ser His Leu Ser Leu Pro Leu Arg His Pro Arg Gln
            35                  40                  45

His Leu Val Val Arg Cys Gly Gly Gly Ser Ala Ser Glu Ser Val
        50                  55                  60

Phe Asn Arg Asp Ser Ala Ala Thr Arg Val Ser Asn Asp His Leu Asp
65                  70                  75                  80

Val Ser Lys Arg Asp Val Lys Leu Lys Ile Ala Ile Gly Phe Gly
                85                  90                  95

Asn Phe Gly Gln Phe Leu Ala Lys Thr Met Ala Lys Gln Gly His Arg
                100                 105                 110

Val Leu Ala Tyr Ser Arg Ser Asp Tyr Ser Arg Ala Ala Lys Glu Ile
            115                 120                 125

Gly Val Glu Tyr Phe Thr Asp Ala Asp Asp Leu Cys Glu Glu His Pro
        130                 135                 140

Glu Val Ile Leu Leu Cys Thr Ser Ile Leu Ser Thr Glu Lys Val Leu
145                 150                 155                 160

Arg Ser Leu Pro Leu His Arg Leu Arg Arg Ser Thr Leu Phe Ala Asp
                165                 170                 175
```

```
Val Leu Ser Val Lys Glu Phe Pro Arg Ser Leu Phe Leu Gln Leu Leu
            180                 185                 190

Pro Lys Asp Phe Asp Ile Leu Cys Thr His Pro Met Phe Gly Pro Asp
        195                 200                 205

Ser Gly Lys Asp Gly Trp Gly Gly Leu Pro Phe Val Phe Asp Lys Val
    210                 215                 220

Arg Val Gly Ser Asp Gln Ser Arg Thr Ser Arg Ala Glu Ala Phe Leu
225                 230                 235                 240

Asp Val Phe Arg Asn Ala Gly Cys Arg Met Val Glu Met Ser Cys Val
                245                 250                 255

Asp His Asp Lys His Ala Ala Gly Ser Gln Phe Ile Thr His Met Met
            260                 265                 270

Gly Arg Val Leu Glu Lys Leu Ala Leu Glu Asn Thr Pro Ile Asn Thr
        275                 280                 285

Lys Gly Tyr Glu Ser Leu Leu Asn Leu Val Asp Asn Thr Ala Arg Asp
    290                 295                 300

Ser Phe Glu Leu Phe Tyr Gly Leu Phe Leu Tyr Asn Lys Asn Ala Met
305                 310                 315                 320

Glu Gln Leu Asp Arg Met Asp Trp Ala Phe Glu Met Val Lys Lys Gln
                325                 330                 335

Leu Ser Gly Tyr Leu His Asp Leu Val Arg Lys Gln Leu Met Leu Glu
            340                 345                 350

Gly Asn Asn Asp Gln Ala Glu Val Thr Phe Asp Lys Pro Leu Met Leu
        355                 360                 365

Pro Ser Pro Thr Ile Asn Pro Pro Gln Ile Val Pro Ser Ala Asp Met
    370                 375                 380

Ala Glu Lys Lys His Asp Leu Val Val Asn Gly Thr Arg
385                 390                 395

<210> SEQ ID NO 4
<211> LENGTH: 398
<212> TYPE: PRT
<213> ORGANISM: Beta vulgaris
<220> FEATURE:
<221> NAME/KEY: misc_feature
<222> LOCATION: (1)..(398)
<223> OTHER INFORMATION: BvADH-alpha Touch Stone yellow beet variety

<400> SEQUENCE: 4

Met Ile Ser Leu Ser Ser Phe His Pro Ser Ser Thr Thr Ala Thr Ala
1               5                   10                  15

Thr Ala Ala Ala Thr Thr His Pro Pro Gln Gln Cys Pro Ala Phe
            20                  25                  30

Ser Ser Pro Pro Ser His Leu Ser Leu Pro Leu Arg His Pro Arg Gln
        35                  40                  45

His Leu Val Val Arg Cys Gly Gly Gly Ser Ala Ser Glu Ser Val
    50                  55                  60

Phe Asn Arg Asp Ser Ala Ala Thr Arg Val Ser Asn Asp His Leu Asp
65                  70                  75                  80

Val Ser Lys Arg Asp Val Lys Leu Lys Ile Ala Ile Ile Gly Phe Gly
                85                  90                  95

Asn Phe Gly Gln Phe Leu Ala Lys Thr Met Ala Lys Gln Gly His Arg
            100                 105                 110

Val Leu Ala Tyr Ser Arg Ser Asp Tyr Ser Arg Ala Ala Lys Glu Ile
        115                 120                 125

Gly Val Glu Tyr Phe Thr Asp Ala Asp Asp Leu Cys Glu Glu His Pro
```

```
                130                 135                 140
Glu Val Ile Leu Leu Cys Thr Ser Ile Leu Ser Thr Glu Lys Val Leu
145                 150                 155                 160

Arg Ser Leu Pro Leu His Arg Leu Arg Arg Ser Thr Leu Phe Ala Asp
                165                 170                 175

Val Leu Ser Val Lys Glu Phe Pro Arg Ser Leu Phe Leu Gln Leu Leu
            180                 185                 190

Pro Lys Asp Phe Asp Ile Leu Cys Thr His Pro Met Phe Gly Pro Asp
                195                 200                 205

Ser Gly Lys Asp Gly Trp Gly Gly Leu Pro Phe Val Phe Asp Lys Val
210                 215                 220

Arg Val Gly Ser Asp Gln Ser Arg Thr Ser Arg Ala Glu Ala Phe Leu
225                 230                 235                 240

Asp Val Phe Arg Asn Ala Gly Cys Arg Met Val Glu Met Ser Cys Val
                245                 250                 255

Asp His Asp Lys His Ala Ala Gly Ser Gln Phe Ile Thr His Met Met
                260                 265                 270

Gly Arg Val Leu Glu Lys Leu Ala Leu Glu Asn Thr Pro Ile Asn Thr
            275                 280                 285

Lys Gly Tyr Glu Ser Leu Leu Asn Leu Val Asp Asn Thr Ala Arg Asp
            290                 295                 300

Ser Phe Glu Leu Phe Tyr Gly Leu Phe Leu Tyr Asn Lys Asn Ala Met
305                 310                 315                 320

Glu Gln Leu Asp Arg Met Asp Trp Ala Phe Glu Met Val Lys Lys Gln
                325                 330                 335

Leu Ser Gly Tyr Leu His Asp Leu Val Arg Lys Gln Leu Met Leu Glu
                340                 345                 350

Gly Asn Asn Asp Gln Ala Glu Val Thr Phe Asp Lys Pro Leu Met Leu
            355                 360                 365

Pro Ser Pro Thr Ile Asn Pro Pro Gln Ile Val Pro Ser Ala Asp Met
            370                 375                 380

Ala Glu Lys Lys His Asp Leu Val Val Val Asn Gly Thr Arg
385                 390                 395

<210> SEQ ID NO 5
<211> LENGTH: 407
<212> TYPE: PRT
<213> ORGANISM: Beta vulgaris
<220> FEATURE:
<221> NAME/KEY: misc_feature
<222> LOCATION: (1)..(407)
<223> OTHER INFORMATION: BvADH-alpha Sea beet PI562585 variety

<400> SEQUENCE: 5

Met Ile Ser Leu Ser Ser Phe His Pro Ser Ser Thr Thr Ala Thr Ala
1               5                   10                  15

Thr Ala Ala Thr Ala Thr Ala Thr Ala Ala Thr Ala Thr Ala Thr Thr
            20                  25                  30

His Pro Pro Gln Gln Cys Pro Ala Phe Ser Ser Pro Pro Ser His Leu
        35                  40                  45

Ser Leu Pro Leu Arg His Pro Arg Gln His Leu Val Val Arg Cys Gly
    50                  55                  60

Gly Gly Gly Ser Ala Ser Glu Ser Val Phe Asn Arg Asp Ser Ala Ala
65              70                  75                  80

Thr Arg Val Ser Asn Asp His Leu Asp Val Ser Lys Arg Asp Val Lys
                85                  90                  95
```

Leu Lys Ile Ala Ile Ile Gly Phe Gly Asn Phe Gly Gln Phe Leu Ala
            100                 105                 110

Lys Thr Met Ala Lys Gln Gly His Arg Val Leu Ala Tyr Ser Arg Ser
        115                 120                 125

Asp Tyr Ser Arg Ala Ala Lys Glu Ile Gly Val Glu Tyr Phe Thr Asp
    130                 135                 140

Ala Asp Asp Leu Cys Glu Glu His Pro Glu Val Ile Leu Leu Cys Thr
145                 150                 155                 160

Ser Ile Leu Ser Thr Glu Lys Val Leu Arg Ser Leu Pro Leu His Arg
                165                 170                 175

Leu Arg Arg Ser Thr Leu Phe Ala Asp Val Leu Ser Val Lys Glu Phe
            180                 185                 190

Pro Arg Ser Leu Phe Leu Gln Leu Leu Pro Lys Asp Phe Asp Ile Leu
        195                 200                 205

Cys Thr His Pro Met Phe Gly Pro Asp Ser Gly Lys Asp Gly Trp Gly
    210                 215                 220

Gly Leu Pro Phe Val Phe Asp Lys Val Arg Val Gly Ser Asp Gln Ser
225                 230                 235                 240

Arg Thr Ser Arg Ala Glu Ala Phe Leu Asp Val Phe Arg Asn Ala Gly
                245                 250                 255

Cys Arg Met Val Glu Met Ser Cys Val Asp His Asp Lys His Ala Ala
            260                 265                 270

Gly Ser Gln Phe Ile Thr His Met Met Gly Arg Val Leu Glu Lys Leu
        275                 280                 285

Ala Leu Glu Asn Thr Pro Ile Asn Thr Lys Gly Tyr Glu Ser Leu Leu
    290                 295                 300

Asn Leu Val Asp Asn Thr Ala Arg Asp Ser Phe Glu Leu Phe Tyr Gly
305                 310                 315                 320

Leu Phe Leu Tyr Asn Lys Asn Ala Met Glu Gln Leu Asp Arg Met Asp
                325                 330                 335

Trp Ala Phe Glu Met Val Lys Lys Gln Leu Ser Gly Tyr Leu His Asp
            340                 345                 350

Leu Val Arg Lys Gln Leu Met Leu Glu Gly Asn Asn Asp Gln Ala Glu
        355                 360                 365

Val Thr Phe Asp Lys Pro Leu Met Leu Pro Ser Pro Thr Ile Asn Pro
    370                 375                 380

Pro Gln Ile Val Pro Ser Ala Asp Met Ala Glu Lys Lys His Asp Leu
385                 390                 395                 400

Val Val Val Asn Gly Thr Arg
                405

<210> SEQ ID NO 6
<211> LENGTH: 346
<212> TYPE: PRT
<213> ORGANISM: Spinacea oleracea
<220> FEATURE:
<221> NAME/KEY: misc_feature
<222> LOCATION: (1)..(346)
<223> OTHER INFORMATION: SoADH-alpha

<400> SEQUENCE: 6

Cys Ala Ala Ser Asp Ser Val Phe Asn His Asp Ile Gly Val Pro Phe
1               5                   10                  15

Val Ser Thr Arg Ala Ser Gly Glu Val Pro Glu Val Asn Ser Arg Asp
            20                  25                  30

```
Ile Lys Leu Lys Ile Ala Ile Gly Phe Gly Asn Phe Gly Gln Phe
            35                  40                  45

Leu Ala Lys Thr Ile Thr Lys Gln Gly His Arg Val Leu Ala Tyr Ser
 50                  55                  60

Arg Ser Asp Tyr Ser Arg Ala Ala Lys Glu Ile Gly Val Glu Tyr Phe
 65                  70                  75                  80

Ser Asp Ala Asp Asp Leu Cys Glu Glu His Pro Glu Val Ile Leu Leu
                 85                  90                  95

Cys Thr Ser Ile Leu Ser Thr Glu Lys Val Leu Arg Ser Leu Pro Leu
                100                 105                 110

His Arg Leu Arg Arg Ser Thr Leu Phe Val Asp Val Leu Ser Val Lys
            115                 120                 125

Glu Phe Pro Arg Ser Leu Phe Leu Gln Val Leu Pro Lys Asp Phe Asp
130                 135                 140

Ile Leu Cys Thr His Pro Met Phe Gly Pro Asp Ser Gly Lys Ser Gly
145                 150                 155                 160

Trp Gly Gly Leu Pro Phe Val Phe Asp Lys Val Arg Val Gly Ser Asp
                165                 170                 175

Pro Thr Arg Ala Ala Arg Thr Glu Ala Phe Leu Asp Ile Tyr Arg Asn
            180                 185                 190

Ala Gly Cys Arg Met Val Glu Met Thr Cys Ala Asp His Asp Lys His
        195                 200                 205

Ala Ala Gly Ser Gln Phe Ile Thr His Met Met Gly Arg Val Leu Glu
    210                 215                 220

Lys Leu Ala Leu Glu Asn Thr Pro Ile Asn Thr Lys Gly Tyr Glu Ser
225                 230                 235                 240

Leu Leu Asn Leu Val Asp Asn Thr Ala Arg Asp Ser Phe Glu Leu Phe
                245                 250                 255

Tyr Gly Leu Phe Leu Tyr Asn Lys Asn Ala Met Glu Gln Leu Asp Arg
            260                 265                 270

Met Asp Trp Ala Phe Glu Met Val Lys Lys Gln Leu Ser Gly Tyr Leu
        275                 280                 285

His Asp Leu Val Arg Lys Gln Leu Met Leu Glu Thr Thr Asn Glu Gln
    290                 295                 300

Val Gly Phe Asp Gln Thr Phe Met Leu Pro Ser Pro Ala Asp Asn Pro
305                 310                 315                 320

Arg Gln Thr Pro Pro Ser Ala Ala Val Ser Glu Asn Ser Lys Pro Asp
                325                 330                 335

Phe Val Val Val Asn Gly Asn Asn Ser Arg
            340                 345

<210> SEQ ID NO 7
<211> LENGTH: 396
<212> TYPE: PRT
<213> ORGANISM: Spergularia marina
<220> FEATURE:
<221> NAME/KEY: misc_feature
<222> LOCATION: (1)..(396)
<223> OTHER INFORMATION: Spergularia marina ADH-alpha

<400> SEQUENCE: 7

Met Met Asn Ser Ile Ser Phe Val Asn Ser Ser Thr Thr Thr Ala
1               5                   10                  15

Asp Ile Ile Tyr Leu Asn His Gln Phe Ser Arg His Lys Cys Phe Ser
                20                  25                  30

Arg Leu Pro Arg Asp Ala Thr Pro Arg Asp Arg Arg Lys Ile Ser Leu
```

```
                35              40              45
Ala Arg Ala Ile Asn Gly Ser Pro Thr Cys Ser His Val Glu Ile Asp
50                  55                  60

Gln Thr Leu Val Ser Ser Gln Ala Thr Thr Arg Ala Cys Ser Asn
65              70                  75              80

Glu Gln Lys Lys Leu Lys Ile Ala Val Val Gly Phe Gly Asn Phe Gly
                85                  90                  95

Gln Phe Leu Ala Arg Glu Met Val Lys Gln Gly His Gln Val Leu Ala
            100                 105                 110

Tyr Ser Arg Ser Asp Tyr Ser Lys Val Ala Lys Glu Ile Gly Val Gln
            115                 120                 125

Phe Phe Arg Asp Pro Asp Asp Leu Cys Glu Glu His Pro Gln Val Val
            130                 135                 140

Leu Leu Cys Thr Ser Ile Leu Ser Thr Glu Lys Val Leu Arg Ser Leu
145                 150                 155                 160

Pro Val Asp Arg Leu Arg Arg Ser Thr Leu Ile Val Asp Val Leu Ser
                165                 170                 175

Val Lys Glu Phe Pro Arg Thr Leu Phe Leu Arg His Leu Pro Glu Asp
            180                 185                 190

Leu Asp Ile Leu Cys Thr His Pro Met Phe Gly Pro Asp Ser Gly Lys
            195                 200                 205

Ser Gly Trp Asp Gly Leu Pro Phe Val Phe Asp Lys Val Arg Val Gly
210                 215                 220

Ser Asp Pro Thr Arg Thr His Arg Val Asn Thr Phe Leu Asp Ile Phe
225                 230                 235                 240

Lys His Ala Gly Cys Arg Met Val Glu Met Thr Cys Met Asp His Asp
                245                 250                 255

Lys His Ala Ala Gly Ser Gln Phe Ile Thr His Met Met Gly Arg Val
            260                 265                 270

Leu Glu Lys Val Gly Leu Ser Asn Thr Pro Ile Asn Thr Lys Gly Tyr
            275                 280                 285

Glu Ser Leu Leu Asn Leu Val Asp Asn Thr Ala Arg Asp Ser Phe Glu
290                 295                 300

Leu Phe Tyr Gly Leu Phe Leu Tyr Asn Lys Asn Ala Met Glu Glu Leu
305                 310                 315                 320

Asp Arg Leu Asp Trp Ala Phe Asp Thr Val Lys Met Gln Leu Ser Gly
                325                 330                 335

Tyr Leu His Asp Phe Ala Ser Lys Lys Leu Met Leu Glu Thr Gly Asn
            340                 345                 350

Glu Leu Ala Gly Ile Val Ser Gly Lys Ile Gly Asp Asp Asn His Asn
            355                 360                 365

Asn Lys Arg Leu Met Leu Ser Pro Pro Thr Asn Ser Tyr Lys Asn Val
            370                 375                 380

Thr Phe Thr Asp Thr Lys Val Ser Glu Lys Met Met
385                 390                 395

<210> SEQ ID NO 8
<211> LENGTH: 375
<212> TYPE: PRT
<213> ORGANISM: Rivina humilis
<220> FEATURE:
<221> NAME/KEY: misc_feature
<222> LOCATION: (1)..(375)
<223> OTHER INFORMATION: RhADH-alpha

<400> SEQUENCE: 8
```

Cys Thr Ala Phe Thr Lys Thr Asn Asn Asn Ala Leu Gly Tyr Gly
1               5                   10                  15

Tyr Gly Tyr Gly Tyr Gly Tyr Gly Asp Lys Asn Lys Val Ser Ser
            20                  25                  30

Thr Glu Gln Gly Asp Glu Val Ser Gly Ser Ser Asn Ser Lys Lys
            35                  40                  45

Leu Lys Ile Gly Ile Ile Gly Phe Gly Asn Phe Gly Gln Phe Met Ala
50                  55                  60

Lys Thr Met Val Lys His Gly His Thr Val Leu Ala Tyr Ser Arg Ser
65                  70                  75                  80

Asp Tyr Ser Arg Ala Ala His Thr Ile Gly Val Arg Tyr Phe Ser Asp
                85                  90                  95

Pro Asp Asp Leu Cys Glu Glu His Pro Glu Val Ile Leu Leu Cys Thr
                100                 105                 110

Ser Ile Leu Ser Thr Glu Arg Val Leu Arg Ser Leu Pro Leu His Arg
            115                 120                 125

Leu Arg Arg Ser Thr Leu Val Ala Asp Val Leu Ser Val Lys Glu Phe
    130                 135                 140

Pro Arg Ser Leu Phe Leu Gln Leu Leu Pro Ser Asp Phe Asp Ile Leu
145                 150                 155                 160

Cys Thr His Pro Met Phe Gly Pro Asp Ser Gly Lys Ala Gly Trp Gly
                165                 170                 175

Gly Leu Pro Phe Val Phe Asp Lys Val Arg Val Gly Ser Gln Pro Glu
            180                 185                 190

Arg Leu Thr Arg Val Glu Ala Phe Leu Asp Ile Phe Arg Asp Ala Gly
            195                 200                 205

Cys Arg Met Val Glu Met Ser Cys Ala Glu His Asp Arg His Ala Ala
    210                 215                 220

Gly Ser Gln Phe Ile Thr His Met Met Gly Arg Val Leu Glu Lys Leu
225                 230                 235                 240

Ala Leu Glu Asp Thr Pro Ile Asn Thr Lys Gly Tyr Glu Ser Leu Leu
                245                 250                 255

Asn Leu Val Asp Asn Thr Ala Arg Asp Ser Phe Glu Leu Phe Tyr Gly
            260                 265                 270

Leu Phe Leu Tyr Asn Lys Asn Ala Met Glu Gln Leu Asp Arg Met His
            275                 280                 285

Trp Ala Phe Glu Thr Val Lys Gln Gln Leu Ser Gly Tyr Leu His Val
290                 295                 300

Leu Val Arg Lys Gln Leu Met Leu Glu Thr Ser Ser Gly Asn Asp Asn
305                 310                 315                 320

Asn Asn Thr Asn Asn Ile Asn Ile Ser Ser Gly Asp Asn Ile Asn Asn
                325                 330                 335

Lys Asp Thr Asn Asn Lys Leu Met Leu Pro Ser Pro Gly Ile Ser Ser
                340                 345                 350

Ala Lys Ile Val Pro Pro Val Gln Glu Lys Glu Lys His Asp Leu Val
                355                 360                 365

Met Leu Asn Gly Ser Lys Arg
    370                 375

<210> SEQ ID NO 9
<211> LENGTH: 341
<212> TYPE: PRT
<213> ORGANISM: Portulaca oleracea
<220> FEATURE:

```
<221> NAME/KEY: misc_feature
<222> LOCATION: (1)..(341)
<223> OTHER INFORMATION: PoADH-alpha

<400> SEQUENCE: 9

Cys Ser Ser Ser Ser Ser Ser Ala Ser Ile Ile Ile Asn Gly Ser
1               5                   10                  15

Gly Ser Ser Thr Thr Asn Ser Ser Val Phe Asp Ala Ser Ser Ser
                20                  25                  30

Asp Ser Asp Val Lys Lys Arg Ser Glu Val Lys Leu Lys Ile Gly Ile
            35                  40                  45

Ile Gly Phe Gly Lys Phe Gly Gln Phe Leu Ala Lys Arg Ile Val Ser
    50                  55                  60

Gln Gly His Asp Val Leu Ala Tyr Ser Arg Ser Asp Tyr Ser Arg Val
65                  70                  75                  80

Ala Ser Glu Ile Gly Val Arg Phe Phe Ser Asp Ala Asp Asp Leu Cys
                85                  90                  95

Glu Glu His Pro Gln Val Ile Leu Leu Cys Thr Ser Ile Leu Ser Thr
                100                 105                 110

Glu Arg Val Leu Arg Ser Leu Pro Leu His Arg Leu Arg Arg Ser Thr
            115                 120                 125

Leu Phe Ala Asp Val Leu Ser Val Lys Glu Phe Pro Arg Ser Leu Phe
130                 135                 140

Leu Gln Leu Leu Pro Ser Asp Phe Asp Ile Leu Cys Thr His Pro Met
145                 150                 155                 160

Phe Gly Pro Asp Ser Gly Lys Ser Gly Trp Asp Ser Leu Pro Phe Val
                165                 170                 175

Phe Asp Lys Val Arg Val Gly Ser Thr Pro Thr Arg Val Thr Arg Ser
            180                 185                 190

Glu Ala Phe Leu Asp Ile Phe Arg Thr Ala Gly Cys Arg Met Val Glu
    195                 200                 205

Met Ser Cys Ala Glu His Asp Lys His Ala Ala Gly Ser Gln Phe Ile
210                 215                 220

Thr His Met Met Gly Arg Val Leu Glu Lys Leu Asp Leu Glu Asn Thr
225                 230                 235                 240

Pro Ile Asn Thr Arg Gly Tyr Glu Ser Leu Arg Asn Leu Val Asp Asn
                245                 250                 255

Thr Ala Arg Asp Ser Phe Glu Leu Phe Tyr Gly Leu Phe Leu Tyr Asn
            260                 265                 270

Lys Asn Ala Thr Glu Gln Leu Asp Arg Met Asp Trp Ala Phe Glu Met
    275                 280                 285

Val Lys Lys Gln Leu Ser Gly Tyr Leu His His Leu Val Arg Lys Gln
290                 295                 300

Leu Met Leu Glu Ser Ser Asn Thr His Glu Asn His Val Asp Asn Lys
305                 310                 315                 320

Leu Leu Leu Pro Glu Asn Lys Gln Lys Gln His Asp Leu Val Val Val
                325                 330                 335

Val Asn Asp Arg Ser
            340

<210> SEQ ID NO 10
<211> LENGTH: 385
<212> TYPE: PRT
<213> ORGANISM: Paronychia polygonifolia
<220> FEATURE:
<221> NAME/KEY: misc_feature
```

<222> LOCATION: (1)..(60)
<223> OTHER INFORMATION: Paronychia polygonifolia ADHa

<400> SEQUENCE: 10

```
Met Asn Ser Ile Ser Ile Val Ser Ser Thr Lys Ser Thr Tyr Tyr Lys
1               5                   10                  15

Val Tyr Gln Phe Pro Ser Pro Lys Ile Cys Phe Phe His Pro Ser Lys
            20                  25                  30

Leu Ser Ile Pro Ser Cys His Leu Lys Phe Gln Asn Phe Ala Val Arg
        35                  40                  45

Cys Asn Ser Ser Asn Asn Pro Lys Asn Val Ser Asn Ser Lys Asp Asn
    50                  55                  60

Lys Trp Lys Pro Ser Glu Ile Asn Lys Gly Ile Lys Leu Lys Ile Ala
65                  70                  75                  80

Val Val Gly Phe Gly Asn Phe Gly Gln Phe Leu Ala Lys Glu Met Val
                85                  90                  95

Lys Gln Gly His Gln Val Val Ala Tyr Ser Arg Thr Asp Tyr Thr Lys
            100                 105                 110

Val Ala Gln Asp Met Gly Val Arg Phe Phe Ser Asp Ala Cys Glu Met
        115                 120                 125

Phe Ile Glu Gln Pro Glu Val Ile Leu Met Cys Thr Ser Ile Leu Ser
    130                 135                 140

Thr Glu Lys Val Leu Arg Ser Leu Pro Leu His Arg Leu Arg Pro Ala
145                 150                 155                 160

Thr Ile Phe Val Asp Val Leu Ser Val Lys Glu Phe Pro Arg Ser Leu
                165                 170                 175

Phe Leu Gln His Leu Pro Lys Asp Phe Gly Ile Leu Cys Thr His Pro
            180                 185                 190

Met Phe Gly Pro Asn Ser Ala Lys Ala Gly Trp Ala Gly Leu Pro Phe
        195                 200                 205

Val Leu Asp Arg Val Arg Val Ser Ile Asp Pro Thr Gln Ala Thr Arg
    210                 215                 220

Thr Glu Ala Phe Leu Asp Ile Phe Arg Asn Ala Gly Cys Arg Met Val
225                 230                 235                 240

Glu Met Thr Cys Glu Asp His Asp Lys His Ala Ala Gly Ser Gln Phe
                245                 250                 255

Ile Thr His Met Met Gly Arg Val Leu Glu Lys Val Gly Leu Arg Asn
            260                 265                 270

Thr Pro Ile Asn Thr Lys Gly Tyr Glu Ser Leu Leu Asn Leu Val Glu
        275                 280                 285

Asn Thr Gly Arg Asp Ser Phe Glu Leu Phe Tyr Gly Leu Phe Leu Tyr
    290                 295                 300

Asn Glu Asn Ala Met Val Gln Leu Glu Arg Leu Asp Trp Ala Phe Lys
305                 310                 315                 320

Lys Val Lys Ser Gln Leu Ser Ala Cys Met His Asp His Val Arg Glu
                325                 330                 335

Ser Leu Met Phe Glu Ser His Gly Asp Gln Asn Lys Ile Met Lys Lys
            340                 345                 350

Ala Ser Tyr Lys Ser Leu Leu Ser Ala Tyr Thr Glu Lys Ser Asn Lys
        355                 360                 365

Ile Val Lys Asp Thr Lys Ile Lys Lys Asp Leu Val Ile Ser Gly Gln
    370                 375                 380

Gln
385
```

<210> SEQ ID NO 11
<211> LENGTH: 239
<212> TYPE: PRT
<213> ORGANISM: Herniaria latifolia
<220> FEATURE:
<221> NAME/KEY: misc_feature
<222> LOCATION: (1)..(239)
<223> OTHER INFORMATION: Herniaria latifolia ADHa

<400> SEQUENCE: 11

Val Gly Phe Gly Asn Phe Gly Gln Phe Leu Ala Lys Glu Met Val Lys
1               5                   10                  15

Gln Gly His Gln Val Leu Ala Tyr Ser Arg Ser Asp Tyr Ser Arg Val
            20                  25                  30

Ala Gln Glu Ile Gly Val Gln Tyr Phe Ser Asn Pro Asp Asp Leu Cys
        35                  40                  45

Lys Glu His Pro Glu Val Ile Leu Leu Cys Thr Ser Ile Leu Ser Thr
50                  55                  60

Glu Lys Val Leu Asn Thr Leu Pro Leu Asp Arg Leu Arg Pro Ser Thr
65                  70                  75                  80

Leu Phe Ser Asp Val Leu Ser Val Lys Glu Phe Pro Arg Thr Leu Phe
                85                  90                  95

Leu Gln Gln Leu Pro Glu Asp Phe Asp Ile Ile Cys Thr His Pro Met
            100                 105                 110

Phe Gly Pro Asp Ser Gly Lys His Gly Trp Ala Gly Leu Pro Tyr Val
        115                 120                 125

Tyr Asp Lys Val Arg Val Gly Leu Asp Pro Thr Arg Ile Arg Arg Ala
    130                 135                 140

Glu Ala Phe Leu Asn Ile Phe Glu Arg Ala Gly Cys Arg Met Val Glu
145                 150                 155                 160

Met Thr Cys Ala Glu His Asp Lys His Ala Ala Gly Ser Gln Phe Ile
                165                 170                 175

Thr His Met Leu Gly Arg Val Leu Glu Lys Val Gly Leu Leu Asn Thr
            180                 185                 190

Pro Ile Asn Thr Lys Gly Tyr Glu Ser Leu Leu Ser Leu Val Asp Asn
        195                 200                 205

Thr Ala Arg Asp Ser Phe Glu Leu Phe Tyr Gly Leu Phe Leu Tyr Asn
    210                 215                 220

Lys Asn Ala Met Glu Gln Leu Asp Arg Leu Asp Trp Ala Phe Asp
225                 230                 235

<210> SEQ ID NO 12
<211> LENGTH: 351
<212> TYPE: PRT
<213> ORGANISM: Corrigiola litoralis
<220> FEATURE:
<221> NAME/KEY: misc_feature
<222> LOCATION: (1)..(351)
<223> OTHER INFORMATION: Corrigiola litoralis ADHa

<400> SEQUENCE: 12

Met Asn Gly Ser Ala Asp His Phe His Pro Asn Ile Lys Val Asn Gly
1               5                   10                  15

Glu Val Leu Asn Pro Met Val Gly Ser Ser Asp Val Ala Glu Asp Val
            20                  25                  30

Lys Leu Lys Ile Ala Ile Val Gly Phe Gly Asn Phe Gly Gln Phe Leu
        35                  40                  45

Ala Lys Glu Ile Val Lys Gln Gly His Lys Val Leu Ala Tyr Ser Arg
 50                  55                  60

Ser Asp Tyr Ser Lys Ala Ala Lys Glu Ile Gly Val Gln Tyr Phe Ser
 65                  70                  75                  80

Asp Ala Asp Asp Leu Cys Glu Glu His Pro Glu Val Ile Leu Leu Cys
                 85                  90                  95

Thr Ser Ile Leu Ser Thr Glu Lys Val Met Arg Ala Leu Pro Ile His
            100                 105                 110

Arg Leu Arg Arg Ser Thr Leu Phe Val Asp Val Leu Ser Val Lys Glu
        115                 120                 125

Phe Pro Arg Ser Leu Phe Leu Gln Val Leu Pro Lys Asp Phe Asp Ile
130                 135                 140

Leu Cys Thr His Pro Met Phe Gly Pro Asp Ser Gly Lys Ala Gly Trp
145                 150                 155                 160

Gly Gly Leu Pro Phe Val Phe Asp Lys Val Arg Val Ala Pro Asp Ser
                165                 170                 175

Thr Arg Ala Thr Arg Ala Glu Ala Phe Leu Asp Ile Phe Arg Arg Ala
            180                 185                 190

Gly Cys Arg Met Val Glu Met Thr Cys Ala Asp His Asp Lys His Ala
        195                 200                 205

Ala Gly Ser Gln Phe Ile Thr His Met Met Gly Arg Val Leu Glu Lys
210                 215                 220

Ile Gly Leu Glu Asn Thr Pro Ile Asn Thr Lys Gly Tyr Glu Ser Leu
225                 230                 235                 240

Leu Asn Leu Val Asp Asn Thr Ala Arg Asp Ser Phe Glu Leu Phe Tyr
                245                 250                 255

Gly Leu Phe Leu Tyr Asn Lys Asn Ala Met Glu Gln Leu Asp Arg Met
            260                 265                 270

Asp Trp Ala Phe Glu Met Ile Lys Lys Arg Leu Ser Gly Tyr Leu His
        275                 280                 285

Asp Leu Val Arg Lys Gln Leu Met Leu Glu Thr Thr Gly Asn Asp Gln
290                 295                 300

Ala Gly Leu Thr Asn Gly Ala Lys Asn Asn His Asp Lys Lys Leu Met
305                 310                 315                 320

Leu Pro Pro Pro Ala Ala Asn Pro Ser Met Ile Val Pro Ser Ala Ala
                325                 330                 335

Thr His Glu Lys Lys His Asp Leu Val His Val Asn Gly Ser Arg
            340                 345                 350

<210> SEQ ID NO 13
<211> LENGTH: 325
<212> TYPE: PRT
<213> ORGANISM: Telephium imperati
<220> FEATURE:
<221> NAME/KEY: misc_feature
<222> LOCATION: (1)..(325)
<223> OTHER INFORMATION: Telephium imperati ADHa

<400> SEQUENCE: 13

Met Val Gly Pro Ser Glu Ser Gly Lys Asp Val Lys Leu Glu Ile Ala
1               5                   10                  15

Val Val Gly Phe Gly Asn Phe Gly Gln Phe Leu Gly Arg Glu Ile Val
                20                  25                  30

Lys Gln Gly His Glu Val Leu Ala Tyr Ser Arg Ser Asp Tyr Ser Lys
            35                  40                  45

Val Ala Lys Glu Ile Gly Val Arg Tyr Phe Ser Asp Ala His Asp Leu

```
            50                  55                  60
Cys Glu Glu His Pro Glu Val Ile Leu Leu Cys Thr Ser Ile Leu Ser
 65                  70                  75                  80

Thr Glu Arg Val Leu His Ser Leu Pro Leu Asn Arg Leu Arg Arg Ser
                 85                  90                  95

Thr Leu Phe Val Asp Val Leu Ser Val Lys Glu Phe Pro Arg Asn Leu
            100                 105                 110

Phe Leu Gln Asn Leu Pro Asn Asp Phe Asp Ile Leu Cys Thr His Pro
            115                 120                 125

Met Phe Gly Pro Asp Ser Gly Lys Ala Gly Trp Asp Gly Leu Pro Phe
        130                 135                 140

Val Phe Asp Lys Val Arg Val Gly Ser Asp Pro Ala Arg Thr Thr Arg
145                 150                 155                 160

Ala Asp Thr Phe Leu Asp Ile Phe Arg Asn Ala Gly Cys Arg Met Val
                165                 170                 175

Glu Met Ser Cys Ala Glu His Asp Arg His Ala Ala Gly Ser Gln Phe
            180                 185                 190

Ile Thr His Met Met Gly Arg Val Leu Glu Lys Ile Gly Leu Glu Asn
        195                 200                 205

Thr Pro Ile Asn Thr Lys Gly Tyr Glu Ser Leu Leu Asn Leu Val Asp
    210                 215                 220

Asn Thr Ala Arg Asp Ser Phe Glu Leu Phe Leu Tyr Tyr Lys Asn Ala
225                 230                 235                 240

Met Glu Gln Leu Asp Arg Met Asp Trp Ala Phe Glu Met Ile Lys Lys
                245                 250                 255

Gln Leu Ser Gly Tyr Leu His Glu Leu Val Arg Lys Gln Leu Met Leu
            260                 265                 270

Glu Thr Asn Asn Asp Gln Ser Gly Ile Ile Asn Gly Lys Thr Asn Cys
        275                 280                 285

Asp Lys Arg Leu Met Leu Pro Pro Ala Ala Asn Pro Ser Val Ile
    290                 295                 300

Val Pro Asp Pro Val Pro Ala Val Lys Lys Lys His Asp Leu Val His
305                 310                 315                 320

Val Asn Gly Ser Arg
                325

<210> SEQ ID NO 14
<211> LENGTH: 360
<212> TYPE: PRT
<213> ORGANISM: Beta vulgaris
<220> FEATURE:
<221> NAME/KEY: misc_feature
<222> LOCATION: (1)..(360)
<223> OTHER INFORMATION: BvADH-beta Big Buck sugar beet variety

<400> SEQUENCE: 14

Met Leu Ser Leu Ser Ser Thr Thr Thr Ala Lys Pro Ser Pro Ser Pro
 1                   5                  10                  15

Ser Pro Ala Asn Phe Pro Ala Lys Leu Ser Ser Leu Ser Thr Ile Thr
                 20                  25                  30

Thr Thr Leu Ser Phe Ser Pro Arg Arg Arg Tyr Phe His Gly Val Lys
            35                  40                  45

Thr Leu Thr Ile Arg Ser Ile Asp Ala Ala Gln Phe Phe Asp Tyr Glu
        50                  55                  60

Ser Lys Leu Ala Ala Ile Asn Thr Thr Ser Ser Ser Ser Ser Ser Ser
 65                  70                  75                  80
```

-continued

Tyr Ser Lys Leu Lys Ile Ala Ile Val Gly Phe Gly Asn Tyr Gly Gln
            85                  90                  95

Phe Leu Ala Lys Thr Leu Val Ser Gln Gly His Thr Val Leu Ala Tyr
            100                 105                 110

Ser Arg Ser Asp Tyr Ser Lys Ile Ala Ala Asn Leu Gly Val Ser Tyr
            115                 120                 125

Phe Ser Asp Pro Asp Leu Cys Glu Glu His Pro Glu Val Ile Met
130                 135                 140

Leu Cys Thr Ser Ile Leu Ser Thr Glu Val Met Leu Asn Ser Leu Pro
145                 150                 155                 160

Leu Gln Arg Leu Lys Arg Ser Thr Leu Phe Val Asp Val Leu Ser Val
            165                 170                 175

Lys Glu Phe Pro Arg Asn Leu Phe Leu Gln Thr Leu Pro Ser Asp Phe
            180                 185                 190

Asp Ile Leu Cys Thr His Pro Met Phe Gly Pro Glu Ser Gly Lys Asn
            195                 200                 205

Gly Trp Gly Ser Leu Pro Phe Val Tyr Asp Lys Val Arg Ile Gly Lys
            210                 215                 220

Asp Glu Gly Arg Ile Lys Arg Cys Glu Ser Phe Leu Asp Val Phe Arg
225                 230                 235                 240

Arg Glu Gly Cys Arg Val Glu Glu Met Thr Cys Ala Glu His Asp Lys
            245                 250                 255

Phe Ala Ala Gly Ser Gln Phe Ile Thr His Phe Leu Gly Arg Val Leu
            260                 265                 270

Glu Lys Leu Asp Leu Glu Asp Thr Pro Ile Asn Thr Lys Gly Tyr Glu
            275                 280                 285

Ser Leu Leu Asn Leu Val Asp Asn Thr Ser Lys Asp Ser Phe Glu Leu
            290                 295                 300

Phe Tyr Gly Leu Phe Leu Tyr Asn Gln Asn Ala Met Glu Gln Leu Glu
305                 310                 315                 320

Arg Leu Asp Trp Ala Phe Glu Leu Val Lys Lys Gln Leu Phe Gly His
            325                 330                 335

Leu His Gly Leu Leu Arg Lys Gln Leu Phe Gly Phe Ser Glu Ile Asp
            340                 345                 350

Glu Arg Ile Gly Lys Ala Lys Glu
            355                 360

<210> SEQ ID NO 15
<211> LENGTH: 60
<212> TYPE: PRT
<213> ORGANISM: Beta vulgaris
<220> FEATURE:
<221> NAME/KEY: misc_feature
<222> LOCATION: (1)..(60)
<223> OTHER INFORMATION: BvADH-beta W357B red beet variety

<400> SEQUENCE: 15

Met Leu Ser Leu Ser Ser Thr Thr Ala Lys Pro Ser Pro Ser Pro
1               5                   10                  15

Ser Pro Ala Asn Phe Pro Ala Lys Leu Ser Ser Leu Ser Thr Ile Thr
            20                  25                  30

Thr Thr Leu Ser Phe Ser Pro Arg Arg Tyr Phe His Gly Val Lys
        35                  40                  45

Thr Leu Thr Ile Arg Ser Ile Asp Ala Ala Gln Phe
        50                  55                  60

<210> SEQ ID NO 16
<211> LENGTH: 386
<212> TYPE: PRT
<213> ORGANISM: Beta vulgaris
<220> FEATURE:
<221> NAME/KEY: misc_feature
<222> LOCATION: (1)..(386)
<223> OTHER INFORMATION: BvADH-beta Touch Stone yellow beet variety

<400> SEQUENCE: 16

```
Met Leu Ser Leu Ser Ser Thr Thr Thr Ala Lys Pro Ser Pro Ser Pro
1               5                   10                  15

Ser Pro Ala Asn Phe Pro Ala Lys Leu Ser Ser Leu Ser Thr Ile Thr
            20                  25                  30

Thr Thr Leu Ser Phe Ser Pro Arg Arg Arg Tyr Phe His Gly Val Lys
        35                  40                  45

Thr Leu Thr Ile Arg Ser Ile Asp Ala Ala Gln Phe Phe Asp Tyr Glu
    50                  55                  60

Ser Lys Leu Ala Ala Ile Asn Thr Thr Ser Ser Ser Ser Ser Ser Ser
65                  70                  75                  80

Tyr Ser Lys Leu Lys Ile Ala Ile Val Gly Phe Gly Asn Tyr Gly Gln
                85                  90                  95

Phe Leu Ala Lys Thr Leu Val Ser Gln Gly His Thr Val Leu Ala Tyr
            100                 105                 110

Ser Arg Ser Asp Tyr Ser Lys Ile Ala Ala Asn Leu Gly Val Ser Tyr
        115                 120                 125

Phe Ser Asp Pro Asp Asp Leu Cys Glu Glu His Pro Glu Val Ile Met
    130                 135                 140

Leu Cys Thr Ser Ile Leu Ser Thr Glu Val Met Leu Asn Ser Leu Pro
145                 150                 155                 160

Leu Gln Arg Leu Lys Arg Ser Thr Leu Phe Val Asp Val Leu Ser Val
                165                 170                 175

Lys Glu Phe Pro Arg Asn Leu Phe Leu Gln Thr Leu Pro Ser Asp Phe
            180                 185                 190

Asp Ile Leu Cys Thr His Pro Met Phe Gly Pro Glu Ser Gly Lys Asn
        195                 200                 205

Gly Trp Gly Ser Leu Pro Phe Val Tyr Asp Lys Val Arg Ile Gly Lys
    210                 215                 220

Asp Glu Gly Arg Ile Lys Arg Cys Glu Ser Phe Leu Asp Val Phe Arg
225                 230                 235                 240

Arg Glu Gly Cys Arg Val Glu Glu Met Thr Cys Ala Glu His Asp Lys
                245                 250                 255

Phe Ala Ala Gly Ser Gln Phe Ile Thr His Phe Leu Gly Arg Val Leu
            260                 265                 270

Glu Lys Leu Asp Leu Glu Asp Thr Pro Ile Asn Thr Lys Gly Tyr Glu
        275                 280                 285

Ser Leu Leu Asn Leu Val Asp Asn Thr Ser Lys Asp Ser Phe Glu Leu
    290                 295                 300

Phe Tyr Gly Leu Phe Leu Tyr Asn Gln Asn Ala Met Glu Gln Leu Glu
305                 310                 315                 320

Arg Leu Asp Trp Ala Phe Glu Leu Val Lys Lys Gln Leu Phe Gly His
                325                 330                 335

Leu His Gly Leu Leu Arg Lys Gln Leu Phe Gly Phe Ser Glu Ile Asp
            340                 345                 350

Glu Arg Ile Gly Lys Ala Lys Glu Ile Lys Phe Leu Ser Asp Ala Ala
```

```
                355                 360                 365
Glu Gln Asn Gly Ser Ala Leu Ser Ala Arg Glu Asn Ala Asn Ser Glu
    370                 375                 380
Thr Asn
385

<210> SEQ ID NO 17
<211> LENGTH: 386
<212> TYPE: PRT
<213> ORGANISM: Beta vulgaris
<220> FEATURE:
<221> NAME/KEY: misc_feature
<222> LOCATION: (1)..(386)
<223> OTHER INFORMATION: BvADH-beta Blankoma white beet variety

<400> SEQUENCE: 17

Met Leu Ser Leu Ser Ser Thr Thr Thr Ala Lys Pro Ser Pro Ser Pro
1               5                   10                  15

Ser Pro Ala Asn Phe Pro Ala Lys Leu Ser Ser Leu Ser Thr Ile Thr
            20                  25                  30

Thr Thr Leu Ser Phe Ser Pro Arg Arg Tyr Phe His Gly Val Lys
        35                  40                  45

Thr Leu Thr Ile Arg Ser Ile Asp Ala Ala Gln Phe Phe Asp Tyr Glu
    50                  55                  60

Ser Lys Leu Ala Ala Ile Asn Thr Thr Ser Ser Ser Ser Ser Ser Ser
65                  70                  75                  80

Tyr Ser Lys Leu Lys Ile Ala Ile Val Gly Phe Gly Asn Tyr Gly Gln
                85                  90                  95

Phe Leu Ala Lys Thr Leu Val Ser Gln Gly His Thr Val Leu Ala Tyr
            100                 105                 110

Ser Arg Ser Asp Tyr Ser Lys Ile Ala Ala Asn Leu Gly Val Ser Tyr
        115                 120                 125

Phe Ser Asp Pro Asp Asp Leu Cys Glu Glu His Pro Glu Val Ile Met
    130                 135                 140

Leu Cys Thr Ser Ile Leu Ser Thr Glu Val Met Leu Asn Ser Leu Pro
145                 150                 155                 160

Leu Gln Arg Leu Lys Arg Ser Thr Leu Phe Val Asp Val Leu Ser Val
                165                 170                 175

Lys Glu Phe Pro Arg Asn Leu Phe Leu Gln Thr Leu Pro Ser Asp Phe
            180                 185                 190

Asp Ile Leu Cys Thr His Pro Met Phe Gly Pro Glu Ser Gly Lys Asn
        195                 200                 205

Gly Trp Gly Ser Leu Pro Phe Val Tyr Asp Lys Val Arg Ile Gly Lys
    210                 215                 220

Asp Glu Gly Arg Ile Lys Arg Cys Glu Ser Phe Leu Asp Val Phe Arg
225                 230                 235                 240

Arg Glu Gly Cys Arg Val Glu Glu Met Thr Cys Ala Glu His Asp Lys
                245                 250                 255

Phe Ala Ala Gly Ser Gln Phe Ile Thr His Phe Leu Gly Arg Val Leu
            260                 265                 270

Glu Lys Leu Asp Leu Glu Asp Thr Pro Ile Asn Thr Lys Gly Tyr Glu
        275                 280                 285

Ser Leu Leu Asn Leu Val Asp Asn Thr Ser Lys Asp Ser Phe Glu Leu
    290                 295                 300

Phe Tyr Gly Leu Phe Leu Tyr Asn Gln Asn Ala Met Glu Gln Leu Glu
305                 310                 315                 320
```

```
Arg Leu Asp Trp Ala Phe Glu Leu Val Lys Lys Gln Leu Phe Gly His
                325                 330                 335

Leu His Gly Leu Leu Arg Lys Gln Leu Phe Gly Phe Ser Glu Ile Asp
            340                 345                 350

Glu Arg Ile Gly Lys Ala Lys Glu Ile Lys Phe Leu Ser Asp Ala Ala
        355                 360                 365

Glu Gln Asn Gly Ser Ala Leu Ser Ala Arg Glu Asn Ala Asn Ser Glu
    370                 375                 380

Thr Asn
385

<210> SEQ ID NO 18
<211> LENGTH: 386
<212> TYPE: PRT
<213> ORGANISM: Beta vulgaris
<220> FEATURE:
<221> NAME/KEY: misc_feature
<222> LOCATION: (1)..(386)
<223> OTHER INFORMATION: BvADH-beta Sea beet PI562585 variety

<400> SEQUENCE: 18

Met Leu Ser Leu Ser Ser Thr Thr Thr Ala Lys Pro Ser Pro Ser Pro
1               5                   10                  15

Ser Pro Ala Asn Phe Pro Ala Lys Leu Ser Ser Leu Ser Thr Ile Thr
            20                  25                  30

Thr Thr Ile Ser Phe Ser Pro Arg Arg Tyr Phe His Gly Val Lys
        35                  40                  45

Thr Leu Thr Ile Arg Ser Ile Asp Ala Ala Gln Phe Phe Asp Tyr Glu
    50                  55                  60

Ser Lys Leu Ala Ala Ile Asn Thr Thr Ser Ser Ser Thr Ser Ser Ser
65                  70                  75                  80

Tyr Ser Lys Leu Lys Ile Ala Ile Val Gly Phe Gly Asn Tyr Gly Gln
                85                  90                  95

Phe Leu Ala Lys Thr Leu Val Ser Gln Gly His Thr Val Leu Ala Tyr
            100                 105                 110

Ser Arg Ser Asp Tyr Ser Lys Ile Ala Ala Asn Leu Gly Val Ser Tyr
        115                 120                 125

Phe Ser Asp Pro Asp Asp Leu Cys Glu Glu His Pro Glu Val Ile Met
    130                 135                 140

Leu Cys Thr Ser Ile Leu Ser Thr Glu Val Met Leu Asn Ser Leu Pro
145                 150                 155                 160

Leu Gln Arg Leu Lys Arg Ser Thr Leu Phe Val Asp Val Leu Ser Val
                165                 170                 175

Lys Glu Phe Pro Arg Asn Leu Phe Leu Gln Thr Leu Pro Ser Asp Phe
            180                 185                 190

Asp Ile Leu Cys Thr His Pro Met Phe Gly Pro Glu Ser Gly Lys Asn
        195                 200                 205

Gly Trp Gly Ser Leu Pro Phe Val Tyr Asp Lys Val Arg Ile Gly Lys
    210                 215                 220

Asp Glu Gly Arg Ile Lys Arg Cys Glu Ser Phe Leu Asp Val Phe Arg
225                 230                 235                 240

Arg Glu Gly Cys Arg Val Glu Glu Met Thr Cys Ala Glu His Asp Lys
                245                 250                 255

Phe Ala Ala Gly Ser Gln Phe Ile Thr His Phe Leu Gly Arg Val Leu
            260                 265                 270
```

Glu Lys Leu Asp Leu Glu Asp Thr Pro Ile Asn Thr Lys Gly Tyr Glu
                275                 280                 285

Ser Leu Leu Asn Leu Val Asp Asn Thr Ser Lys Asp Ser Phe Glu Leu
                290                 295                 300

Phe Tyr Gly Leu Phe Leu Tyr Asn Gln Asn Ala Met Glu Gln Leu Glu
305                 310                 315                 320

Arg Leu Asp Trp Ala Phe Glu Leu Val Lys Lys Gln Leu Phe Gly His
                325                 330                 335

Leu His Gly Leu Leu Arg Lys Gln Leu Phe Gly Phe Ser Glu Ile Asp
                340                 345                 350

Glu Arg Ile Gly Lys Ala Lys Glu Ile Lys Phe Leu Ser Asp Ala Ala
                355                 360                 365

Glu Gln Asn Gly Ser Ala Leu Ser Ala Arg Glu Asn Ala Asn Ser Glu
                370                 375                 380

Thr Asn
385

<210> SEQ ID NO 19
<211> LENGTH: 321
<212> TYPE: PRT
<213> ORGANISM: Spinacea oleracea
<220> FEATURE:
<221> NAME/KEY: misc_feature
<222> LOCATION: (1)..(321)
<223> OTHER INFORMATION: SoADH-beta

<400> SEQUENCE: 19

Ala Ala Thr Asn Thr Ser Thr Ala Thr Ser Ser Gln Ser Ser Tyr
1               5                   10                  15

Ser Lys Leu Lys Val Ala Ile Val Gly Phe Gly Asn Tyr Gly Gln Phe
                20                  25                  30

Leu Ala Lys Thr Met Val Ser Gln Gly His Thr Val Leu Ala Tyr Ser
                35                  40                  45

Arg Ser Asp Tyr Ser Lys Ile Ala Pro Asn Leu Gly Val Ser Phe Phe
50                  55                  60

Ser Asp Pro Asp Asp Leu Cys Glu Glu His Pro Glu Val Ile Leu Leu
65                  70                  75                  80

Cys Thr Ser Ile Leu Ser Thr Glu Phe Met Leu Asn Ser Leu Pro Leu
                85                  90                  95

Gln Arg Leu Lys Arg Ser Thr Leu Phe Val Asp Val Leu Ser Val Lys
                100                 105                 110

Glu Phe Pro Arg Asn Leu Phe Leu Gln Thr Leu Pro Pro Asp Phe Asp
                115                 120                 125

Ile Leu Cys Thr His Pro Met Phe Gly Pro Glu Ser Gly Lys Asn Gly
                130                 135                 140

Trp Gly Gly Leu Pro Phe Val Tyr Asp Lys Val Arg Ile Gly Lys Ala
145                 150                 155                 160

Glu Arg Arg Ile Arg Arg Cys Glu Asn Phe Leu Asp Val Phe Arg Arg
                165                 170                 175

Ala Gly Cys Arg Val Glu Glu Met Thr Cys Ala Glu His Asp Lys Tyr
                180                 185                 190

Ala Ala Gly Ser Gln Phe Ile Thr His Phe Leu Gly Arg Val Leu Glu
                195                 200                 205

Lys Leu Asp Leu Glu Asp Thr Pro Ile Asn Thr Lys Gly Tyr Glu Ser
                210                 215                 220

Leu Leu Asn Leu Val Asp Asn Thr Ser Lys Asp Ser Phe Glu Leu Phe

```
               225                 230                 235                 240

Tyr Gly Leu Phe Leu Tyr Asn Gln Asn Ala Met Glu Gln Leu Glu Arg
                245                 250                 255

Leu Asp Trp Ala Phe Glu Leu Val Lys Lys Gln Leu Phe Gly His Leu
            260                 265                 270

His Gly Leu Leu Arg Gly Gln Leu Phe Gly Cys Thr Glu Ile Asp Glu
        275                 280                 285

Arg Leu Glu Lys Ala Lys Glu Leu Lys Phe Leu Ser Asp Ala Thr Thr
    290                 295                 300

Gln Asn Gly Ser Ala Ser Ala Pro Arg Glu Asn Ala Asn Ser Glu Ile
305                 310                 315                 320

Asn

<210> SEQ ID NO 20
<211> LENGTH: 321
<212> TYPE: PRT
<213> ORGANISM: Nepenthes alata
<220> FEATURE:
<221> NAME/KEY: misc_feature
<222> LOCATION: (1)..(321)
<223> OTHER INFORMATION: NaADH-beta

<400> SEQUENCE: 20

Ala Ala Leu Pro Asn Asp Tyr Glu Thr Lys Leu Ser His Leu Pro Ser
1               5                   10                  15

Ser Phe Ala Lys Leu Lys Val Gly Ile Ile Gly Phe Gly Asn Tyr Gly
            20                  25                  30

Gln Phe Leu Ala Lys Thr Leu Val Arg Gln Gly His Thr Val Leu Ala
        35                  40                  45

His Ser Arg Ser Asn Tyr Ser Gln Asn Ala Ala Lys Leu Gly Val Ser
    50                  55                  60

Phe Phe Tyr Asp Pro Asn Asp Leu Cys Glu Glu His Pro Glu Val Ile
65                  70                  75                  80

Leu Leu Cys Thr Ser Ile Leu Ser Thr Glu Ser Val Leu Arg Ser Leu
                85                  90                  95

Pro Leu Gln Arg Leu Lys Arg Ser Thr Leu Phe Val Asp Val Leu Ser
            100                 105                 110

Val Lys Glu Phe Pro Arg Ser Leu Leu Leu Gln Ile Leu Pro Pro Asp
        115                 120                 125

Leu Asp Ile Leu Cys Thr His Pro Met Phe Gly Pro Glu Ser Gly Lys
    130                 135                 140

Asn Gly Trp Ser Gly Leu Pro Phe Val Tyr Asp Lys Val Arg Ile Gly
145                 150                 155                 160

Glu His Glu Ile Arg Val Asn Arg Cys Asp Asn Phe Ile Glu Val Phe
                165                 170                 175

Arg Arg Glu Gly Cys Arg Met Val Gln Met Ser Cys Ala Glu His Asp
            180                 185                 190

Arg His Ala Ala Gly Ser Gln Phe Ile Thr His Met Met Gly Arg Val
        195                 200                 205

Leu Glu Lys Leu Lys Leu Glu Asp Thr Pro Ile Asn Thr Lys Gly Tyr
    210                 215                 220

Glu Ser Leu Leu Asn Leu Val Glu Asn Thr Ala Arg Asp Ser Phe Glu
225                 230                 235                 240

Leu Phe Tyr Gly Leu Phe Leu Tyr Asn Lys Asn Val Met Glu Gln Leu
                245                 250                 255
```

Glu Arg Met Asp Leu Ala Phe Glu Met Val Lys Lys Gln Leu Phe Gly
            260                 265                 270

His Leu His Gly Leu Leu Arg Ser Gln Leu Phe Asp Gly Ser Glu Met
        275                 280                 285

Glu Val Arg Val Glu Glu Arg Lys Leu Leu Ser Asp Gly Ser Gln
    290                 295                 300

Asn Gly His Val Phe Ser Ser Phe Ser Asp Ser Lys Asn Val Glu Arg
305                 310                 315                 320

Asn

<210> SEQ ID NO 21
<211> LENGTH: 1197
<212> TYPE: DNA
<213> ORGANISM: Beta vulgaris
<220> FEATURE:
<221> NAME/KEY: misc_feature
<222> LOCATION: (1)..(1197)
<223> OTHER INFORMATION: Beta vulgaris Big Buck arogenate dehydrogenase
      alpha, complete CDS

<400> SEQUENCE: 21

```
atgatttcac tctcttcttt tcatccttcc tccaccaccg ccaccgccac cgccgccacc      60
gccaccaccc acccaccaca caatgtccc gcttttcct ctcctccatc gcatctctcg      120
cttcctttac gccaccctcg ccaacaccti gtagttcggt gcggtggagg tggttcggcc     180
tccgaatcgg tatttaaccg tgatagtgct gctactcgtg tttctaatga tcatcttgac    240
gttagtaaaa gagatgttaa gcttaagatt gctattattg ggtttggtaa ctttggccag    300
ttttggcta agacaatggc taagcaaggt catagagtgt tggcttactc acgctcggac     360
tactcccgcg ctgctaagga gatcggcgtc gagtatttta ctgacgccga tgacctctgc    420
gaggagcacc ctgaggttat tcttttgtgc acgtccatcc tctcaacgga gaaggtcctc    480
cgatcactcc ccctccaccg gctccgtcgt tcaaccctct tgcggatgt tctctcggtc     540
aaggaatttc ctcgatcgct cttccttcaa ctacttccta aggactttga tatcctatgc    600
acccacccta tgtttggccc agactcgggc aaagacgggt ggggtggact accctttgtg   660
tttgataaag ttagagtcgg atcagatcag agtcggacgt ctcgtgctga ggcattccta   720
gacgtgttta ggaatgccgg gtgtaggatg gtggaaatga ttgtgttga tcatgacaag     780
catgcagccg gtctcaatt tattacacat atgatgggac gagttttgga gaaattggcc     840
ttggaaaata caccaattaa tacaaaaggg tacgaaagtt tgttaaattt ggtggataat    900
actgcaaggg atagttttga gttgttttat gggttgtttt tgtacaataa aaatgcaatg   960
gagcaattgg atagaatgga ttgggctttc gagatggtaa aaaagcaact ttcgggatat   1020
ttgcatgatc ttgttagaaa acaattgatg ttggagggta ataatgatca agctgaggtt  1080
acttttgaca aaccattaat gcttccttct cctactatta atcctccaca aatagttcct   1140
tctgctgata tggctgagaa gaagcatgat ttagtggtgg ttaatggtac tagatag      1197
```

<210> SEQ ID NO 22
<211> LENGTH: 1197
<212> TYPE: DNA
<213> ORGANISM: Beta vulgaris
<220> FEATURE:
<221> NAME/KEY: misc_feature
<222> LOCATION: (1)..(1197)
<223> OTHER INFORMATION: Beta vulgaris W357B arogenate dehydrogenase
      alpha, complete CDS

<400> SEQUENCE: 22

```
atgatttcac tctcttcttt tcatccttcc tccaccaccg ccaccgccac cgccgccgcc       60
gccaccaccc acccacctca acaatgtccc gcttttcct ctcctccgtc gcatctctcg       120
cttcctttac gccacccctcg ccaacaccctt gtagttcggt gcggtggagg tggttcggcc    180
tccgaatcgg tatttaaccg tgatagtgct gctactcgtg tttctaatga tcatcttgac     240
gttagtaaaa gagatgttaa gcttaagatt gctattattg ggtttggtaa ctttggccag     300
ttttggccta agacaatggc taagcaaggt catagagtgt tggcttactc acgctcggac     360
tactcccgcg ctgctaagga gatcggcgtc gagtatttta ctgacgccga tgacctctgc    420
gaggagcacc ctgaggttat tctgttgtgc acatccatcc tctcaacgga gaaggtcctc    480
cgatcactcc ccctccaccg gctccgtcgt tcaaccctct tgcggatgt tctctcggtc     540 aaggaatttc ctcgatcgct cttccttcaa ctacttccta aggactttga tatcctatgc    600
acccacccta tgtttggccc agactcgggc aaagacgggt ggggtggact accttttgtg    660
ttcgataaag ttagagtcgg atcagatcag agtcggacat ctcgtgctga ggcattccta    720
gacgtgttta ggaatgccgg gtgtaggatg gtggaaatga gttgtgttga tcatgacaag    780
catgcagccg gtctcaatt tattacacat atgatgggac gagttttgga gaaattggcc     840
ttggaaaata caccaattaa tacaaaaggg tacgaaagtt tgttaaattt ggtggataat    900
actgcaaggg atagttttga gttgttttac gggttgtttt tgtacaataa aaatgcaatg    960
gagcaattgg atagaatgga ttgggctttc gagatggtaa aaaagcaact ttcgggatat   1020
ttgcatgatc ttgttagaaa acaattgatg ttggagggta ataatgatca agctgaggtt   1080 actttttgaca aaccattgat gcttccttct cctactatta atcctccaca aatagttccc   1140
tctgctgata tggctgagaa gaagcatgat ttagtggtgg ttaatggtac tagatag      1197
```

<210> SEQ ID NO 23
<211> LENGTH: 1197
<212> TYPE: DNA
<213> ORGANISM: Beta vulgaris
<220> FEATURE:
<221> NAME/KEY: misc_feature
<222> LOCATION: (1)..(1197)
<223> OTHER INFORMATION: Beta vulgaris Blankoma arogenate dehydrogenase alpha, complete CDS

<400> SEQUENCE: 23

```
atgatttcac tctcttcttt tcatccttcc tccaccaccg ccaccgccac cgccgccgcc       60
gccaccaccc acccaccaca acaatgtccc gcttttcct ctcctccgtc gcatctctcg      120
cttcctttac gccacccctcg ccaacaccctt gtagttcggt gcggtggagg tggttcggcc   180
tccgaatcgg tatttaaccg tgatagtgct gctactcgtg tttctaatga tcatcttgac     240
gttagtaaaa gagatgttaa gcttaagatt gctattattg ggtttggtaa ctttggccag    300
ttttggccta agacaatggc taagcaaggt catagagtgt tggcttactc acgctcggac    360
tactcccgcg ctgctaagga gatcggcgtc gagtatttta ctgacgccga tgacctctgc   420
gaggagcacc ctgaggttat tctgttgtgc acgtccatcc tctcaacgga gaaggtcctc   480
cgatcactcc ccctccaccg gctccgtcgt tcaaccctct tgcggatgt tctctcggtc    540 aaggaatttc ctcgatcgct cttccttcaa ctacttccta aggactttga tatcctatgc   600
acccacccta tgtttggccc agactcgggc aaagacgggt ggggtggact accttttgtg   660
ttcgataaag ttagagtcgg atcagatcag agtcggacat ctcgtgctga ggcattccta   720
gacgtgttta ggaatgccgg gtgtaggatg gtggaaatga gttgtgttga tcatgacaag   780
```

```
catgcagccg ggtctcaatt tattacacat atgatgggac gagttttgga gaaattggcc    840
ttggaaaata caccaattaa tacaaaaggg tacgaaagtt tgttaaattt ggtggataat    900
actgcaaggg atagttttga gttgttttac gggttgtttt tgtacaataa aaatgcaatg    960
gagcaattgg atagaatgga ttgggctttc gagatggtaa aaaagcaact ttcgggatat   1020
ttgcatgatc ttgttagaaa acaattgatg ttggagggta ataatgatca agctgaggtt   1080
acttttgaca aaccattgat gcttccttct cctactatta atcctccaca aatagttccc   1140
tctgctgata tggctgagaa gaagcatgat ttagtggtgg ttaatggtac tagatag     1197
```

```
<210> SEQ ID NO 24
<211> LENGTH: 1197
<212> TYPE: DNA
<213> ORGANISM: Beta vulgaris
<220> FEATURE:
<221> NAME/KEY: misc_feature
<222> LOCATION: (1)..(1197)
<223> OTHER INFORMATION: Beta vulgaris Touch Stone arogenate
      dehydrogenase alpha, complete CDS

<400> SEQUENCE: 24
```

```
atgatttcac tctcttcttt tcatccttcc tccaccaccg ccaccgccac cgccgccgcc     60
gccaccaccc acccacctca acaatgtccc gcttttccct ctcctccgtc gcatctctcg    120
cttcctttac gccaccctcg ccaacacctt gtagttcggt gcggtggagg tggttcggcc    180
tccgaatcgg tatttaaccg tgatagtgct gctactcgtg tttctaatga tcatcttgac    240
gttagtaaaa gagatgttaa gcttaagatt gctattattg ggtttggtaa ctttggccag    300
tttttggcta agacaatggc taagcaaggt catagagtgt tggcttactc acgctcggac    360
tactcccgcg ctgctaagga gatcggcgtc gagtattta ctgacgccga tgacctctgc    420
gaggagcacc ctgaggttat tctgttgtgc acatccatcc tctcaacgga gaaggtcctc    480
cgatcactcc ccctccaccg gctccgtcgt tcaaccctct ttgcggatgt tctctcggtc    540
aaggaatttc ctcgatcgct cttccttcaa ctacttccta aggactttga tatcctatgc    600
acccacccta tgtttggccc agactcgggc aaagacgggt ggggtggact acctttgtg    660 ttcgataaag ttagagtcgg atcagatcag agtcggacat ctcgtgctga ggcattccta    720
gacgtgttta ggaatgccgg tgtaggatg gtggaaatga gttgtgttga tcatgacaag    780
catgcagccg ggtctcaatt tattacacat atgatgggac gagttttgga gaaattggcc    840
ttggaaaata caccaattaa tacaaaaggg tacgaaagtt tgttaaattt ggtggataat    900
actgcaaggg atagttttga gttgttttac gggttgtttt tgtacaataa aaatgcaatg    960
gagcaattgg atagaatgga ttgggctttc gagatggtaa aaaagcaact ttcgggatat   1020
ttgcatgatc ttgttagaaa acaattgatg ttggagggta ataatgatca agctgaggtt   1080
acttttgaca aaccattgat gcttccttct cctactatta atcctccaca aatagttccc   1140
tctgctgata tggctgagaa gaagcatgat ttagtggtgg ttaatggtac tagatag     1197
```

```
<210> SEQ ID NO 25
<211> LENGTH: 1224
<212> TYPE: DNA
<213> ORGANISM: Beta vulgaris
<220> FEATURE:
<221> NAME/KEY: misc_feature
<222> LOCATION: (1)..(1224)
<223> OTHER INFORMATION: Beta vulgaris subsp.maritima PI562585 arogenate
      dehydrogenase alpha, complete CDS
```

<400> SEQUENCE: 25

| | | | | |
|---|---|---|---|---|
| atgatttcac | tctcttcttt | tcatccttcc | tccaccaccg | ccaccgccac cgccgccacc | 60 |
| gccaccgcca | ccgccgccac | cgccaccgcc | accacccacc | caccacaaca atgtcccgct | 120 |
| ttttcctctc | ctccatcgca | tctctcgctt | cctttacgcc | accctcgcca acaccttgta | 180 |
| gttcggtgcg | gtggaggtgg | ttcggcctcc | gaatcggtat | ttaaccgtga tagtgctgct | 240 |
| actcgtgttt | ctaatgatca | tcttgacgtt | agtaaaagag | atgttaagct taagattgct | 300 |
| attattgggt | ttggtaactt | tggccagttt | ttggctaaga | caatggctaa gcaaggtcat | 360 |
| agagtgttgg | cttactcacg | ctcggactac | tcccgcgctg | ctaaggagat cggcgtcgag | 420 |
| tattttactg | acgccgatga | cctctgcgag | gagcaccctg | aggttattct tttgtgcacg | 480 |
| tccatcctct | caacggagaa | ggtcctccga | tcactccccc | tccaccggct ccgtcgttca | 540 |
| accctctttg | cggatgttct | ctcggtcaag | gaatttcctc | gatcgctctt ccttcaacta | 600 |
| cttcctaagg | actttgatat | cctatgcacc | caccctatgt | ttggcccaga ctcgggcaaa | 660 |
| gacgggtggg | gtggactacc | ctttgtgttt | gataaagtta | gagtcggatc agatcagagt | 720 |
| cggacgtctc | gtgctgaggc | attcctagac | gtgtttagga | atgccgggtg taggatggtg | 780 |
| gaaatgagtt | gtgttgatca | tgacaagcat | gcagccgggc | tcaatttat tacacatatg | 840 |
| atgggacgag | ttttggagaa | attggccttg | gaaaatacac | caattaatac aaaagggtac | 900 |
| gaaagtttgt | taaatttggt | ggataatact | gcaaggata | gttttgagtt gttttatggg | 960 |
| ttgtttttgt | acaataaaaa | tgcaatggag | caattggata | gaatggattg ggctttcgag | 1020 |
| atggtaaaaa | agcaactttc | gggatatttg | catgatcttg | ttagaaaaca attgatgttg | 1080 |
| gagggtaata | atgatcaagc | tgaggttact | tttgacaaac | cattaatgct tccttctcct | 1140 |
| actattaatc | ctccacaaat | agttccttct | gctgatatgg | ctgagaagaa gcatgattta | 1200 |
| gtggtggtta | atggtactag | atag | | | 1224 |

<210> SEQ ID NO 26
<211> LENGTH: 1041
<212> TYPE: DNA
<213> ORGANISM: Spinacia oleracea
<220> FEATURE:
<221> NAME/KEY: misc_feature
<222> LOCATION: (1)..(1041)
<223> OTHER INFORMATION: Spinacia oleracea arogenate dehydrogenase
      alpha, partial CDS

<400> SEQUENCE: 26

| | | | | |
|---|---|---|---|---|
| tgcgccgcct | ctgactccgt | gttcaaccac | gatattggtg | tgccttttgt ctcaacacgc | 60 |
| gcttccggcg | aggtgccgga | ggttaacagt | agagatatta | agcttaagat cgcgatcatt | 120 |
| gggttcggga | actttggtca | gttttttggct | aagactatta | ctaagcaagg tcacagagtt | 180 |
| ttggcttact | cccggtcaga | ttactcccgt | gctgctaagg | agatcggcgt cgagtatttc | 240 |
| tccgacgccg | atgatctttg | cgaagagcat | cccgaggtga | tactcctatg cacttcaatc | 300 |
| ctctcaacag | agaaggtcct | ccgttcgctc | cccctccacc | gccttcgccg gtccacctc | 360 |
| ttcgtggacg | tcctctcggt | gaaggagttc | ccgcgttcac | ttttcctcca agtccttcct | 420 |
| aaagactttg | catccttttg | cacccacccc | atgttcggcc | cagactcagg caaaagcgga | 480 |
| tggggtgggc | tccccttttgt | cttcgacaaa | gtccgagtcg | gtcggaccc aacccgggcg | 540 |
| gctcggactg | aggcgttcct | agacatttat | aggaacgccg | ggtgtaggat ggtggaaatg | 600 |
| acatgcgcgg | accacgacaa | gcacgcggct | gggtcgcaat | tcataaccca catgatgggc | 660 |

```
cgggttttgg agaaattagc cctcgaaaac acaccgatta acacgaaagg gtacgagagt      720
ttgttgaact tggtggataa tacggcccgg gacagctttg agttgtttta cggactgttt      780
ttgtacaaca agaacgcgat ggaacaattg gatagaatgg attgggcttt cgagatggta      840
aagaagcaac tttcgggtta tttgcatgat cttgttagga aacaattgat gctagagact      900
accaatgaac aagttgggtt tgatcagacg ttcatgcttc cttctcctgc cgataatcct      960
cgtcaaacac caccctcggc tgccgtttcc gagaattcga aacccgatttt tgtggtggta     1020 aatggtaata attctagata g                                               1041
```

<210> SEQ ID NO 27
<211> LENGTH: 1128
<212> TYPE: DNA
<213> ORGANISM: Rivina humilis
<220> FEATURE:
<221> NAME/KEY: misc_feature
<222> LOCATION: (1)..(1128)
<223> OTHER INFORMATION: Rivina humilis arogenate dehydrogenase alpha, partial CDS

<400> SEQUENCE: 27

```
tgcacggcct tcactaaaac taataataat aatgccttgg gttatggtta cggttatggt       60
tatggttatg gctatgacaa aaacaaggtg tctagtactg aacagggtga tgaggtttcg      120
ggttcgagtt cgaattcgaa gaagctgaag attggtataa ttgggttcgg aactttggt      180 cagtttatgg caaagacgat ggtgaaacat ggtcacactg tgcttgctta ttctcgttcc      240
gattactcac gtgctgctca taccatcggt gttcgctact ctctgatcc tgatgacttg      300 tgcgaagagc accctgaggt gattctactg tgcacctcca tcttatccac tgaaagggtg      360
cttcggtcac taccgcttca tcgcctacgc cgctcaacac tcgttgcgga tgtgctgtcg      420
gtcaaggaat tcccacgttc actcttccta caactcctcc cttctgactt tgacatcctt      480
tgcactcatc ctatgttcgg accggactcc ggcaaggccg ggtggggcgg tcttcctttc      540
gtctttgaca aagtccgggt tggatcccaa cccgaacgcc tcacccgtgt tgaggccttc      600
ctggacattt tccgggatgc cgggtgccga atggtggaga tgagttgtgc tgagcatgac      660
aggcatgctg ctgggtcaca attcataaca cacatgatgg gacgtgtgtt agagaagctt      720
gcacttgagg acacaccaat taacaccaaa gggtatgaga gttgtgaa cttggttgat       780 aacactgcta gggacagttt tgagctgttt tatggactct ttttatacaa caagaatgca      840
atggaacagc ttgatagaat gcattgggca tttgagacag tgaagcaaca gctctctggt      900
tatttgcatg tccttgttag gaagcagttg atgttggaga cttcttccgg taatgacaat      960
aataatacta ataatattaa tattagcagt ggtgataata ttaataataa ggacacaaat     1020
aataaattaa tgttaccttc tcctgggatt agttctgcta aaattgttcc accagtacag     1080
gagaaggaga aacatgactt ggtgatgctc aatggatcaa agcggtag                  1128
```

<210> SEQ ID NO 28
<211> LENGTH: 1026
<212> TYPE: DNA
<213> ORGANISM: Portulaca oleracea
<220> FEATURE:
<221> NAME/KEY: misc_feature
<222> LOCATION: (1)..(1026)
<223> OTHER INFORMATION: Portulaca oleracea arogenate dehydrogenase alpha, partial CDS

<400> SEQUENCE: 28

```
tgctcatcat catcatcatc cagtgccagc atcatcatca atggttccgg tagctccacg       60
```

```
acaaactcga gcgtcttcga tgctagttct tcctccgatt cagacgtaaa aaaaaggtca    120
gaagtgaagc tgaaaatcgg gatcattgga tttgggaagt ttggacagtt tctagcgaag    180
agaattgtga gtcagggtca tgatgtcttg gcgtattctc ggtcggatta ctcacgggtg    240
gcatcggaga ttggcgtacg gttcttctct gacgccgatg acctctgcga ggagcaccct    300
caggtgatcc tgttatgcac atcaatcctg tcaaccgagc gcgttctgcg ctcgcttcca    360
ctacacaggc tccgtcgatc caccctgttc gcggatgtcc tgtccgtaaa agagttcccg    420
cggtcactct tcttacaatt actcccctcc gacttcgaca ttctatgcac acccccatg     480 ttcggacccg actcaggcaa gtccgggtgg acagtcttc cctttgtctt cgacaaggtc     540
cgggtcggat ccaccccctac tcgggtcacc cggtccgagg ccttcctaga catcttccgg   600
accgccgggt gtaggatggt ggaaatgagc tgcgccgagc acgacaaaca cgcagccggg   660
tcccagttca taacccatat gatgggccgg gttctcgaga agttagactt ggaaaacaca   720
cccataaaca ccagaggata tgagagtttg agaaacctgg tggacaacac ggcaagggac   780
agctttgagc tgttttatgg attgttttg tacaacaaaa acgcgacgga gcagcttgac   840
aggatggatt gggcattcga gatggttaag aaacaacttt ctgggtatct tcatcatcta   900
gttaggaaac agttgatgtt agagagtagt aatacacatg aaaatcatgt tgacaacaaa   960
ttgttgcttc cagagaataa gcagaagcaa catgacttgg tcgtcgtcgt caacgataga   1020
tcatag                                                              1026
```

<210> SEQ ID NO 29
<211> LENGTH: 1191
<212> TYPE: DNA
<213> ORGANISM: Spergularia marina
<220> FEATURE:
<221> NAME/KEY: misc_feature
<222> LOCATION: (1)..(1191)
<223> OTHER INFORMATION: Spergularia marina arogenate dehydrogenase alpha mRNA, complete CDS

<400> SEQUENCE: 29

```
atgatgaatt ctatctcctt tgtcaactct tcctcaacaa caaccgcgga tattatctac     60
ttaaaccacc aatttttcgcg tcacaagtgt ttttctcgtc ttcctcggga cgcaactcct   120
agggaccgtc ggaagatttc cttggctaga gccatcaacg gctcacctac gtgtagccat   180
gttgaaatcg accaaacgtt ggttagctct agccaagcta ctactagagc ttgtagtaat   240
gagcaaaaga agcttaaaat cgcggtcgta gggttcggga attttggaca gtttttggct   300
agagaaatgg ttaagcaagg acatcaagtg ttggcttact ctcgctctga ttactcaaag   360
gttgctaaag agattggtgt ccaattcttt agggaccctg atgacctttg cgaggaacat   420
cctcaggtgg ttcttttatg cacctctatt ctctcaacgg agaaggtcct tcgctccctc   480
ccggttgacc gccttcgccg ttccacccct attgttgacg tcctctcggt taaggagttt   540
ccgcgcaccc ttttcctccg gcacttgcct gaggacttgg acatcctttg cacccatcca   600
atgtttggcc cggactctgg caagtccggg tgggatgggc tacccttttgt atttgataaa   660 gtccgagttg atcagaccc aaccccggacc cacagagtca acacattctt ggatatattt   720
aaacacgcag ggtgtagaat ggttgagatg acgtgtatgg accatgacaa gcatgcagcc   780
ggttcccagt ttataaccca catgatgggt cgggtcttag agaaagtggg cctttcaaat   840
acacccatta atacaaaagg gtatgagagt ttgttgaatt tggtggataa tacagcaaga   900
gatagctttg agttgtttta tggactgttt ttgtacaaca aaaatgcaat ggaggagttg   960
```

```
gatagattgg actgggcctt tgatacggta aaaatgcagc tttctgggta tttgcatgat    1020
tttgctagta aaaagttgat gttggagact ggtaatgaac tagctgggat tgttagtggt    1080
aaaattggcg acgacaatca taataacaag aggttaatgc tctcccctcc tacaaattct    1140
tacaagaatg ttacttttac tgatacgaaa gtttcggaga aaatgatgtg a             1191
```

<210> SEQ ID NO 30
<211> LENGTH: 1158
<212> TYPE: DNA
<213> ORGANISM: Paronychia polygonifolia
<220> FEATURE:
<221> NAME/KEY: misc_feature
<222> LOCATION: (1)..(1158)
<223> OTHER INFORMATION: Paronychia polygonifolia dehydrogenase alpha
      mRNA, complete CDS

<400> SEQUENCE: 30

```
atgaattcta tctctattgt aagctctact aagtctactt attacaaagt ctaccaattt     60
ccatcaccta agatatgttt cttccaccct tctaagctct ctattccttc ttgccaccct    120
aagtttcaaa attttgccgt acgttgcaat agtagtaaca acccaaaaaa tgtttcaaac    180
tctaaggata ataaatggaa gcctagtgaa attaacaagg gaattaagct taaaatcgcg    240
gtagtggggt tcggcaactt tgggcagttc ttggctaagg aaatggttaa gcaaggccat    300
caagtggtgg cgtactctcg tactgattat actaaggttg ctcaagatat gggtgttcgc    360
ttcttttctg atgcttgtga atgttcatt gagcaacccg aggtgattct aatgtgcacc     420
tctatcctct ctacggagaa ggtgttgcgc tccctccctc tccaccgtct ccggccagcc    480
accatcttcg tggacgtcct ctccgtgaag gagttccccc ggtccctctt cctccaacac    540
ctccccaagg acttcggcat cctttgcact cacccaatgt ttgggccaaa ctcagccaag    600
gccgggtggg ccgggctccc cttcgttcta gacagggttc gggtcagtat tgacccgacc    660
caagccaccc ggacagaggc attcctagac atattccgaa atgcagggtg taggatggtg    720
gaaatgactt gtgaagacca tgacaagcat gcagccgggt cacagttcat aacccacatg    780
atgggtcggt tcttgagaa agtggggctc cgaaatacac ccattaatac aaaagggtac    840
gaaagtttgt tgaatttggt ggagaataca ggaagagata gctttgagtt gttttatggg    900
ttgttcttgt acaatgaaaa tgcaatggtg caattagaga ggttggactg ggcttttaag    960
aaggttaaga gtcaactttc tgcatgtatg catgatcatg ttagggagag ccttatgttt    1020
gagtctcatg gagatcaaaa taagattatg aaaaaggcga gttacaagtc actcctatca    1080
gcctatacag aaaaaagtaa taagattgtc aaagatacaa agattaagaa ggacttggtg    1140
attagtgggc aacaataa                                                  1158
```

<210> SEQ ID NO 31
<211> LENGTH: 720
<212> TYPE: DNA
<213> ORGANISM: Herniaria latifolia
<220> FEATURE:
<221> NAME/KEY: misc_feature
<222> LOCATION: (1)..(720)
<223> OTHER INFORMATION: Herniaria latifolia arogenate dehydrogenase
      alpha mRNA, partial CDS

<400> SEQUENCE: 31

```
agtcgggttt gggaactttg gcagttcctt agccaaagaa atggtgaagc aaggtcatca     60
agtgttggct tattctcgct ctgattattc aagggttgct caggagattg gcgtacagta    120
```

```
tttctcaaat cccgacgacc tttgcaaaga gcatcctgag gttatcctcc tgtgcacatc    180
catcctctcc actgaaaaag tcctaaatac ccttcccctc gaccgcctcc gaccatcaac    240
tctcttctcc gatgtgctct ccgtcaagga attccctcgt acacttttcc tccagcaact    300
acccgaggac tttgacatca tctgtaccca tccaatgttc ggcccggact cgggcaaaca    360
cgggtgggca gggctcccct acgtctacga caaagtacgt gtcgggttgg atccgacccg    420
gatccgccga gcgaggcat ttcttaacat tttcgaaagg gcagggtgta ggatggtgga    480
gatgacgtgt gcagagcatg acaagcatgc agctgggtcc cagttcataa cccacatgtt    540
gggccgagtt ttggagaaag tgggccttt  aaatacgccc attaacacaa aagggtacga    600
gagtttgttg agcttggtgg ataatacagc aagagacagc tttgagttgt tttatgggct    660
ttttttgtac aacaaaaatg caatggagca gttggatcga ttggattggg cctttgacat    720
```

<210> SEQ ID NO 32
<211> LENGTH: 1077
<212> TYPE: DNA
<213> ORGANISM: Corrigiola litoralis
<220> FEATURE:
<221> NAME/KEY: misc_feature
<222> LOCATION: (1)..(1077)
<223> OTHER INFORMATION: Corrigiola litoralis arogenate dehydrogenase
      alpha, partial CDS

<400> SEQUENCE: 32

```
tgcagcaagg gtgtgcatgg catgaatggc tcagctgatc attttcatcc taacattaag     60
gttaatggtg aggttttgaa ccctatggtt ggctctagtg atgtagccga ggatgttaag    120
ctaaaaatcg ccatagttgg gtttggaaac ttcggacaat tcttggctaa ggaaattgtt    180
aagcagggtc ataaggtgtt ggcttactct cggtctgatt actctaaggc tgctaaggag    240
attggtgtgc agtatttttc cgatgctgat gacctgtgtg aggagcatcc tgaggtgatc    300
ctcctttgca cctctatcct ctcaacggag aaggtgatgc gcgccctccc tatccaccgc    360
cttcgccggt ccaccctctt cgtcgatgtt ctctcagtga aggagttccc ccgctcactc    420
ttcctccaag ttctccctaa ggactttgac atcctctgca cccacccaat gttcggccct    480
gactccggca aagccgggtg gggtggactc ccttttgtct ttgacaaagt tcgggttgcg    540
ccagactcca cccgggctac tagggccgag gcatttctag acatcttcag aagagcaggg    600
tgccgaatgg tagaaatgac ttgtgcagac cacgacaagc atgcagcagg atcgcagttc    660
atcacacaca tgatgggtcg ggtgctagag aaaatagggc ttgaaaatac tcccatcaac    720
acaaaagggt acgagagttt gctcaatttg gtggacaata cggcgagaga cagctttgag    780
ttgttttatg ggttgttttt gtataataag aacgcaatgg agcagttaga tagaatggac    840
tgggcttttg agatgataaa gaagcgactt tcaggatact tgcatgatct tgttaggaag    900
cagttgatgc tagaaactac tggtaatgat caagctggtc taactaacgg tgcaaaaaat    960
aatcatgaca agaagctcat gcttcctcct cctgctgcca atccttctat gattgttcct   1020
tctgctgcta ctcatgagaa gaagcatgat ttggtgcatg tcaatggaag cagatga      1077
```

<210> SEQ ID NO 33
<211> LENGTH: 990
<212> TYPE: DNA
<213> ORGANISM: Telephium imperati
<220> FEATURE:
<221> NAME/KEY: misc_feature
<222> LOCATION: (1)..(990)
<223> OTHER INFORMATION: Telephium imperati arogenate dehydrogenase
      alpha, partial CDS

<400> SEQUENCE: 33

```
gtattgggga gtatggttgg tcctagtgag agtgggaagg atgttaagct tgaaatcgcg    60
gtagtcgggt tcgggaactt tgggcagttt ttgggtaggg aaattgttaa gcaggggcat   120
gaggtgttgg cttattctcg gtctgattac tccaaagttg ctaaggagat tggtgtacgt   180
tatttttccg acgctcatga cttgtgtgag gagcatcctg aggtgatcct cctatgcaca   240
tccatcctct caacagagag ggtcctccac tccctccctc taaaccgcct ccgccgctcc   300
accctcttcg tcgacgtcct ctccgtgaag gagttccccc gaaacctctt cctccaaaac   360
ctccccaacg acttcgacat cctctgcacc cacccaatgt tcggcccgga ctccggcaaa   420
gccggctggg acgggctccc cttcgtgttc gacaaggtcc gggtcgggtc agacccggcc   480
cggaccaccc gggccgacac attcctagac atattcagga atgcagggtg caggatggtg   540
gaaatgtcct gtgcagagca tgacaggcac gcagccgggt cacaattcat aacccacatg   600
atgggtcggg ttttggagaa atcgggctc gaaaacacac ccattaacac aaaagggtac   660
gagagtttgt tgaatttggt ggataataca gcaagggata gctttgaatt gttttttgtat   720
tataagaatg caatggagca attagatagg atggattggg cttttgagat gattaagaag   780
cagcttctg ggtatttgca tgagcttgtt aggaagcaat tgatgctaga gactaataat   840
gatcaatccg ggataattaa tggtaaaact aattgtgata acgactaat gcttcctcct    900
ccggccgcta atccgtctgt aattgttcct gatcctgttc ctgctgtgaa gaagaagcat   960
gatttggtgc atgtcaatgg aagtagatga                                     990
```

<210> SEQ ID NO 34
<211> LENGTH: 1161
<212> TYPE: DNA
<213> ORGANISM: Beta vulgaris
<220> FEATURE:
<221> NAME/KEY: misc_feature
<222> LOCATION: (1)..(1161)
<223> OTHER INFORMATION: Beta vulgaris W357B arogenate dehydrogenase
      betta mRNA, complete CDS

<400> SEQUENCE: 34

```
atgctttctc tctcctccac aaccaccgca aaccctcgc cgtcgccatc tccggcgaat    60
tttccggcga aactttcttc tctctccacc atcaccacca ctctctcttt ctctcctcgc   120
cggagatatt ttcatggcgt caaaacccta acaattcgca gcatcgacgc cgcacaattc   180
ttcgattacg aatcaaaact tgccgccatt aacacaacct cttcgtcttc atcttcatct   240
tattcgaagc tcaaaatcgc aatcgtaggg ttcggaaatt acggacaatt tctcgcgaaa   300
accctagttt ctcaaggtca tactgttctc gcttattctc gctctgatta ctctaaaatc   360
gctgcgaatc tcggcgtttc ttacttttct gatcctgatg atctttgcga agaacatcct   420
gaggtaatta tgttgtgtac ttcgattta tcaactgaag ttatgttgaa ttcgttacca   480
ttgcagcgac ttaaacgatc gacgctttt gttgatgttt tatcggtgaa agaatttccg   540
cgtaatttgt tcttcaaac tttaccgtct gattttgata tattatgtac tcatcctatg   600
tttgggcctg aatctgggaa aaatggttgg ggaagtttgc cttttgttta tgataaggtt   660
aggattggga aagatgaggg tagaattaag agatgtgaga gttttttgga tgttttagg    720
agagaaggtt gtagggttga ggaaatgact tgtgctgagc atgataagtt tgcagcaggg   780
tctcagttta taacacattt cttagggagg gttttggaga gcttgatttt ggaggatacg   840
ccgattaata cgaaagggta tgagagtttg ttgaatttgg tggataatac gtcgaaggat   900
```

```
agtttcgagt tgttttatgg gttgttttg tataatcaga atgctatgga gcagttagag    960
aggttagatt gggcgtttga gttggttaag aagcaattgt ttggacactt gcatgggttg   1020
ctaaggaaac agttgtttgg gttttctgag atagatgaac gtattgggaa ggcgaaggag   1080
atcaaatttc tctctgatgc tgcagaacag aatggctctg ccttgtctgc tagggagaat   1140
gcaaattcgg agacaaattg a                                             1161

<210> SEQ ID NO 35
<211> LENGTH: 1161
<212> TYPE: DNA
<213> ORGANISM: Beta vulgaris
<220> FEATURE:
<221> NAME/KEY: misc_feature
<222> LOCATION: (1)..(1161)
<223> OTHER INFORMATION: Beta vulgaris Big Buck arogenate dehydrogenase
      betta mRNA, complete CDS

<400> SEQUENCE: 35
atgctttctc tctcctccac aaccaccgca aaaccctcgc cgtcgccatc tccggcgaat     60
tttccggcga aactttcttc tctctccacc atcaccacca ctctctcttt ctctcctcgc    120
cggagatatt ttcatggcgt caaaacccta acaattcgca gcatcgacgc cgcacaattc    180
ttcgattacg aatcaaaact tgccgccatt aacacaacct cttcgtcttc atcttcatct    240
tattcgaagc tcaaaatcgc aatcgtaggg ttcggaaatt acggacaatt ctcgcgaaa     300 accctagttt ctcaaggtca tactgttctc gcttattctc gctctgatta ctctaaaatc    360
gctgcgaatc tcggcgtttc ttactttct gatcctgatg atctttgcga agaacatcct    420
gaggtaatta tgttgtgtac ttcgatttta tcaactgaag ttatgttgaa ttcgttacca    480
ttgcagcgac ttaaacgatc gacgcttttt gttgatgttt tatcggtgaa agaatttccg    540
cgtaatttgt ttcttcaaac tttaccgtct gattttgata tattatgtac tcatcctatg    600
tttgggcctg aatctgggaa aaatggttgg ggaagtttgc cttttgttta tgataaggtt    660
aggattggga aagatgaggg tagaattaag agatgtgaga gttttttgga tgttttagg    720 agagaaggtt gtagggttga ggaaatgact tgtgctgagc atgataagtt tgcagcaggg    780
tctcagttta ttacacattt cttagggagg gttttggaga agcttgattt ggaggatacg    840
ccgattaata cgaaagggta tgagagtttg ttgaatttgg tggataatac gtcgaaggat    900
agtttcgagt tgttttatgg gttgttttg tataatcaga atgctatgga gcagttagag    960
aggttagatt gggcgtttga gttggttaag aagcaattgt ttggacactt gcatgggttg   1020
ctaaggaaac agttgtttgg gttttctgag atagatgaac gtattgggaa ggcgaaggag   1080
atcaaatttc tctctgatgc tgcagaacag aatggctctg ccttgtctgc tagggagaat   1140
gcaaattcgg agacaaattg a                                             1161

<210> SEQ ID NO 36
<211> LENGTH: 1161
<212> TYPE: DNA
<213> ORGANISM: Beta vulgaris
<220> FEATURE:
<221> NAME/KEY: misc_feature
<222> LOCATION: (1)..(1161)
<223> OTHER INFORMATION: Beta vulgaris Touch Stone arogenate
      dehydrogenase betta mRNA, complete CDS

<400> SEQUENCE: 36
atgctttctc tctcctccac aaccaccgca aaaccctcgc cgtcgccatc tccggcgaat     60
```

```
tttccggcga aactttcttc tctctccacc atcaccacca ctctctcttt ctctcctcgc    120
cggagatatt ttcatggcgt caaaaccccta acaattcgca gcatcgacgc cgcacaattc    180
ttcgattacg aatcaaaact tgccgccatt aacacaacct cttcgtcttc atcttcatct    240
tattcgaagc tcaaaatcgc aatcgtaggg ttcggaaatt acggacaatt tctcgcgaaa    300
accctagttt ctcaaggtca tactgttctc gcttattctc gctctgatta ctctaaaatc    360
gctgcgaatc tcggcgtttc ttactttttct gatcctgatg atctttgcga agaacatcca    420
gaggtaatta tgttgtgtac ttcgatttta tcaactgaag ttatgttgaa ttcgttacca    480
ttgcagcgac ttaaacgatc gacgcttttt gttgatgttt tatcggtgaa agaatttccg    540
cgtaatttgt ttcttcaaac tttaccgtct gattttgata tattatgtac tcatcctatg    600
tttgggcctg aatctgggaa aaatggttgg ggaagtttgc cttttgttta tgataaggtt    660
aggattggga aagatgaggg tagaattaag agatgtgaga gttttttgga tgtttttagg    720
agagaaggtt gtagggttga ggaaatgact tgtgctgagc atgataagtt tgcagcaggg    780
tctcagttta taacacattt cttagggagg gttttggaga agcttgatt ggaggatacg    840 ccgattaata cgaaagggta tgagagtttg ttgaatttgg tggataatac gtcgaaggat    900
agtttcgagt tgtttatgg gttgttttg tataatcaga atgctatgga gcagttagag    960
aggttagatt gggcgtttga gttggttaag aagcaattgt ttggacactt gcatgggttg    1020
ctaaggaaac agttgtttgg gttttctgag atagatgaac gtattgggaa ggcgaaggag    1080
atcaaatttc tctctgatgc tgcagaacag aatggctctg ccttgtctgc tagggagaat    1140
gcaaattcgg agacaaattg a                                              1161
```

<210> SEQ ID NO 37
<211> LENGTH: 1161
<212> TYPE: DNA
<213> ORGANISM: Beta vulgaris
<220> FEATURE:
<221> NAME/KEY: misc_feature
<222> LOCATION: (1)..(1161)
<223> OTHER INFORMATION: Beta vulgaris Blankoma arogenate dehydrogenase
      betta mRNA, complete CDS

<400> SEQUENCE: 37

```
atgctttctc tctcctccac aaccaccgca aaccctcgc cgtcgccatc tccggcgaat    60
tttccggcga aactttcttc tctctccacc atcaccacca ctctctcttt ctctcctcgc    120
cggagatatt ttcatggcgt caaaaccccta acaattcgca gcatcgacgc cgcacaattc    180
ttcgattacg aatcaaaact tgccgccatt aacacaacct cttcgtcttc atcttcatct    240
tattcgaagc tcaaaatcgc aatcgtaggg ttcggaaatt acggacaatt tctcgcgaaa    300
accctagttt ctcaaggtca tactgttctc gcttattctc gctctgatta ctctaaaatc    360
gctgcgaatc tcggcgtttc ttactttttct gatcctgatg atctttgcga agaacatcct    420
gaggtaatta tgttgtgtac ttcgatttta tcaactgaag ttatgttgaa ttcgttacca    480
ttgcagcgac ttaaacgatc gacgcttttt gttgatgttt tatcggtgaa agaatttccg    540
cgtaatttgt ttcttcaaac tttaccgtct gattttgata tattatgtac tcatcctatg    600
tttgggcctg aatctgggaa aaatggttgg ggaagtttgc cttttgttta tgataaggtt    660
aggattggga aagatgaggg tagaattaag agatgtgaga gttttttgga tgtttttagg    720
agagaaggtt gtagggttga ggaaatgact tgtgctgagc atgataagtt tgcagcaggg    780
tctcagttta taacacattt cttagggagg gttttggaga agcttgattt ggaggatacg    840
```

```
ccgattaata cgaaagggta tgagagtttg ttgaatttgg tggataatac gtcgaaggat      900
agtttcgagt tgttttatgg gttgttttg tataatcaga atgctatgga gcagttagag       960
aggttagatt gggcgtttga gttggttaag aagcaattgt ttggacactt gcatgggttg     1020
ctaaggaaac agttgtttgg gttttctgag atagatgaac gtattgggaa ggcgaaggag     1080
atcaaatttc tctctgatgc tgcagaacag aatggctctg ccttgtctgc tagggagaat     1140
gcaaattcgg agacaaattg a                                               1161
```

<210> SEQ ID NO 38
<211> LENGTH: 1161
<212> TYPE: DNA
<213> ORGANISM: Beta vulgaris
<220> FEATURE:
<221> NAME/KEY: misc_feature
<222> LOCATION: (1)..(1161)
<223> OTHER INFORMATION: Beta vulgaris subsp.maritima PI562585 arogenate
      dehydrogenase betta, complete CDS

<400> SEQUENCE: 38

```
atgctttctc tctcctccac aaccaccgca aaaccctcgc cgtcgccatc tccggcgaat       60
tttccggcaa aactttcttc tctctccacc atcaccacca ctatctcctt ctctcctcgc      120
cggagatatt ttcatggcgt caaaaccta acaattcgca gcatcgacgc tgcacaattc      180
ttcgattacg aatcaaaact cgccgccatt aacacaacct cttcatctac atcgtcatct      240
tattcgaaac tcaaaatcgc aatcgtaggt ttcggaaatt acggacaatt tctcgcgaaa     300
accctagttt ctcaaggtca tactgttctc gcttattctc gctctgatta ctctaaaatc      360
gctgcgaatc tcggcgtttc ttactttct gatcctgatg atctttgcga agaacatcct      420
gaggtaatta tgttgtgtac ttcgatttta tcaactgaag ttatgttgaa ttcgttacca     480
ttgcagcgac ttaaacgatc gacgcttttt gttgatgttt tatcggtgaa agaatttccg     540
cgtaatttgt ttcttcaaac tttaccgtct gatttgata tattatgtac tcatcctatg      600
tttgggcctg aatctgggaa aaatggttgg ggaagtttgc cttttgttta tgataaggtt     660
aggattggga aagatgaggg tagaattaag agatgtgaga gttttttgga tgttttagg     720 agagaaggtt gtaggggttga ggaaatgact tgtgctgagc atgataagtt tgcagcaggg     780 tctcagtta ttacacattt cttagggagg gttttggaga agcttgattt ggaggatacg     840
ccgattaata cgaaagggta tgagagtttg ttgaatttgg tggataatac gtcgaaggat     900
agtttcgagt tgttttatgg gttgttttg tataatcaga atgctatgga gcagttagag      960
aggttagatt gggcatttga gttggttaag aagcaattgt ttggacactt gcatgggttg     1020
ctaaggaaac agttgtttgg gttttctgag atagatgaac gtattgggaa ggcgaaggag     1080
atcaaatttc tctctgatgc tgcagaacag aatggctctg ccttgtctgc tagggagaat     1140
gcaaattcgg agacaaattg a                                               1161
```

<210> SEQ ID NO 39
<211> LENGTH: 966
<212> TYPE: DNA
<213> ORGANISM: Spinacia oleracea
<220> FEATURE:
<221> NAME/KEY: misc_feature
<222> LOCATION: (1)..(966)
<223> OTHER INFORMATION: Spinacia oleracea arogenate dehydrogenase
      betta, partial CDS

<400> SEQUENCE: 39

```
gccgctacca ataccctccac cgccaccctct tcctcacagt cgtcgtactc gaagctcaag       60
```

```
gtggcaatcg ttgggttcgg aaactatgga caatttctcg caaaaactat ggtttctcaa    120
ggtcatactg ttcttgcata ttctcggtct gattactcga aaatagctcc aaatctgggc    180
gtttcgttct tttccgatcc tgatgattta tgtgaagaac atccggaggt aattttgctg    240
tgcacttcga ttttatcaac tgaatttatg ttgaattcac taccattgca acgtcttaag    300
aggtcgacgc tttttgttga tgttttatcg gttaaggagt ttccccgtaa cttgtttctt    360
cagactttgc cgcctgattt tgatatttta tgcactcatc ctatgtttgg tcctgaatct    420
gggaaaaatg gatggggagg tttgccgttt gtttatgata aggttaggat tgggaaagca    480
gagcgtagaa ttaggaggtg tgagaatttt ttggatgttt ttaggagagc agggtgtagg    540
gttgaggaga tgacttgtgc agagcatgat aaatacgcgg cgggttcaca gtttattacg    600
catttcctgg ggagggtttt ggagaagctt gatttggagg ataccgat taacacgaaa    660 gggtacgaga gtttgttgaa tttggtggat aatacgtcga aggatagttt cgagttgttt    720
tatgggttgt ttttgtacaa ccagaatgct atggagcagt ggagaggtt agattgggca    780 ttcgagttgg ttaagaagca gttgtttggg catttgcatg gtttgttaag gggtcagttg    840
tttgggtgta ctgagattga tgaacgtctt gagaaggcaa aggagttgaa gtttcttcct    900
gatgccacga cacaaaatgg ctctgcctcc gctcctagag aaaatgcaaa ttcagagatc    960
aattga                                                              966

<210> SEQ ID NO 40
<211> LENGTH: 966
<212> TYPE: DNA
<213> ORGANISM: Nepenthes ventricosa
<220> FEATURE:
<221> NAME/KEY: misc_feature
<222> LOCATION: (1)..(966)
<223> OTHER INFORMATION: Nepenthes ventricosa x Nepenthes alata
      arogenate dehydrogenase betta, partial CDS

<400> SEQUENCE: 40
gccgcgctgc caaacgacta cgaaacgaag cttcccatc tccctagttc tttcgcgaaa      60
ctcaaggtcg ggatcattgg gttcggcaat tacgggcagt tccttgccaa aaccctagtc    120
cggcaaggcc acaccgttct cgctcattct cgctccaatt actcccaaaa cgccgcgaag    180
ctcggcgtct ctttcttcta tgatcccaat gacctatgcg aggaacaccc ggaagttatc    240
ctcctctgca cctcgattct gtcgacggaa tctgtcctcc ggagcctgcc attgcagcgg    300
ctcaagcggt ctactctctt cgtcgacgtt ttgtcggtga aggagtttcc tcgatcgctt    360
ttgctccaaa ttctgccccc tgacttagac attctctgca ctcaccccat gttcgggccg    420
gaatccggca agaacggctg gagcgggctg ccgttcgttt acgataaggt tagaatcggc    480
gaacatgaga ttagggttaa caggtgtgat aattttatcg aagtgttcag gagggaaggg    540
tgtaggatgg tacagatgag ctgtgcggag cacgatcggc atgcggctgg ctctcagttt    600
ataactcata tgatggggag agtttttggag aagttgaaat tagaggatac gcccattaat    660
acgaaaggct atgagagttt gttgaatttg gtggagaaca ctgcgaggga tagtttcgag    720 ttgtttttatg ggctgtttct gtataataag aacgttatgg agcagctgga gaggatggat    780
ttagcgttcg agatggttaa aaagcagttg tttggccatt tacatggggtt gttgaggagc    840 cagttgtttg atggttccga aatggaagtt agagtggagg aggagagaaa attgttgtcc    900
gatgggtctc agaatgggca cgttttttct tcttttttcag atagtaaaaa tgttgagaga    960
aattga                                                              966
```

```
<210> SEQ ID NO 41
<211> LENGTH: 53
<212> TYPE: PRT
<213> ORGANISM: Beta vulgaris
<220> FEATURE:
<221> NAME/KEY: misc_feature
<222> LOCATION: (1)..(53)
<223> OTHER INFORMATION: BvADHa N-terminal plastid transit peptide

<400> SEQUENCE: 41

Met Ile Ser Leu Ser Ser Phe His Pro Ser Ser Thr Thr Ala Thr Ala
1               5                   10                  15

Thr Ala Ala Ala Ala Thr Thr His Pro Pro Gln Gln Cys Pro Ala Phe
            20                  25                  30

Ser Ser Pro Pro Ser His Leu Ser Leu Pro Leu Arg His Pro Arg Gln
        35                  40                  45

His Leu Val Val Arg
    50

<210> SEQ ID NO 42
<211> LENGTH: 74
<212> TYPE: PRT
<213> ORGANISM: Beta vulgaris
<220> FEATURE:
<221> NAME/KEY: misc_feature
<222> LOCATION: (1)..(74)
<223> OTHER INFORMATION: BvADHb N-terminal plastid transit peptide

<400> SEQUENCE: 42

Met Leu Ser Leu Ser Ser Thr Thr Thr Ala Lys Pro Ser Pro Ser Pro
1               5                   10                  15

Ser Pro Ala Asn Phe Pro Ala Lys Leu Ser Ser Leu Ser Thr Ile Thr
            20                  25                  30

Thr Thr Leu Ser Phe Ser Pro Arg Arg Arg Tyr Phe His Gly Val Lys
        35                  40                  45

Thr Leu Thr Ile Arg Ser Ile Asp Ala Ala Gln Phe Phe Asp Tyr Glu
    50                  55                  60

Ser Lys Leu Ala Ala Ile Asn Thr Thr Ser
65                  70

<210> SEQ ID NO 43
<211> LENGTH: 398
<212> TYPE: PRT
<213> ORGANISM: Beta vulgaris
<220> FEATURE:
<221> NAME/KEY: misc_feature
<222> LOCATION: (1)..(398)
<223> OTHER INFORMATION: BvADH-alpha Boltardy red beet variety

<400> SEQUENCE: 43

Met Ile Ser Leu Ser Ser Phe His Pro Ser Ser Thr Thr Ala Thr Ala
1               5                   10                  15

Thr Ala Ala Ala Ala Thr Thr His Pro Pro Gln Gln Cys Pro Ala Phe
            20                  25                  30

Ser Ser Pro Pro Ser His Leu Ser Leu Pro Leu Arg His Pro Arg Gln
        35                  40                  45

His Leu Val Val Arg Cys Gly Gly Gly Ser Ala Ser Glu Ser Val
    50                  55                  60

Phe Asn Arg Asp Ser Ala Ala Thr Arg Val Ser Asn Asp His Leu Asp
65                  70                  75                  80
```

```
Val Ser Lys Arg Asp Val Lys Leu Lys Ile Ala Ile Gly Phe Gly
                85                  90                  95

Asn Phe Gly Gln Phe Leu Ala Lys Thr Met Ala Lys Gln Gly His Arg
            100                 105                 110

Val Leu Ala Tyr Ser Arg Ser Asp Tyr Ser Arg Ala Ala Lys Glu Ile
            115                 120                 125

Gly Val Glu Tyr Phe Thr Asp Ala Asp Leu Cys Glu His Pro
            130                 135                 140

Glu Val Ile Leu Leu Cys Thr Ser Ile Leu Ser Thr Glu Lys Val Leu
145                 150                 155                 160

Arg Ser Leu Pro Leu His Arg Leu Arg Arg Ser Thr Leu Phe Ala Asp
                165                 170                 175

Val Leu Ser Val Lys Glu Phe Pro Arg Ser Leu Phe Gln Leu Leu
            180                 185                 190

Pro Lys Asp Phe Asp Ile Leu Cys Thr His Pro Met Phe Gly Pro Asp
                195                 200                 205

Ser Gly Lys Asp Gly Trp Gly Gly Leu Pro Phe Val Phe Asp Lys Val
            210                 215                 220

Arg Val Gly Ser Asp Gln Ser Arg Thr Ser Arg Ala Glu Ala Phe Leu
225                 230                 235                 240

Asp Val Phe Arg Asn Ala Gly Cys Arg Met Val Glu Met Ser Cys Val
                245                 250                 255

Asp His Asp Lys His Ala Ala Gly Ser Gln Phe Ile Thr His Met Met
            260                 265                 270

Gly Arg Val Leu Glu Lys Leu Ala Leu Glu Asn Thr Pro Ile Asn Thr
            275                 280                 285

Lys Gly Tyr Glu Ser Leu Leu Asn Leu Val Asp Asn Thr Ala Arg Asp
            290                 295                 300

Ser Phe Glu Leu Phe Tyr Gly Leu Phe Leu Tyr Asn Lys Asn Ala Met
305                 310                 315                 320

Glu Gln Leu Asp Arg Met Asp Trp Ala Phe Glu Met Val Lys Lys Gln
                325                 330                 335

Leu Ser Gly Tyr Leu His Asp Leu Val Arg Lys Gln Leu Met Leu Glu
            340                 345                 350

Gly Asn Asn Asp Gln Ala Glu Val Thr Phe Asp Lys Pro Leu Met Leu
            355                 360                 365

Pro Ser Pro Thr Ile Asn Pro Pro Gln Ile Val Pro Ser Ala Asp Met
            370                 375                 380

Ala Glu Lys Lys His Asp Leu Val Val Val Asn Gly Thr Arg
385                 390                 395

<210> SEQ ID NO 44
<211> LENGTH: 1197
<212> TYPE: DNA
<213> ORGANISM: Beta vulgaris
<220> FEATURE:
<221> NAME/KEY: misc_feature
<222> LOCATION: (1)..(1197)
<223> OTHER INFORMATION: BvADH-alpha Boltardy red beet variety

<400> SEQUENCE: 44
atgatttcac tctcttcttt tcatccttcc tccaccaccg ccaccgccac cgccgccgcc      60
gccaccaccc acccacctca acaatgtccc gcttttcct ctcctccgtc gcatctctcg     120
cttcctttac gccaccctcg ccaacacctt gtagttcggt gcggtggagg tggtcggcc     180 tccgaatcgg tatttaaccg tgatagtgct gctactcgtg tttctaatga tcatcttgac    240
```

```
gttagtaaaa gagatgttaa gcttaagatt gctattattg ggtttggtaa ctttggccag      300
tttttggcta agacaatggc taagcaaggt catagagtgt tggcttactc acgctcggac      360
tactcccgcg ctgctaagga gatcggcgtc gagtatttta ctgacgccga tgacctctgc      420
gaggagcacc ctgaggttat tctgttgtgc acatccatcc tctcaacgga gaaggtcctc      480
cgatcactcc ccctccaccg gctccgtcgt tcaaccctct tgcggatgt tctctcggtc       540 aaggaatttc ctcgatcgct cttccttcaa ctacttccta aggactttga tatcctatgc      600
acccacccta tgtttggccc agactcgggc aaagacgggt ggggtggact acctttgtg      660 ttcgataaag ttagagtcgg atcagatcag agtcggacat ctcgtgctga ggcattccta      720
gacgtgttta ggaatgccgg gtgtaggatg gtggaaatga gttgtgttga tcatgacaag      780
catgcagccg atctcaatt tattacacat atgatgggac gagttttgga gaaattggcc       840
ttggaaaata caccaattaa tacaaaaggg tacgaaagtt tgttaaattt ggtggataat      900
actgcaaggg atagttttga gttgttttac gggttgtttt tgtacaataa aaatgcaatg      960
gagcaattgg atagaatgga ttgggctttc gagatggtaa aaaagcaact ttcgggatat     1020
ttgcatgatc ttgttagaaa acaattgatg ttggagggta ataatgatca agctgaggtt     1080
acttttgaca aaccattgat gcttccttct cctactatta atcctccaca aatagttccc     1140
tctgctgata tggctgagaa gaagcatgat ttagtggtgg ttaatggtac tagatag        1197
```

<210> SEQ ID NO 45
<211> LENGTH: 323
<212> TYPE: PRT
<213> ORGANISM: Mirabilis jalapa
<220> FEATURE:
<221> NAME/KEY: misc_feature
<222> LOCATION: (1)..(323)
<223> OTHER INFORMATION: Mirabilis jalapa ADH-alpha

<400> SEQUENCE: 45

```
Ile Ala Ile Val Gly Phe Gly Asn Phe Gly Gln Phe Leu Gly Lys Glu
1               5                   10                  15

Ile Val Lys Gln Gly His Thr Val Leu Ala Tyr Ser Arg Ser Asp Tyr
            20                  25                  30

Leu Arg Ala Ala His Asn Ile Gly Val Lys Phe Phe Ser Asp Ala Asp
        35                  40                  45

Asp Leu Cys Glu Glu His Pro Gln Val Ile Leu Leu Cys Thr Ser Ile
    50                  55                  60

Leu Ser Thr Glu Arg Val Leu Arg Ser Leu Pro Leu His Arg Leu Arg
65                  70                  75                  80

Arg Ser Thr Leu Met Val Asp Val Leu Ser Val Lys Glu Phe Pro Arg
                85                  90                  95

Ser Leu Phe Leu Gln Leu Leu Pro Pro Asp Phe Asp Ile Leu Cys Thr
            100                 105                 110

His Pro Met Phe Gly Pro Asp Ser Gly Lys Ala Gly Trp Gly Gly Leu
        115                 120                 125

Pro Phe Val Phe Glu Lys Val Arg Val Gly Ser Asn Pro Thr Arg Ser
    130                 135                 140

Cys Arg Val Glu Ser Phe Leu Gly Ile Phe Gln Glu Ala Gly Cys Arg
145                 150                 155                 160

Met Val Glu Met Ser Cys Ala Glu His Asp Arg His Ala Ala Gly Ser
                165                 170                 175

Gln Phe Ile Thr His Met Met Gly Arg Val Leu Glu Lys Leu Ala Leu
```

```
                180             185             190
Glu Asp Thr Pro Ile Asn Thr Lys Gly Tyr Glu Ser Leu Leu Asn Leu
            195                 200                 205

Val Asp Asn Thr Ala Arg Asp Ser Phe Glu Leu Phe Tyr Gly Leu Phe
        210                 215                 220

Leu Tyr Asn Lys Asn Ala Met Glu Gln Leu Asp Arg Met His Trp Ala
225                 230                 235                 240

Phe Glu Thr Val Lys Gln Gln Leu Ser Gly Tyr Leu His Asp Leu Val
                245                 250                 255

Arg Lys Gln Leu Met Leu Glu Ser Ser Ser Asn Asp Asn Asn Asp Phe
            260                 265                 270

Val Gly Asn Tyr Tyr Asp Asn Asn Glu Asn Asp Lys Ser Ser Asp Glu
        275                 280                 285

Lys Lys Leu Met Leu Pro Ala Pro Gly Val Ala Ala Ala Ala Gln Ile
            290                 295                 300

Leu Pro Ser Ser Glu Arg Gln Gln Asn His Asp Leu Leu Tyr Ile Asn
305                 310                 315                 320

Gly Arg Arg

<210> SEQ ID NO 46
<211> LENGTH: 972
<212> TYPE: DNA
<213> ORGANISM: Mirabilis jalapa
<220> FEATURE:
<221> NAME/KEY: misc_feature
<222> LOCATION: (1)..(972)
<223> OTHER INFORMATION: Mirabilis jalapa ADH-alpha

<400> SEQUENCE: 46
atagcgatag ttgggtttgg taactttggt cagttttttgg gtaaagaaat agtaaagcaa    60
ggtcatactg ttttggctta ttcacgctct gattacttac gtgctgctca caacatcggc   120
gtcaaattct tttctgacgc cgatgacctt tgtgaggaac atcctcaggt gatactgcta   180
tgcacatcca tcctatcaac agagcgagtc cttcgctcac tccctctcca ccgcctgcgc   240
cgctcaacac tcatggtaga cgtactgtcg gtcaaggagt tcccccgttc attattcctt   300
caacttctac caccggactt tgacatcctg tgcacacacc ccatgtttgg acctgactca   360
ggcaaggccg gtggggagg gctcccattc gtgtttgaaa aagtgcgagt tggatccaac   420
ccaacccgct cttgccgggt tgagtccttt cttggaatat tccaagaagc ggggtgtcgg   480
atggtggaaa tgagttgtgc agaacatgac aggcatgctg cagggtcaca gttcataact   540
cacatgatgg gtcgtgtttt ggagaaatta gcattagaag acactccaat taacacaaaa   600
ggatatgaaa gtttactgaa tttggttgat aacacggcaa gagatagctt tgagttgttt   660
tatggactgt ttttgtacaa caagaatgca atggaacaac ttgataggat gcattgggca   720
ttcgaaactg ttaagcaaca gttatctggt tacttacacg atctggttcg caaacaattg   780
atgttagaat cttcaagtaa tgataacaat gactttgtcg gtaattatta tgataataat   840
gaaaatgata gagtagtga tgaaaagaaa ttgatgcttc ctgctcctgg agttgcagct   900
gctgctcaga ttctaccttc ttctgaaagg caacaaaatc atgacttgct ctatatcaat   960
ggtcgtcgat ag                                                      972

<210> SEQ ID NO 47
<211> LENGTH: 386
<212> TYPE: PRT
<213> ORGANISM: Beta vulgaris
```

-continued

```
<220> FEATURE:
<221> NAME/KEY: misc_feature
<222> LOCATION: (1)..(386)
<223> OTHER INFORMATION: BvADH-beta Boltardy red beet variety

<400> SEQUENCE: 47
```

Met Leu Ser Leu Ser Ser Thr Thr Thr Ala Lys Pro Ser Pro Ser Pro
1               5                   10                  15

Ser Pro Ala Asn Phe Pro Ala Lys Leu Ser Ser Leu Ser Thr Ile Thr
            20                  25                  30

Thr Thr Leu Ser Phe Ser Pro Arg Arg Tyr Phe His Gly Val Lys
        35                  40                  45

Thr Leu Thr Ile Arg Ser Ile Asp Ala Ala Gln Phe Phe Asp Tyr Glu
    50                  55                  60

Ser Lys Leu Ala Ala Ile Asn Thr Thr Ser Ser Thr Ser Ser Ser
65                  70                  75                  80

Tyr Ser Lys Leu Lys Ile Ala Ile Val Gly Phe Gly Asn Tyr Gly Gln
                85                  90                  95

Phe Leu Ala Lys Thr Leu Val Ser Gln Gly His Thr Val Leu Ala Tyr
            100                 105                 110

Ser Arg Ser Asp Tyr Ser Lys Ile Ala Ala Asn Leu Gly Val Ser Tyr
            115                 120                 125

Phe Ser Asp Pro Asp Asp Leu Cys Glu Glu His Pro Glu Val Ile Met
130                 135                 140

Leu Cys Thr Ser Ile Leu Ser Thr Glu Val Met Leu Asn Ser Leu Pro
145                 150                 155                 160

Leu Gln Arg Leu Lys Arg Ser Thr Leu Phe Val Asp Val Leu Ser Val
                165                 170                 175

Lys Glu Phe Pro Arg Asn Leu Phe Leu Gln Thr Leu Pro Ser Asp Phe
            180                 185                 190

Asp Ile Leu Cys Thr His Pro Met Phe Gly Pro Glu Ser Gly Lys Asn
            195                 200                 205

Gly Trp Gly Ser Leu Pro Phe Val Tyr Asp Lys Val Arg Ile Gly Lys
        210                 215                 220

Asp Glu Gly Arg Ile Lys Arg Cys Glu Ser Phe Leu Asp Val Phe Arg
225                 230                 235                 240

Arg Glu Gly Cys Arg Val Glu Glu Met Thr Cys Ala Glu His Asp Lys
                245                 250                 255

Phe Ala Ala Gly Ser Gln Phe Ile Thr His Phe Leu Gly Arg Val Leu
            260                 265                 270

Glu Lys Leu Asp Leu Glu Asp Thr Pro Ile Asn Thr Lys Gly Tyr Glu
        275                 280                 285

Ser Leu Leu Asn Leu Val Asp Asn Thr Ser Lys Asp Ser Phe Glu Leu
290                 295                 300

Phe Tyr Gly Leu Phe Leu Tyr Asn Gln Asn Ala Met Glu Gln Leu Glu
305                 310                 315                 320

Arg Leu Asp Trp Ala Phe Glu Leu Val Lys Lys Gln Leu Phe Gly His
                325                 330                 335

Leu His Gly Leu Leu Arg Lys Gln Leu Phe Gly Phe Ser Glu Ile Asp
            340                 345                 350

Glu Arg Ile Gly Lys Ala Lys Glu Ile Lys Phe Leu Ser Asp Ala Ala
        355                 360                 365

Glu Gln Asn Gly Ser Ala Leu Ser Ala Arg Glu Asn Ala Asn Ser Glu
    370                 375                 380

Thr Asn
385

<210> SEQ ID NO 48
<211> LENGTH: 1161
<212> TYPE: DNA
<213> ORGANISM: Beta vulgaris
<220> FEATURE:
<221> NAME/KEY: misc_feature
<222> LOCATION: (1)..(1161)
<223> OTHER INFORMATION: BvADH-beta Boltardy red beet variety

<400> SEQUENCE: 48

| | | | | |
|---|---|---|---|---|
| atgctttctc | tctcctccac | aaccaccgca | aaaccctcgc | cgtcgccatc | tccggcgaat | 60 |
| tttccggcaa | aactttcttc | tctctccacc | atcaccacca | ctctctcctt | ctctcctcgc | 120 |
| cggagatatt | tcatggcgt | caaaaccta | acaattcgca | gcatcgacgc | tgcacaattc | 180 |
| ttcgattacg | aatcaaaact | cgccgccatt | aacacaacat | cttcatctac | atcttcatct | 240 |
| tattcgaaac | tcaaaatcgc | aatcgtaggt | ttcggaaatt | acggacaatt | tctggcgaaa | 300 |
| accctagttt | ctcaaggtca | tactgttctc | gcttattctc | gctctgatta | ctctaaaatc | 360 |
| gctgcgaatc | tcggtgtttc | ttactttcct | gatcctgatg | atctttgcga | agaacatccc | 420 |
| gaggtaatta | tgttgtgtac | ttcgatttta | tcaactgaag | ttatgttgaa | ttcgttacca | 480 |
| ttgcagcgac | ttaaacgatc | gacgcttttt | gttgatgttt | tatcggtgaa | agaatttccg | 540 |
| cgtaatttgt | tcttcagac | tttaccgtct | gattttgata | tattatgtac | tcatcctatg | 600 |
| tttgggcctg | aatctgggaa | aaatggttgg | ggaagtttgc | cgtttgttta | tgataaagtt | 660 |
| aggattggga | aagatgaggg | tagaattaag | agatgtgaga | gttttttgga | tgtttttagg | 720 |
| agagaaggtt | gtagggttga | ggaaatgact | tgtgctgagc | atgataagtt | tgcagcagga | 780 |
| tctcagttta | taacacattt | cttagggagg | gttttggaga | agcttgatttt | ggaggatacg | 840 |
| ccgattaata | cgaaagggta | tgagagtttg | ttgaatttgg | tggataatac | gtcgaaggat | 900 |
| agtttcgagt | tgttttatgg | gttgttttg | tataatcaga | atgctatgga | gcagttagag | 960 |
| aggttagatt | gggcgtttga | gttggttaag | aagcaattgt | ttggacactt | gcatggggttg | 1020 |
| ctaaggaaac | agttgtttgg | gttttctgag | atagatgaac | gtattgggaa | ggcgaaggag | 1080 |
| atcaaatttc | tctctgatgc | tgcagaacag | aatggctctg | ccttgtctgc | tagggagaat | 1140 |
| gcaaattcgg | agacaaattg | a | | | | 1161 |

<210> SEQ ID NO 49
<211> LENGTH: 33
<212> TYPE: DNA
<213> ORGANISM: Artificial Sequence
<220> FEATURE:
<223> OTHER INFORMATION: Synthetic primer

<400> SEQUENCE: 49
ggttccgcgt ggatccctaa caattcgcag cat                33

<210> SEQ ID NO 50
<211> LENGTH: 34
<212> TYPE: DNA
<213> ORGANISM: Artificial Sequence
<220> FEATURE:
<223> OTHER INFORMATION: Synthetic primer

<400> SEQUENCE: 50
aattcggaga caaattgaga attcatcgtg actg               34

<210> SEQ ID NO 51
<211> LENGTH: 36
<212> TYPE: DNA
<213> ORGANISM: Artificial Sequence
<220> FEATURE:
<223> OTHER INFORMATION: Synthetic primer

<400> SEQUENCE: 51
ctggttccgc gtggatcctg cggtggaggt ggttcg                36

<210> SEQ ID NO 52
<211> LENGTH: 35
<212> TYPE: DNA
<213> ORGANISM: Artificial Sequence
<220> FEATURE:
<223> OTHER INFORMATION: Synthetic primer

<400> SEQUENCE: 52
gttaatggta ctagatagga attcatcgtg actga                 35

<210> SEQ ID NO 53
<211> LENGTH: 36
<212> TYPE: DNA
<213> ORGANISM: Artificial Sequence
<220> FEATURE:
<223> OTHER INFORMATION: Synthetic primer

<400> SEQUENCE: 53
ctggttccgc gtggatccgc aatcgacgcc gcccaa                36

<210> SEQ ID NO 54
<211> LENGTH: 35
<212> TYPE: DNA
<213> ORGANISM: Artificial Sequence
<220> FEATURE:
<223> OTHER INFORMATION: Synthetic primer

<400> SEQUENCE: 54
tcatcatcat catcttaaga attcatcgtg actga                 35

<210> SEQ ID NO 55
<211> LENGTH: 36
<212> TYPE: DNA
<213> ORGANISM: Artificial Sequence
<220> FEATURE:
<223> OTHER INFORMATION: Synthetic primer

<400> SEQUENCE: 55
ctggttccgc gtggatccgc cgctaccaat acctcc                36

<210> SEQ ID NO 56
<211> LENGTH: 35
<212> TYPE: DNA
<213> ORGANISM: Artificial Sequence
<220> FEATURE:
<223> OTHER INFORMATION: Synthetic primer

<400> SEQUENCE: 56
aattcagaga tcaattgaga attcatcgtg actga                 35

<210> SEQ ID NO 57
<211> LENGTH: 36
<212> TYPE: DNA
<213> ORGANISM: Artificial Sequence
<220> FEATURE:
<223> OTHER INFORMATION: Synthetic primer -continued

```
<400> SEQUENCE: 57
ctggttccgc gtggatcctg cgccgcctct gactcc                                    36

<210> SEQ ID NO 58
<211> LENGTH: 36
<212> TYPE: DNA
<213> ORGANISM: Artificial Sequence
<220> FEATURE:
<223> OTHER INFORMATION: Synthetic primer

<400> SEQUENCE: 58
tggtaataat tctagatagg aattcatcgt gactga                                    36

<210> SEQ ID NO 59
<211> LENGTH: 37
<212> TYPE: DNA
<213> ORGANISM: Artificial Sequence
<220> FEATURE:
<223> OTHER INFORMATION: Synthetic primer

<400> SEQUENCE: 59
ctggttccgc gtggatccgc cgcgctgcca aacgact                                   37

<210> SEQ ID NO 60
<211> LENGTH: 36
<212> TYPE: DNA
<213> ORGANISM: Artificial Sequence
<220> FEATURE:
<223> OTHER INFORMATION: Synthetic primer

<400> SEQUENCE: 60
aaatgttgag agaaattgag aattcatcgt gactga                                    36

<210> SEQ ID NO 61
<211> LENGTH: 37
<212> TYPE: DNA
<213> ORGANISM: Artificial Sequence
<220> FEATURE:
<223> OTHER INFORMATION: Synthetic primer

<400> SEQUENCE: 61
ctggttccgc gtggatcctg ctcatcatca tcatcat                                   37

<210> SEQ ID NO 62
<211> LENGTH: 36
<212> TYPE: DNA
<213> ORGANISM: Artificial Sequence
<220> FEATURE:
<223> OTHER INFORMATION: Synthetic primer

<400> SEQUENCE: 62
cgtcaacgat agatcatagg aattcatcgt gactga                                    36

<210> SEQ ID NO 63
<211> LENGTH: 37
<212> TYPE: DNA
<213> ORGANISM: Artificial Sequence
<220> FEATURE:
<223> OTHER INFORMATION: Synthetic primer

<400> SEQUENCE: 63
ctggttccgc gtggatccat agcgatagtt gggtttg                                   37

<210> SEQ ID NO 64
```

<210> SEQ ID NO 64
<211> LENGTH: 36
<212> TYPE: DNA
<213> ORGANISM: Artificial Sequence
<220> FEATURE:
<223> OTHER INFORMATION: Synthetic primer

<400> SEQUENCE: 64
tatcaatggt cgtcgatagg aattcatcgt gactga          36

<210> SEQ ID NO 65
<211> LENGTH: 38
<212> TYPE: DNA
<213> ORGANISM: Artificial Sequence
<220> FEATURE:
<223> OTHER INFORMATION: Synthetic primer

<400> SEQUENCE: 65
ctggttccgc gtggatcctg cacggccttc actaaaac       38

<210> SEQ ID NO 66
<211> LENGTH: 37
<212> TYPE: DNA
<213> ORGANISM: Artificial Sequence
<220> FEATURE:
<223> OTHER INFORMATION: Synthetic primer

<400> SEQUENCE: 66
tcaatggatc aaagcggtag gaattcatcg tgactga        37

<210> SEQ ID NO 67
<211> LENGTH: 23
<212> TYPE: DNA
<213> ORGANISM: Artificial Sequence
<220> FEATURE:
<223> OTHER INFORMATION: Synthetic primer

<400> SEQUENCE: 67
tcaagctgag gttacttttg aca                        23

<210> SEQ ID NO 68
<211> LENGTH: 23
<212> TYPE: DNA
<213> ORGANISM: Artificial Sequence
<220> FEATURE:
<223> OTHER INFORMATION: Synthetic primer

<400> SEQUENCE: 68
aagaagcatg atttagtggt ggt                        23

<210> SEQ ID NO 69
<211> LENGTH: 20
<212> TYPE: DNA
<213> ORGANISM: Artificial Sequence
<220> FEATURE:
<223> OTHER INFORMATION: Synthetic primer

<400> SEQUENCE: 69
tgcagcgact taaacgatcg                            20

<210> SEQ ID NO 70
<211> LENGTH: 20
<212> TYPE: DNA
<213> ORGANISM: Artificial Sequence
<220> FEATURE:
<223> OTHER INFORMATION: Synthetic primer

<400> SEQUENCE: 70
ttggggaagt ttgccgtttg                                               20

<210> SEQ ID NO 71
<211> LENGTH: 19
<212> TYPE: DNA
<213> ORGANISM: Artificial Sequence
<220> FEATURE:
<223> OTHER INFORMATION: Synthetic primer

<400> SEQUENCE: 71
agttccctct gctgatatg                                                19

<210> SEQ ID NO 72
<211> LENGTH: 21
<212> TYPE: DNA
<213> ORGANISM: Artificial Sequence
<220> FEATURE:
<223> OTHER INFORMATION: Synthetic primer

<400> SEQUENCE: 72
gtggttaatg gtactagata g                                             21

<210> SEQ ID NO 73
<211> LENGTH: 20
<212> TYPE: DNA
<213> ORGANISM: Artificial Sequence
<220> FEATURE:
<223> OTHER INFORMATION: Synthetic primer

<400> SEQUENCE: 73
gcgaaggaga tcaaatttct                                               20

<210> SEQ ID NO 74
<211> LENGTH: 21
<212> TYPE: DNA
<213> ORGANISM: Artificial Sequence
<220> FEATURE:
<223> OTHER INFORMATION: Synthetic primer

<400> SEQUENCE: 74
tcaatttgtc tccgaatttg c                                             21

<210> SEQ ID NO 75
<211> LENGTH: 26
<212> TYPE: DNA
<213> ORGANISM: Artificial Sequence
<220> FEATURE:
<223> OTHER INFORMATION: Synthetic primer

<400> SEQUENCE: 75
atgatttcac tctcttcttt tcatcc                                        26

<210> SEQ ID NO 76
<211> LENGTH: 30
<212> TYPE: DNA
<213> ORGANISM: Artificial Sequence
<220> FEATURE:
<223> OTHER INFORMATION: Synthetic primer

<400> SEQUENCE: 76
gatttagtgg tggttaatgg tactagatag                                    30

<210> SEQ ID NO 77
<211> LENGTH: 20
<212> TYPE: DNA

```
<213> ORGANISM: Artificial Sequence
<220> FEATURE:
<223> OTHER INFORMATION: Synthetic primer

<400> SEQUENCE: 77
atgctttctc tctcctccac                                                      20

<210> SEQ ID NO 78
<211> LENGTH: 20
<212> TYPE: DNA
<213> ORGANISM: Artificial Sequence
<220> FEATURE:
<223> OTHER INFORMATION: Synthetic primer

<400> SEQUENCE: 78
caaattcgga gacaaattga                                                      20

<210> SEQ ID NO 79
<211> LENGTH: 20
<212> TYPE: DNA
<213> ORGANISM: Artificial Sequence
<220> FEATURE:
<223> OTHER INFORMATION: Synthetic primer

<400> SEQUENCE: 79
tctatccttg catctctcag                                                      20

<210> SEQ ID NO 80
<211> LENGTH: 20
<212> TYPE: DNA
<213> ORGANISM: Artificial Sequence
<220> FEATURE:
<223> OTHER INFORMATION: Synthetic primer

<400> SEQUENCE: 80
tctccaaggg cgagtatgat                                                      20

<210> SEQ ID NO 81
<211> LENGTH: 20
<212> TYPE: DNA
<213> ORGANISM: Artificial Sequence
<220> FEATURE:
<223> OTHER INFORMATION: Synthetic primer

<400> SEQUENCE: 81
cattggttca ggaagtgcaa                                                      20

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
cctttgattc atggcttcgt                                                      20

<210> SEQ ID NO 83
<211> LENGTH: 19
<212> TYPE: DNA
<213> ORGANISM: Artificial Sequence
<220> FEATURE:
<223> OTHER INFORMATION: Synthetic primer

<400> SEQUENCE: 83
tatcaaacga gggcacttc                                                       19
```

```
<210> SEQ ID NO 84
<211> LENGTH: 19
<212> TYPE: DNA
<213> ORGANISM: Artificial Sequence
<220> FEATURE:
<223> OTHER INFORMATION: Synthetic primer

<400> SEQUENCE: 84
gatggtcttt gatagcagc                                          19

<210> SEQ ID NO 85
<211> LENGTH: 23
<212> TYPE: DNA
<213> ORGANISM: Artificial Sequence
<220> FEATURE:
<223> OTHER INFORMATION: Synthetic primer

<400> SEQUENCE: 85
cttttcagtg gaattagccc acc                                     23

<210> SEQ ID NO 86
<211> LENGTH: 24
<212> TYPE: DNA
<213> ORGANISM: Artificial Sequence
<220> FEATURE:
<223> OTHER INFORMATION: Synthetic primer

<400> SEQUENCE: 86
tggaacatta tggaagatat tggg                                    24

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
ggctggaaga gtgatcggag                                         20

<210> SEQ ID NO 88
<211> LENGTH: 22
<212> TYPE: DNA
<213> ORGANISM: Artificial Sequence
<220> FEATURE:
<223> OTHER INFORMATION: Synthetic primer

<400> SEQUENCE: 88
acgctactgt tgagcatctt ca                                      22

<210> SEQ ID NO 89
<211> LENGTH: 56
<212> TYPE: DNA
<213> ORGANISM: Artificial Sequence
<220> FEATURE:
<223> OTHER INFORMATION: Synthetic primer

<400> SEQUENCE: 89
gctgtcaacg atacgctacg taacggcatg acagtgtttt tttttttttt tttttt    56

<210> SEQ ID NO 90
<211> LENGTH: 21
<212> TYPE: DNA
<213> ORGANISM: Artificial Sequence
<220> FEATURE:
```

<223> OTHER INFORMATION: Synthetic primer

<400> SEQUENCE: 90
agctttacct cccaagtcat c                                              21

<210> SEQ ID NO 91
<211> LENGTH: 20
<212> TYPE: DNA
<213> ORGANISM: Artificial Sequence
<220> FEATURE:
<223> OTHER INFORMATION: Synthetic primer

<400> SEQUENCE: 91
ccaagattga caggcgttct                                                20

<210> SEQ ID NO 92
<211> LENGTH: 358
<212> TYPE: PRT
<213> ORGANISM: Artificial Sequence
<220> FEATURE:
<223> OTHER INFORMATION: Synthetic: AtADH2

<400> SEQUENCE: 92

Met Leu Leu His Phe Ser Pro Ala Lys Pro Leu Ile Ser Pro Pro Asn
1               5                   10                  15

Leu Arg Arg Asn Ser Pro Thr Phe Leu Ile Ser Pro Arg Ser Leu
            20                  25                  30

Arg Ile Arg Ala Ile Asp Ala Ala Gln Ile Phe Asp Tyr Glu Thr Gln
        35                  40                  45

Leu Lys Ser Glu Tyr Arg Lys Ser Ser Ala Leu Lys Ile Ala Val Leu
    50                  55                  60

Gly Phe Gly Asn Phe Gly Gln Phe Leu Ser Lys Thr Leu Ile Arg His
65                  70                  75                  80

Gly His Asp Leu Ile Thr His Ser Arg Ser Asp Tyr Ser Asp Ala Ala
                85                  90                  95

Asn Ser Ile Gly Ala Arg Phe Phe Asp Asn Pro His Asp Leu Cys Glu
            100                 105                 110

Gln His Pro Asp Val Val Leu Leu Cys Thr Ser Ile Leu Ser Thr Glu
        115                 120                 125

Ser Val Leu Arg Ser Phe Pro Phe Gln Arg Leu Arg Arg Ser Thr Leu
    130                 135                 140

Phe Val Asp Val Leu Ser Val Lys Glu Phe Pro Lys Ala Leu Phe Ile
145                 150                 155                 160

Lys Tyr Leu Pro Lys Glu Phe Asp Ile Leu Cys Thr His Pro Met Phe
                165                 170                 175

Gly Pro Glu Ser Gly Lys His Ser Trp Ser Gly Leu Pro Phe Val Tyr
            180                 185                 190

Asp Lys Val Arg Ile Gly Asp Ala Ala Ser Arg Gln Glu Arg Cys Glu
        195                 200                 205

Lys Phe Leu Arg Ile Phe Glu Asn Glu Gly Cys Lys Met Val Glu Met
    210                 215                 220

Ser Cys Glu Lys His Asp Tyr Tyr Ala Ala Gly Ser Gln Phe Val Thr
225                 230                 235                 240

His Thr Met Gly Arg Val Leu Glu Lys Tyr Gly Val Glu Ser Ser Pro
                245                 250                 255

Ile Asn Thr Lys Gly Tyr Glu Thr Leu Leu Asp Leu Val Glu Asn Thr
            260                 265                 270

```
Ser Ser Asp Ser Phe Glu Leu Phe Tyr Gly Leu Phe Met Tyr Asn Pro
            275                 280                 285

Asn Ala Leu Glu Gln Leu Glu Arg Leu Asp Met Ala Phe Glu Ser Val
        290                 295                 300

Lys Lys Glu Leu Phe Gly Arg Leu His Gln Gln Tyr Arg Lys Gln Met
305                 310                 315                 320

Phe Gly Gly Glu Val Gln Ser Pro Lys Lys Thr Gln Lys Leu Leu
                325                 330                 335

Asn Asp Gly Gly Val Val Pro Met Asn Asp Ile Ser Ser Ser Ser
                340                 345                 350

Ser Ser Ser Ser Ser Ser
            355
```

<210> SEQ ID NO 93
<211> LENGTH: 311
<212> TYPE: PRT
<213> ORGANISM: Artificial Sequence
<220> FEATURE:
<223> OTHER INFORMATION: Synthetic: AaPDH

<400> SEQUENCE: 93

```
Met Ala Ile Leu Ser Ser Met Phe Asn Pro Ser Pro Pro Gln Gly Phe
1               5                   10                  15

Cys Lys Lys Asn Ile Ile Lys Ile Leu Lys Ser Leu Ser Met Gln Asn
            20                  25                  30

Val Leu Ile Val Gly Val Gly Phe Met Gly Gly Ser Phe Ala Lys Ser
        35                  40                  45

Leu Arg Arg Ser Gly Phe Lys Gly Lys Ile Tyr Gly Tyr Asp Ile Asn
    50                  55                  60

Pro Glu Ser Ile Ser Lys Ala Val Asp Leu Gly Ile Ile Asp Glu Gly
65                  70                  75                  80

Thr Thr Ser Ile Ala Lys Val Glu Asp Phe Ser Pro Asp Phe Val Met
                85                  90                  95

Leu Ser Ser Pro Val Arg Thr Phe Arg Glu Ile Ala Lys Lys Leu Ser
            100                 105                 110

Tyr Ile Leu Ser Glu Asp Ala Thr Val Thr Asp Gln Gly Ser Val Lys
        115                 120                 125

Gly Lys Leu Val Tyr Asp Leu Glu Asn Ile Leu Gly Lys Arg Phe Val
130                 135                 140

Gly Gly His Pro Ile Ala Gly Thr Glu Lys Ser Gly Val Glu Tyr Ser
145                 150                 155                 160

Leu Asp Asn Leu Tyr Glu Gly Lys Lys Val Ile Leu Thr Pro Thr Lys
                165                 170                 175

Lys Thr Asp Lys Lys Arg Leu Lys Leu Val Lys Arg Val Trp Glu Asp
            180                 185                 190

Val Gly Gly Val Val Glu Tyr Met Ser Pro Glu Leu His Asp Tyr Val
        195                 200                 205

Phe Gly Val Val Ser His Leu Pro His Ala Val Ala Phe Ala Leu Val
    210                 215                 220

Asp Thr Leu Ile His Met Ser Thr Pro Glu Val Asp Leu Phe Lys Tyr
225                 230                 235                 240

Pro Gly Gly Gly Phe Lys Asp Phe Thr Arg Ile Ala Lys Ser Asp Pro
                245                 250                 255

Ile Met Trp Arg Asp Ile Phe Leu Glu Asn Lys Glu Asn Val Met Lys
            260                 265                 270
```

```
Ala Ile Glu Gly Phe Glu Lys Ser Leu Asn His Leu Lys Glu Leu Ile
            275                 280                 285

Val Arg Glu Ala Glu Glu Leu Val Glu Tyr Leu Lys Glu Val Lys
        290                 295                 300

Ile Lys Arg Met Glu Ile Asp
305                 310

<210> SEQ ID NO 94
<211> LENGTH: 279
<212> TYPE: PRT
<213> ORGANISM: Artificial Sequence
<220> FEATURE:
<223> OTHER INFORMATION: Synthetic: SyADH

<400> SEQUENCE: 94

Met Lys Ile Gly Val Val Gly Leu Gly Leu Ile Gly Ala Ser Leu Ala
1               5                   10                  15

Gly Asp Leu Arg Arg Gly His Tyr Leu Ile Gly Val Ser Arg Gln
            20                  25                  30

Gln Ser Thr Cys Glu Lys Ala Val Glu Arg Gln Leu Val Asp Glu Ala
            35                  40                  45

Gly Gln Asp Leu Ser Leu Leu Gln Thr Ala Lys Ile Ile Phe Leu Cys
    50                  55                  60

Thr Pro Ile Gln Leu Ile Leu Pro Thr Leu Glu Lys Leu Ile Pro His
65                  70                  75                  80

Leu Ser Pro Thr Ala Ile Val Thr Asp Val Ala Ser Val Lys Thr Ala
                85                  90                  95

Ile Ala Glu Pro Ala Ser Gln Leu Trp Ser Gly Phe Ile Gly Gly His
            100                 105                 110

Pro Met Ala Gly Thr Ala Ala Gln Gly Ile Asp Gly Ala Glu Glu Asn
        115                 120                 125

Leu Phe Val Asn Ala Pro Tyr Val Leu Thr Pro Thr Glu Tyr Thr Asp
    130                 135                 140

Pro Glu Gln Leu Ala Cys Leu Arg Ser Val Leu Glu Pro Leu Gly Val
145                 150                 155                 160

Lys Ile Tyr Leu Cys Thr Pro Ala Asp His Asp Gln Ala Val Ala Trp
                165                 170                 175

Ile Ser His Leu Pro Val Met Val Ser Ala Ala Leu Ile Gln Ala Cys
            180                 185                 190

Ala Gly Glu Lys Asp Gly Asp Ile Leu Lys Leu Ala Gln Asn Leu Ala
        195                 200                 205

Ser Ser Gly Phe Arg Asp Thr Ser Arg Val Gly Gly Asn Pro Glu
    210                 215                 220

Leu Gly Thr Met Met Ala Thr Tyr Asn Gln Arg Ala Leu Leu Lys Ser
225                 230                 235                 240

Leu Gln Asp Tyr Arg Gln His Leu Asp Gln Leu Ile Thr Leu Ile Ser
                245                 250                 255

Asn Gln Gln Trp Pro Glu Leu His Arg Leu Leu Gln Gln Thr Asn Gly
            260                 265                 270

Asp Arg Asp Lys Tyr Val Glu
        275
```

AROGENATE DEHYDROGENASE POLYNUCLEOTIDES, POLYPEPTIDES AND METHODS OF USING THE SAME

CROSS-REFERENCE TO RELATED PATENT APPLICATIONS

The present application claims the benefit of priority to U.S. Provisional Patent Application No. 62/459,798, filed on Feb. 16, 2017, the content of which is incorporated herein by reference in its entirety.

STATEMENT REGARDING FEDERALLY SPONSORED RESEARCH

This invention was made with United States government support under grant number 2015-67013-22955 awarded by the US Department of Agriculture, National Institute of Food and Agriculture. The government has certain rights in this invention.

SEQUENCE LISTING

This application is being filed electronically via EFS-Web and includes an electronically submitted Sequence Listing in .txt format. The .txt file contains a sequence listing entitled "2024-06-19_960296-02416_ST25_Replacement.txt," which was created on Jun. 19, 2024, and is 129,437 bytes in size. The Sequence Listing contained in this .txt file is part of the specification and is hereby incorporated by reference herein in its entirety.

INTRODUCTION

Plants synthesize numerous specialized metabolites (also known as secondary metabolites), which play crucial roles in plant adaptation. In contrast to well-documented diversification of plant enzymes directly involved in specialized metabolism, relatively little is known about the evolution of primary metabolic enzymes that provide precursors to the production of various specialized metabolites.

L-Tyrosine (Tyr) is an aromatic amino acid required for protein biosynthesis in all organisms; however, it is synthesized de novo only in bacteria, fungi and plants, but not in animals. Consequently, animals have to consume Tyr, or L-phenylalanine (Phe) that can be hydroxylated to Tyr. Besides protein biosynthesis, plants also use Tyr to produce a diverse array of specialized metabolites that are important for defense (e.g. dhurrin), antioxidants (e.g. tocopherols), and pollinator attraction (e.g., betalains). Notably, humans have a long history of utilizing Tyr-derived specialized metabolites, such as the psychedelic alkaloid mescaline derived from the cactus *Lophophora williamsii* and the analgesic morphine derived from *Papaver somniferum* (opium poppy).

Tyr is synthesized from prephenate, which is converted from the final product of the shikimate pathway, chorismate. In most bacteria and fungi, prephenate is oxidatively decarboxylated by prephenate dehydrogenase (TyrA$_p$/PDH, hereafter referred only as PDH; EC 1.3.1.12) to produce 4-hydroxyphenylpyruvate (HPP), which is subsequently transaminated to Tyr (See, e.g., FIG. 1). On the other hand, most plants first transaminate prephenate into arogenate and subsequently decarboxylate into Tyr by arogenate dehydrogenase (TyrA$_a$/ADH, hereafter referred only as ADH; EC 1.3.1.78), both steps occurring in the plastids. The Tyr pathway is usually highly regulated at PDH and ADH. These homologous enzymes are strongly feedback inhibited by Tyr and control carbon flow between the two competing Tyr and Phe pathways. A recent report showed that, in addition to plastidic ADH enzymes, some plants possess a PDH enzyme(s) that is not inhibited by Tyr and is localized to the cytosol. Clearly, there is evolutionary variation in the Tyr pathway(s) in different plant lineages that warrants investigation. In addition, the contribution of Tyr biosynthesis and its regulation to the generation of Tyr-derived plant natural products is currently unknown.

Betalains are a class of pigments that, within the flowering plants, occur exclusively in the order Caryophyllales where they replace the otherwise ubiquitous anthocyanins. Within Caryophyllales, the majority of families are betalain pigmented. In two families, Molluginaceae and Caryophyllaceae, however, evolutionary reversions from betalain to anthocyanin pigmentation have occurred, highlighting the fact that these two classes of water-soluble pigments have never been found in the same organism. Betalains and anthocyanins are synthesized from Tyr and Phe, respectively, but have similar chemical properties and physiological functions in pollinator attraction and stress tolerance. Betalains are also used as a natural food dye (E162) and have anticancer and antidiabetic properties. Furthermore, intermediates in the betalain pathway are important pharmaceuticals [e.g. L-dihydroxyphenylalanine (L-DOPA) for the treatment of Parkinson's disease) or are substrates for other pharmaceutical agents (e.g. the production of dopamine and isoquinoline alkaloids such as morphine). Consequently, understanding the coordinated regulation of Tyr and betalain biosynthesis has the potential to enhance the production of Tyr, and the yield of Tyr-derived plant natural products important for human health and nutrition.

SUMMARY

In one aspect, ADH polynucleotides encoding ADH polypeptides are provided. The polynucleotides may encode a polypeptide having at least 50%, 55%, 60%, 65%, 70%, 75%, 80%, 85%, 90%, 95%, or 99% sequence identity to any one of the polypeptides of SEQ ID NOS: 1-20, 43, 45, or 47. SEQ ID NOS: 1-20, 43, 45, or 47 are polypeptide sequences of ADHα and ADHβ polypeptides identified in W357B red beet variety, Big Buck sugar beet variety, Touch Stone yellow beet variety, Blankoma white beet variety, Sea beet PI562585 variety, and other Caryophyllales species.

In another aspect, constructs are provided. The constructs may include a heterologous promoter operably linked to any one of the polynucleotides described herein.

In a further aspect, vectors including any of the constructs or polynucleotides described herein are provided.

In another aspect, cells including any of the polynucleotides, constructs, or vectors described herein are provided.

In a further aspect, plants including any of the polynucleotides, constructs, vectors, or cells described herein are also provided.

In a still further aspect, methods for increasing production of at least one product of the tyrosine or HPP pathways in a cell are provided. The methods may include introducing any of the polynucleotides, constructs, or vectors described herein into the cell. Optionally, the methods may further include purifying the product of the tyrosine or HPP pathways from the cells.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-1D shows *Beta vulgaris* have two ADH enzymes localized in the plastids. FIG. 1A shows tyrosine and betalain biosynthetic pathways in plants. L-Tyrosine (Tyr) can be synthesized from prephenate via arogenate dehydrogenase (ADH/TyrA$_a$) or prephenate dehydrogenase (PDH/TyrA$_p$). Tyr is exported from the plastid to cytosol and then converted to L-dihydroxyphenylalanine (L-DOPA) by CYP76AD1α, CYP76AD5, and CYP76AD6 (CYP76AD1α/5/6). L-DOPA is then eventually converted to betalains, red betacyanins and yellow betaxanthins. Biosynthesis of Tyr competes for arogenate or prephenate substrate with that of L-phenylalanine (Phe), the precursor of anthocyanins. Dashed lines denote feedback regulation by Tyr. DODA, L-DOPA dioxygenase. FIG. 1B is a graph showing arogenate substrate was incubated with the purified recombinant enzymes of BvADHα or BvADHβ together with NADP$^+$ cofactor and the production of Tyr was analyzed. The High Pressure Liquid Chromatography (HPLC) traces were offset for presentation. *Arabidopsis thaliana* ADH2 (AtADH2) was used as a control for the ADH assay. In FIG. 1C green fluorescence protein (GFP) was fused at the C-terminal of BvADHα and BvADHβ and transiently expressed in *Arabidopsis* protoplasts. Free GFP and GFP-fused *Arabidopsis* ADH2 (AtADH2) were used as controls for cytosolic and plastidic localization, respectively. Representative images show GFP fluorescence and chlorophyll autofluorescence. Scale bars, 10 μm. FIG. 1D is a set of graphs showing expression levels of BvADHα and BvADHβ were compared with those of betalain pathway genes in the cotyledon and hypocotyl of 7 day-old sugar beet and red beet (W357B). Asterisks indicate significant differences between the two genotypes (p<0.05, Student's t-test). Bars represent percent expression relative to the sample with the highest expression. Data are means of three biological replicates±s.e.m. N.D., not detectable.

FIG. 2A shows the location and physical distance of BvADHα and BvADHβ on chromosome 8 of the *B. vulgaris* genome. FIG. 2B shows amino acid identity of ADH and PDH proteins from different plants and bacteria. AaPDH, *Aquifex aeolicus*; AtADH1 and AtADH2, *Arabidopsis thaliana*; GmPDH1, *Glycine max*; EcPDH, *Escherichia coli*; and SyADH, *Synechocysti* ssp. PCC6803.

FIGS. 3A-3C shows ADH but not PDH activity detected from *B. vulgaris* tissues (FIGS. 3A, 3B) or recombinant enzyme (FIG. 3C). Arogenate (FIG. 3A) or prephenate (FIGS. 3B, 3C) substrates were incubated with NADP$^+$ cofactor and desalted protein crude extract (FIGS. 3A, 3B) of beet leaf (L), root/stem (R/S) tissues or recombinant enzyme of BvADHα or BvADHβ together with NADP$^+$ cofactor (FIG. 3C). The production of Tyr (FIG. 3A) or HPP (which was converted to 4-hydroxyphenyllactic acid, HPLA) FIGS. 3B, 3C were analyzed by HPLC. The HPLC traces were offset for presentation. *Arabidopsis thaliana* ADH2 (AtADH2) [17,18] and *Medicago truncatula* PDH (MtPDH) [22] were used as a control for the ADH and PDH assay, respectively.

FIG. 4 shows BvADHs prefer NADP$^+$ over NAD$^+$ as cofactor. ADH activity was analyzed using NADP$^+$ or NADP$^+$ cofactor, which is expressed as the mean of three independent experiments±s.e.m. in nmols-1 mg-1 of protein.

FIGS. 5A1-5D show no amino acid changes were found in the mature protein coding region of BvADHα among different *B. vulgaris* varieties. The BvADHα and BvADHβ genes were sequenced from five different varieties of domesticated (red 1 [W357B], red 2 [Boltardy], sugar, yellow, and white) and a wild beet (sea beet ascension number PI562585). In nucleotide sequence comparisons of BvADHα (FIG. 5A, SEQ ID NOs: 21-25, 44) and BvADHβ (FIG. 5B SEQ ID NOs: 34-38, 48), several single nucleotide polymorphisms (SNPs) were found among varieties. Amino acid sequence alignments of BvADHα (FIG. 5C, SEQ ID NOs: 1-5, 43) and BvADHβ (FIG. 5D, SEQ ID NOs: 14-18, 47), however, showed that these SNPs were mostly synonymous (no changes in amino acid), with two exceptions found in the N-terminal predicted chloroplast transit peptide, which was eliminated for recombinant enzyme expression. The predicted chloroplast transit peptide cleavage sites are denoted by triangles.

FIGS. 9A-9B show transgene expression and tyrosine levels of individual leaf samples of infiltrated *Nicotiana benthamiana*. *Agrobacterium tumefaciens* carrying the construct of 35S::GFP, 35S::BvADHα, or 35S::BvADHβ was infiltrated to *Nicotiana benthamiana* leaves (sample names ending with G, a, and b, respectively). 1a-1 and 1a-2 are technical replicates of the same leaf infiltrated with 35S::BvADHα, so do 1b-1 and 1b-2 for 35S::BvADHβ. FIG. 9A shows expression of respective transgenes shown by RTPCR. (+) denotes a positive control using the original plasmid as a template, while (−) indicates a negative control cDNA from a leaf area without infiltration. (−RT) is an additional negative control without reverse transcriptase to detect genomic DNA contamination. FIG. 9B shows tyrosine contents of individual samples. Two technical replicates showed very similar results. Means±s.e.m. of Tyr and other amino acids analysis are shown in FIGS. 10A-10B and Table 2.

FIGS. 11A-11C show phylogenetic distribution of ADHα in Caryophyllales. FIG. 11A shows maximum-likelihood phylogeny of ADH genes in Caryophyllales. The blue and pink branches represent anthocyanin and betalain-producing families, respectively, while families with unclear/unidentified pigmentation are shown in gray. Scale bar indicates inferred number of amino acid substitution per site. ADH enzymes characterized in this study are indicated at the end of each branch. FIG. 11B shows presence and absence of BvADHα and BvADHβ orthologs detected from genome or transcriptome data was mapped to the family-level phylogenetic tree of the Caryophyllales order. Filled circles denote that corresponding orthologs were detected in all species within the family, whereas partially filled circles indicate that the filled portion of the species within each family had corresponding orthologs. Open circles denote no corresponding orthologs were detected. Dark lines on the left, labeled "ADHα/β" and "CYP76AD1α/β DODAα/β," indicate estimating timings of duplication events of ADH and betalain pathway genes (CYP76AD1 and DODA). Dash lines (–) represent families with no available transcriptomic or genomic data. FIG. 11C shows Tyr contents analyzed in various Caryophyllales species. *Arabidopsis thaliana* was used as outgroup. Young leaf tissues were used for all samples except a Cactaceae species, in which flowers were used to avoid succulent tissues. Asterisks denote significant difference from *Arabidopsis* (p<0.05) based on fixed effect model (see method). Also, a statistical analysis based on the mixed effect model showed significant differences between two groups, plants with and without ADHα (p<0.0001). Bars represent means±s.e.m. (n=four biological replicates).

FIGS. 14A and 14B show ADHα orthologs of Caryophyllaceae (branches below the dashed lines, designated as test branches in RELAX analysis, Table 5), as compared to those betalain-producing Caryophyllales species (branches above the dashed lines, designated as reference branches in RELAX analysis, Table 5). The test branches showed no obvious acceleration of substitution in their coding sequences (CDS, FIG. 14A), whereas there was apparent acceleration in their peptide sequences (FIG. 14B). Tips marked with '@' are from assembled transcriptomes. The rest of the sequences are from PCR and Sanger sequencing from DNA (*H. latifolia*, *S. marina*, and *P. polygonifolia*) or RNA.

DETAILED DESCRIPTION

Figure 1A:
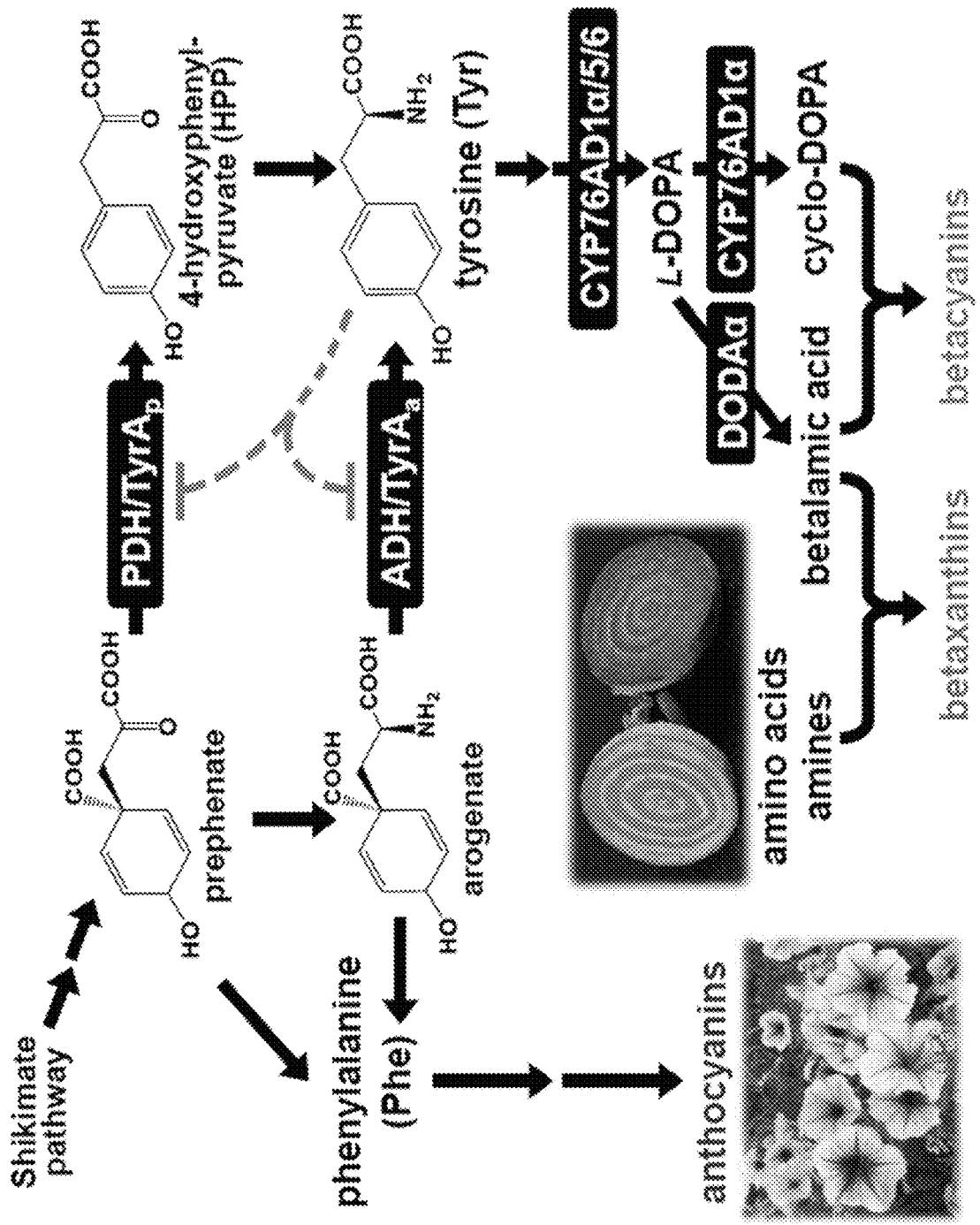

The present inventors investigated the Tyr biosynthetic pathway and its regulation in table beet (*Beta vulgaris* L.), which produces high levels of betalains. Using comparative genomics, biochemical, and cellular analyses, they found that *B. vulgaris* possesses two paralogous genes encoding two ADH enzymes, which they named ADHα and ADHβ. Interestingly, ADHα but not ADHβ exhibited relaxed sensitivity to Tyr inhibition. Although the present inventors recently reported that legume PDH enzymes are also Tyr insensitive, BvADHα and legume PDHs have two major differences. First, legume PDHs are localized in the cytosol, whereas BvADHα (and BvADHβ) was targeted to the plastids. Second, legume PDHs completely lost Tyr sensitivity but BvADHα was still inhibited by Tyr at higher concentrations.

Other insensitive ADH/PDH enzymes have been previously found in microorganisms and the structural analyses of Tyr sensitive and insensitive enzymes identified histidine 217 as a possible residue responsible for its Tyr sensitivity. However, the corresponding histidine residue was still present in BvADHα, suggesting that different mechanisms, and as yet unidentified residues, are involved in the relaxed Tyr sensitivity of BvADHα. The identified BvADHα and other Caryophyllales ADHα enzymes may be introduced into various types of cells to deregulate Tyr biosynthesis and redirect carbon flow from Phe to Tyr, to improve the production of Tyr-derived products (e.g., vitamin E, isoquinoline alkaloids including morphine).

ADH polynucleotides encoding ADH polypeptides are provided. The polynucleotides may encode a polypeptide having at least 50%, 55%, 60%, 65%, 70%, 75%, 80%, 85%, 90%, 95%, or 99% sequence identity to any one of the polypeptides of SEQ ID NOS: 1-20, 43, 45, or 47. SEQ ID NOS: 1-20, 43, 45, or 47 are polypeptide sequences of ADHα and ADHβ polypeptides identified in W357B red beet variety, Big Buck sugar beet variety, Touch Stone yellow beet variety, Blankoma white beet variety, Sea beet PI562585 variety, and other Caryophyllales species.

As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of natural or synthetic origin (which may be single-stranded or double-stranded and may represent the sense or the antisense strand). The polynucleotides may be cDNA or genomic DNA.

In some embodiments, the polynucleotides of the present invention may include any one of the polynucleotide sequences of SEQ ID NOS: 21-40, 44, 46, or 48 or a polynucleotide having at least 50%, 55%, 60%, 65%, 70%, 75%, 80%, 85%, 90%, 95%, or 99% sequence identity to any one of the polynucleotide sequences of SEQ ID NOs: 21-40, 44, 46, or 48. SEQ ID NOS: 21-40, 44, 46, or 48 are polynucleotide sequences of ADHα and ADHβ polynucleotides that encode the ADHα and ADHβ polypeptides of SEQ ID NOS: 1-20, 43, 45, or 47 and identified in W357B red beet variety, Big Buck sugar beet variety, Touch Stone yellow beet variety, Blankoma white beet variety, Sea beet PI562585 variety, and other plant species. The polynucleotide sequences of SEQ ID NO: 21-40, 44, 46, or 48 are cDNA sequences.

Polynucleotides homologous to the polynucleotides described herein are also provided. Those of skill in the art understand the degeneracy of the genetic code and that a variety of polynucleotides can encode the same polypeptide. In some embodiments, the polynucleotides (i.e., polynucleotides encoding the ADH polypeptides) may be codon-optimized for expression in a particular cell including, without limitation, a plant cell, bacterial cell, or fungal cell. While particular polynucleotide sequences which are found in plants are disclosed herein any polynucleotide sequences may be used which encode a desired form of the polypeptides described herein. Thus, non-naturally occurring sequences may be used. These may be desirable, for example, to enhance expression in heterologous expression systems of polypeptides or proteins. Computer programs for generating degenerate coding sequences are available and can be used for this purpose. Pencil, paper, the genetic code, and a human hand can also be used to generate degenerate coding sequences.

Regarding ADH polypeptides, the phrases "% sequence identity," "percent identity," or "% identity" refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Polypeptide sequence identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Suitably, the polypeptides encoded by the polynucleotides provided herein are not sensitive to tyrosine inhibition. The polypeptide is considered to not be sensitive, i.e. to lack sensitivity to tyrosine feedback inhibition, if at least 50% of the activity in the absence of tyrosine is maintained in the presence of 1-100 µM (or any range therein) tyrosine. The polypeptide is considered to lack tyrosine feedback sensitivity if at least 40% of the activity in the absence of tyrosine is maintained in the presence of 1 mM tyrosine.

The ADH polypeptides disclosed herein may include "variant" polypeptides, "mutants," and "derivatives thereof." As used herein the term "wild-type" is a term of the art understood by skilled persons and means the typical form of a polypeptide as it occurs in nature as distinguished from variant or mutant forms. As used herein, a "variant, "mutant," or "derivative" refers to a polypeptide molecule having an amino acid sequence that differs from a reference protein or polypeptide molecule. A variant or mutant may have one or more insertions, deletions, or substitutions of an amino acid residue relative to a reference molecule. For example, a ADH polypeptide mutant or variant may have one or more insertions, deletions, or substitution of at least one amino acid residue relative to the ADH "wild-type" polypeptides disclosed herein. The polypeptide sequences of the "wild-type" ADH polypeptides from beets and other plant species are presented in SEQ ID NOS: 1-20, 43, 45, or 47. These sequences may be used as reference sequences.

The ADH polypeptides provided herein may be full-length polypeptides or may be fragments of the full-length polypeptide. As used herein, a "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide. A fragment of an ADH polypeptide may comprise or consist essentially of a contiguous portion of an amino acid sequence of the full-length ADH polypeptide (See SEQ ID NOS: 1-20, 43, 45, or 47). A fragment may include an N-terminal truncation, a C-terminal truncation, or both truncations relative to the full-length ADH polypeptide.

A "deletion" in an ADH polypeptide refers to a change in the amino acid sequence resulting in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide).

"Insertions" and "additions" in an ADH polypeptide refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A variant of an ADH polypeptide may have N-terminal insertions, C-terminal insertions, internal insertions, or any combination of N-terminal insertions, C-terminal insertions, and internal insertions.

The amino acid sequences of the ADH polypeptide variants, mutants, derivatives, or fragments as contemplated herein may include conservative amino acid substitutions relative to a reference amino acid sequence. For example, a variant, mutant, derivative, or fragment polypeptide may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed variant and fragment ADH polypeptides described herein may have one or more functional or biological activities exhibited by a reference polypeptide (e.g., one or more functional or biological activities exhibited by wild-type ADH polypeptides (i.e, SEQ ID NOS: 1-20, 43, 45, or 47). Suitably, the disclosed variant or fragment ADH polypeptides retain at least 20%, 40%, 60%, 80%, or 100% of the arogenate dehydrogenase activity of the reference polypeptide (i.e., SEQ ID NOS: 1-20, 43, 45, or 47). As used herein, a "functional fragment" of an ADH polypeptide is a fragment of, for example, one of the polypeptides of SEQ ID NOS: 1-20 that retains at least 20%, 40%, 60%, 80%, or 100% of the arogenate dehydrogenase activity of the full-length ADH polypeptide. Exemplary functional fragments of the ADH polypeptides disclosed herein may include, for example, fragment ADH polypeptides of the polypeptides of SEQ ID NOS: 1-20 that lack the N-terminal plastid transit peptide within these sequences. The N-terminal plastid transit peptide (identified by SEQ ID NO: 41 for BvADHα and SEQ ID NO: 42 for BvADHβ) functions to localize the ADH polypeptides of SEQ ID NOS: 1-20, 43, 45, or 47 to the plastid in plant cells. This function is not necessarily required for the ADH polypeptides arogenate dehydrogenase activity and thus may be removed from SEQ ID NOS: 1-20, 43, 45, or 47.

FIGS. 5A1-5D and FIG. 15 show sequence alignments including some of the ADH polypeptides disclosed as SEQ ID NOs: 1-20. Based on these alignments it becomes immediately apparent to a person of ordinary skill in the art that various amino acid residues may be altered (i.e. substituted, deleted, etc.) without substantially affecting the arogenate dehydrogenase activity of the polypeptide. For example, a person of ordinary skill in the art would appreciate that substitutions in a reference ADH polypeptide could be based on alternative amino acid residues that occur at the corresponding position in other ADH polypeptides from other species. SEQ ID NOS: 1-20, 43, 45, or 47 may also include ADH polypeptides that are not shown in FIGS. 5 and 15. A person of ordinary skill in the art, however, could easily align these polypeptide sequences with the polypeptide sequences shown in FIGS. 5 and 15 to determine what additional variants could be made to the ADH polypeptides.

In another aspect of the present invention, constructs are provided. As used herein, the term "construct" refers to recombinant polynucleotides including, without limitation, DNA and RNA, which may be single-stranded or double-stranded and may represent the sense or the antisense strand. Recombinant polynucleotides are polynucleotides formed by laboratory methods that include polynucleotide sequences derived from at least two different natural sources or they may be synthetic. Constructs thus may include new modifications to endogenous genes introduced by, for example, genome editing technologies. Constructs may also include recombinant polynucleotides created using, for example, recombinant DNA methodologies.

The constructs provided herein may be prepared by methods available to those of skill in the art. Notably each of the constructs claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The constructs provided herein may include a heterologous promoter operably linked to any one of the polynucleotides described herein. As used herein, the terms "heterologous promoter," "promoter," "promoter region," or "promoter sequence" refer generally to transcriptional regulatory regions of a gene, which may be found at the 5' or 3' side of the ADH polynucleotides described herein, or within the coding region of the ADH polynucleotides, or within introns in the ADH polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the disclosed ADH polynucleotides are operably connected to the heterologous promoter. As used herein, a polynucleotide is "operably connected" or "operably linked" when it is placed into a functional relationship with a second polynucleotide sequence. For instance, a promoter is operably linked to an ADH polynucleotide if the promoter is connected to the ADH polynucleotide such that it may affect transcription of the ADH polynucleotides. In various embodiments, the ADH polynucleotides may be operably linked to at least 1, at least 2, at least 3, at least 4, at least 5, or at least 10 promoters.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be a plant, animal, bacterial, fungal, or synthetic promoter. Suitable promoters for expression in plants include, without limitation, the 35S promoter of the cauliflower mosaic virus, ubiquitine, tCUP cryptic constitutive promoter, the Rsyn7 promoter, pathogen-inducible promoters, the maize In2-2 promoter, the tobacco PR-1a promoter, glucocorticoid-inducible promoters, estrogen-inducible promoters, tetracycline-inducible promoters, tetracycline-repressible promoters, and promoters for monocots like actin. Other promoters include the T3, T7 and SP6 promoter sequences, which are often used for in vitro transcription of RNA. In mammalian cells, typical promoters include, without limitation, promoters for Rous sarcoma virus (RSV), human immunodeficiency virus (HIV-1), cytomegalovirus (CMV), SV40 virus, and the like as well as the translational elongation factor EF-Iα promoter or ubiquitin promoter. Those of skill in the art are familiar with a wide variety of additional promoters for use in various cell types. In some embodiments, the heterologous promoter includes a plant promoter, either endogenous to the plant host or heterologous.

Vectors including any of the constructs or polynucleotides described herein are provided. The term "vector" is intended to refer to a polynucleotide capable of transporting another polynucleotide to which it has been linked. In some embodiments, the vector may be a "plasmid," which refers to a circular double-stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome, such as some viral vectors or transposons. Plant mini-chromosomes are also included as vectors. Vectors may carry genetic elements, such as those that confer resistance to certain drugs or chemicals.

Cells including any of the polynucleotides, constructs, or vectors described herein are provided. Suitable "cells" that may be used in accordance with the present invention include eukaryotic or prokaryotic cells. Suitable eukaryotic cells include, without limitation, plant cells, fungal cells, and animal cells. Suitable prokaryotic cells include, without limitation, gram-negative and gram-positive bacterial species. In some embodiments, the cell is a plant cell such as, without limitation, a soybean plant cell, a mung bean plant cell, an opium poppy plant cell, a quinoa plant cell, an alfalfa plant cell, a rice plant cell, a wheat plant cell, a corn plant cell, a sorghum plant cell, a barley plant cell, a millet plant cell, an oat plant cell, a rye plant cell, a rapeseed plant cell, a beet plant cell, and a miscanthus plant cell. In some embodiments, the cell is a bacterial or fungal cell.

Plants including any of the polynucleotides, constructs, vectors, or cells described herein are also provided. Suitable plants may include, without limitation, a beet plant, a soybean plant, a mung bean plant, an opium poppy plant, a quinoa plant, an alfalfa plant, a rice plant, a wheat plant, a corn plant, a sorghum plant, a barley plant, a millet plant, an oat plant, a rye plant, and a rapeseed plant as well as perennial grasses such as a miscanthus plant. For example, ADH polynucleotides encoding any one of the ADH polypeptides of SEQ ID NOS: 1-20, 43, 45, or 47 may be used to generate transgenic plants.

Portions or parts of these plants are also useful and provided. Portions and parts of plants includes, without limitation, plant cells, plant tissue, plant progeny, plant asexual propagates, plant seeds. The plant may be grown from a seed comprising transgenic cells or may be grown by any other means available to those of skill in the art. Chimeric plants comprising transgenic cells are also provided and encompassed.

As used herein, a "plant" includes any portion of the plant including, without limitation, a whole plant, a portion of a plant such as a part of a root, leaf, stem, seed, pod, flower, cell, tissue plant germplasm, asexual propagate, or any progeny thereof. Germplasm refers to genetic material from an individual or group of individuals or a clone derived from a line, cultivar, variety or culture. Plant refers to whole plants or portions thereof including, without limitation, plant cells, plant protoplasts, plant tissue culture cells or calli. For example, a beet plant refers to whole beet plant or portions thereof including, without limitation, beet plant cells, beet plant protoplasts, beet plant tissue culture cells or calli. A plant cell refers to cells harvested or derived from any portion of the plant or plant tissue culture cells or calli.

Methods for increasing production of at least one product of the tyrosine or HPP pathways in a cell are provided. The methods may include introducing any of the polynucleotides, constructs, or vectors described herein into the cell. Suitable products of the tyrosine or HPP pathways include, without limitation, vitamin E, plastoquinone, a cyanogenic glycoside, a benzylisoquinoline alkaloid, rosmarinic acid, betalains, suberin, mescaline, morphine, salidroside, a phenylpropanoid compound, dhurrin, a tocochromanol, ubiquinone, lignin, a catecholamine such as epinephrine (adrenaline) or dopamine (i.e., L-dihydroxyphenylalanine (L-DOPA)), melanin, an isoquinoline alkaloid, hydroxycinnamic acid amide (HCAA), an amaryllidaceae alkaloid, hordenine, hydroxycinnamate, hydroxylstyrene, or tyrosine. Phenylpropanoid compounds (i.e., lignin, tannins, flavonoids, stilbene) may be produced from tyrosine, for example, by combining the polypeptides disclosed herein with a tyrosine-ammonia lyase (TAL) or by using cells that naturally have a TAL such as grass cells.

As used herein, "introducing" describes a process by which exogenous polynucleotides (e.g., DNA or RNA) are introduced into a recipient cell. Methods of introducing polynucleotides into a cell are known in the art and may include, without limitation, microinjection, transformation, and transfection methods. Transformation or transfection may occur under natural or artificial conditions according to various methods well known in the art, and may rely on any known method for the insertion of foreign nucleic acid sequences into a host cell. The method for transformation or transfection is selected based on the type of host cell being transformed and may include, but is not limited to, the floral dip method, *Agrobacterium*-mediated transformation, bacteriophage or viral infection, electroporation, heat shock, lipofection, and particle bombardment. Microinjection of polynucleotides may also be used to introduce polynucleotides into cells.

In some embodiments, the present methods may further include purifying the product of the tyrosine or HPP pathways from the cells. As used herein, the term "purifying" is used to refer to the process of ensuring that the product of the tyrosine or HPP pathways is substantially or essentially free from cellular components and other impurities. Purification of products of the tyrosine or HPP pathways is typically performed using analytical chemistry techniques such as high performance liquid chromatography (HPLC)

and other chromatographic techniques. Methods of purifying such products are well known to those skilled in the art. A "purified" product of the tyrosine or HPP pathways means that the product is at least 85% pure, more preferably at least 95% pure, and most preferably at least 99% pure.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Relaxation of Tyrosine Pathway Regulation Underlies the Evolution of Betalain Pigmentation in Caryophyllales This Example is based on data reported in Lopez-Nieves et al., "Relaxation of Tyrosine Pathway Regulation Underlies the Evolution of Betalain Pigmentation in Caryophyllales," *New Phytologist*, 217(2): 896-908 (2018), the contents of which (including all supplemental data, figures, and associated materials) is incorporated herein by reference.

Summary

Diverse natural products are synthesized in plants by specialized metabolic enzymes, which are often lineage-specific and derived from gene duplication followed by functional divergence. However, little is known about the contribution of primary metabolism to the evolution of specialized metabolic pathways.

Betalain pigments, uniquely found in the plant order Caryophyllales, are synthesized from the aromatic amino acid L-tyrosine (Tyr) and replaced the otherwise ubiquitous phenylalanine-derived anthocyanins. This study combined biochemical, molecular and phylogenetic analyses and uncovered coordinated evolution of Tyr and betalain biosynthetic pathways in Caryophyllales.

We found that *Beta vulgaris*, which produces high levels of betalains, synthesizes Tyr via plastidic arogenate dehydrogenases (TyrA$_a$/ADH) encoded by two ADH genes (BvADHα and BvADHβ). Unlike BvADHβ and other plant ADHs that are strongly inhibited by Tyr, BvADHα exhibited relaxed sensitivity to Tyr. Also, Tyr-insensitive BvADHα orthologs arose during the evolution of betalain pigmentation in the core Caryophyllales and later experienced relaxed selection and gene loss in lineages that reverted from betalain to anthocyanin pigmentation, such as Caryophyllaceae.

These results suggest that relaxation of Tyr pathway regulation increased Tyr production and contributed to the evolution of betalain pigmentation, highlighting the significance of upstream primary metabolic regulation for the diversification of specialized plant metabolism.

Introduction

Plants synthesize numerous specialized metabolites (also known as secondary metabolites), which play crucial roles in plant adaptation. In contrast to well-documented diversification of plant enzymes directly involved in specialized metabolism (Chen et al., 2011; Mizutani & Ohta, 2010; Moghe & Last, 2015; Pichersky & Lewinsohn, 2011; Weng, 2014), relatively little is known about the evolution of primary metabolic enzymes that provide precursors to the production of various specialized metabolites.

L-Tyrosine (Tyr) is an essential aromatic amino acid required for protein biosynthesis in all organisms; however, it is synthesized de novo only in bacteria, fungi, and plants, but not in animals. Consequently, animals have to consume Tyr or L-phenylalanine (Phe) that can be hydroxylated to Tyr (Pencharz et al., 2007). Besides protein biosynthesis, plants also use Tyr to produce a diverse array of specialized metabolites that are important for defense (e.g. dhurrin, Gleadow & Møller, 2014), stress tolerance (e.g. tocopherols, Mene-Saffrane et al., 2010), and pollinator attraction (e.g., betalains, Tanaka et al., 2008). Notably, humans have a long history of utilizing Tyr-derived specialized metabolites, such as the psychedelic alkaloid mescaline derived from the cactus *Lophophora williamsii* (Ibarra-Laclette et al., 2015) and the analgesic morphine derived from *Papaver somniferum* (opium poppy, Beaudoin & Facchini, 2014; Millgate et al., 2004).

Tyr is synthesized from prephenate, which is converted from the final product of the shikimate pathway, chorismate (Maeda & Dudareva, 2012; Siehl, 1999; Tzin, V. & Galili, 2010). In most bacteria and fungi, prephenate is oxidatively decarboxylated by prephenate dehydrogenase (TyrA$_p$/PDH, hereafter referred only as PDH; EC 1.3.1.12) to 4-hydroxyphenylpyruvate (HPP), which is transaminated to Tyr (Bentley, 1990, FIG. 1A). On the other hand, most plants first transaminate prephenate into arogenate and subsequently decarboxylate into Tyr by arogenate dehydrogenase (TyrA$_a$/ADH, hereafter referred only as ADH; EC 1.3.1.78, Rippert & Matringe, 2002a,b), both steps occurring in the plastids (Dal Cin et al., 2011; Rippert et al., 2009; FIG. 1A). The Tyr pathway is usually highly regulated at PDH and ADH. These homologous enzymes are strongly feedback inhibited by Tyr and control carbon flow between the two competing Tyr and Phe pathways (Gaines et al., 1982; Bentley, 1990; Rippert & Matringe, 2002a,b; FIG. 1B). A recent report showed that, in addition to plastidic ADH enzymes, some plants possess a PDH enzyme(s) that is not inhibited by Tyr and is localized to the cytosol (Rubin & Jensen, 1979; Schenck et al., 2015; 2017; Siehl, 1999). Clearly, there is evolutionary variation in the Tyr pathway(s) in different plant lineages that warrants investigation.

Betalains are a class of Tyr-derived pigments that, within the flowering plants, occur exclusively in the order Caryophyllales where they replace the otherwise ubiquitous anthocyanins (Mabry, 1964; Tanaka et al., 2008). Within Caryophyllales, the majority of families are betalain pigmented. In two families, Molluginaceae and Caryophyllaceae, however, evolutionary reversions from betalain to anthocyanin pigmentation have occurred (Brockington et al., 2015), highlighting the fact that these two classes of water-soluble pigments have never been found in the same organism (Bate-Smith, 1962; Brockington et al., 2011; Clement & Mabry, 1996; Mabry, 1964). Betalains and anthocyanins are synthesized from Tyr and Phe, respectively, but have similar physiological functions in pollinator attraction and stress tolerance (Tanaka et al., 2008). Betalains are also used as a natural food dye (E162) and have anticancer and antidiabetic properties (Khan, 2015; Lee et al., 2014; Neelwarne & Halagur, 2012). Furthermore, intermediates in the betalain pathway are important pharmaceuticals [e.g. L-dihydroxyphenylalanine (L-DOPA) for the treatment of Parkinson's disease] or are substrates for other pharmaceutical agents (e.g. the production of dopamine and isoquinoline alkaloids such as morphine). Consequently, understanding the coordinated regulation of Tyr and betalain biosynthesis has the potential to enhance the production of Tyr, and the yield of Tyr-derived plant natural products important for human health and nutrition.

Betalain biosynthesis starts with hydroxylation of Tyr to L-DOPA by at least three closely related cytochrome P450 enzymes (CYP76AD1, CYP76AD5, and CYP76AD6, FIG. 1A) (Polturak et al., 2016; Sunnadeniya et al., 2016). L-DOPA is further converted into betalamic acid or cyclo-DOPA by L-DOPA dioxygenases (DODA, Christinet et al., 2004; Gandía-Herrero & García-Carmona, 2012) or CYP76AD1 (Hatlestad et al., 2012), respectively (FIG. 1A). Betalamic acid then spontaneously reacts with cyclo-DOPA or amines to produce various forms of betacyanins or betaxanthins, respectively, which are usually further glycosylated. Recent studies found that the two key enzymes within the betalain pathway, DODA, and CYP76AD1, duplicated just prior to the emergence of betalain pigmentation (Brockington et al., 2015). Subsequently, one of the duplicated copies (DODAα and CYP76AD1α) in both genes became specialized for betalain biosynthesis and were lost or downregulated in the anthocyanin-producing families such as Molluginaceae and Caryophyllaceae (Brockington et al., 2015). Despite recent and rapid progress in understanding the betalain pathway enzymes and their evolution, little is known about the regulation of primary Tyr metabolism in relation to the evolution of this novel Tyr-dependent betalain pathway.

Here we first investigated the Tyr biosynthetic pathway and its regulation in table beet (*Beta vulgaris* L.), which produces high levels of betalains (Goldman, 1996). Using comparative genomics, biochemical, and cellular analyses, we found plastidic ADH enzymes from *B. vulgaris* that exhibit relaxed sensitivity to Tyr inhibition in vitro and in vivo. Phylogenetic analysis combined with recombinant enzyme characterization further demonstrated that de-regulated ADH enzymes emerged during the evolution of betalain pigmentations in the core Caryophyllales, and were lost or downregulated following disappearance of betalains. Furthermore, transient expression of the de-regulated ADH in *Nicotiana benthamiana* led to high accumulation of Tyr in planta. The results revealed the important contribution of primary Tyr pathway regulation to the unique evolution of a plant specialized metabolic pathway, betalain biosynthesis.

Materials and Methods

Plant Source and Growth Conditions *B. vulgaris* varieties, red beet (W357B), yellow beet (Touch Stone), and white beet (Blankoma), were provided by Dr. Irwin Goldman from the University of Wisconsin-Madison, Department of Horticulture (Goldman, 1996), whereas sugar beet (Big Buck) and sea beet (PI 562585) were commercial sugar beets obtained from the Heirloom Seeds (West Finley, PA, USA) and the National Plant Germplasm System (NPGS), respectively. Spinach (*Spinacia oleraceae*), Pigeonberry (*Rivina humilis*), four o'clock (*Mirabilis jalapa*), and common purslane (*Portulaca oleracea*) were grown from seed with a growing mix soil (Fafard®, Agawam, MA, USA) in a growth chamber under 12 hr light (100 µE), 22° C. and 60% humidity. After one month of growth, their leaves were harvested for RNA extraction.

Identification and Cloning of ADH Homologs from Caryophyllales

Figures 2A, 2B:
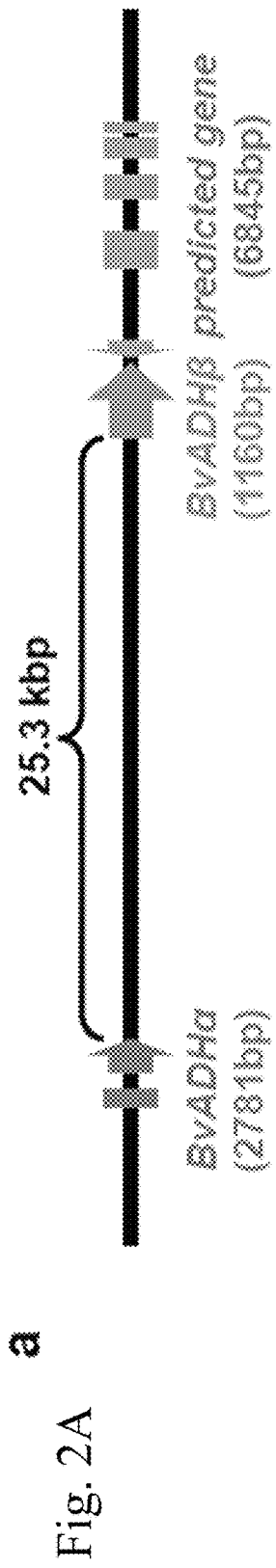
FIGS. 2A-2B show physical location, homology, and phylogeny of BvADHα and BvADHβ.

BLASTP searches were performed using the protein sequences of ADH and PDH enzymes from *A. thaliana* (AtADH1/At5g34930, NP_173023; AtADH2/At1g15710, NP_198343), *Glycine max* (GmPDH, KM507071), *Synechocystis* sp. PCC6803 (SyADH, WP_010872597), *Escherichia coli* (EcPDH, WP_052912694), *Aquifex aeolicus* (AaPDH, WP_010881139) as queries against the sugar beet genome (*Beta vulgaris* molgen.mpg.de/) (FIG. 2B). Potential ADH candidates were identified based on a broad phylogenetic analysis that included various plant ADH and PDH sequences.

Genomic DNA was extracted using Tris-sodium chloride-EDTA/sodium dodecyl sulfate buffer and precipitated with isopropanol and 200 mM ammonium acetate. For RNA isolation, the method described by Wang et al (2011) was used with some modifications. The tissues were ground in a mortar with liquid nitrogen and powder polyvinylpyrrolidone (PVP). After addition of 700 μL fresh pre-warmed lysis buffer (2% CTAB, 2 M NaCl, 100 mM Tris-HCl pH 8, 25 mM EDTA and 5% β-mercaptoethanol), the samples were shaken vigorously for 2 min and incubated in a water bath at 65° C. for 5 min. The RNA was converted into complementary DNA (cDNA) using the High-Capacity cDNA Reverse Transcription Kit (Applied Biotechnology, USA) and SuperScript IV Reverse Transcriptase with oligo $dT_{20}$ primer or random primers (Invitrogen, USA).

Cloning primers were designed with the Invitrogen primer design (lifetechnologies.com) and the PCR In-Fusion® primers designing program (clontech.com, Clontech, Mount View, CA). All ADH candidate genes, except for PoADHα (see below), were PCR amplified from cDNA using gene-specific primers (Table 1) and Phusion DNA polymerase (Thermo, Waltham, MA) with the following conditions: initial denaturation at 95° C. for 5 min, 35 cycles of amplification at 95° C. for 30 s, 58° C. for 30 s, 72° C. for 30 s, with a final extension at 72° C. for 10 min. The PCR fragments were purified using QIAquick gel extraction kit (Qiagen, Valencia, CA) and were inserted into the pGEX-2T vector (GE Healthcare) at EcoRI and BamHI sites using the In-Fusion cloning method (Clontech). PoADHα was gene synthesized (Biomatik, Cambridge, Ontario, Canada) and directly cloned into the same pGEX-2T vector. For generation of His-tagged proteins, the cloned PCR fragments were inserted into the pET28a vector (Novagen, Madison WI, USA) at NdeI and EcoRI site.

TABLE 1

Primers used as indicated in the description and methods

| Species (gene) | Purpose | Primer name | Primer sequence 5' to 3' |
| --- | --- | --- | --- |
| *Beta vulgaris* (BvADHβ) | RT-PCR | pHM0290SLN BvADHβF | GGTTCCGCGTGGATCCCTAACAATTC GCAGCAT (SEQ ID NO: 49) |
| *Beta vulgaris* (BvADHβ) | RT-PCR | pHM0291SLN RBvADHβR | AATTCGGAGACAAATTGAGAATTCAT CGTGACTG (SEQ ID NO: 50) |
| *Beta vulgaris* (BvADHα) | RT-PCR | pHM0372SLN BvADHαF | CTGGTTCCGCGTGGATCCTGCGGTGG AGGTGGTTCG (SEQ ID NO: 51) |
| *Beta vulgaris* (BvADHα) | RT-PCR | pHM0373SLN BvADHαR | GTTAATGGTACTAGATAGGAATTCAT CGTGACTGA (SEQ ID NO: 52) |
| *Arabidopsis thaliana* (AtADH2) | Cloning | pHM0384SLN AtADHαF | CTGGTTCCGCGTGGATCCGCAATCGA CGCCGCCCAA (SEQ ID NO: 53) |
| *Arabidopsis thaliana* (AtADH2) | Cloning | pHM0385SLN AtADHαR | TCATCATCATCATCTTAAGAATTCATC GTGACTGA (SEQ ID NO: 54) |
| *Spinacea oleracea* (SoADHβ) | Cloning | pHM0582SoA DHβF | CTGGTTCCGCGTGGATCCGCCGCTAC CAATACCTCC (SEQ ID NO: 55) |
| *Spinacea oleracea* (SoADHβ) | Cloning | pHM0583SoA DHβR | AATTCAGAGATCAATTGAGAATTCAT CGTGACTGA (SEQ ID NO: 56) |
| *Spinacea oleracea* (SoADHα) | Cloning | pHM0584SoA DHαF | CTGGTTCCGCGTGGATCCTGCGCCGC CTCTGACTCC (SEQ ID NO: 57) |
| *Spinacea oleracea* (SoADHα) | Cloning | pHM0585SoA DHαR | TGGTAATAATTCTAGATAGGAATTCA TCGTGACTGA (SEQ ID NO: 58) |
| *Nepenthes alata* (NaADHβ) | Cloning | pHM0603SLN NaADHF | CTGGTTCCGCGTGGATCCGCCGCGCT GCCAAACGACT (SEQ ID NO: 59) |
| *Nepenthes alata* (NaADHβ) | Cloning | pHM0604SLN NaADHR | AAATGTTGAGAGAAATTGAGAATTCA TCGTGACTGA (SEQ ID NO: 60) |
| *Portulaca oleracea* (PoADHα) | RT-PCR | pHM0609SLN PoADHαAF | CTGGTTCCGCGTGGATCCTGCTCATCA TCATCATCAT (SEQ ID NO: 61) |
| *Portulaca oleracea* (PoADHα) | RT-PCR | pHM0610SLN PoADHαAR | CGTCAACGATAGATCATAGGAATTCA TCGTGACTGA (SEQ ID NO: 62) |
| *Mirabilis jalapa* (MjADHα) | Cloning | pHM0624SLN MjADHαAF | CTGGTTCCGCGTGGATCCATAGCGAT AGTTGGGTTTG (SEQ ID NO: 63) |
| *Mirabilis jalapa* (MjADHα) | Cloning | pHM0625SLN MjADHαAR | TATCAATGGTCGTCGATAGGAATTCA TCGTGACTGA (SEQ ID NO: 64) |
| *Rivina hurndis* (RhADHα) | Cloning | pHM0647SLN RhADHαF | CTGGTTCCGCGTGGATCCTGCACGGC CTTCACTAAAAC (SEQ ID NO: 65) |

TABLE 1-continued

Primers used as indicated in the description and methods

| Species (gene) | Purpose | Primer name | Primer sequence 5' to 3' |
|---|---|---|---|
| Rivina humilis(RhADHα) | Cloning | pHM0648SLN RhADHαR | TCAATGGATCAAAGCGGTAGGAATTC ATCGTGACTGA (SEQ ID NO: 66) |
| Beta vulgaris (BvADHα) | RT-PCR | BvADHα_q_F | TCAAGCTGAGGTTACTTTTGACA (SEQ ID NO: 67) |
| Beta vulgaris (BvADHα) | RT-PCR | BvADHα_q_R | AAGAAGCATGATTTAGTGGTGGT (SEQ ID NO: 68) |
| Beta vulgaris (BvADHβ) | RT-PCR | BvADHα_q_F | TGCAGCGACTTAAACGATCG (SEQ ID NO: 69) |
| Beta vulgaris (BvADHβ) | RT-PCR | BvADHα_q_R | TTGGGGAAGTTTGCCGTTTG (SEQ ID NO: 70) |
| Beta vulgaris (BvADHα) | RT-PCR | pHM0793SLN BvADHαF | AGTTCCCTCTGCTGATATG (SEQ ID NO: 71) |
| Beta vulgaris (BvADHα) | RT-PCR | pHM0794SLN BvADHαR | GTGGTTAATGGTACTAGATAG (SEQ ID NO: 72) |
| Beta vulgaris (BvADHβ) | qPCR | pHM0791SLN BvADHβF | GCGAAGGAGATCAAATTTCT (SEQ ID NO: 73) |
| Beta vulgaris (BvADHβ) | qPCR | pHM0792SLN BvADHβR | TCAATTTGTCTCCGAATTTGC (SEQ ID NO: 74) |
| Beta vulgaris (BvADHα) | qPCR | BvADHα_F | ATGATTTCACTCTCTTCTTTTCATCC (SEQ ID NO: 75) |
| Beta vulgaris (BvADHα) | qPCR | BvADHα_R | GATTTAGTGGTGGTTAATGGTACTAG ATAG (SEQ ID NO: 76) |
| Beta vulgaris (BvADHβ) | qPCR | BvADHβ_F | ATGCTTTCTCTCTCCTCCAC (SEQ ID NO: 77) |
| Beta vulgaris (BvADHβ) | qPCR | BvADHβ_R | CAAATTCGGAGACAAATTGA (SEQ ID NO: 78) |
| Beta vulgaris (BvActin) | qPCR | pHM0001HM BvACT | TCTATCCTTGCATCTCTCAG (SEQ ID NO: 79) |
| Beta vulgaris (BvActin) | qPCR | pHM0002HM BvACT | TCTCCAAGGGCGAGTATGAT (SEQ ID NO: 80) |
| Beta vulgaris (BvDODA) | qPCR | pHM0003HM BvDODA | CATTGGTTCAGGAAGTGCAA (SEQ ID NO: 81) |
| Beta vulgaris (BvDODA) | qPCR | pHM0004HM BvDODA | CCTTTGATTCATGGCTTCGT (SEQ ID NO: 82) |
| Beta vulgaris (BvMYB1) | qPCR | pHM057613vMYB1F | TATCAAACGAGGGCACTTC (SEQ ID NO: 83) |
| Beta vulgaris (BvMYB1) | qPCR | pHM0577BvMYB1R | GATGGTCTTTGATAGCAGC (SEQ ID NO: 84) |
| Beta vulgaris (BvCYP76AD1) | qPCR | pHM0005HM BvCYP76AD1 | CTTTTCAGTGGAATTAGCCCACC (SEQ ID NO: 85) |
| Beta vulgaris (BvCYP76AD1) | qPCR | pHM0006HM BvCYP76AD1 | TGGAACATTATGGAAGATATTGGG (SEQ ID NO: 86) |
| GFP | qPCR | tGFP_q_F | GGCTGGAAGAGTGATCGGAG (SEQ ID NO: 87) |
| GFP | qPCR | tGFP_q_R | ACGCTACTGTTGAGCATCTTCA (SEQ ID NO: 88) |
| Gene Racer oligoT | RT-PCR | GeneRacer OligoT | GCTGTCAACGATACGCTACGTAACGGCA TGACAGTG(T)20 (SEQ ID NO: 89) |

TABLE 1 -continued

Primers used as indicated in the description and methods

| Species (gene) | Purpose | Primer name | Primer sequence 5' to 3' |
|---|---|---|---|
| Eukaryotic translational elongation factor 1α | qPCR | EF1α_q_F | AGCTTTACCTCCCAAGTCATC (SEQ ID NO: 90) |
| Eukaryotic translational elongation factor 1α | qPCR | EF1α_q_R | CCAAGATTGACAGGCGTTCT (SEQ ID NO: 91) |

Recombinant Enzyme Expression and Purification

The His-tagged recombinant protein expression was carried out as we described previously (Dornfeld et al., 2014). For GST-tagged recombinant protein expression, the cloned pGEX-2T vectors were introduced into Rosetta-2 E. coli competent cells (Novagen, Madison WI, USA) and cultured overnight at 37° C., 200 r.p.m. in 10 mL LB medium containing Ampicillin (100 µg/mL). The ten milliliters of the overnight culture were transferred to 1 L LB medium with Ampicillin (100 µg/mL and further incubated at 37° C. and 200 r.p.m. until the $OD_{600}$ reached 0.3. The temperature was then changed to 18° C. and, after 1 hr, isopropyl β-D-1-thiogalactopyranoside (IPTG, 400 mM final concentration) was added to induce recombinant protein expression. After overnight incubation at 18° C. under constant shaking at 200 r.p.m., cultures were harvested by centrifugation at 2,000 g for 10 min at 4° C., and the pellet was washed with 0.9% NaCl solution. The samples were harvested and resuspended in 25 mL of lysis buffer [phosphate-buffered saline (PBS) pH 7.4, 1 mM phenylmethylsulfonyl fluoride (PMSF), 1 mM dithiothreitol (DTT) and plant proteases inhibitor cocktail (Amresco, Solon, OH, USA)]. The resuspended cells were sonicated for periods of 20 s for 5 min. The cell lysate was centrifuged at 10,000 g for 30 min at 4° C., and the supernatant was applied to Fast Protein Liquid Chromatography (FPLC, AKTApure25 FPLC system, GE Healthcare) equipped with GSTtrap™MFF (GE Healthcare, USA). Prior and after injection, the column was washed with five times bed volume wash buffer A (PBS, pH 7.6) followed by five times bed volume of wash buffer B (10 mM glutathione, 1.54 g of reduced glutathione dissolved in 500 mL of 50 mM Tris-HCl, pH 8). The recombinant enzymes containing GST-tag were eluted with ten-bed volumes of the elution buffer B and collected into Eppendorf tubes containing 500 µL. Recombinant enzymes eluted in the fraction five and six, which were combined and desalted using a gel filtration column (Sephadex G50-80 resin, Sigma-Aldrich, St Louis, MO, USA) in the reaction buffer [200 mM HEPES (pH 7.6), 50 mM KCl, 10% ethylene glycol]. Enzyme concentrations were measured using Bradford assay (Bio-Rad, Des Plaines, IL, USA) and the enzyme purity was estimated by running on SDS-PAGE gel and analyzing with ImageJ (imagej.nih.gov).

ADH and PDH Activity Assays In Vitro

ADH and PDH activity from beet tissues (FIGS. 3A, 3B) were analyzed by using the leaves and stem/root crude protein extract of red beet (W357B). The beets were grown in a greenhouse for 12 weeks with a temperature of 22-25° C. and 16 hr of ambient and supplemented lights. Protein extraction was performed by grinding 1 g of tissues in liquid nitrogen and resuspending the powder in the extraction buffer [200 mM HEPES (pH 7.6), 50 mM KCl, 10% ethylene glycol, 1 mM PMSF, 1 mM DTT and plant proteases inhibitor cocktail (Ameresco)]. The extracts were desalted using the gel filtration column (Sephadex G50-80 resin, Sigma-Aldrich St. Louis, MO, USA) into the reaction buffer. The ADH or PDH assays were performed by mixing the desalted protein extract with 1 mM $NADP^+$ and 1 mM L-arogenate or prephenate in a total volume of 10 µL or 25 µL, respectively. L-Arogenate was prepared by enzymatic conversion from prephenate (Sigma-Aldrich, St. Louis, MO, USA), as previously described (Schenck et al., 2015). The reactions were started by adding the enzyme (crude extract or recombinant enzyme) and incubated at 37° C. for 45 min. The reaction was stopped with two times volume of methanol. The same ADH and PDH assay protocols were used for initial characterization of purified recombinant BvADH enzymes For detection of Tyr product from the ADH assays, 10 µL of the reaction mixture was first derivatized with the equal volume of the 40.26 mM OPA solution [5.4 mg OPA (Sigma-Aldrich, St. Louis, MO, USA) mixed in 100 µL methanol, 5 µL 2-mercaptoethanol and 900 µL 0.4M boric acid) for 3 min, injected to high pressure liquid chromatography (HPLC, Agilent 1260) equipped with the Eclipse XDH-C18 column (5 µm, 3.0×150 mm, Agilent, USA), and separated by a 30 min linear gradient from 20-45% methanol in 0.1% ammonium acetate at a flow rate of 0.8 ml/min. The substrate and product of ADH assays (Tyr and arogenate, respectively) were detected by a fluorescence detector (Agilent, USA) with excitation at 360 nm and emission of 455 nm. For PDH assays, the reactions were stopped by addition of $NaBH_4$, which converts the reaction product HPP into hydroxyphenyllactic acid (HPLA), followed by neutralization with 100 µl of 6 N HCl as described by Schenck et al. 2015. The HPLC was equipped with ZORBAX SB-C18 column (Agilent, USA) using a 6 min isocratic elution at 25% methanol in 0.1% phosphoric acid, followed by a 20 min linear gradient of 25-60% methanol at a flow rate of 1.0 mL/min. The HPLA were monitored by absorption at 270 nm.

To test the electron donor and substrate preferences of purified recombinant enzymes, the ADH and PDH reactions were performed as described above, except for 12 min with 400 µM L-arogenate and 1 mM cofactor ($NAD^+$ or $NADP^+$). The reaction was stopped by placing the tubes on ice and immediately measured for the production of the reduced cofactor, NAD (P) H, at 340 nm by spectrophotometer (NanoDrop 2000, Thermo Scientific, USA). The quantification was based on the standard curve of authentic NADPH.

To examine Tyr sensitivity of the purified recombinant enzymes, ADH assay was performed as described previously (Schenck et al., 2015) but in the presence or absence of different concentrations of L-Tyr. Tyr was first dissolved in 0.025 N NaOH at 100 mM (as the water solubility of Tyr is very low, <2 mM), which was diluted to 4 mM to 10 µM final concentration in 0.0025 N NaOH. The reactions contained 500 mM HEPES (pH 7.6) to maintain the final pH at 7.6. The production of reduced cofactor (NADPH) was monitored at 340 nm using a spectrophotometer every two minutes for 10 min. In addition, other effectors (L-Phe, L-Trp, and betanin) were used to test possible inhibition of the enzyme ADH activity at a final concentration of 1 mM. All of the reactions were performed under non-saturated condition, where activity increased linearly depending on reaction times and enzyme concentrations.

Transient Expression of BvADHα and BvADHβ in *Nicotiana benthamiana*

ADHα and ADHβ sequences used for *N. benthamiana* agroinfiltration were amplified from *Beta vulgaris* var. *vulgaris* variety "Boltardy" (Chiltern Seeds, UK) swollen hypocotyl and leaf tissue cDNA libraries respectively, which were prepared using BioScript Reverse Transcriptase (Bioline Reagents, London, UK). Transcripts were amplified by PCR using gene specific primers (Table S1) and Phusion High-Fidelity DNA polymerase (Thermo Fisher Scientific, Waltham, MA, USA). Vectors for transient transformation were constructed with Golden Gate cloning using the MoClo Tool Kit (Weber et al., 2011; Addgene, Cambridge, MA, USA), with the BpiI and BsaI restriction sites eliminated after cloning. The turboGFP sequence used in this assay was a variant codon-optimized for plants contained in the MoClo Plant Parts Kit (Engler et al., 2014; Addgene, Cambridge, MA, USA). BvADHα, BvADHβ, and turboGFP sequences were ultimately cloned into the pICH86988 binary vector under control of the Cauliflower Mosaic Virus 35S promoter and the *Agrobacterium tumefaciens* octopine synthase (OCS) terminator.

Transient gene expression assays in *N. benthamiana* were performed according to the previously described agroinfiltration method with some modifications (Sparkes et al., 2006). All constructs were transformed into the *Agrobacterium tumefaciens* GV3101 strain, and grown in LB media supplemented with kanamycin (50 mg/L), gentamycin (25 mg/L) and rifampicin (50 mg/L) until reaching an $OD_{600}$ of 1.5. Cultures were then brought to a final $OD_{600}$ of 0.5 in infiltration media (10 mM $MgCl_2$, 0.1 mM acetosyringone, 10 mM MES at pH 5.6) for three hours prior to infiltration. Infiltration spots corresponding to 35S:BvADHα, 35S:BvADHβ, and 35S::turboGFP were performed in the same leaves of 6-week old *N. benthamiana* plants alternating the position of the spots between plants in a clockwise manner to account for intra-leaf variation (Barshandy et al., 2015). Infiltrated tissue was sampled three days post-infiltration from five biological replicates for tyrosine quantification and qRT-PCR analysis.

For quantification of tyrosine and other amino acids, ~40 mg fresh weight tissues were harvested, lyophilized, sent from the University of Cambridge (UK) to the University of Wisconsin-Madison (USA), and analyzed exactly as described. Tyrosine and other amino acids were extracted and measured as described previously (Wang et al., 2017). Amino acid standards (Sigma-Aldrich, St. Louis, MO, USA) of 4 to 1000 µM were prepared the same way to make standard curves.

Phylogenetic Analysis

Amino acid sequences from genomes (full open reading frame) and transcriptomes (full or partial open reading frame) of Brockington et al. (2015) were used for phylogenetic analysis following methods described in Brockington et al. (2015) with minor modifications. In addition, we carried out analysis of dN/dS ratio in ADHα to test for relaxed selection in anthocyanic lineages (Table 2).

TABLE 2

Sequences of Caryophyllales (ingroups) and non-Caryophyllales (outgroups) used in this Example.

| Tason | Source | Accession code | Citation |
|---|---|---|---|
| Ingroups | | | |
| Achatocarpaceae_Phaulothamnus_spinescens | Smith Lab | MJM1677 | (Brockington et al., 2015) |
| Aizoaceae_Cypselea_humifusum | 1KP | GJNX | (Matasci et al., 2014) |
| Aizoaceae_Delosperma_echinatum | 1KP | BJKT | (Matasci et al., 2014) |
| Aizoaceae_Sesuvium_porfulacastrum | 1KP | HZTS | (Matasci et al., 2014) |
| Aizoaceae_Sesuvium_verrucosum | 1KP | EDIT | (Matasci et al., 2014) |
| Aizoaceae_Trianthemum_porfulacastrum | 1KP | OMYK | (Matasci et al., 2014) |
| Aizoaceae_Zaleya_penfandra | 1KP | BERS | (Matasci et al., 2014) |
| Amaranthaceae_Aerva_javanica | 1KP | HDSY | (Matasci et al., 2014) |
| Amaranthaceae_Aerva_lanata | 1KP | PDQH | (Matasci et al., 2014) |
| Amaranthaceae_Alternanthera_brasiliana | 1KP | ZBPY | (Matasci et al., 2014) |
| Amaranthaceae_Alternanthera_caracasana | 1KP | OHKC | (Matasci et al., 2014) |
| Amaranthaceae_Alternanthera_sessilis | 1KP | BWRK | (Matasci et al., 2014) |
| Amaranthaceae_Alternanthera_fenella | 1KP | EYRD | (Matasci et al., 2014) |
| Amaranthaceae_Amaranthus_cruentus | 1KP | XSSD | (Matasci et al., 2014) |
| Amaranthaceae_Amaranthus_retroflexus | 1KP | WMLW | (Matasci et al., 2014) |
| Amaranthaceae_Atriplex_hortensis | 1KP | ONLQ | (Matasci et al., 2014) |
| Amaranthaceae_Atriplex_prostrata | 1KP | AAXJ | (Matasci et al., 2014) |
| Amaranthaceae_Atriplex_rosea | 1KP | CBJR | (Matasci et al., 2014) |
| Amaranthaceae_Bassia_scoparia | 1KP | WGET | (Matasci et al., 2014) |
| AmaranthEceae_Beta_maritima | 1KP | FVXD | (Matasci et al., 2014) |
| Amaranthaceae_Beta_vulgaris | Genome | v1.1 | (Dohm et al., 2014) |
| Amaranthaceae_Blutaparon_vermiculare | 1KP | CUTE | (Matasci et al., 2014) |
| Amaranthaceae_Chenopodium_amaranticolor | SRA | SRX151423 | (Zhang et al., 2012) |
| Amaranthaceae_Chenopodium_quinoa | 1KP | SMMC | (Matasci et al., 2014) |
| Amaranthaceae_Froelichia_floridana | Smith Lab | MJM1665 | (Brockington et al., 2015) |
| Amaranthaceae_Salicornia_europaea | SRA | SRX302090 | (Fan et al., 2013) |
| Basellaceae_Basella_alba | 1KP | CTYH | (Matasci et al., 2014) |
| Cactaceae_Lophophora_williamsii | 1KP | CPKP | (Matasci et al., 2014) |
| Cactaceae_Pereskia_aculeata | 1KP | JLOV | (Matasci et al., 2014) |

TABLE 2-continued

Sequences of Caryophyllales (ingroups) and non-Caryophyllales (outgroups) used in this Example.

| Taxon | Source | Accession code | Citation |
|---|---|---|---|
| Caryophyllaceae_Cerastium_arvense | Smith Lab | MJM1767 | (Brockington et al., 2015) |
| Caryophyllaceae_Dianthus_caryophyllus | Genome | v1.0 | (Yagi et al., 2014) |
| Caryophyllaceae_Drymaria_cordata | Smith Lab | LCMsn | (Brockington et al., 2015) |
| Caryophyllaceae_Polycarpaea_repens | 1KP | RXEN | (Matasci et al., 2014) |
| Caryophyllaceae_Saponaria_officinalis | 1KP | SKNL | (Matasci et al., 2014) |
| Caryophyllaceae_Schiedea_membranacea | 1KP | OLES | (Matasci et al., 2014) |
| Caryophyllaceae_Silene_latifolia | 1KP | FZQN | (Matasci et al., 2014) |
| Caryophyllaceae_Silene_latifoliaSRA | SRA | SRX118777-SRX118782 | (Muyle et al., 2012) |
| Caryophyllaceae_Silene_vulgaris | SRA | SRX096120 | N/A[1] |
| Caryophyllaceae_Spergulana_media | 1KP | TJES | (Matasci et al., 2014) |
| Droseraceae_Aldrovanda_vesiculosa | Smith Lab | MJM1652 | (Brockington et al., 2015) |
| Droseraceae_Dionaea_muscipula | SRA | SRX312294 | (Jensen et al., 2015) |
| Frankeniaceae_Frankenia_laevis | 1KP | WPYJ | (Matasci et al., 2014) |
| Microteaceae_Microtea_debilis | 1KP | YNFJ | (Matasci et al., 2014) |
| Molluginaceae_Mollugo_cerviana | 1KP | RNBN | (Matasci et al., 2014) |
| Molluginaceae_Mollugo_nudicaulis | 1KP | SCAO | (Matasci et al., 2014) |
| Molluginaceae_Mollugo_verticillata | 1KP | NXTS | (Matasci et al., 2014) |
| Nepenthaceae_Nepenthes_alata | 1KP | WQUF | (Matasci et al., 2014) |
| Nyctaginaceae_Abronia_carletonii | Smith Lab | MJM1751 | (Brockington et al., 2015) |
| Nyctaginaceae_Acleisanthes_lanceolata | Smith Lab | MJM1741 | (Brockington et al., 2015) |
| Nyctaginaceae_Acleisanthes_obtusa | Smith Lab | MJM1697 | (Brockington et al., 2015) |
| Nyctaginaceae_Anulocaulis_leiosolenus | Smith Lab | SRX717838 | (Yang et al., 2015) |
| Nyctaginaceae_Boerhavia_burbidgeana | 1KP | VJPU | (Matasci et al., 2014) |
| Nyctaginaceae_Boerhavia_coccinea | 1KP | ZBTA | (Matasci et al., 2014) |
| Nyctaginaceae_Bougainvillea_spectabilis | 1KP | JAFJ | (Matasci et al., 2014) |
| Nyctaginaceae_Bougainvillea_stipitata | Smith Lab | SRX718672 | (Yang et al., 2015) |
| Nyctaginaceae_Cyphomeris_gypsophiloides | Smith Lab | MJM1714 | (Brockington et al., 2015) |
| Nyctaginaceae_Guapira_obtusata | Smith Lab | SRX718384 | (Yang et al., 2015) |
| Nyctaginaceae_Mirabilis_jalapa | 1KP | JGAB | (Matasci et al., 2014) |
| Nyctaginaceae_Mirabilis_multiflora | Smith Lab | MJM1771 | (Brockington et al., 2015) |
| Nyctaginaceae_Pisonia_aculeata | Smith Lab | SRX718389 | (Yang et al., 2015) |
| Nyctaginaceae_Pisonia_umbellifera | Smith Lab | SFB29 | (Brockington et al., 2015) |
| Physenaceae_Physena_madagascariensis | 1KP | RUUB | (Matasci et al., 2014) |
| Phytolaccaceae_Ercilla_volubilis | Smith Lab | MJM1649 | (Brockington et al., 2015) |
| Phytolaccaceae_Hilleria_latifolia | 1KP | SFKQ | (Matasci et al., 2014) |
| Phytolaccaceae_Petiveria_alliacea | 1KP | AZBL | (Matasci et al., 2014) |
| Phytolaccaceae_Phytolacca_americana | 1KP | BKQU | (Matasci et al., 2014) |
| Phytolaccaceae_Phytolacca_bogotensis | 1KP | MRKX | (Matasci et al., 2014) |
| Phytolaccaceae_Phytolacca_diuica | Smith Lab | SFB31 | (Brockington et al., 2015) |
| Phytolaccaceae_Rivina_humilis | Smith Lab | SRX718277 | (Yang et al., 2015) |
| Phytolaccaceae_Seguieria_aculeata | Smith Lab | SRX718486 | (Yang et al., 2015) |
| Plumbaginaceae_Limonium_spectabile | 1KP | WOBD | (Matasci et al., 2014) |
| Polygonaceae_Antigonon_leptopus | Smith Lab | MJM1811 | (Brockington et al., 2015) |
| Polygonaceae_Fagopyrum_esculentum | SRA | SRX112838 | N/A[1] |
| Polygonaceae_Polygonum_convolvulus | 1KP | FYSJ | (Matasci et al., 2014) |
| Polygonaceae_Polygonum_cuspidatum | SRA | SRX079484 | (Hao et al., 2012) |
| Polygonaceae_Rheum_nobile | SRA | SRX621187 | N/A[1] |
| Polygonaceae_Rheum_rhabarbarum | SRA | SRX286365 | N/A[1] |
| Polygonaceae_Rumes_acetosa | SRA | ERX190940 | N/A[1] |
| Polygonaceae_Rumex_palustris | SRA | ERX190941, ERX190942 | N/A[1] |
| Portulacaceae_Portulaca_amilis | 1KP | LDEL | (Matasci et al., 2014) |
| Portulacaceae_Portulaca_cryptopetala | 1KP | LLQV | (Matasci et al., 2014) |
| Portulacaceae_Portulaca_grandiflora | 1KP | CPLT | (Matasci et al., 2014) |
| Portulacaceae_Portulaca_molokiniensis | 1KP | UQCB | (Matasci et al., 2014) |
| Portulacaceae_Portulaca_oleracea | 1KP | EZGR | (Matasci et al., 2014) |
| Portulacaceae_Portulaca_pilosa | 1KP | IWLS | (Matasci et al., 2014) |
| Portulacaceae_Portulaca_suffruticosa | 1KP | GCYL | (Matasci et al., 2014) |
| Sarcobataceae_Sarcobatus_vermiculatus | 1KP | GIWN | (Matasci et al., 2014) |
| Summondsiaceae_Simmondsia_chinensis | 1KP | CVDF | (Matasci et al., 2014) |
| Talinaceae_Talinum_sp | 1KP | LKKX | (Matasci et al., 2014) |
| Tamaricaceae_Reaumuria_trigyna | SRA | SRX099851, SRX105466 | N/A1 |
| Tamaricaceae_Tamarix_hispida | SRA | All 8 runs in PRJNA170420 | (Wang et al., 2014) |
| | Outgroups | | |
| Arabidopsis_thaliana | Genome | Accessed May 28, 2014 | (Goodstein et al., 2012) |
| Oryza_sativa | Genome | Accessed April 21, 2015 | (Goodstein et al., 2012) |

TABLE 2-continued

Sequences of Caryophyllales (ingroups) and non-Caryophyllales (outgroups) used in this Example.

| Tason | Source | Accession code | Citation |
| --- | --- | --- | --- |
| Solanum_lycopersicum | Genome | Accessed May 28, 2014 | (Goodstein et al., 2012) |
| Vitis_vinifera | Genome | Accessed April 21, 2015 | (Goodstein et al., 2012) |

[1]N/A, not available

Subcellular Localization of GFP-Fused ADH Enzymes

The subcellular localization experiments of GFP-fused ADH enzymes were conducted as we described previously (Schenck et al., 2015).

Accession Numbers

The Genbank accession numbers for the sequences mentioned in this article are: BvADHβ W357B red beet variety (KY207366), BvADHβ Boltardy red beet variety (MF346292), BvADHβ Big Buck sugar beet variety (KY207367), BvADHβ Touch Stone yellow beet variety (KY207368), BvADHβ Blankoma white beet variety (KY207369), BvADHβ Sea beet PI562585 variety (KY207370), BvADHα Big Buck sugar beet variety (KY207371), BvADHα W357B red beet variety (KY207372), BvADHα Boltardy red beet variety (MF346291), BvADHα Blankoma white beet variety (KY207373), BvADHα Touch Stone yellow beet variety (KY207374), BvADHα Sea beet PI562585 variety (KY207375), SoADHβ (KY207376), SoADHα (KY207378), NaADHβ (KY207377), MjADHα (KU881770), RhADHα (KY207379), PoADHα (KY207380), SmADHα (KY274179), PpADHα (KY274180), and HLADHα (KY274181).

Results

B. vulgaris has Two ADH Enzymes.

Figure 3B:
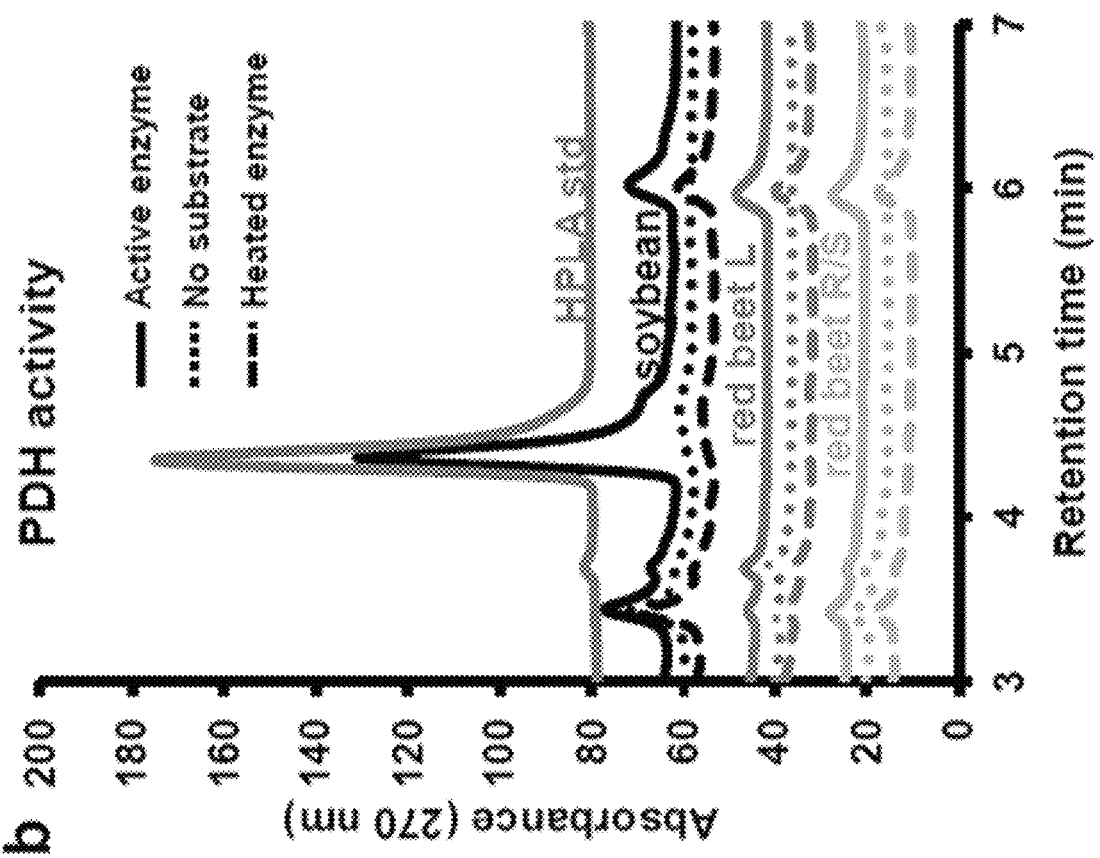
Figure 3A:
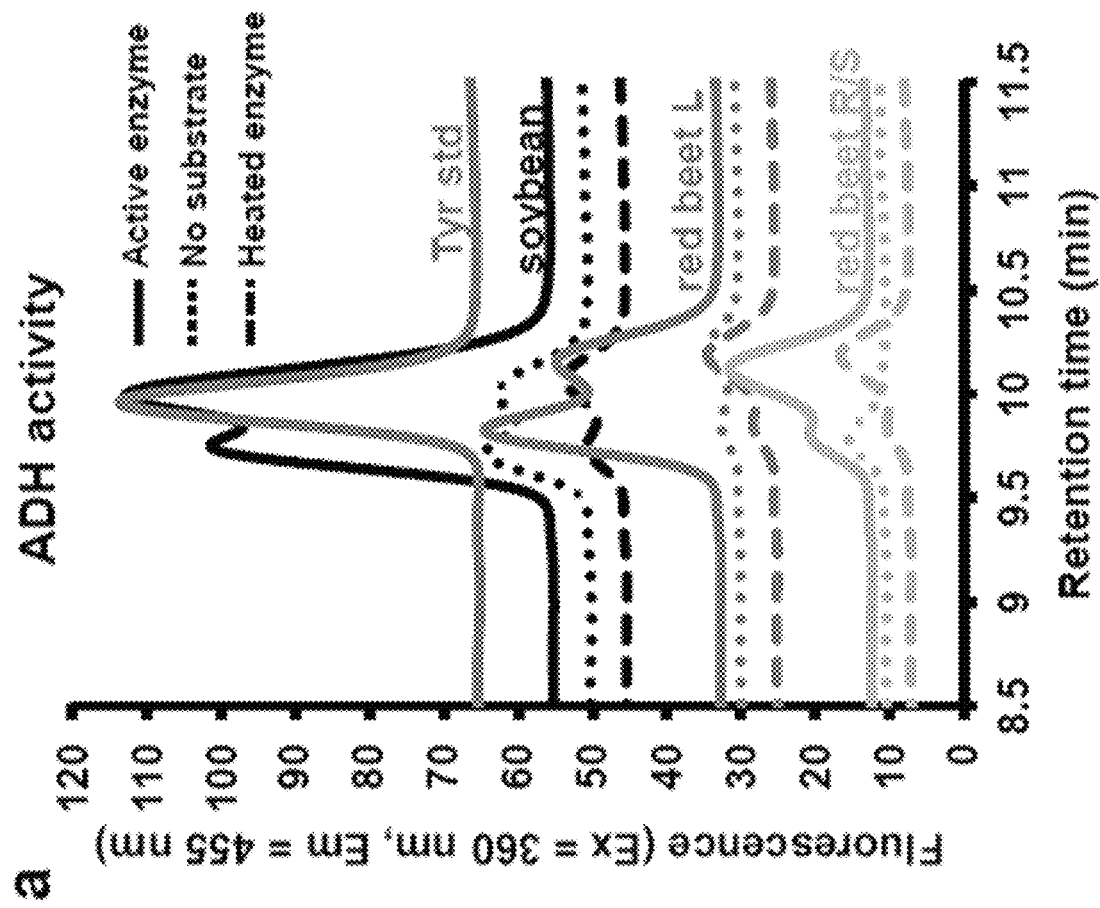

To first investigate how B. vulgaris synthesizes Tyr, protein crude extracts of red beet leaf and root/stem tissues were analyzed for ADH and PDH activity, the production of Tyr or HPP from arogenate or prephenate, respectively. Tyr was produced from arogenate in the red beet extracts of both leaves and roots/stems (FIG. 3A) similar to soybean leaf extract, which was previously shown to have both ADH and PDH activity (Schenck et al., 2015). On the other hand, unlike the soybean leaf extract, HPP production was not detected in the leaf and root/stem extracts of red beet (FIG. 3B). These results showed that red beet has ADH but not PDH activity.

To identify the gene(s) responsible for the ADH activity in B. vulgaris, previously reported plant and microbial ADH and PDH genes (Bonvin et al., 2006; Hudson et al., 1984; Legrand et al., 2006; Rippert & Matringe, 2002a,b; Schenck et al., 2015, FIG. 2B) were used to BLAST against the genome of sugar beet, another cultivar of B. vulgaris (Dohm et al., 2014) (assembly v.1.2 molgen.mpg.de). Two B. vulgaris sequences homologous to these ADH and PDH genes were found on chromosome 8 of the B. vulgaris genome 25.3 kbp apart (FIG. 2A). They were more similar to plant ADHs and PDHs (59 to 61% similarity at amino acid levels) than bacterial ones (24 to 40% similarity, FIG. 2B). Within plants, the two ADH candidate genes from B. vulgaris both belong to the canonical ADH clade containing Arabidopsis ADHs (Rippert & Matringe, 2002a,b), rather than the non-canonical clade containing legume PDHs (Schenck et al., 2015; 2017), and appear to be derived from a recent duplication within the order Caryophyllales.

For biochemical characterization, these two putative BvADHs were expressed in E. coli as recombinant enzymes, which were further purified using affinity chromatography and subjected to ADH and PDH assays. Both of the beet recombinant enzymes showed ADH activity (i.e. the production of Tyr from arogenate, FIG. 1B) and strongly preferred NADP$^+$ over NAD$^+$ (FIG. 4) similar to other plant ADH enzymes and activities (Gaines et al., 1986; Rippert & Matringe, 2002a,b). On the other hand, neither of the beet enzymes exhibited detectable PDH activity (FIG. 3C), which is consistent with the lack of PDH activity in beet tissues (FIG. 3B) and also confirmed the absence of E. coli PDH contamination (Hudson et al., 1984). Therefore, these two genes were designated as B. vulgaris arogenate dehydrogenases (BvADHα and BvADHβ).

Both BvADHs are Plastid Localized but Only BvADHα Expression is Correlated with Betalain Pathway Genes.

Most plant enzymes involved in the aromatic amino acid pathways are localized within the plastids (Dal Cin et al., 2011; Maeda & Dudareva, 2012; Rippert et al., 2009), and both BvADH proteins also have a predicted N-terminal plastid transit peptide (FIGS. 5A-5D). To experimentally determine the subcellular localization of BvADHs, a green fluorescent protein (GFP) was fused to the C-terminal of BvADHs, expressed in Arabidopsis protoplasts, and analyzed for their localization using confocal microscopy. The fluorescence signal of GFP fused with BvADHα or BvADHβ overlapped with chlorophyll autofluorescence, which was different from the free GFP control and similar to GFP fused with plastidic Arabidopsis ADH (Rippert et al., 2009) (AtADH2, FIG. 1C). These results suggest that both BvADHs are targeted to the plastids and that Tyr is mainly produced by the plastidic arogenate pathway in B. vulgaris.

Figure 1D:
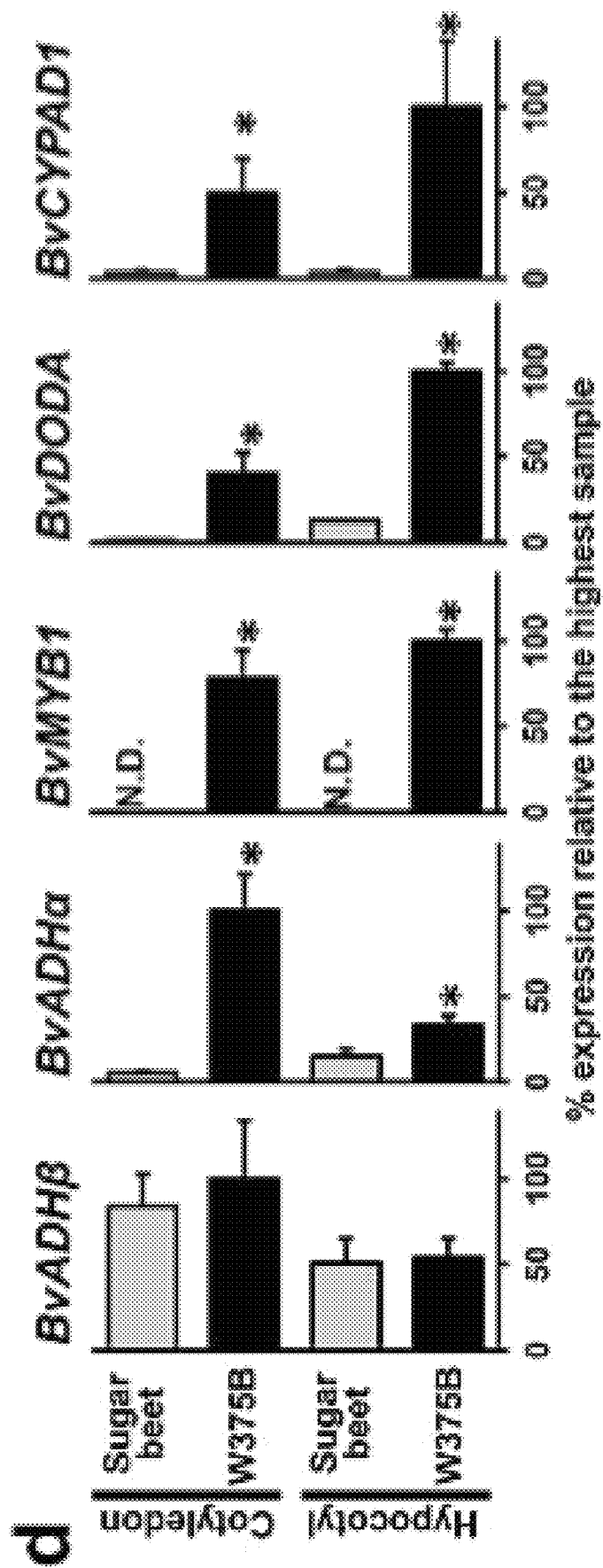

To examine expression patterns of BvADHs, especially in comparison to the betalain pathway genes, expression levels of BvADHα and BvADHβ were analyzed and compared with those of DODAα, CYP76AD1α, and BvMYB1 in cotyledon and hypocotyl tissues of sugar and red beets (FIG. 1D). Consistent with previous studies (Hatlestad et al., 2012; 2015), DODAα and CYP76AD1α, as well as BvMYB1 transcription factor, were much more highly expressed in red than sugar beet. Interestingly, BvADHα expression showed similar trends and was significantly higher in red than sugar beet in both cotyledon and hypocotyl tissues. On the other hand, BvADHβ expression levels were very similar between genotypes in both tissue types (FIG. 1D). These results showed that expression of BvADHα, but not BvADHβ, is correlated with those of betalain pathway genes in B. vulgaris.

BvADHα but not BvADHβ Exhibits Relaxed Sensitivity to Tyr

Figure 6:
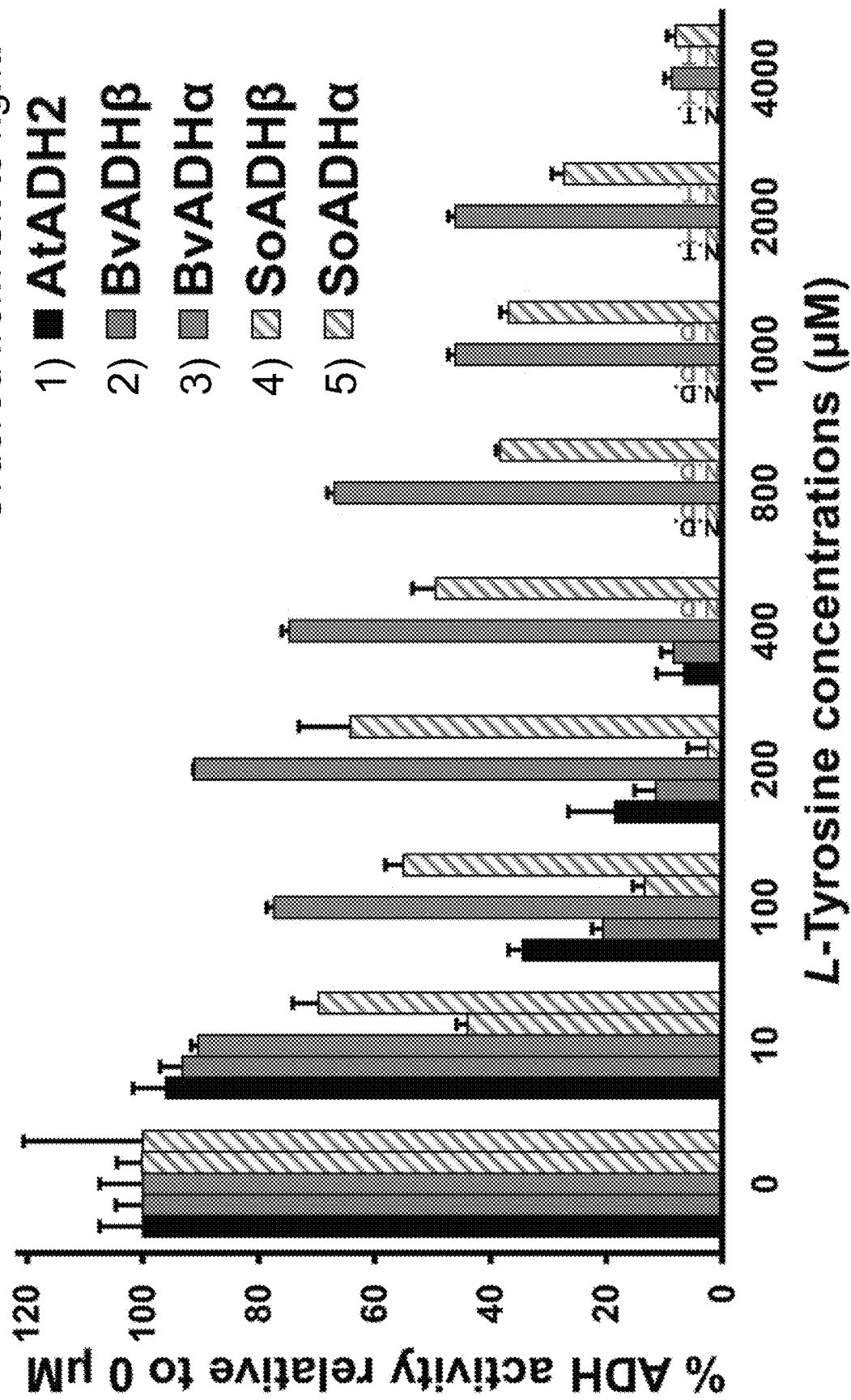
FIG. 6 shows beet and spinach ADHα but not ADHβ have reduced sensitivity to Tyr. ADH activity was measured at different Tyr concentrations using NADP$^+$ cofactor and purified recombinant ADH enzymes of beet (BvADHα, BvADHβ), spinach (SoADHα, SoADHβ), and *Arabidopsis* (AtADH2). Data are expressed as the percentage of respective control activity without Tyr (0 μM) and means of three independent experiments±s.e.m. N.D., not detectable; N.T., not tested.
Figure 7:
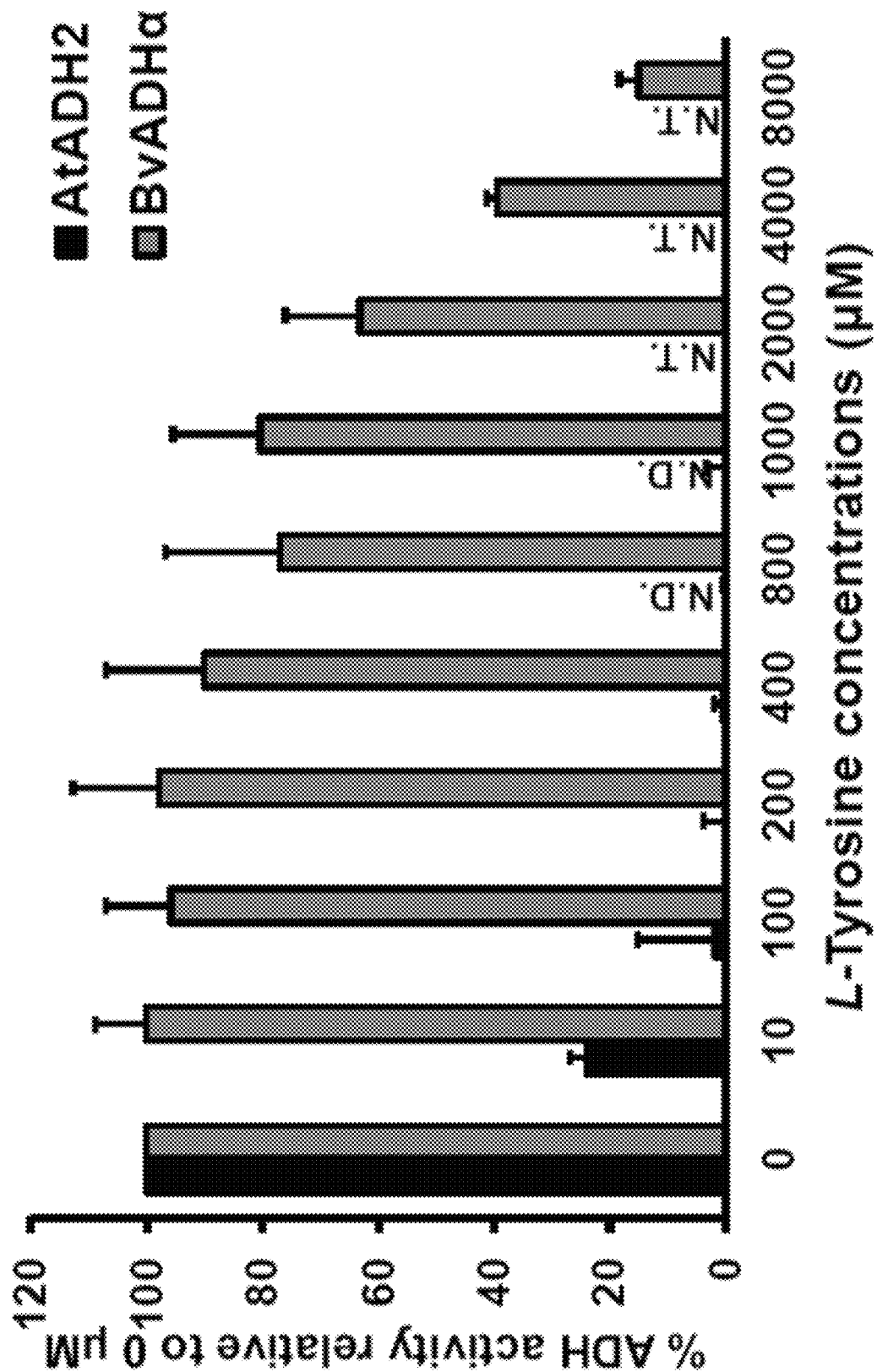
FIG. 7 shows recombinant His-tagged BvADHα also exhibits reduced sensitivity to Tyr relative to AtADH2. BvADHα and AtADH2 recombinant enzymes were also generated as 6× His-tag proteins to determine if GST-tag affects Tyr sensitivity of BvADHα. The His-BvADHα recombinant enzyme still exhibited relaxed sensitive to Tyr inhibition. Data are expressed as the percentage of respective control activity without Tyr (0 μM) and the means of three independent experiments±s.e.m. N.D., not detectable; N.T., not tested.
Figure 8:
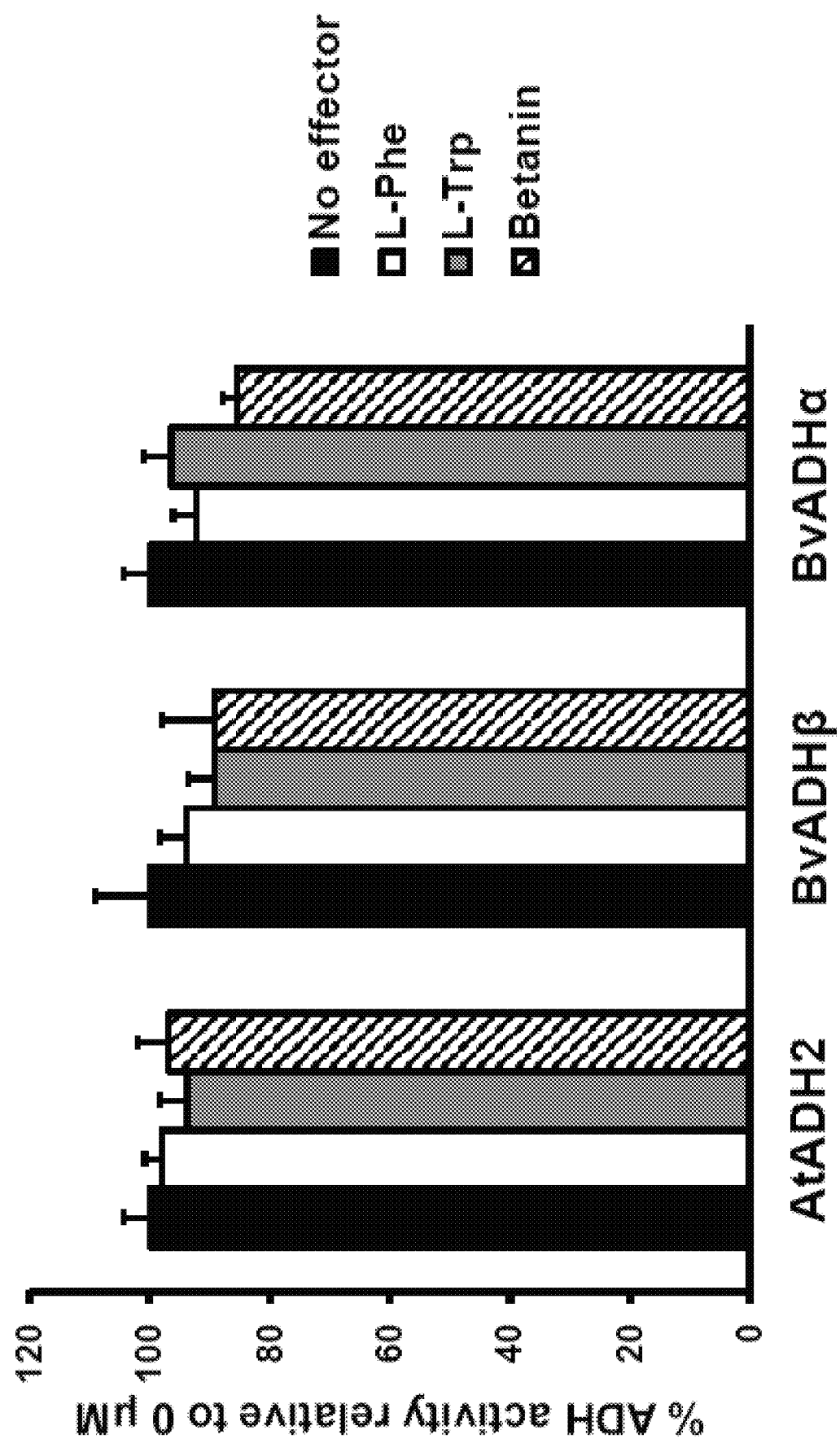
FIG. 8 shows BvADHs are not inhibited by phenylalanine, tryptophan, and betanin. ADH activity of BvADHα, BvADHβ and AtADH2 was measured in the presence and absence of 1 mM final concentration of L-phenylalanine (L-Phe), L-tryptophan (L-Trp), and betanins as an effector. Data are expressed as the percentage of respective control activity without effector and the mean of three independent experiments±s.m.e. No significant reduction was observed by any effector treatment relative to respective no effector control (P<0.05, student t test).

Both ADH and PDH enzymes are usually inhibited by Tyr in most organisms (Bentley, 1990; Connelly & Conn, 1986; Gaines et al., 1982; Rippert & Matringe, 2002a,b; Sun, 2009). To determine if the BvADHs are also feedback regulated by Tyr, ADH activity of the recombinant BvADH enzymes were analyzed in the presence and absence of Tyr as an effector molecule. The ADH activity of glutathione S-transferase (GST)-tagged BvADHβ was inhibited by 80% and 100% in the presence of 100 μM and 1 mM Tyr, respectively (FIG. 6), similar to the Tyr-sensitive Arabidopsis AtADH2 (Rippert & Matringe, 2002a,b). In contrast, ADH activity of BvADHα was reduced only by half at 1 mM Tyr (FIG. 6). Similar results were obtained for histidine (His)-tagged ADH enzymes, where BvADHα showed much less sensitivity to Tyr than AtADH2 (FIG. 7), though the expression of His-tagged BvADHβ was not successful. Other aromatic amino acids (Phe and tryptophan) as well as betanin, the major betacyanin accumulated in red beet, did not significantly reduce the ADH activity of BvADHα, BvADHβ, or AtADH2 at 1 mM (FIG. 8). These results revealed that BvADHα, but not BvADHβ, has relaxed sensitivity to Tyr inhibition.

Heterologous Expression of BvADHα but not BvADHβ Increase Tyr Accumulation in Plants.

Figure 10A:
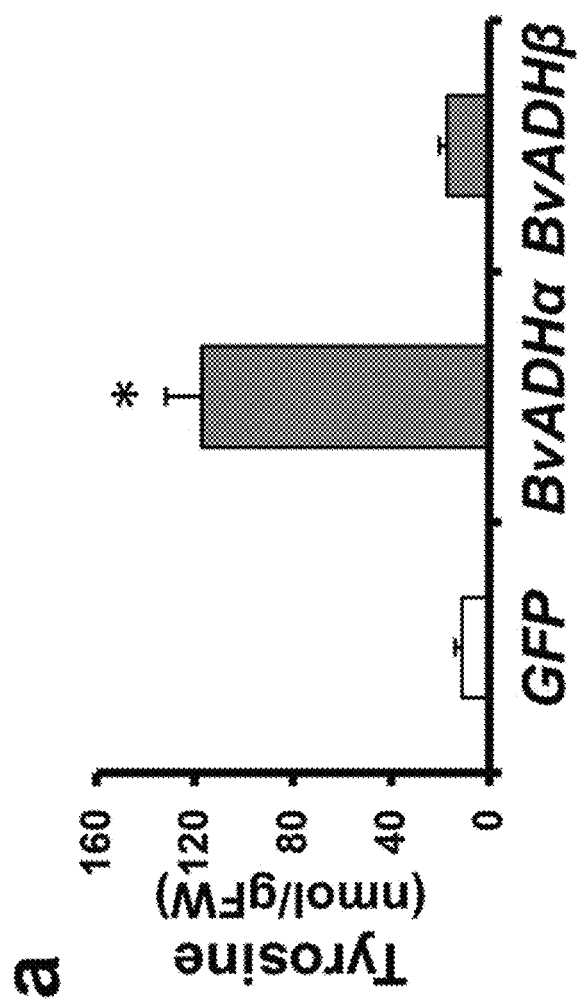
FIGS. 10A-10B shows heterologous expression of BvADHα but not BvADHβ increases tyrosine levels in *Nicotiana benthamiana*. *Agrobacterium tumefaciens* carrying the construct of 35S::GFP, 35S::BvADHα, or 35S::BvADHβ was infiltrated to *N. benthamiana* leaves, which were analyzed for amino acid contents using GC-MS. The levels of tyrosine (FIG. 10A) and phenylalanine (FIG. 10B) are shown. Asterisks indicate significant differences from the 35S::GFP control (p<0.05, Student's t-test). Data are means+S.E.M. (n=5).
Figure 10B:
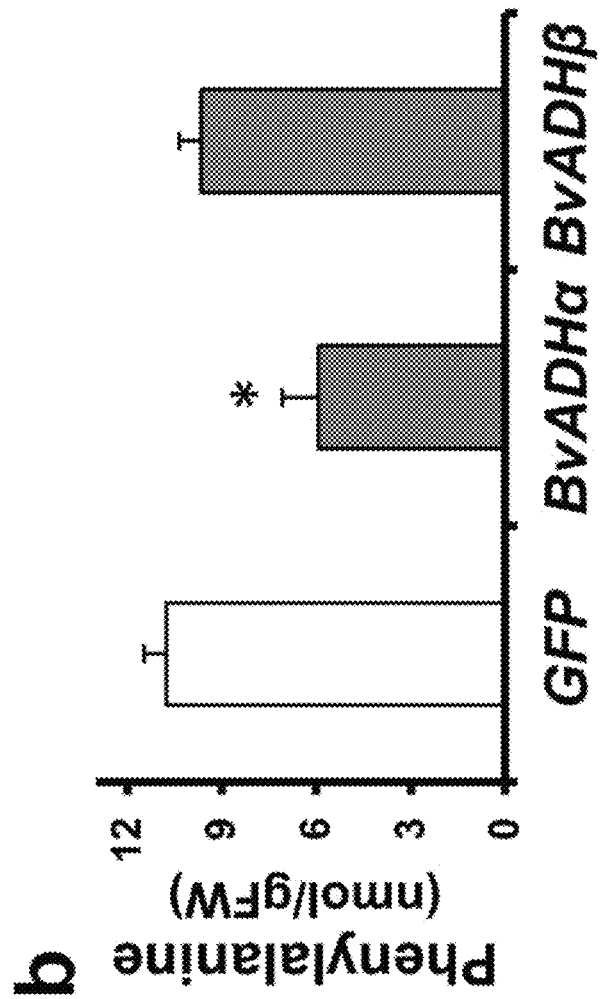

To test if BvADHα having relaxed sensitivity to Tyr can enhance the production of Tyr in planta, BvADHα and BvADHβ were transiently expressed in N. benthamiana through Agrobacteria infiltration (FIG. 9A, Sparkes et al., 2006) and their impacts on Tyr production were analyzed. A control vector expressing GFP was also infiltrated as a negative control (FIG. 9A). BvADHα expression resulted in >10-fold increase in Tyr levels relative to the GFP control, while the increase of Tyr due to BvADHβ expression was not significantly different (FIGS. 10A & 9B, Table 3). Interestingly, phenylalanine (Phe) levels were decreased significantly under BvADHα, but not BvADHβ expression (FIG. 10B). Other amino acid levels were largely unaffected by BvADHα or BvADHβ expression (Table 3). These results demonstrate that BvADHα expression leads to elevated accumulation of Tyr in planta.

TABLE 3

Amino Acid levels of Nicotiana benthamiana leaves expressing GFP, BvADHα, BvADHβ. Agrobacteria carrying the 35S::GFP, 35S::BvADHα, or 35S::BvADHβ construct were infiltrated to Nicotiana benthamiana leaves and the levels of amino acids were analyzed after three days post-infiltration. Data are mean ± s.e.m. (nmol/gFW, n = 5 biological replications). Asterisks denote values significantly different from the control 35S::GFP sample (Student t-test, p < 0.01). Tryptophan, lysine, cysteine, and histidine levels were below quantification threshold.

| Amino Acids | 35S::GFP | 35S::BvADHα | 35S::BvADHβ |
|---|---|---|---|
| alanine | 99.8 ± 15.5 | 93.0 ± 14.8 | 88.1 ± 20.0 |
| glycine | 15.5 ± 1 | 17.5 ± 2.1 | 13.6 ± 0.2 |
| valine | 23.9 ± 9.7 | 23.8 ± 8.3 | 22.1 ± 8.4 |
| leucine | 21.3 ± 10.4 | 21.8 ± 9.2 | 18.8 ± 8.3 |
| isoleucine | 13.8 ± 7 | 13.3 ± 5.7 | 13.3 ± 6.7 |
| proline | 154.8 ± 67.4 | 126.7 ± 56.3 | 137.3 ± 75.4 |
| methionine | 2.8 ± 0.4 | 3.1 ± 0.4 | 2.6 ± 0.2 |
| serine | 57.4 ± 8 | 58.6 ± 11.7 | 43.9 ± 3.9 |
| threonine | 69.4 ± 7.5 | 67.8 ± 8.6 | 58.1 ± 6.5 |
| phenylalanine | 10.8 ± 0.7 | 5.9 ± 1.2* | 9.7 ± 0.7 |
| aspartic acid | 173.5 ± 45.5 | 176.8 ± 40.6 | 132.7 ± 41.5 |
| glutamic acid | 941.6 ± 45.8 | 968.1 ± 91.6 | 746.4 ± 111.4 |
| ornithine[a] | 54.9 ± 1.6 | 56.2 ± 2.4 | 48.4 ± 2.9 |
| asparagine | 6.8 ± 1.2 | 6.9 ± 1.5 | 4.9 ± 1.0 |
| glutamine | 345.2 ± 116.1 | 348.7 ± 138.4 | 291.3 ± 107.7 |
| tyrosine | 11.2 ± 2.8 | 116.8 ± 15.1* | 17.2 ± 3.2 |

[a]Arginine was quantified as its non-enzymatic degradation product ornithine.

BvADHα Orthologs Emerged During the Evolution of Betalain Pigmentation in Caryophyllales.

Domestication has modified metabolic traits in various crops (Hanson et al., 1996; Rapp et al., 2010; Rong et al., 2014). Thus, we hypothesized that the BvADHα enzyme with relaxed Tyr regulation was selected during domestication and intensification of color in table beets, that have been used at least since the Roman times (Biancardi et al., 2012; Dohm et al., 2014). To test this hypothesis, the nucleotide and protein sequences of BvADHα (and BvADHβ) were compared among different domesticated beets, red beet (W357B), sugar beet (Big Buck), yellow beet (Touch Stone), and white beet (Blankoma), as well as their wild relative, sea beet (Biancardi et al., 2012) (Beta vulgaris subsp. maritima). Several single nucleotide polymorphisms (SNPs) were detected among different lines in both BvADHα and BvADHβ (FIGS. 5A, 5B). However, only a few of them affected the amino acid sequences and were within and near the N-terminal signal peptide of BvADHα and BvADHβ, respectively (FIGS. 5C, 5D). Thus, the mature enzyme regions of BvADHα were unaltered during domestication.

To further test if the ADHα enzymes with reduced Tyr sensitivity are restricted to the species B. vulgaris, the corresponding genes for BvADHα and BvADHβ were cloned from a closely related species within the same Amaranthaceae family, spinach (Spinacia oleracea), whose draft genome is available (molgen.mpg.de). Spinach ADHα and ADHβ orthologs (SoADHα and SoADHβ) had 77 and 83% identity at amino acid levels to the corresponding BvADHs in the mature enzymatic regions. The recombinant enzymes of spinach ADHs showed similar Tyr sensitivity to beet ADHs: SoADHα, but not SoADHβ, exhibited reduced Tyr sensitivity (FIG. 6). These results suggest that the reduced Tyr sensitivity of BvADHα at least at the enzyme level was not the result of selection during domestication of beet cultivars, but was already present in the common ancestor of the beet and spinach ADHα enzymes.

Figure 11A:
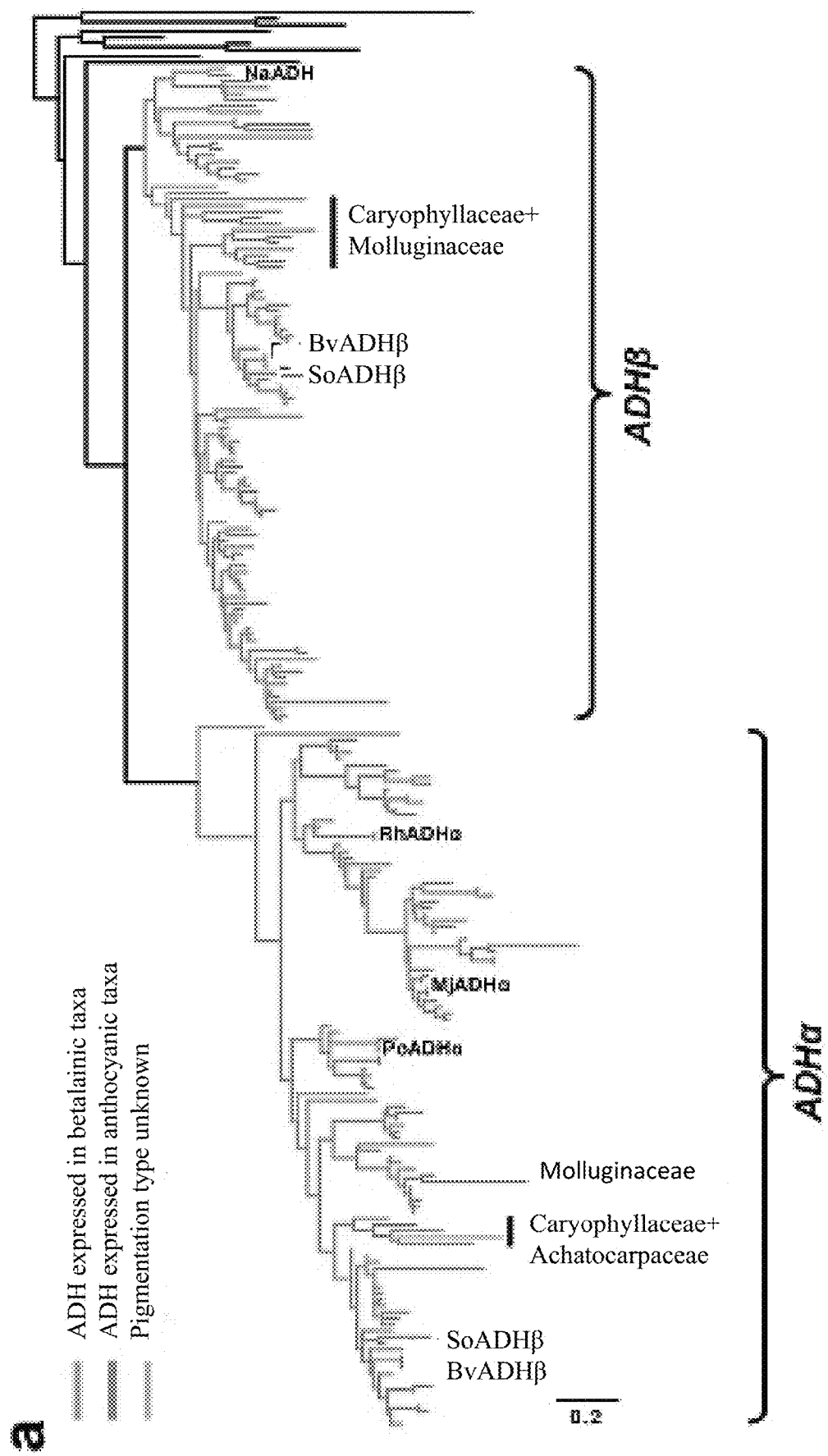

To determine the origin and molecular evolution of BvADHα, we mined genome and transcriptomic data across the Caryophyllales for ADH orthologs and performed a phylogenetic analysis (FIG. 11A). The results indicate that a gene duplication event on the branch leading to stem Caryophyllales produced ADHα and ADHβ lineages. While ADHβ orthologs were expressed across the entire Caryophyllales, expression of ADHα closely parallels betalain production in Caryophyllales. ADHα expression is undetectable from the anthocyanic clade that diverged prior to the earliest inferred origin of betalain synthesis (hereafter referred to as non-core Caryophyllales; Brockington et al., 2009). Two families in the Caryophyllales, Molluginaceae and Caryophyllaceae have reverted from betalain to anthocyanin pigmentation (Brockington et al., 2011, 2015). Presence of the ADHα orthologs in the transcriptomes of Molluginaceae and Caryophyllaceae was much less common than the presence of BvADHβ (FIGS. 11A, 11B). Thus the presence of ADHα, but not ADHβ, closely mirrors the distribution of betalain pigmentation across Caryophyllales, similar to the pattern in two other genes of the betalain pathway, CYP76AD1α and DODAα (Brockington et al., 2015).

Betalain-Producing Species have Deregulated BvADHα Enzyme and Elevated Tyr Levels.

Figure 12:
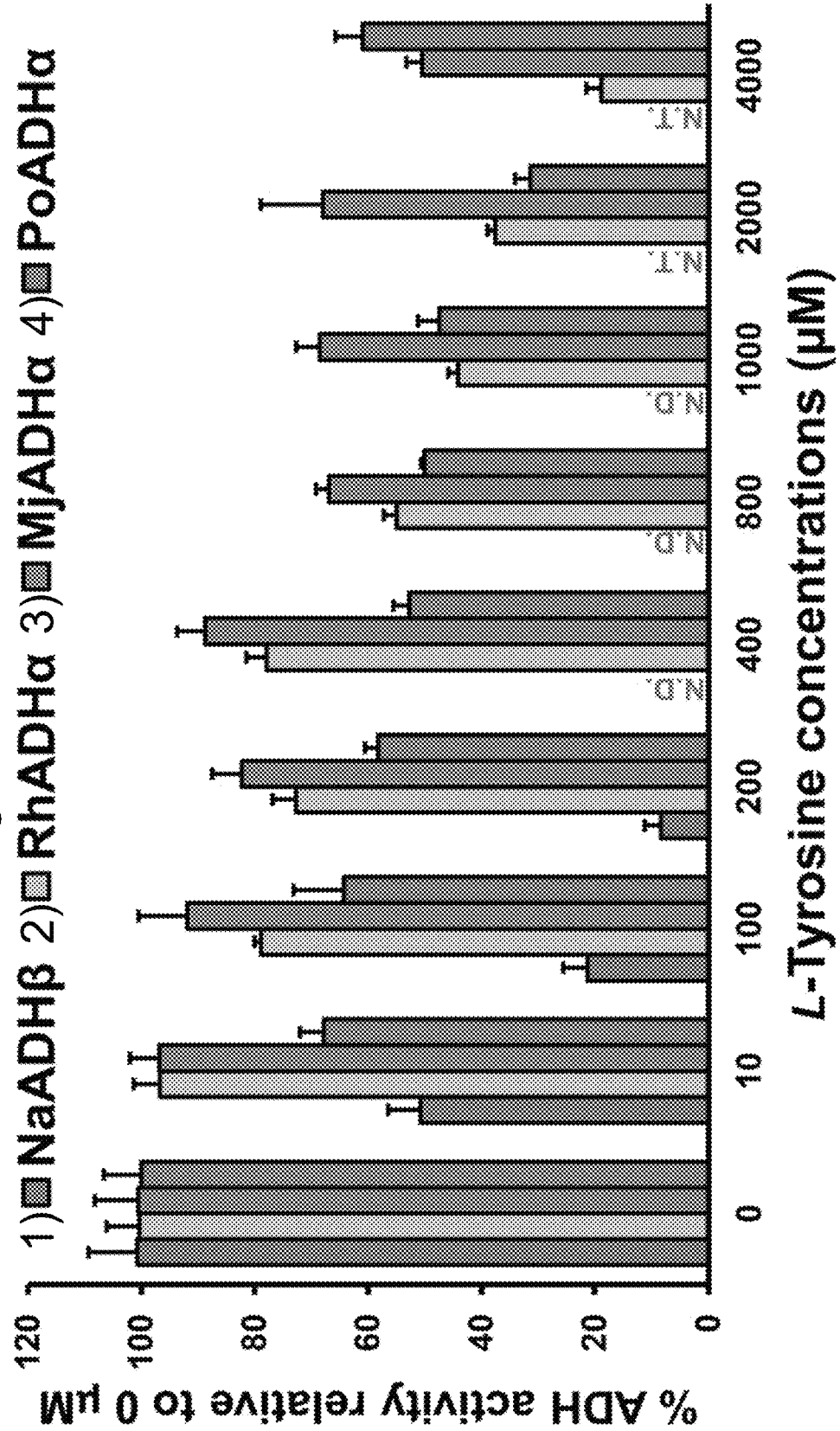
FIG. 12 shows ADHα from various species of core Caryophyllales also exhibit relaxed sensitivity. ADH activity was measured under different Tyr concentrations using purified recombinant ADH enzymes of *Nepenthes ventricosa* x *alata* (NaADHβ), *Rivina humilis* (RhADHα), *Mirabilis jalapa* (MjADHα), and *Portulaca oleracea* (PoADHα) ADH. Data are expressed as the percentage of respective control activity without Tyr (0 µM) and the mean of three independent experiments±s.e.m. N.D., not detectable; N.T., not tested.

To further test experimentally if ADHα orthologs across Caryophyllales share the unique property of reduced Tyr inhibition, ADH genes from representative members of Caryophyllales (Brockington et al., 2011) were cloned and the Tyr sensitivity of encoded enzymes was evaluated. An ADHβ enzyme from the anthocyanin-producing non-core Caryophyllales, *Nepenthes ventricosa* x *alata* (NaADHβ, Nepenthaceae, FIG. 11B), was strongly inhibited by Tyr (FIG. 12) similar to beet and spinach ADHβ (FIG. 6). On the other hand, ADHα orthologs from betalain-producing families, *Rivina humilis* (RhADHα, Rivinaceae), *Mirabilis jalapa* (MjADHα, Nyctaginaceae), and *Portulaca oleracea* (PoADHα, Portulacaceae), all shared relaxed Tyr inhibition and retained 42% to 68% of ADH activity even at 1 mM Tyr (FIG. 12).

Figure 13:
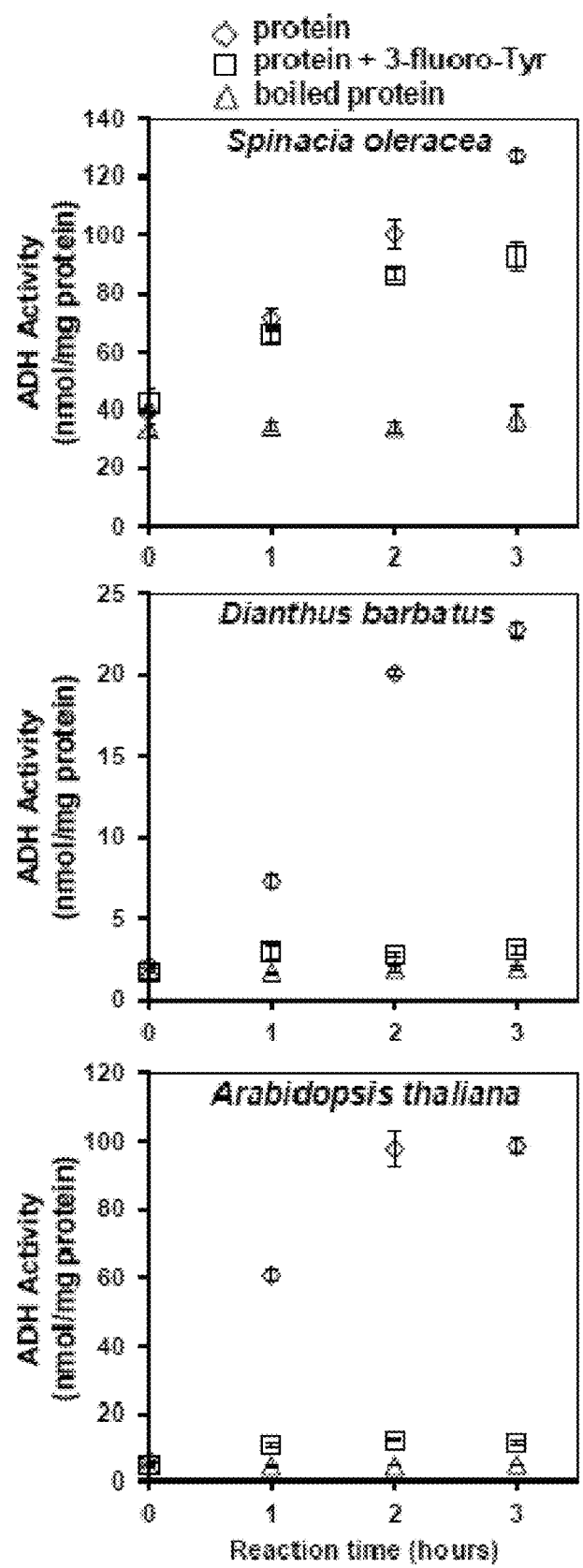
FIG. 13 shows Tyr sensitivity of ADH activity from plant tissues. The plastid extracts of spinach (*Spinacia oleracea*), and the crude extracts of *Dianthus barbatus* and *Arabidopsis thaliana* were incubated with Im Marogenate substrate and 1 mM NADP+ cofactor for indicated times. Plastids were isolated for spinach ADH assays to eliminate strong polyphenoloxidase activity present in the crude extracts. Data are means±s.e.m. (n=4). Activity increased linearly during the first two hours, which were used to calculate ADH activity presented in Table 4.

To test if Tyr-insensitivity of the recombinant ADHα enzyme is also detectable in vivo, Tyr sensitivity of leaf ADH activity was analyzed from species containing ADHα (i.e. spinach) and ones lacking ADHα [i.e. *Arabidopsis thaliana*, *Dianthus barbatus*, Caryophyllaceae]. Spinach rather than beet was used due to its cleaner background during HPLC-based enzyme assay. As shown in Table 4 and FIG. 13, ADH activity of *Arabidopsis* and *Dianthus barbatus* tissues was strongly inhibited (92-95%) by 0.5 mM of Tyr effector, whereas that of spinach was much more resistant to Tyr inhibition (only ~21% inhibited), consistent with the presence of SoADHα with relaxed sensitivity to Tyr (FIG. 6).

ADHα-containing species all had significantly higher Tyr levels (from 12 to 180 nmol/gFW) than *Arabidopsis* (FIG. 11C). These results demonstrate that betalain-producing species have ADHα with relaxed sensitivity to Tyr inhibition and accumulate elevated levels of Tyr.

Figure 14A:
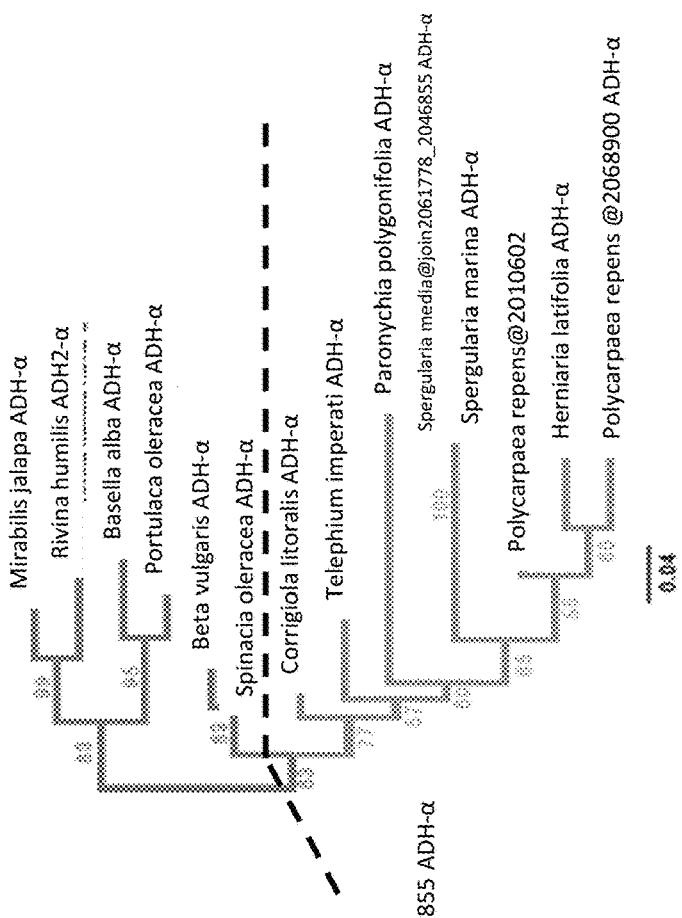
FIGS. 14A-14B shows ADHα sequences used for texting relax selection.
Figure 14B:
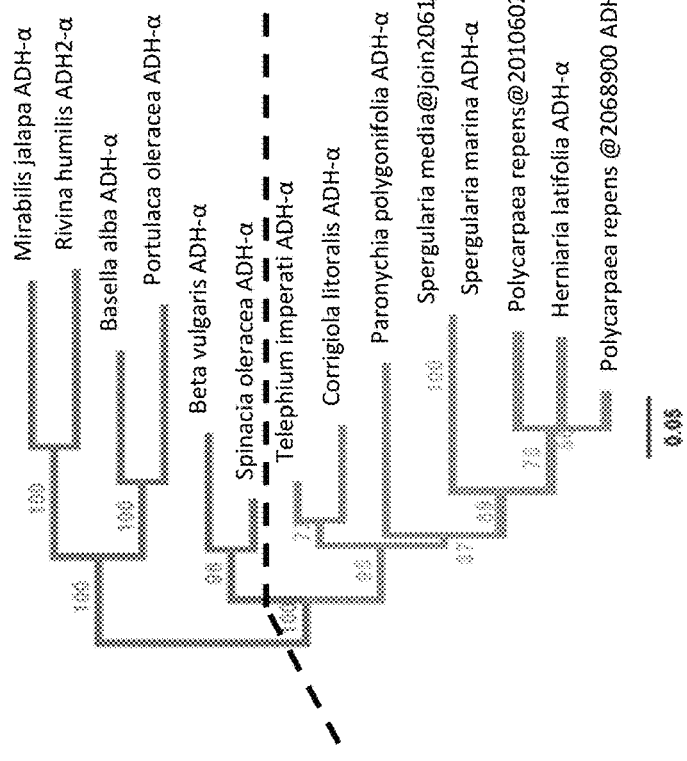
Figure 15:
FIG. 15 shows the Histidine 217 residue responsible for Tyr sensitivity of *Aquifex aeolicus* PDH (AaPDH) is still present in BvADHα. Previous studies showed that the H217 residue of AaPDH (denoted by triangles) is absent in Tyr-insensitive ADH of *Synechocystis* sp. PCC6803 (SyADH) and confers Tyr sensitivity of AaPDH (Sun et al., 2009, Legrand, P. et al. 2008). The amino acid alignment of AaPDH, SyADH together with BvADHα, BvADHβ, and *Arabidopsis* ADH (AtADH2) (SEQ ID NOs: 1, 14, and 92-94) showed that corresponding His residues are present in all plant ADHs. This result suggests that yet to be identified novel residues and mechanism are involved in the relaxed Tyr sensitivity of BvADHα.

ADHα Orthologs Underwent Relaxed Selection and Gene Loss in Lineages that have Reverted from Betalain to Anthocyanin Pigmentation Interestingly, when ADHα orthologs were recovered from Caryophyllaceae or Molluginaceae transcriptomic data, they were often recovered in partial sequences, indicating general low abundance. Within the Caryophyllaceae, ADHα orthologs was only detected in the subfamily Paronychioideae (Greenberg & Donoghue, 2011), which forms a grade paraphyletic to the rest of the family. To test for relaxed selection in anthocyanic lineages we further examined a subset of ADHα orthologs with sequences either verified by Sanger sequencing or by transcriptome read mapping and manual inspection of read coverage. Although no obvious acceleration of substitution was observed in Caryophyllaceae from nucleotide coding sequences (CDS, FIG. 14A), there was apparent acceleration in their amino acid sequences (FIG. 14B). Furthermore, the dN/dS ratio in Caryophyllaceae ADHα (0.166) was elevated compared to the rate among betalain-producing ADHα (0.0743) under the Partitioned MG94xREV Model, assuming homogenous synonymous and nonsynonymous rates across sites. In addition, we found evidence of relaxed selection (as opposed to intensification of positive selection) that contributes to the increase in nonsynonymous rate in Caryophyllaceae under the RELAX framework (p=5.6E-8, Table 5) (Wertheim et al., 2014). Moreover, the genome assembly of the antho-

TABLE 4

Tyr sensitivity of ADH activity from plant tissue extracts. Total protein extracts of spinach, *Dianthus barbatus*, and *Arabidopsis* leaf tissues were used to analyze ADH activity in the presence and absence of 0.5 mM Tyr analog (3-fluoro-Tyr), which were used to calculate percent inhibition. ADH activity was measured with 1 mM arogenate substrate and 1 mM NADP$^+$ cofactor during 2 hr incubation (see FIG. 13). Data are means ± s.e.m. (n = 4).

| species | ADH activity (nmol/mg protein) | | inhibition (%) |
| --- | --- | --- | --- |
| | 0 mM 3-fluoro-Tyr | 0.5 mM 3-fluoro-Tyr | |
| *Spinach oleracea* | 66.4 ± 5.0 | 52.7 ± 1.9 | 20.7% |
| *Dianthus barbatus* | 18.1 ± 0.3 | 0.9 ± 0.2 | 95.0% |
| *Arabidopsis thaliana* | 93.5 ± 5.2 | 7.8 ± 0.5 | 91.6% |

To further test if the presence of deregulated ADHα leads to increased Tyr accumulation in betalain-producing species, Tyr levels were quantified in young leaves of a variety of Caryophyllales species with or without ADHα and also in *Arabidopsis thaliana* as a comparison. Anthocyanin-producing species from non-core Caryophyllales (e.g. *Nepenthes ventricosa* x *alata*) and Caryophyllaceae (e.g. *Dianthus barbatus*) had Tyr levels (2.1 to 8.8 nmol/gFW) comparable to that of *Arabidopsis* (5.3 nmol/gFW). On the other hand, while large variations were observed, betalain-producing cyanic carnation (*Dianthus caryophyllus*, Caryophyllaceae subfamily Caryophylloideae that nested within subfamily Paronychioideae, Greenberg & Donoghue, 2011; Yagi et al., 2014) lacked ADHα ortholog and only contained ADHβ ortholog, suggesting complete gene loss of ADHα in the subfamily Caryophylloideae (Greenberg & Donoghue, 2011). Species within the anthocyanic Caryophyllaceae, therefore, exhibit the transition from relaxed selection to gene loss of ADHα orthologs, which associates with the loss of betalain pigmentation in Caryophyllaceae.

TABLE 5

RELAX analysis support the acceleration in amino acid substitution in Caryophyllales is due to relaxed purifying selection, instead of intensified positive selection

| Model | log L | # par. | AICc | Ltree | Branch set | ω1 (purifying selection) | ω2 (nearly neutral) | ω3 (positive selection) |
|---|---|---|---|---|---|---|---|---|
| Partitioned MG94xREV | −5484.8 | 38 | 11046.5 | 2.23 | Reference | 0.0743 (100%) | | |
| | | | | | Test | 0.166 (100%) | | |
| Null | −5374.3 | 41 | 10831.7 | 11.9 | Reference | 0.00 (83%) | 0.550 (15%) | 30.9 (1.4%) |
| | | | | | Test | 0.00 (83%) | 0.550 (15%) | 30.9 (1.4%) |
| Alternative | −5359.6 | 42 | 10804.2 | 84.5 | Reference | 0.00598 (91%) | 0.650 (7.9%) | 540 (1.5%) |
| | | | | | Test | 0.0646 (91%) | 0.794 (7.9%) | 29.0 (1.5%) |

K = 0.54. Test for selection relaxation (K < 1) was significant (p = 5.6e−8, LR = 29.48)

Discussion

This study found that *B. vulgaris* has ADH but no PDH enzymes or activity (FIG. 1B, FIGS. 3, 4). This is similar to most plants (Connelly & Conn, 1986; Gaines et al., 1982; Rippert & Matringe, 2002a,b) but different from legumes that have both ADH and PDH (Rubin & Jensen, 1979; Schenck et al., 2015; 2017; Siehl, 1999). Thus, *B. vulgaris* synthesizes Tyr via the ADH pathway that occurs within the plastids (Rippert et al., 2009) (FIG. 1C). We also found that *B. vulgaris* possesses two paralogous genes encoding the ADH enzymes, namely ADHα and ADHβ. Interestingly, ADHα but not ADHβ exhibited relaxed sensitivity to Tyr inhibition (FIG. 6). Although recent studies reported that the legume PDH enzymes are also Tyr insensitive (Schenck et al., 2015; 2017), BvADHα and legume PDHs have two major differences. First, legume PDHs are localized in the cytosol (Schenck et al., 2015), whereas BvADHα (and BvADHβ) was targeted to the plastids (FIG. 1C). Second, legume PDHs completely lost Tyr sensitivity (Schenck et al., 2015) but BvADHα was still inhibited by Tyr at higher concentrations (FIG. 6, FIG. 7). The maintenance of inhibition at higher concentration is likely necessary because Phe biosynthesis is also localized within the plastids, and thus BvADHα is directly competing for the arogenate substrate with Phe biosynthesis (FIG. 1A). Complete loss of ADH regulation by Tyr would, therefore, deplete Phe and essential Phe-derived compounds (e.g., proteins, lignin).

Other insensitive ADH/PDH enzymes have been previously found in microorganisms (Legrand et al., 2006) and the structural analyses of Tyr sensitive and insensitive enzymes identified histidine 217 as a possible residue responsible for its Tyr sensitivity (Legrand et al., 2006; Sun et al., 2009). Also, phylogeny-guided structure-function analysis revealed that converting a single active site aspartate 222 residue into a non-acidic residue played a key role in the evolution of the legume PDH enzymes and simultaneously introduced prephenate substrate specificity and Tyr insensitivity (Schenck et al., 2017). However, the corresponding histidine and aspartate residues are still present in BvADHα (FIG. 15), suggesting that different mechanisms, and as yet unidentified residues are involved in the relaxed Tyr sensitivity of BvADHα.

Previous analyses of molecular evolution of DODAa and CYP76AD1α, two enzymes which convert Tyr into betalains (Christinet et al., 2004; Gandía-Herrero & García-Carmona, 2012; Hatlestad et al., 2012), revealed that both of these genes arose through gene duplication, just prior to the origin of betalain pigmentation in Caryophyllales (Brockington et al., 2015). Similarly, this study found that ADHα orthologs arose by gene duplication, prior to the emergence of DODAα and CYP76AD1α (FIGS. 11A and 11B), intimately associated with the origin of betalain pigmentation. One of the duplicated copies, ADHα, underwent neofunctionalization and became much less sensitive to Tyr inhibition, which is the key regulatory mechanism of Tyr biosynthesis (Maeda & Dudareva, 2012; Rippert & Matringe, 2002a,b). ADHα enzymes with relaxed Tyr sensitivity are maintained in all betalain-producing species of Caryophyllales, at least the ones that we analyzed (FIGS. 6 and 12). Furthermore, the expression pattern of BvADHα is distinct from that of BvADHβ and similar to those of the betalain biosynthetic genes (DODAα and CYP76AD1α) and MYB1 transcription factor (FIG. 1D), suggesting that the alteration of ADHα enzyme property was accompanied by changes in its expression profile. Although similar examples of biochemical and transcriptional changes during the evolution of plant specialized metabolic enzymes/genes have been reported (Kajikawa et al., 2017; Moghe & Last, 2015; Panchy et al., 2016; Weng et al., 2012; Xu et al., 2017), here we revealed a unique example of coordinated evolution of primary amino acid pathway (i.e. Tyr biosynthesis) and its downstream specialized metabolism (i.e. betalain biosynthesis).

In the anthocyanic Caryophyllaceae, the transition of betalain pigmentation to anthocyanin pigmentation was associated with down-regulation, relaxed natural selection, and deletion of ADHα (FIGS. 11, and 14, Table 5). Similar down-regulation and deletion of genes were also observed during the loss of flower petals (Zhang et al., 2013) and arbuscular mycorrhizal symbiosis (Delaux et al., 2014) in various plant lineages. Together these lines of evidence suggest that maintenance of the ADHα is superfluous, following loss of betalain pigmentation. The ultimate cause of reversion of betalain to anthocyanin pigmentation in multiple lineages within the core Caryophyllales is currently unknown. It may be due to a number of factors, including: i) metabolic cost of nitrogen-containing alkaloid betalain pigments, ii) shift in pollinator populations that are attracted by unique spectra (e.g. blue) of some anthocyanins, iii) increased demand for other Phe-derived compounds (e.g. tannins, flavonoids), or iv) simple genetic drift enabled by the presence of still intact Phe, phenylpropanoid, core flavonoid pathways in betalain-producing plants (Brockington et al, 2011; Shimada et al., 2005; Xu et al., 2016).

A mechanism underlying the mutually exclusive distribution of betalain and anthocyanin pigments has long fascinated evolutionary biologists (Brockington et al, 2011; Des Marais, 2015). Our analyses now provide one possible explanation. The relaxation of the Tyr-mediated feedback inhibition may direct more carbon flow towards Tyr, and away from Phe biosynthesis (FIG. 1A), as demonstrated by increased Tyr and decreased Phe levels upon transient expression of ADHα (FIG. 10). This may create a surplus of Tyr at the expense of Phe-derived products such as anthocyanins. Furthermore, betalain-producing, ADHα-containing core Caryophyllales species accumulated more Tyr than plants not possessing ADHα (FIG. 11C). The involvement of other factors such as transcriptional regulation of betalain, anthocyanin, and Tyr/Phe pathway genes remain to be examined (Hatlestad et al., 2015; Ambawat et al, 2013), however our data provide a fascinating insight into the contribution of Tyr biosynthesis regulation to the evolution of a novel betalain pigment biosynthesis.

Prior heterologous reconstructions of specialized metabolic pathways resulted in significant accumulations of Tyr-derived plant natural products, such as a cyanogenic glycoside, dhurrin, in *Arabidopsis* (~4% per dry weight, Tattersall et al., 2001; Kristensen et al., 2005) and betalains in tobacco (330 mg kg$^{-1}$ approaching red beet extract of 760 mg kg$^{-1}$, Polturak et al., 2016). In other cases, however, DODA and CYP76AD1 expression in *Arabidopsis* still required feeding of Tyr for betalain production (Harris et al., 2012; Sunnadeniya et al., 2016). Therefore, "pulling" a precursor (e.g. Tyr) may not be always enough to efficiently produce its downstream product, and "pushing" the precursor supply may be also important. Indeed, in red beets, increased Tyr levels have a strong positive correlation with enhanced accumulation of betalains (Wang et al., 2017), suggesting that elevated production of Tyr plays important role in overall production of betalains. Over 100-fold increase in Tyr accumulation observed in *N. benthamiana* leaves expressing ADHα (FIG. 10) further demonstrates an exciting opportunity to introduce Caryophyllales ADHα enzymes into other plants and microbes, deregulate Tyr biosynthesis, and boost the availability of Tyr and the production of Tyr-derived products (e.g., vitamin E, isoquinoline alkaloids including morphine).

Additional Materials and Methods

ADH Activity from Plant Tissue Extracts

Spinach *oleracea* seeds (HighMowing, Wolcott, VT) and pink *Dianthus barbatus* (BloomIQ, Lansing, MI) seedlings were purchased from a nursery and were grown together with *Arabidopsis thaliana* (ecotype Columbia) in 22° C., 60% humidity, and 12/12 h light cycle growth chamber. Leaves of spinach and *Arabidopsis* seedlings were harvested at 3-week-old, and *Dianthus barbatus* leaves were harvested at 6-week-old. The crude extracts of *Arabidopsis* or *Dianthus barbatus* were prepared from ~1 g leaf tissues according to Aryal et al. (2014). For spinach, ~10 g leaf tissues were used to isolate the plastids according to Aryal et al. (2014) in order to avoid the undesired cytosolic polyphenol oxidase activity. Crude or plastid fractions were desalted by Sephadex G50 column to obtain protein extracts, and protein concentration of all biological replicates were adjusted to 0.06, 0.85, and 0.6 mg/mL for spinach, *Dianthus barbatus*, and *Arabidopsis* extracts, respectively. Time course ADH activity assays at 0, 1, 2, and 3 hr were performed in the presence and absence of 500 μM Tyr analog, 3-fluoro-Tyr, in 10 μL reaction containing 50 mM sodium phosphate (pH 8.0), 1 mM arogenate, 1 mM NADP$^+$, 10 μg/mL tetracycline (to inhibit prokaryotic-type protein synthesis of plastids or bacterial contamination), and 0.3, 4.25, and 3 μg of spinach, *Dianthus*, and *Arabidopsis* protein, respectively. The reaction was stopped by adding 20 μL methanol containing 10 μM norvaline as an internal standard. Respective boiled protein extracts were used as negative controls. ADH activity was quantified by the formation of tyrosine according to (Schenck et al., 2015), except that tyrosine was detected as o-phthalaldehyde derivative with excitation/emission wavelength of 360/455 nm by fluorescence detector, and o-phthalaldehyde derivative of the norvaline internal standard was quantified at 336 nm by DAD detector.

Analysis of Tyr Contents from Caryophyllales Tissues

Metabolite extracts of thirteen Caryophyllales species were prepared from ~70 mg of youngest leaves, except for flowers of a Cactaceae species to avoid succulent tissues. All plants were grown and harvested at Botany Greenhouse of the University of Wisconsin-Madison. Young leaf tissues of ~4 weeks-old *Arabidopsis* Columbia ecotype were used as a control. Harvested tissues were extracted by adding 400 μL extraction buffer containing methanol:chloroform (2:1, v/v) and 100 μM 4-chlorobenzoic acid (an internal standard). After adding 300 μL water and 125 μL chloroform, the mixture was vigorously mixed by a vortex mixer for 5 min and centrifuged at 20,000 g for 5 min for phase separation. The upper polar phase of 400 μL was transferred to a new centrifuge tube and dried down in a benchtop speed vacuum (Labconco, Kansas City, MO, USA). The dried polar phase was resuspended in 200 μL methanol. After centrifugation at 20,000 g for 5 min, 20 μL was injected into the Agilent 1260 HPLC equipped with Atlantis T3 C-18 column (3 μm, 2.1×150 mm, Waters, Milford, MA), and separated by the following gradient of acetonitrile (B) in 0.1% formic acid (A): 1% B for the first 5 min, followed by a linear increase to 76% B at 10 min, an isocratic elution at 76% B until 16 min, followed by re-equilibration at 1% B. Tyr was monitored with the fluorescence detector at 274 and 303 nm for excitation and emission, respectively. The internal standard was monitored by photodiode array detector at 270 nm. Statistical analyses were conducted by the Statistica Analysis Software (SAS) based on the "mixed" effect model (Pinheiro, 2000) to compare between the two groups having and not-having ADHα and using the "fixed" effect model (Milliken, 2009) to compare individual samples against *Arabidopsis* control.

Reverse Transcription PCR (RT-PCR) Analysis

RT-PCR was carried out on five biological replicates for each infiltrated vector (FIG. 9B). Two technical replicates were additionally analyzed for one sample each for BvADHα and BvADHβ infiltrations. RNA was extracted and DNAse treated using the RNeasy Plant Mini Kit and the RNAse-free DNAse set (Qiagen, Hilden, Germany). cDNA was prepared using BioScript Reverse Transcriptase (Bioline Reagents, London, UK) and an oligo (dT) 18 primer according to the manufacturer's recommendations. A control with no reverse transcription was included to test the presence of genomic DNA. RT-PCR was performed on a 1:10 cDNA dilution with the KAPA 2G Fast DNA Polymerase kit (KAPA Biosystems, Wilmington, MA, USA) and an Eppendorf Mastercycler Nexus (Eppendorf, Hamburg, Germany). Amplification conditions were as follow: initial step of 1 min at 95° C. followed by 30 cycles of 10 s at 95° C., 10 s at 60° C. and 2 s at 72° C., and a final step of 5 min at 72° C. Amplicons were visualised on 2% agarose gel electrophoresis using ethidium bromide (0.1 μg/ml) and run at 120V for 20 min. The expected size for the reactions is 140, 90 and 111 bp for BvADHα, BvADHβ, and tGFP, respectively. Primers used are described in Table 1.

Quantitative Real-Time PCR (qRT-PCR) Analysis

For quantification of endogenous expression of BvACTIN (internal control), BvADHα, BvADHβ, BvDODA, BvMYB1 and BvCYP76AD1, red beet (W357B) and sugar beet (Big Buck) plants were grown in 22° C., 60% humidity, and 12/12 hr light cycle in a growth chamber. The seedlings were harvested at 7-days after germination and the tissue was divided into cotyledon and hypocotyl. RNA was extracted (Oñate-Sánchez and Vicente-Carbajosa, 2008) and DNAse treated (Ambion, Austin TX, USA) following by cDNA preparation using MLV Reverse Transcriptase (Promega, Madison, WI, USA). qRT-PCR was performed using the GoTaq qPCR Master Mix (Promega, Madison, WI, USA), and the Stratagene Mx3000P qPCR System (Agilent Technologies, Stratagene, La Jolla, CA, USA). Amplification conditions were as follow: an initial step of 1 min at 95° C. followed by 45 cycles of 15 s at 95° C., 30 s at 60° C. and 30 s at 72° C. The gene expression of BvADH was normalized using BvACTIN as an internal control and analyzed by using the relative expression of the genes. The results are shown in % expression relative to the highest sample (FIG. 1D). Primers used in all qPCR analysis are listed in Table 1.

Phylogenetic Analysis

Amino acids from genomes (full open reading frame) and transcriptomes (full or partial open reading frame) of Brockington et al. (2015) were used in this analysis with minor modifications in species included (Table 2). The final taxon sampling in this study consisted of 95 species, with 91 ingroup species (89 transcriptomes and 2 genomes) representing 26 of the 39 families in Caryophyllales (Hernández-Ledesma et al., 2015) and four outgroup genomes from eudicots and monocots (Table 2). Amino acid sequences of the 11 functionally characterized ADH genes were used as baits to search against each of the 95 species. To maximize the sensitivity of homology searches in order to identify short and incomplete sequences from de novo assembled transcriptomes, we used SWIPE v2.0.11 (Rognes, 2011) with a high E-value cutoff of 10 and low minimal bitscore cutoff of 30. Hits from all 11 query sequences against each species were ranked from high to low by bitscore, and the top 10 hits from each species were pooled and used for the initial phylogenetic analysis.

The pooled top hits from each of the 95 species, together with the 11 baits were used as the starting sequence file (948 sequences). An initial phylogenetic analysis was conducted using MAFFT v7.215 with "--genafpair --maxiterate 1000" (Katoh & Standley, 2013). Columns with more than 90% missing data in the resulting alignment were trimmed using Phyutility v2.2.6 with "-clean 0.1" (Smith & Dunn, 2008) and a phylogeny was estimated using RAXML v8.1.5 with the model "PROTCATWAG" (Stamatakis, 2014). After visually examining the alignment and tree, tips with branch lengths that were outliers were removed (any terminal branches that had on average more than two substitutions for each amino acid site; or more than ten times longer than its sister group and on average had more than one substitution per site; Yang and Smith, 2014). Monophyletic or paraphyletic tips that belonged to the same species from transcriptome data most often resulted from isoforms produced during de novo assembly. These were masked, leaving only the tip with the highest number of aligned characters (Yang and Smith, 2014). Internal branches with molecular branch lengths longer than 1 were likely due to distantly related paralogs or assembly artifacts and were pruned. A large number of distantly related genes, isoforms, and assembly errors were removed during the tip trimming and long branch removing process, with 251 sequences left. A new fasta file was written from remaining tips, and this alignment, tree building, and tree trimming procedure was repeated once, with 229 sequences left. Following the homology search and filtering, we extracted the Caryophyllales ADH gene lineage rooted by outgroup genomes (Yang and Smith, 2014). While visually examining alignment and tree we found the sequence Cham@c36044_g1_12_242_1480_minus that belonged to *Chenopodium giganteum*, but were placed in between ADHα and ADHβ, outside of Chenopodiaceae. Further examination of the alignment showed that the half of the sequence was closely related to ADHα, and the other half closely related to ADHβ. Although this can be real, it is most likely an assembly error and was removed from the analysis. Indeed, *Chenopodium giganteum* had additional, correctly assembled ADHα and ADHβ copies nested in respective Chenopodiaceae clades. Therefore this putative chimeric sequence was removed.

Remaining sequences belonged to the Caryophyllales ADH lineage were aligned with MAFFT with "--genafpair --maxiterate 1000" and trimmed by Phyutility with "-clean 0.3". An alternative alignment was constructed with PRANK v140603 using default settings (Löytynoja & Goldman, 2008; 2010), poorly aligned sequences were manually removed, and trimmed by Phyutility with "-clean 0.1". We used two alternative alignment methods because MAFFT tends to force regions to align even when they are highly divergent whereas PRANK tends to introduce lots of gaps in highly divergent regions. On the other hand, PRANK is an iterative alignment, tree building, and refinement pipeline that we run five iterations before obtaining the final alignment. For both trimmed alignments, a phylogenetic tree was constructed using RAxML with "-m PROTCATAUTO" and 200 rapid bootstrap replicates to evaluate support. Given that the resulting tree topologies and support values using both alignments were very similar we are presenting the results from MAFFT. The code used in the phylogenetic analysis is available from bitbucket.org/yangya/adh_2016.

Testing for Relaxed Section in Caryophyllaceae

To test for shift in selection pressure in ADHα associated with loss of betalain, we carried out selection analysis on a reduced data set that included representative sequences across ADHα that were either verified by Sanger sequencing or by mapping reads back to the de novo assembled contigs and carefully examining read coverages visually.

Within the family Caryophyllaceae, ADHα expression was detected in the transcriptome of only the subfamily Paronychioideae. Those ADHα transcripts from *Corrigiola litoralis* and *Telephium imperati* were both confirmed by PCR and Sanger sequencing. Two *Spergularia media* fragments from transcriptome assembly were both belonged to ADHα and are non-overlapping in the alignment. These two fragments could be from two loci or from a single locus. To distinguish between these two scenarios, we first extended the two fragments separately using Assembly by Reduced Complexity (Hunter et al., 2015, ARC v.1.1.3) with maximum 10 cycles, Bowtie 2 v2.2.8 (Langmead & Salzberg, 2012) for read mapping and Newbler v2.9 (454 Life Sciences, downloaded Mar. 17, 2015) for assembly. After extending the original assembly and aligning it with other ADHα sequences, the two extended fragments were still 22 base pairs apart. To evaluate whether these two fragments were supported by raw reads we concatenated the two fragments by fixing the direction and adding 22 Ns to the middle, and mapped raw reads to the concatenated reference using Bowtie 2 with the setting "--phred64 --very-fast-local". The 22 bp gap was highly supported by read pairs and the joined read were kept for subsequent dN/dS analysis. We carried out the same procedure for *Polycarpaea repens* but were unable to join the reads nor confirm they are paralogs due to low read coverage and a longer gap between the two fragments. Therefore, the two fragments were kept in the alignments for phylogenetic analysis but were removed for dN/dS analysis.

To obtain ADHα sequences from additional species of Caryophyllaceae, primers were designed to the conserved portion of the *Spergularia media* contig, and were used to amplify ADHα sequences from the closely related *Spergularia marina*. Inverse PCR was used to obtain ADHα sequences from *Spergularia marina, Paronychia polygonifolia* and *Herniaria latifolia*. For inverse PCR, genomic DNA was digested with restriction enzymes EcoRI and Mfel, and fragments were circularised with T4 ligase (Biolabs, New England). Nested primers were used to amplify the fragment containing the ADHα ortholog. Amplified products were sanger sequenced to acquire the 5' and 3' terminals of the locus. In summary, a total of six well-supported ADHα sequences were then taken forward for the dN/dS selection analyses.

Our final alignment for selection analysis included eight ADHα sequences in Caryophyllaceae and six additional sequences from representative betalain-producing species across rest of the ADHα lineage. We first trimmed the alignment to remove signal peptide and poorly aligned ends, leaving the region from BvADHα amino acid no. 79 to 354 that covered the enzyme active domain. We then carried out phylogenetic analyses for both alignments in RAXML, with the model "GTRCAT" for the codon alignment and "PROTCATAUTO" for the amino acids alignment, and 200 rapid bootstrap replicates to evaluate node support (FIG. 14A, 14B). To quantify the rate shift, we carried out RELAX analysis (Wertheim et al., 2014) as implemented in the online portal Datamonkey (Kosakovsky Pond & Frost, 2005, accessed Mar. 19, 2016), using the trimmed CDS matrix with *Polycarpaea repens* removed. RELAX has the advantage of distinguishing between increased positive selection vs. reduced purifying selection, both of which would result in accelerated average dN/dS values. We designated all crown branches in Caryophyllaceae as the testing branches and the rest branches as the background. We fitted the partitioned MG94xREV model that assumes all sites having unified dN and dS value, allowing the rate to vary between the test and background branches. We also fitted the RELAX model that takes site heterogeneity into account. The RELAX null model assumes all background and test branches share the same rate in each rate category, whereas the RELAX alternative model allows substitution rate to vary between the test and background branches in each rate category, and sites can move among rate categories.

Example 2: Overexpression of BvADHα but not BvADHβ Leads to High Accumulation of Tyrosine in *Arabidopsis thaliana*

Figure 16:
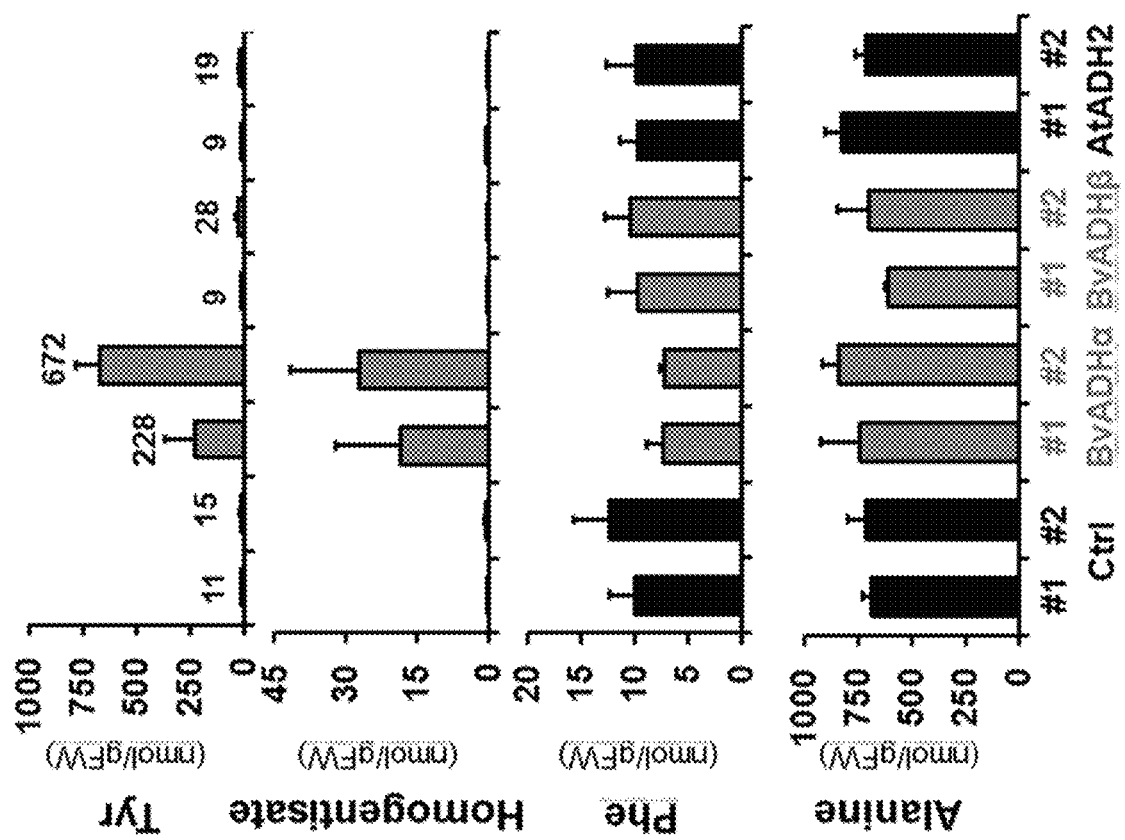
FIG. 16 shows expression of BvADHα in *Arabidopsis* leads to hyper-accumulation of tyrosine. Overexpression of tyrosine-insensitive BvADHα, but not BvADHβ or AtADH2, in *Arabidopsis* drastically enhanced accumulation of tyrosine and homogentisate, the downstream product of tyrosine and precursor of tocopherols and plastoquinone. Four-week old *Arabidopsis* leaf tissue was submitted to chemical analysis by GC-MS. Two representative homozygous lines for each construct were selected. Control plants (Ctrl) are lines transformed with the empty vector. The content of tyrosine (Tyr), homogentisate, phenylalanine (Phe), and alanine (Ala) are shown as nmol/g of fresh weight. Samples were normalized by the internal recovery standard, norvaline. Values are mean of 3 biological replicates±SD (standard deviation). The above experiments were repeated at least 3 times with similar results.

*Beta vulgaris* accumulates high amounts of endogenous tyrosine as well as its derived metabolites betalains due to the presence of the tyrosine-insensitive BvADHα enzyme. To further test if the lack of BvADHα feedback regulation is a critical factor for high tyrosine accumulation in plant tissues, BvADHα, BvADHβ, and *Arabidopsis* ADH2 (AtADH2) were individually overexpressed by the 35S promoter of the cauliflower mosaic virus (CaMV) in *A. thaliana* Col-0 background. The empty vector containing no gene was also introduced as a negative control. Gas chromatography-mass spectrometry (GC-MS) based metabolite analysis showed that overexpression of BvADHα but not BvADHβ or AtADH2 leads to much higher accumulation of tyrosine than the empty vector control (nearly 50-fold increase, FIG. 16). In addition, BvADHα expression resulted in a slightly reduction of an aromatic amino acid phenylalanine and drastic increase in homogentisate, the downstream product of tyrosine and precursor of tocopherols (vitamin E). No differences were observed for most amino acids, including alanine. These results provide proof-of-concept demonstration that the production of tyrosine can be substantially enhanced by the expression of a tyrosine-insensitive ADH enzyme (i.e. BvADHα) in plant tissues. In addition, the observed increase of homogentisate as a consequence of high levels of tyrosine suggests that Tyr availability is a limit-step for the production of Tyr-derived secondary metabolites in plants such as tocopherols or betalains.

Material and Methods

Cloning of BvADHα, BvADHβ and AtADH2 cDNAs into Overexpression Binary Vector

Total RNA isolated from *Beta vulgaris* and *Arabidopsis thaliana* leaf tissues were used to synthesize cDNA using random primers and the High Capacity cDNA Reverse Transcription Kit (Applied Biosystems). Specific oligonucleotides to amplify each of the desired cDNAs were designed using In-Fusion® Primer design tool (Clontech). PCR fragments were obtained using Phusion High-Fidelity DNA polymerase and cloned into the binary vector DF 264 vector, downstream of the 35S CaMV promoter, using the In-Fusion® HD cloning kit. Plasmid was linearized with the restriction enzymes Xbal and BamHI (FastDigest, Thermo Scientific) and the enzymes sites were preserved after cloning. Xbal site is upstream of ATG start codon and BamHI is downstream of TAA stop codon. All reactions were performed accordingly with the instructions of the manufacturer. In-Fusion cloning reactions were transformed into *E. coli* Stellar™ Competent cells (Clontech) and positive colonies were selected on LB agar plates containing 50 μg/mL Spectinomycin. Antibiotic resistance colonies were confirmed for the presence of the cDNA insert by colony PCR and submitted to plasmid isolation. cDNA inserts were checked for possible point mutations by SANGER sequencing the obtained plasmids using primers annealing at the 35S CaMV promoter and NOS terminator. Confirmed vectors were transformed into *Agrobacterium tumefaciens* GV3101 by freeze-thaw method.

*Arabidopsis* Transformation and Transgenic Selection.

Flowering *A. thaliana* Col-0, 5-6 weeks old, were used to plant transformation by floral dip (Bent A (2006) *Arabidopsis thaliana* floral dip transformation method. Methods Mol Biol. 343:87-103). Briefly, flower buds were submerged into *Agrobacterium* GV3101 solution. The excess of solution was removed using absorbent paper. Plants were transfer to a close container to preserve humidity and kept in a dark environment for 16 hours after transformation. After this period of time, plants were acclimated back to the growth chamber. The transformation process was repeated after 5 days of the first transformation and plants were kept in the growth chamber until harvesting. To seeds were chlorine sterilized and germinated on ½ Force Murashige and Skoog (MS) agar plates supplemented with 1% Sucrose and 100 μg/mL of Gentamycin. 10 positive $T_1$ seedlings for each construct were transferred to soil and seeds were harvested for each individual plant. Transgenic lines were then checked for the number of insertions based on the segregation ratio of antibiotic resistant $T_2$ seedlings. Single-insertion homozygous $T_2$ lines were then germinated on soil and 4-weeks old plants were analyzed for Tyr and other organic acids contents by gas chromatography-mass spectrometry analysis (GC-MS).

GC-MS Analysis

Four-week old *Arabidopsis* plants overexpressing BvADHα, BvADHβ, AtADH2 or empty vector were submitted to GC-MS analysis. Briefly, approximately 30 mg of fresh leaf tissue was excised from at least 3 plants of each transgenic line to compound one biological replicate. Tissue sample was transferred to a 1.5 mL microcentrifuge tube and 400 µL of solvent extraction solution [Methanol:Chloroform (2:1) with 100 µM norvaline]. Three 3 mm glass beads were added to each tube and samples were submitted to GenoGrindr (1500 strokes/min) for 5 min. After a brief spin 300 µL of water, followed by 125 µL of Chloroform were added to each sample. Samples were vortex on high for 30 seconds and centrifuged at 21000×g for 5 minutes to achieve phase separation. The aqueous phase was carefully transferred to a new 1.5 mL tube and transfer to speedvac system at room temperature until completely dry. After dry, the polar phase compounds were resuspended in 210 µL of methanol containing 100 µM 4-chlorobenzoic acid. Samples were sonicated for 10 min and insoluble remaining debris was removed by centrifugation at 21000×g for 5 min. at room temperature. 100 µL of supernatant was transferred into a glass vial and the methanol was dry out in the speed vac. After dry, the inserts were transferred to a glass vial and the pellets were ressuspended in 40 µL pyridine. Samples were submitted to sonication for 10 min and 40 µL of N-methyl-N-(tert-butyldimethylsilyl) trifluoroacetamide with 1% tertbutyldimetheylchlorosilane (MTBSTFA+1% t-BDMCS) was added to each sample. Samples were incubated at 80° C. for 1 hour and transferred to analysis on GC-MS. The GC-MS was stablished as Hold at 70° C. for 2 min, increased to 250° C. by 5° C. per min., then hold at 300° C. for 10 min. Amino acid standard (Sigma, #AAS18) was used to stablish the standard curve of each amino acid. Peak areas were normalized by the internal standard norvaline and by fresh tissue weight (g).

Example 3—In Planta Expression of Tyr-Insensitive BvADHα Leads to Enhanced Accumulation of Tyr in *Arabidopsis*

Figure 17:
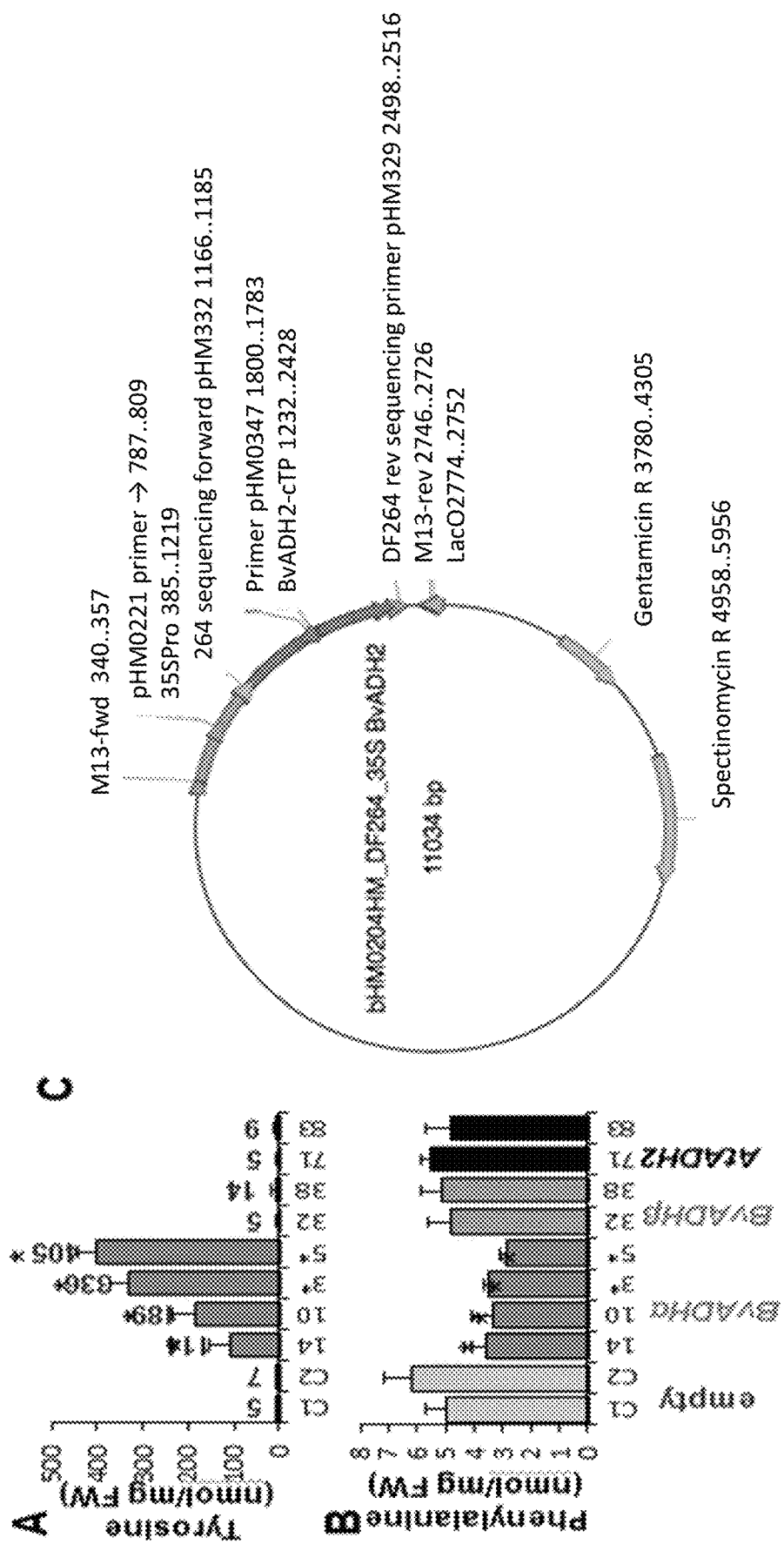
FIG. 17 shows in planta expression of de-regulated BvADHα leads to enhanced accumulation of Tyr in *Arabidopsis*.

BvADHα was heterologously expressed in *Arabidopsis*, which only has Tyr-inhibited ADH enzymes (Rippert and Matringe, 2002a; Rippert and Matringe, 2002b; Schenck et al., 2015). Overexpression of BvADHα, but not Tyr-inhibited BvADHβ or AtADH2, resulted in elevated Tyr accumulation by up to 60-fold compared to empty vector controls in T3 single insertion homozygous lines (FIG. 17). Also, the BvADHα lines reduced levels of Phe. Thus, expression of de-regulated BvADHα can increase the carbon flow through the shikimate pathway and direct away from Phe biosynthesis to drastically enhance availability of Tyr.

Example 4—Heterologous Expression of Tyr-Insensitive BvADHα Leads to Hyper-Accumulation of Tyr in *Glycine max* (Soybean)

Figure 18:
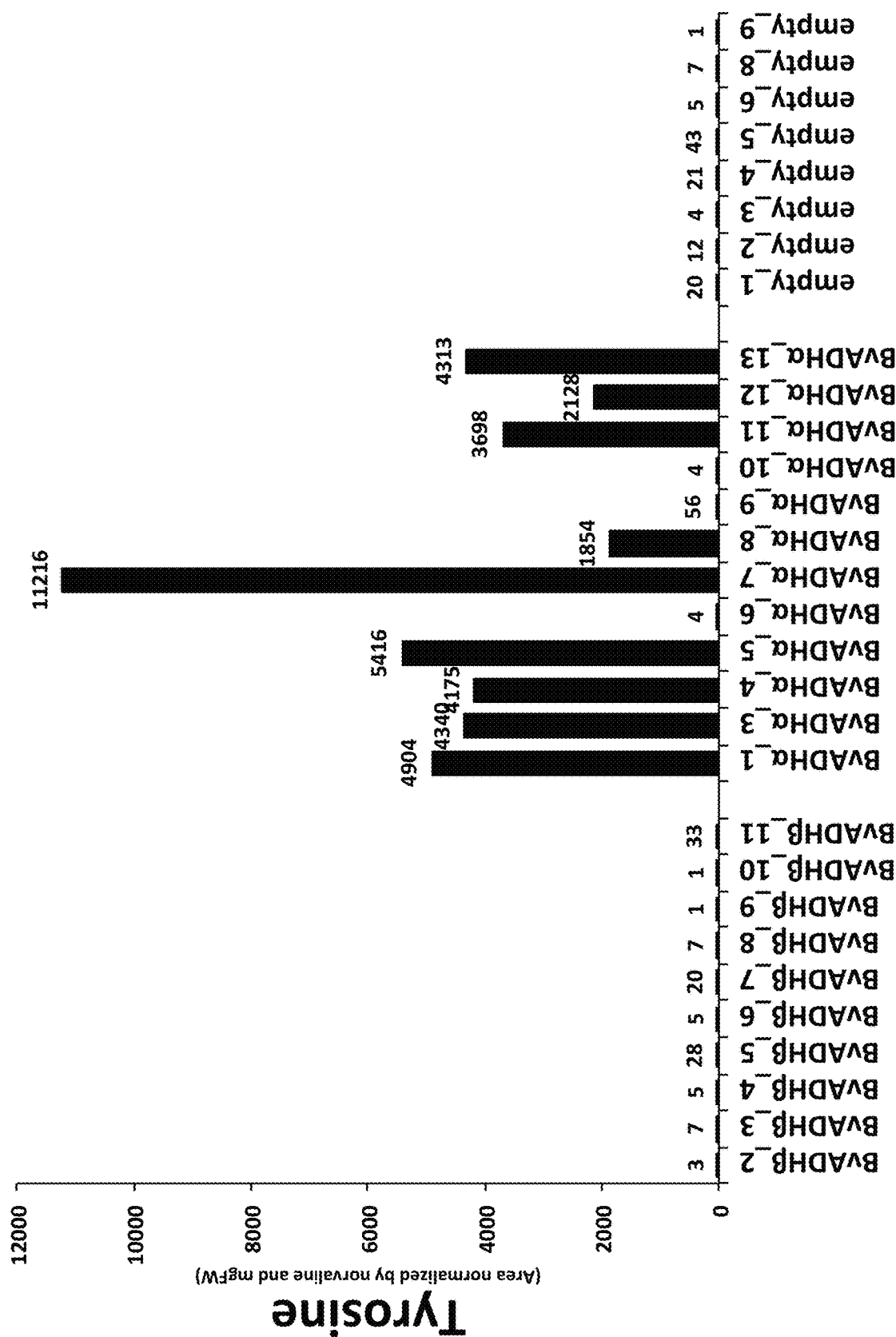
FIG. 18 shows heterologous expression of de-regulated BvADHα leads to hyper-accumulation of Tyr in *Glycine max* (soybean).

BvADHα or BvADHβ was also heterologously expressed in *Glycine max* (soybean), which has both Tyr-inhibited ADH and Tyr-insensitive PDH enzymes (Schenck et al., 2015). When Tyr levels were analyzed in the leaves of antibiotic resisitant $T_1$ transgenic lines, nine out of twelve BvADHα overexpression lines showed nearly 1,000 fold increase in Tyr relative to empty vector control (FIG. 18). All of BvADHβ transgenic lines showed basal levels of Tyr similar to empty vector controls. Three BvADHα lines with low Tyr were likely unsuccessful transformants.

REFERENCES

Ambawat S, Sharma P, Yadav N R, Yadav R C. 2013. MYB transcription factor genes as regulators for plant responses: an overview. *Physiology and Molecular Biology of Plants* 19: 307-321.

Bate-Smith E C. 1962. The phenolic constituents of plants and their taxonomic significance. *Botanical Journal of the Linnean Society* 58: 95-173.

Barshandy H, Jalkanen S, Teeri T H. 2015. Within leaf variation is the largest source of variation in agroinfiltration of *Nicotiana benthamiana*. *Plant Methods* 11: 47.

Beaudoin G A W, Facchini P J. 2014. Benzylisoquinoline alkaloid biosynthesis in opium poppy. *Planta* 240: 19-32.

Bentley R. 1990. The ahikimate pathway-A metabolic tree with many branche. *Critical Reviews in Biochemistry and Molecular Biology* 25: 307-84.

Biancardi E, Panella L W, and Lewellen R. 2012. *Beta maritima: The origin of beets*. New York: Springer.

Bonvin J, Aponte R A, Marcantonio M, Singh S, Christendat D, Turnbull J L. 2006. Biochemical characterization of prephenate dehydrogenase from the hyperthermophilic bacterium *Aquifex aeolicus*. *Protein Science* 15: 1417-32.

Brockington S F, Walker R H, Glover B J, Soltis P S, Soltis D E. 2011. Complex pigment evolution in the Caryophyllales. *New Phytologist* 190: 854-864.

Brockington S F, Yang Y, Gandia-Herrero F, Covshoff S, Hibberd J M, Sage R F, Wong G K S, Moore M J, Smith S A. 2015. Lineage-specific gene radiations underlie the evolution of novel betalain pigmentation in Caryophyllales. *New Phytologist* 207:1170-1180.

Byng G, Whitaker R, Elick C, Jensen ROYA. 1981. Enzymology of L-tyrosine biosynthesis in corn (*Zea mays*). *Phytochemistry* 20: 1289-1292.

Chen F, Tholl D, Bohlmann J, Pichersky E. 2011. The family of terpene synthases in plants: A mid-size family of genes for specialized metabolism that is highly diversified throughout the kingdom. *Plant Journal* 66: 212-229.

Christinet L, Burdet F, Zaiko M, Hinz U, Zrÿd J P. 2004. Characterization and functional identification of a novel plant 4,5-extradiol dioxygenase involved in betalain pigment biosynthesis in *Portulaca grandiflora*. *Plant Physiology* 134: 265-274.

Clement J S, Mabry T J. 1996. Pigment evolution in the caryophyllales: A systematic overview. *Botanica Acta* 109: 360-367.

Connelly J A and, Conn E E. 1986. Tyrosine biosynthesis in *Sorghum bicolor*: isolation and regulatory properties of arogenate dehydrogenase. *Zeitschrift für Naturforschung C* 41: 69-78.

Dal Cin V, Tieman D M, Tohge T, McQuinn R, de Vos R C H, Osorio S, Schmelz E, Taylor M G, Smits-Kroon M T, Schuurink R C, et al. 2011. Identification of genes in the phenylalanine metabolic pathway by ectopic expression of a MYB transcription factor in tomato fruit. *The Plant Cell* 23: 2738-2753.

Delaux P M, Varala K, Edger P P, Coruzzi G M, Pires J C, Ané J M. 2014. Comparative phylogenomics uncovers the impact of symbiotic associations on host genome evolution. *PLOS Genetics* 10: e1004487.

Brockington S F, Alexandre R, Ramdial J, Moore M J, Crawley S, Dhingra A, Hilu K, Soltis P S. 2009. Phylogeny of the Caryophyllales sensu lato: Revisiting hypotheses on pollination biology and perianth differentiation in the core Caryophyllales. *International Journal of Plant Sciences* 170: 627-643.

Dohm J C, Minoche A E, Holtgrawe D, Capella-Gutierrez S, Zakrzewski F, Tafer H, Rupp O, Sörensen T R, Stracke R, Reinhardt R, et al. 2014. The genome of the recently domesticated crop plant sugar beet (*Beta vulgaris*). *Nature* 505: 546-549.

Dornfeld C, Weisberg A J, C R K, Dudareva N, Jelesko J G, Maeda H A. 2014. Phylobiochemical characterization of class-Ib aspartate/prephenate aminotransferases reveals evolution of the plant arogenate phenylalanine pathway. *The Plant Cell* 26: 3101-3114.

Engler C, Youles M, Gruetzner R, Ehnert T M, Werner S, Jones J D G, Patron N J, and Marillonnet S. 2014. A golden gate modular cloning toolbox for plants. *ACS Synthetic Biology* 3: 839-843.

Gaines, C. G., Byng G S, Whitaker R J and, Jensen R A. 1982. L-Tyrosine regulation and biosynthesis via arogenate dehydrogenase in suspension-cultured cells of *Nicotiana silvestris* Speg. et Comes. *Planta* 156: 233-240.

Gandía-Herrero F, García-Carmona F. 2012. Characterization of recombinant *Beta vulgaris* 4,5-DOPA-extradiol-dioxygenase active in the biosynthesis of betalains. *Planta* 236: 91-100.

Gleadow R M, Møller B L. 2014. Cyanogenic glycosides: synthesis, physiology, and phenotypic plasticity. *Annual Review of Plant Biology* 65: 155-185.

Greenberg A K and Donoghue M J. 2011. Molecular systematics and character evolution in Caryophyllaceae. *TAXON* 60: 1637-1652

Goldman I L. 1996. A list of germplasm releases from the University of Wisconsin table beet breeding program. *HortScience* 31: 880-881.

Hanson M et al. 1996. Evolution of anthocyanin biosynthesis in maize kernels: the role of regulatory and enzymatic loci. *Genetics* 143: 1395-1407.

Hatlestad G J, Sunnadeniya R M, Akhavan N, Gonzalez A, Goldman I L, McGrath J M, Lloyd A M. 2012. The beet R locus encodes a new cytochrome P450 required for red betalain production. *Nature Genetics* 44: 816-820.

Hudson, G S, Wong, V., and Davidson B. 1984. Chorismate mutase/prephenate dehydrogenase from *Escherichia coli* K12: purification, characterization, and identification of a reactive cysteine. *Biochemistry* 23: 6240-6249.

Ibarra-Laclette E, Zamudio-Hernández F, Pérez-Torres C A, Albert V A, Ramírez-Chávez E, Molina-Torres J, Fernandez-Cortes A, Calderon-Vazquez C, Olivares-Romero J L, Herrera-Estrella A, et al. 2015. De novo sequencing and analysis of *Lophophora williamsii* transcriptome, and searching for putative genes involved in mescaline biosynthesis. *BMC Genomics* 16: 657.

Khan M I. 2015. Plant betalains: safety, antioxidant activity, clinical efficacy, and bioavailability. *Comprehensive Reviews in Food Science and Food Safety* 15: 316-330.

Kajikawa M, Sierro N, Kawaguchi H, Bakaher N, Ivanov N V, Hashimotp T, Shoji T. 2017. Genomic insights into the evolution of the nicotine biosynthesis pathway in tobacco. *Plant Physiology* 4: 999-1011.

Kristensen C, Morant M, Olsen C E, Ekstrom C T, Galbraith D W, Moller B L, Bak S. 2005. Metabolic engineering of dhurrin in transgenic *Arabidopsis* plants with marginal inadvertent effects on the metabolome and transcriptome. *Proceedings of the National Academy of Sciences of the United States of America* 102: 1779-1784.

Lee, E. J., An, D., Nguyen, C. T. T. Lee, E. J., An, D. Nguyen, C. T., Patill, B. S., Kim, J., & Yoo K. 2014. Betalain and betaine composition of greenhouse or field produced beetroot (*Beta vulgaris* L.) and inhibition of HepG2 cell proliferation. *Journal of Agriculture and Food Chemistry* 62: 1324-1331.

Legrand P, Dumas R, Seux M, Rippert P, Ravelli R, Ferrer J L, Matringe M. 2006. Biochemical characterization and crystal structure of *Synechocystis* arogenate dehydrogenase provide insights into catalytic reaction. *Structure* 14: 767-776.

Mabry T J. 1964. The betacyanins, a new class of red violet pigments, and their phylogenetic significance. In: Leone C A, ed. *Taxonomic biochemistry, physiology, and serology*. New York, NY, USA: Ronald Press: 239-254.

Maeda H, Dudareva N. 2012. The shikimate pathway and aromatic amino acid biosynthesis in plants. *Annual Review of Plant Biology* 63:73-105.

Mene-Saffrane L, Jones A D, DellaPenna D. 2010. Plastochromanol-8 and tocopherols are essential lipid-soluble antioxidants during seed desiccation and quiescence in *Arabidopsis*. *Proceedings of the National Academy of Sciences of the United States of America* 107: 17815-17820.

Millgate A G, Pogson B J, Wilson I W, Kutchan T M, Zenk M H, Gerlach W L, first A J, Larkin P J. 2004. Analgesia: Morphine-pathway block in top1 poppies. *Nature* 431: 413-414.

Mizutani M, Ohta D. 2010. Diversification of P450 genes during land plant evolution. *Annual Review of Plant Biology* 61: 291-315.

Moghe G D, Last R L. 2015. Something old, something new: Conserved enzymes and the evolution of novelty in plant specialized metabolism. *Plant Physiology* 169: 1512-23.

Neelwarne B, & Halagur SB. 2012. Red beet: an overview. In B. Neelwarne (Ed.), Red Beet Biotechnology: Food and Pharmaceutical Applications. New York, New York USA, Springer: 1-43.

Panchy N, Lehti-Shiu M, Shiu S-H. 2016. Evolution of gene duplication in plants. *Plant Physiology* 171: 2294-2316.

Pencharz P B, Hsu J W-C, Ball R O. 2007. Aromatic amino acid requirements in healthy human subjects. *The Journal of Nutrition* 137: 1576S-1578S.

Pichersky E, Lewinsohn E. 2011. Convergent evolution in plant specialized metabolism. *Annual Review of Plant Biology* 62:549-566.

Polturak G, Breitel D, Grossman N, Sarrion-Perdigones A, Weithorn E, Pliner M, Orzaez D, Granell A, Rogachev I, Aharoni A. 2016. Elucidation of the first committed step in betalain biosynthesis enables the heterologous engineering of betalain pigments in plants. *New Phytologist* 210: 269-283.

Rapp R A, Haigler C H, Flagel L, Hovav R H, Udall J A, Wendel J F. 2010. Gene expression in developing fibres of upland cotton (*Gossypium hirsutum* L.) was massively altered by domestication. *BMC Biology* 8: 1-15.

Rippert P, Matringe M. 2002a. Purification and kinetic analysis of the two recombinant arogenate dehydrogenase isoforms of *Arabidopsis thaliana*. *European Journal of Biochemistry* 269: 4753-4761.

Rippert P, Matringe M. 2002b. Molecular and biochemical characterization of an *Arabidopsis thaliana* arogenate dehydrogenase with two. *Plant Molecular Biology* 48: 361-368.

Rippert P, Puyaubert J, Grisollet D, Derrier L, Matringe M. 2009. Tyrosine and phenylalanine are synthesized within the plastids in *Arabidopsis*. *Plant Physiology* 149: 1251-1260.

Rong J, Lammers Y, Strasburg J L, Schidlo N S, Ariyurek Y, de Jong T J, Klinkhamer P G L, Smulders M J M, Vrieling K. 2014. New insights into domestication of carrot from root transcriptome analyses. *BMC Genomics* 15: 895.

Rubin J L, Jensen R a. 1979. Enzymology of L-tyrosine biosynthesis in mung bean (*Vigna radiata* [L.] Wilczek). *Plant Physiology* 64: 727-734.

Schenck C A, Holland C K, Schneider M R, Men Y, Lee S G, Jez J M & Maeda H A. 2017. Molecular Basis of the evolution of alternative tyrosine biosynthetic routes in plants. *Nature Chemocal Biology* 13: 1029-1035.

Schenck C A, Chen S, Siehl D L, Maeda H A. 2015. Non-plastidic, tyrosine-insensitive prephenate dehydrogenases from legumes. *Nature Chemical Biology* 11: 52-57.

Shimada S, Inoue Y T, Sakuta M. 2005. Anthocyanidin synthase in non-anthocyanin-producing Caryophyllales species. *The Plant Journal* 44: 950-959.

Siehl D L. 1999. The biosynthesis of tryptophan, tyrosine, and phenylalanine from chorismate in Plant Amino Acids: Biochemistry and Biotechnology. Singh B, ed. New York: CRC Press, New York, 171-204.

Sparkes I A, Runions J, Kearns A, and Hawes C. 2006. Rapid, transient expression of fluorescent fusion proteins in tobacco plants and generation of stably transformed plants. *Nature Protocols* 1: 2019-2025.

Sun W, Shahinas D, Bonvin J, Hou W, Kimber M S, Turnbull J, Christendat D. 2009. The crystal structure of *Aquifex aeolicus* prephenate dehydrogenase reveals the mode of tyrosine inhibition. *Journal of Biological Chemistry* 284: 13223-13232.

Sunnadeniya R, Bean A, Brown M, Akhavan N, Hatlestad G, Gonzalez A, Symonds V V, Lloyd A. 2016. Tyrosine hydroxylation in betalain pigment biosynthesis is performed by cytochrome P450 enzymes in beets (*Beta vulgaris*). *PLoS ONE* 11: 1-16.

Tanaka Y, Sasaki N, Ohmiya A. 2008. Biosynthesis of plant pigments: anthocyanins, betalains and carotenoids. *Plant Journal* 54: 733-749.

Tattersall D B, Bak S, Jones P R, Olsen C E, Nielsen J K, Hansen M L, Høj P B, Møller B L. 2001. Resistance to an herbivore through engineered cyanogenic glucoside synthesis. *Science* 293: 1826-1828.

Tzin, V. & Galili G. 2010. The biosynthetic pathways for shikimate and aromatic amino acids in *Arabidopsis thaliana*. *The Arabidopsis Book/American Society of Plant Biologists* 8: e0132.

Wang M, Lopez-Nieves S, Goldman IL, and Maeda HA. 2017. Limited tyrosine utilization explains lower betalain contents in yellow than red table beet genotypes. *Journal of Agricultural and Food Chemistry* 65:4305-4313.

Wang X, Xiao H, Chen G, Zhao X, Huang C, Chen C, Wang F. 2011. Isolation of high-quality RNA from *Reaumuria soongorica*, a desert plant rich in secondary metabolites. *Molecular Biotechnology* 48: 165-172.

Weber E, Engler C, Gruetzner R, Werner S, and Marillonnet S. 2011. A modular cloning system for standardized assembly of multigene constructs. *PLoS One* 18: 6:e16765.

Weng J K. 2014. The evolutionary paths towards complexity: A metabolic perspective. *New Phytologist* 201: 1141-1149.

Weng J K, Philippe R N, Noel J P. 2012. The rise of chemodiversity in plants. *Science* 336; 1667-1670.

Wertheim J O, Murrell B, Smith M D, Kosakovsky Pond S L, Scheffler K. 2014. RELAX: detecting relaxed selection in a phylogenetic framework. *Molecular Biology and Evolution* 32: 1-13.

Xu S, Brockmöller T, Navarro-Quezada A, Kuhl H, Gase K, Ling Z, Zhou W, Kreitzer C, Stanke M, Tang H, Lyons E, Pandey P, Pandey S P, Timmermann B, Gaquerel E, Baldwin I T. 2017. Wild tobacco genomes reveal the evolution of nicotine biosynthesis. *Proceedings of the National Academy of Sciences of the United States of America* 114: 6133-6138.

Xu S, Huang Q, Lin C, Lin L, Zhou Q, Lin F and He E. 2016. Transcriptome comparison reveals candidate genes responsible for the betalain-/anthocyanidin-production in bougainvilleas. *Functional Plant Biology* 43: 278-286.

Yagi M, Kosugi S, Hirakawa H, Ohmiya A, Tanase K, Harada T, Kishimoto K, Nakayama M, Ichimura K, Onozaki T, et al. 2014. Sequence analysis of the genome of carnation (*Dianthus caryophyllus* L.). *DNA Research* 21: 231-241.

Zhang R, Guo C, Zhang W, Wang P, Li L, Duan X, Du Q, Zhao L, Shan H, Hodges S a, et al. 2013. Disruption of the petal identity gene APETALA3-3 is highly correlated with loss of petals within the buttercup family (Ranunculaceae). *Proceedings of the National Academy of Sciences of the United States of America* 110: 5074-9.

Aryal U K, Xiong Y, McBride Z, Kihara D, Xie J, Hall M C, Szymanski D B. 2014. A proteomic strategy for global analysis of plant protein complexes. *The Plant Cell* 26: 3867-3882.

Brockington S F, Yang Y, Gandia-Herrero F, Covshoff S, Hibberd J M, Sage R F, Wong G K S, Moore M J, Smith S A. 2015. Lineage-specific gene radiations underlie the evolution of novel betalain pigmentation in Caryophyllales. *New Phytologist* 207: 1170-1180.

Hernandez-Ledesma P, Berendsohn W G, Borsch T, Mering S V, Akhani H, Arias S, Castañeda-Noa I, Eggli U, Eriksson R, Flores-Olvera H, Fuentes-Bazán S, Kadereit G, Klak C, Korotkova N, Nyffeler R, Ocampo G, Ochoterena H, Oxelman B, Rabeler R K, Sanchez A, Schlumpberger B O & Uotila P. 2015. A taxonomic backbone for the global synthesis of species diversity in the angiosperm order Caryophyllales. *Willdenowia* 45: 281-383.

Hunter S S, Lyon R T, Sarver B A J, Hardwick K, Forney L J, Settles M L. 2015. Assembly by Reduced Complexity (ARC): a hybrid approach for targeted assembly of homologous sequences. *bioRxiv*. doi: 10.1101/014662.

Katoh K, Standley D M. 2013. MAFFT multiple sequence alignment software version 7: Improvements in performance and usability. *Molecular Biology and Evolution* 30: 772-780.

Kosakovsky Pond S L, Frost S D W. 2005. Datamonkey: Rapid detection of selective pressure on individual sites of codon alignments. *Bioinformatics* 21: 2531-2533.

Langmead B, Salzberg S L. 2012. Fast gapped-read alignment with Bowtie 2. *Nature Methods* 9: 357-359.

Löytynoja A, Goldman N. 2008. Phylogeny-aware gap placement prevents errors in sequence alignment and evolutionary analysis. *Science (New York, N.Y.)* 320: 1632-1635.

Löytynoja A, Goldman N. 2010. webPRANK: a phylogeny-aware multiple sequence aligner with interactive alignment browser. *BMC Bioinformatics* 11: 579.

Milliken, G A. 2009. Analysis of messy data. Boca Raton: CRC Press.

Oñate-Sánchez L, and Vicente-Carbajosa J. 2008. DNA-free RNA isolation protocols for *Arabidopsis thaliana*, including seeds and siliques. *BMC Research Note* 1: 93.

Pinheiro, J C. 2000. *Mixed-effects models in S and S-PLUS*. New York: Springer.

Rognes T. 2011. Faster Smith-Waterman database searches with inter-sequence SIMD parallelisation. *BMC bioinformatics* 12: 221.

Schenck C A, Chen S, Siehl D L, Maeda H A. 2015. Non-plastidic, tyrosine-insensitive prephenate dehydrogenases from legumes. *Nature Chemical Biology* 11: 52-57.

Smith S A, Dunn C W. 2008. Phyutility: A phyloinformatics tool for trees, alignments and molecular data. *Bioinformatics* 24: 715-716.

Stamatakis A. 2014. RAXML version 8: A tool for phylogenetic analysis and post-analysis of large phylogenies. *Bioinformatics* 30: 1312-1313.

Wertheim J O, Murrell B, Smith M D, Kosakovsky Pond S L, Scheffler K. 2014. RELAX: Detecting relaxed selection in a phylogenetic framework. *Molecular biology and evolution* 32: 1-13.

Yang, Y. and S. A. Smith. 2014. Orthology inference in non-model organisms using transcriptomes and low-coverage genomes: improving accuracy and matrix occupancy for phylogenomics. *Molecular Biology and Evolution* 31: 3081-3092.

We claim:

1. A construct comprising a heterologous promoter operably linked to a polynucleotide encoding an arogenate dehydrogenase (ADH) polypeptide selected from:
   a) the group consisting of any one of SEQ ID NOS: 1, 5, 7, 10, 12, 13, and 43; and
   b) a functional fragment of SEQ ID NO: 43 consisting of amino acids 54-398 of SEQ ID NO: 43;
   wherein the polypeptide maintains at least 50% of its ADH activity in the presence of 10 µM tyrosine.

2. The construct of claim 1, wherein the polynucleotide encoding the ADH polypeptide is codon-optimized for expression in a cell.

3. The construct of claim 2, wherein the cell is a plant cell, bacterial cell, or fungal cell.

4. The construct of claim 1, wherein the heterologous promoter is a plant promoter.

5. The construct of claim 1, wherein the heterologous promoter is an inducible promoter or a tissue-specific promoter.

6. A vector comprising the construct of claim 1.

7. The vector of claim 6, wherein the vector comprises a plasmid.

8. A cell comprising the construct of claim 1.

9. The cell of claim 8, wherein the cell is a plant cell.

10. The cell of claim 9, wherein the plant cell is selected from a soybean plant cell, a mung bean plant cell, an opium poppy plant cell, a *quinoa* plant cell, an alfalfa plant cell, a rice plant cell, a wheat plant cell, a corn plant cell, a sorghum plant cell, a barley plant cell, a millet plant cell, an oat plant cell, a rye plant cell, a rapeseed plant cell, a beet plant cell, and a miscanthus plant cell.

11. A seed comprising the construct of claim 1.

12. A plant comprising the construct of claim 1.

13. The plant of claim 12, wherein the plant is selected from a beet plant, a soybean plant, a mung bean plant, an opium poppy plant, a quinoa plant, an alfalfa plant, a rice plant, a wheat plant, a corn plant, a sorghum plant, a barley plant, a millet plant, an oat plant, a rye plant, a rapeseed plant, and a miscanthus plant.

* * * * *

UNITED STATES PATENT AND TRADEMARK OFFICE
CERTIFICATE OF CORRECTION

PATENT NO. : 12,378,567 B2  
APPLICATION NO. : 15/932337  
DATED : August 5, 2025  
INVENTOR(S) : Hiroshi A. Maeda et al.

Page 1 of 1

It is certified that error appears in the above-identified patent and that said Letters Patent is hereby corrected as shown below:

In the Specification

Column 5, Line 50, "Im" should be --1m--.

Column 21, Line 42, "GSTtrap™MMF" should be --GSTtrap™FF--.

Table 2, Column 25, Line 67, "N/A1" should be --N/A$^1$--.

Column 27, Line 36, "HLADAα" should be --H1ADHα--.

Column 37, Line 42, "RAXML" should be --RAxML--.

Column 37, Lines 66-67, "Cham@c36044_g1_12_242_1480_minus" should be --Cham@c36044_g1_i2_242_1480_minus--.

Column 39, Line 7, "Mefl" should be --MfeI--.

Column 39, Line 21, "RAXML" should be --RAxML--.

Column 40, Line 25, "Xbal" should be --XbaI--.

Column 40, Line 27, "Xbal" should be --XbaI--.

Column 40, Line 52, "To" should be --T$_0$--.

Signed and Sealed this  
Ninth Day of December, 2025

John A. Squires  
*Director of the United States Patent and Trademark Office*